US007291464B2

(12) United States Patent
Kuo

(10) Patent No.: US 7,291,464 B2
(45) Date of Patent: Nov. 6, 2007

(54) AUTOCATALYSIS/YEAST TWO-HYBRID ASSAY

(75) Inventor: Min-Hao Kuo, East Lansing, MI (US)

(73) Assignee: Michigan State University, Lansing, MI (US)

(*) Notice: Subject to any disclaimer, the term of this patent is extended or adjusted under 35 U.S.C. 154(b) by 0 days.

(21) Appl. No.: 10/773,911

(22) Filed: Feb. 6, 2004

(65) Prior Publication Data

US 2004/0259122 A1 Dec. 23, 2004

Related U.S. Application Data

(60) Provisional application No. 60/482,188, filed on Jun. 24, 2003, provisional application No. 60/448,068, filed on Feb. 18, 2003.

(51) Int. Cl.

| | |
|---|---|
| ***C12Q 1/68*** | (2006.01) |
| ***G01N 33/53*** | (2006.01) |
| ***G01N 53/567*** | (2006.01) |
| *C12N 15/63* | (2006.01) |

(52) U.S. Cl. .......................... 435/6; 435/7.2; 435/7.21

(58) Field of Classification Search .................... None
See application file for complete search history.

(56) References Cited

OTHER PUBLICATIONS

Van Criekinge et al, Yeast Two-Hybrid: State of the Art, Biological Procedures Online 2(1): 1-38, 1999.*

* cited by examiner

*Primary Examiner*—Nancy Vogel
*Assistant Examiner*—Michele K. Joike
(74) *Attorney, Agent, or Firm*—Medlen + Carroll, LLP

(57) ABSTRACT

The present invention provides compounds and methods for the detection of protein-protein interactions wherein said interactions are dependent on the presence or absence of post-translational modifications (PTMs) of at least one of the proteins.

5 Claims, 77 Drawing Sheets

Lane 1. Vector control
Lane 2. H3-GST-Gcn5(wt)-Ras
Lane 3. H3-GST-Gcn5(mut)-Ras
Lane 4. GST-Gcn5(wt)-Ras
Lane 5. BSA, 150 ng control Lane 1. H4-GST-Gcn5(wt)-Ras
Lane 2. H4-GST-Gcn5(mut)-Ras
Lane 3. GST-Gcn5(wt)-Ras
Lane 4. Vector control (Ras only)

Lane 1. Vector control (GDBD only)
Lane 2. GDBD-H3-Gcn5(wt)-HA
Lane 3. GDBD-H3-Gcn5(mut)-HA 1. H3-Gcn5 (wt) + vector
2. H3-Gcn5 (wt) + PCAF
3. H4-Gcn5 (wt) + vector
4. H4-Gcn5 (wt) + PCAF
5. H3-Gcn5 (F221A) + vector
6. H3-Gcn5 (F221A) + PCAF
7. H4-Gcn5 (F221A) + vector
8. H4-Gcn5 (F221A) + PCAF (A)
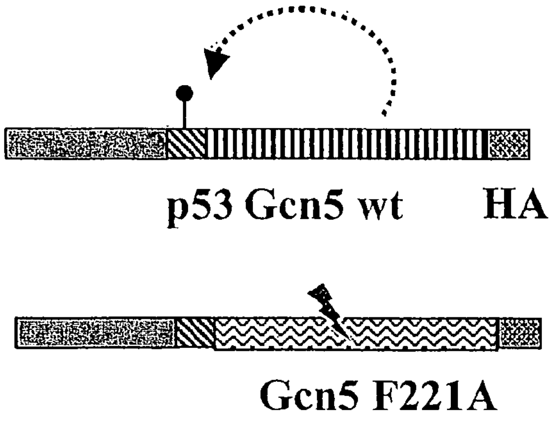
(B)
| IP: | HA | K320.Ac | HA |
|---|---|---|---|
| Western: | K320.Ac | HA | HA |
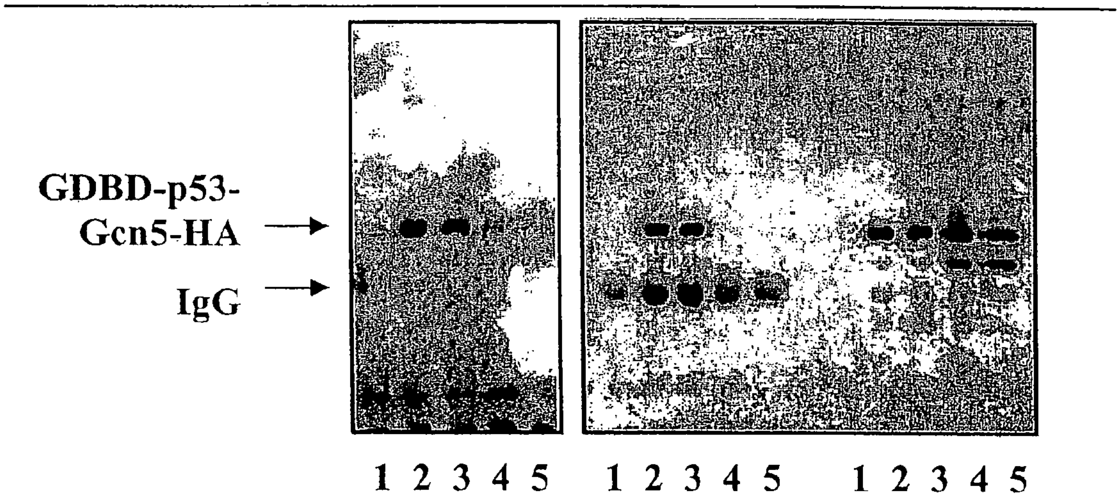
1. Antibody only control
2. Wildtype Gcn5
3. Wildtype Gcn5
4. Mutant Gcn5
5. Mutant Gcn5
FIG. 10

434-2059: Gal4 DBD-H3-Gcn5-HA
434-874: Gal4 DBD (amino acids 1-147)
953-1129: H3 (amino acids 1-59)
1208-1912: Gcn5 (amino acids 18-252)
1946-2035: trimeric HA
...-...: CEN/ARS
...-...: TRP1

Translation: Gal4-DBD-H3-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMFMARTKQTARKSTGGKAPRKQLASKAARKSAPSTGGVKKPHRYKPGTVALREIRRFQKSTEPGSPILGY
WKGRRDHPPKSDLIEGRGDPEVKRVKLENNVEEIQPEQAETNKQEGTDKENKGKFEKETERIGGSEVVTDVEKGIVKFEF
DGVEYTFKERPSVVEENEGKIEFRVVNNDNTKENMMVLTGLKNIFQKQLPKMPKEYIARLVYDRSHLSMAVIRKPLTVVG
GITYRPFDKREFAEIVFCAISSTEQVRGYGAHLMNHLKDYVRNTSNIKYFLTYADNYAIGYFKKQGFTKEITLDKSIWMG
YIKDYEGGTLMQCNMAIPGGGRIFYPYDVPDYAGYPYDVPDYAGSYPYDVPDYAAQCGRSS ; DNA sequence PDG1 8285 b.p. complete sequence
;
gtggtacataacgaactaatactgtagccctagacttgatagccatcatcatatcgaagtttcactaccctttttccatt
tgccatctattgaagtaataataggcgcatgcaacttcttttctttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGCTGACCACCATGTTTatggccagaac
aaagcaaacagcaagaaagtccactggtggtaaggccccaagaaagcaattagcttctaaggctgccagaaaatccgccc
catctaccggtggtgttaagaagcctcacagatataagccaggtactgttgctttgagagaaatcagaagattccaaaaa
tctactgaaCCCgggtcccctatactaggttattggaaaggtcgacgcgaccatcctccaaaatcggatctgatcgaagg
tcgtggaGATCCCGAAGTTAAACGGGTAAAATTAGAAAACAACGTTGAAGAAATACAACCTGAGCAGGCTGAGACCAATA
AACAAGAGGGCACCGATAAAGAGAATAAAGGAAAGTTCGAGAAAGAAACTGAGAGAATAGGAGGATCTGAAGTGGTTACA
GATGTGGAAAAAGGAATTGTCAAATTTGAATTTGATGGTGTTGAATACACATTCAAAGAGAGACCCAGTGTCGTAGAGGA
AAATGAAGGTAAAATTGAGTTTAGGGTGGTGAATAATGATAATACTAAAGAAAACATGATGGTCCTAACTGGATTAAAAA
ACATTTTTCAAAAGCAATTACCAAAAATGCCCAAAGAATACATTGCCAGGTTAGTCTATGATCGAAGTCATCTTTCCATG
GCTGTCATTAGGAAGCCATTGACTGTCGTAGGTGGCATAACATATCGACCTTTCGATAAGAGAGAATTCGCAGAAATTGT
TTTCTGTGCCATCAGTTCGACGGAACAGGTACGCGGTTATGGTGCGCATCTAATGAATCACTTAAAAGACTATGTTAGAA
ATACCTCGAACATAAAATATTTTTTGACATATGCAGATAATTACGCTATTGGATACTTTAAAAAGCAAGGCTTTACTAAA
GAAATCACGTTGGATAAAAGTATATGGATGGGATATATTAAAGATTATGAAGGTGGTACGCTGATGCAATGTAACATGGC
AATTCCCGGtggcggccgcatcttttacccatacgatgttcctgactatgcgggctatccctatgacgtcccggactatg
caggatcctatccatatgacgttccagattacgctgctcagtgcggccgctctagctagaactagtggatcccccGATAC
CGTCGACCTGCAGAGATCTAtgaatcgtagatactgaaaaaccccgcaagttcacttcaactgtgcatcgtgcaccatct
caatttctttcatttatacatcgttttgccttcttttatgtaactatactcctctaagtttcaatcttggccatgtaacc
tctgatctatagaatttttaaatgactagaattaatgcccatcttttttttggacctaaattcttcatgaaaatatatt
acgagggcttattcagaagctttggacttcttcgccagaggtttggtcaagtctccaatcaaggttgtcggcttgtctac
cttgccagaaatttacgaaaagatggaaaagggtcaaatcgttggtagatacgttgttgacacttctaaataagcgaatt

FIG. 12 tcttatgatttatgattttattattaaataagttataaaaaaataagtgtatacaaattttaaagtgactcttaggtt
ttaaaacgaaaattcttattcttgagtaactctttcctgtaggtcaggttgctttctcaggtatagcatgaggtcgctct
tattgaccacacctctaccggcatgccgagcaaatgcctgcaaatcgctccccatttcacccaattgtagatatgctaac
tccagcaatgagttgatgaatctcggtgtgtattttatgtcctcagaggacaacacctgttgtaatcgttcttccacacg
gatcctggcgtaatagcgaagaggcccgcaccgatcgcccttcccaacagttgcgcagcctgaatggcgaatggcgcctg
atgcggtattttctccttacgcatctgtgcggtatttcacaccgcatatatcgctgggccattctcatgaagaatatctt
gaatttattgtcatattactagttggtgtggaagtccatatatcggtgatcaatatagtggttgacatgctggctagtca
acattgagccttttgatcatgcaaatatattacggtattttacaatcaaatatcaaacttaactattgactttataactt
atttaggtggtaacattcttataaaaagaaaaaaattactgcaaaacagtactagcttttaacttgtatcctaggttat
ctatgctgtctcaccatagagaatattacctatttcagaatgtatgtccatgattcgccgggtaaatacatataatacac
aaatctggcttaataaagtctataatatatctcataaagaagtgctaaattggctagtgctatatattttaagaaaatt
tcttttgactaagtccatatcgactttgtaaaagttcactttagcatacatatattacacgagccagaaattgtaacttt
tgcctaaaatcacaaattgcaaaatttaattgcttgcaaaaggtcacatgcttataatcaactttttaaaaatttaaaa
tactttttatttttatttttaaacataaatgaaataatttatttattgtttatgattaccgaaacataaaacctgctc
aagaaaaagaaactgttttgtccttggaaaaaaagcactacctaggagcggccaaaatgccgaggctttcatagcttaaa
ctctttacagaaaataggcattatagatcagttcgagttttcttattcttccttccggttttatcgtcacagttttacag
taaataagtatcacctcttagagttcgatgataagctgtcaaacatgagaattaattccacatgttaaaatagtgaagga
gcatgttcggcacacagtggaccgaacgtggggtaagtgcactagggtccggttaaacggatctcgcattgatgaggcaa
cgctaattatcaacatatagattgttatctatctgcatgaacacgaaatctttacttgacgacttgaggctgatggtgtt
tatgcaaagaaaccactgtgtttaatatgtgtcactgtttgatattactgtcagcgtagaagataatagtaaaagcggtt
aataagtgtatttgagataagtgtgataaagtttttacagcgaaaagacgataaatacaagaaaatgattacgaggatac
ggagagaggtatgtacatgtgtatttatatactaagctgccggcggttgtttgcaagaccgagaaaaggctagcaagaat
cgggtcattgtagcgtatgcgcctgtgaacattctcttcaacaagtttgattccattgcggtgaaatggtaaaagtcaac
cccctgcgatgtatattttcctgtacaatcaatcaaaaagccaaatgatttagcattatctttacatcttgttattttac
agattttatgtttagatcttttatgcttgcttttcaaaaggcttgcaggcaagtgcacaaacaatacttaaataaatact
actcagtaataacctaTTTCTTAGCATTTTTGACGAAATTTGCTATTTTGTTAGAGTCTTTTACACCATTTGTCTCCACA
CCTCCGCTTACATCAACACCAATAACGCCATTTAATCTAAGCGCATCACCAACATTTTCTGGCGTCAGTCCACCAGCTAA
CATAAAATGTAAGCTCTCGGGGCTCTCTTGCCTTCCAACCCAGTCAGAAATCGAGTTCCAATCCAAAAGTTCACCTGTCC
CACCTGCTTCTGAATCAAACAAGGGAATAAACGAATGAGGTTTCTGTGAAGCTGCACTGAGTAGTATGTTGCAGTCTTTT
GGAAATACGAGTCTTTTAATAACTGGCAAACCGAGGAACTCTTGGTATTCTTGCCACGACTCATCTCCATGCAGTTGGAC
GATATCAATGCCGTAATCATTGACCAGAGCCAAAACATCCTCCTTAGGTTGATTACGAAACACGCCAACCAAGTATTTCG
GAGTGCCTGAACTATTTTTATATGCTTTTACAAGACTTGAAATTTTCCTTGCAATAACCGGGTCAATTGTTCTCTTTCTA
TTGGGCACACATATAATACCCAGCAAGTCAGCATCGGAATCTAGTGCACATTCTGCGGCCTCTGTGCTCTGCAAGCCGCA
AACTTTCACCAATGGACCAGAACTACCTGTGAAATTAATAACAGACATactccaagctgcctttgtgtgcttaatcacgt
atactcacgtgctcaatagtcaccaatgccctccctcttggccctctccttttctttttcgaccgaattaattcttgaa
gacgaaagggcctcgtgatacgcctatttttataggttaatgtcatgataataatggtttcttagacgtcaggtggcact
tttcggggaaatgtgcgcggaacccctatttgtttatttttctaaatacattcaaatatgtatccgctcatgagacaata
accctgataaatgcttcaataatattgaaaaaggaagagtATGAGTATTCAACATTTCCGTGTCGCCCTTATTCCCTTTT
TTGCGGCATTTTGCCTTCCTGTTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACCAAACG
ACGAGCGTGACACCACGATGCCTGTAGCAATGGCAACAACGTTGCGCAAACTATTAACTGGCGAACTACTTACTCTAGCT
TCCCGGCAACAATTAATAGACTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACTGGGGCCAGATGGTAAGCCCT
CCCGTATCGTAGTTATCTACACGACGGGGAGTCAGGCAACTATGGATGAACGAAATAGACAGATCGCTGAGATAGGTGCC
TCACTGATTAAGCATTGGtaactgtcagaccaagtttactcatatatactttagattgatttaaaacttcatttttaatt
taaaaggatctaggtgaagatcctttttgataatctcatgaccaaaatcccttaacgtgagttttcgttccactgagcgt
cagaccccgtagaaaagatcaaaggatcttcttgagatcctttttttctgcgcgtaatctgctgcttgcaaacaaaaaaa
ccaccgctaccagcggtggtttgtttgccggatcaagagctaccaactctttttccgaaggtaactggcttcagcagagc
gcagataccaaatactgtccttctagtgtagccgtagttaggccaccacttcaagaactctgtagcaccgcctacatacc
tcgctctgctaatcctgttaccagtggctgctgccagtggcgataagtcgtgtcttaccgggttggactcaagacgatag

FIG. 12 Cont.

ttaccggataaggcgcagcggtcgggctgaacggggggttcgtgcacacagcccagcttggagcgaacgacctacaccga
actgagatacctacagcgtgagctatgagaaagcgccacgcttcccgaagggagaaaggcggacaggtatccggtaagcg
gcagggtcggaacaggagagcgcacgagggagcttccagggggaaacgcctggtatctttatagtcctgtcgggtttcgc
cacctctgacttgagcgtcgatttttgtgatgctcgtcaggggggcggagcctatggaaaaacgccagcaacgcggcctt
tttacggttcctggccttttgctggccttttgctcacatgttctttcctgcgttatcccctgattctgtggataaccgta
ttaccgcctttgagtgagctgataccgctcgccgcagccgaacgaccgagcgcagcgagtcagtgagcgaggaagcggaa
gagcgcccaatacgcaaaccgcctctccccgcgcgttggccgattcattaatgcaggatccgggatcgaagaaatgatgg
taaatgaaataggaaatcaaggagcatgaaggcaaaagacaaatataagggtcgaacgaaaaataaagtgaaaagtgttg
atatgatgtatttggctttgcggcgccgaaaaaacgagtttacgcaattgcacaatcatgctgactctgtggcggacccg
cgctcttgccggcccggcgataacgctgggcgtgaggctgtgcccggcggagtttttgcgcctgcattttccaaggttt
accctgcgctaagggcgagattggagaagcaataagaatgccggttggggttgcgatgatgacgaccacgacaactggt
gtcattatttaagttgccgaaagaacctgagtgcatttgcaacatgagtatactagaagaatgagccaagacttgcgaga
cgcgagtttgccggtggtgcgaacaatagagcgaccatgaccttgaaggtgagacgcgcataaccgctagagtactttga
agaggaaacagcaatagggttgctaccagtataaatagacaggtacatacaacactggaaatggttgtctgtttgagtac
gctttcaattcatttgggtgtgcactttattatgttacaatatggaagggaactttacacttctcctatgcacatatatt
aattaaagtccaatgctagtagagaagggggtaacacccctccgcgctcttttccgatttttttctaaaccgtggaata
tttcggatatcctttgttgtttccgggtgtacaatatggacttcctcttttctggcaaccaaacccatacatcgggatt
cctataataccttcgttggtctccctaacatgtaggtggcggaggggagatatacaatagaacagataccagacaagaca
taatgggctaaacaagactacaccaattacactgcctcattgatg
//

FIG. 12 Cont.

434-2059: Gal4 DBD-H3-Gcn5 (F221A)-HA
434-874: Gal4 DBD (amino acids 1-147)
953-1129: H3 (amino acids 1-59)
1208-1912: Gcn5 (amino acids 18-252)
1817-1819: F221A (1817TTT changed to GCT)
1945-2035: trimeric HA Translation: Gal4-DBD-H3-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMFMARTKQTARKSTGGKAPRKQLASKAARKSAPSTGGVKKPHRYKPGTVALREIRRFQKSTEPGSPILGY
WKGRRDHPPKSDLIEGRGDPEVKRVKLENNVEEIQPEQAETNKQEGTDKENKGKFEKETERIGGSEVVTDVEKGIVKFEF
DGVEYTFKERPSVVEENEGKIEFRVVNNDNTKENMMVLTGLKNIFQKQLPKMPKEYIARLVYDRSHLSMAVIRKPLTVVG
GITYRPFDKREFAEIVFCAISSTEQVRGYGAHLMNHLKDYVRNTSNIKYFLTYADNYAIGYAKKQGFTKEITLDKSIWMG
YIKDYEGGTLMQCNMAIPGGGRIFYPYDVPDYAGYPYDVPDYAGSYPYDVPDYAAQCGRSS ; DNA sequence PDG1 8285 b.p. complete sequence
;
gtggtacataacgaactaatactgtagccctagacttgatagccatcatcatatcgaagtttcactaccctttttccatt
tgccatctattgaagtaataataggcgcatgcaacttcttttcttttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGCTGACCACCATGTTTatggccagaac
aaagcaaacagcaagaaagtccactggtggtaaggccccaagaaagcaattagcttctaaggctgccagaaaatccgccc
catctaccggtggtgttaagaagcctcacagatataagccaggtactgttgctttgagagaaatcagaagattccaaaaa
tctactgaaCCCgggtcccctatactaggttattggaaaggtcgacgcgaccatcctccaaaatcggatctgatcgaagg
tcgtggaGATCCCGAAGTTAAACGGGTAAAATTAGAAAACAACGTTGAAGAAATACAACCTGAGCAGGCTGAGACCAATA
AACAAGAGGGCACCGATAAAGAGAATAAAGGAAAGTTCGAGAAAGAAACTGAGAGAATAGGAGGATCTGAAGTGGTTACA
GATGTGGAAAAAGGAATTGTCAAATTTGAATTTGATGGTGTTGAATACACATTCAAAGAGAGACCCAGTGTCGTAGAGGA
AAATGAAGGTAAAATTGAGTTTAGGGTGGTGAATAATGATAATACTAAAGAAAACATGATGGTCCTAACTGGATTAAAAA
ACATTTTTCAAAAGCAATTACCAAAAATGCCCAAAGAATACATTGCCAGGTTAGTCTATGATCGAAGTCATCTTTCCATG
GCTGTCATTAGGAAGCCATTGACTGTCGTAGGTGGCATAACATATCGACCTTTCGATAAGAGAGAATTCGCAGAAATTGT
TTTCTGTGCCATCAGTTCGACGGAACAGGTACGCGGTTATGGTGCGCATCTAATGAATCACTTAAAAGACTATGTTAGAA
ATACCTCGAACATAAAATATTTTTTGACATATGCAGATAATTACGCTATTGGATACTTTAAAAAGCAAGGCTTTACTAAA
GAAATCACGTTGGATAAAAGTATATGGATGGGATATATTAAAGATTATGAAGGTGGTACGCTGATGCAATGTAACATGGC
AATTCCCGGtggcggccgcatcttttacccatacgatgttcctgactatgcgggctatccctatgacgtcccggactatg
caggatcctatccatatgacgttccagattacgctgctcagtgcggccgctctagctagaactagtggatcccccGATAC
CGTCGACCTGCAGAGATCTAtgaatcgtagatactgaaaaaccccgcaagttcacttcaactgtgcatcgtgcaccatct
caatttctttcatttatacatcgttttgccttcttttatgtaactatactcctctaagtttcaatcttggccatgtaacc
tctgatctatagaatttttaaatgactagaattaatgcccatcttttttttggacctaaattcttcatgaaaatatatt
acgagggcttattcagaagctttggacttcttcgccagaggtttggtcaagtctccaatcaaggttgtcggcttgtctac
cttgccagaaatttacgaaaagatggaaaagggtcaaatcgttggtagatacgttgttgacacttctaaataagcgaatt

FIG. 13 tcttatgatttatgattttattattaaataagttataaaaaaataagtgtatacaattttaaagtgactcttaggtt
ttaaaacgaaaattcttattcttgagtaactctttcctgtaggtcaggttgctttctcaggtatagcatgaggtcgctct
tattgaccacacctctaccggcatgccgagcaaatgcctgcaaatcgctccccatttcacccaattgtagatatgctaac
tccagcaatgagttgatgaatctcggtgtgtattttatgtcctcagaggacaacacctgttgtaatcgttcttccacacg
gatcctggcgtaatagcgaagaggcccgcaccgatcgcccttcccaacagttgcgcagcctgaatggcgaatggcgcctg
atgcggtatttctccttacgcatctgtgcggtatttcacaccgcatatatcgctgggccattctcatgaagaatatctt
gaatttattgtcatattactagttggtgtggaagtccatatatcggtgatcaatatagtggttgacatgctggctagtca
acattgagccttttgatcatgcaaatatattacggtattttacaatcaaatatcaaacttaactattgactttataactt
atttaggtggtaacattcttataaaaaagaaaaaattactgcaaaacagtactagcttttaacttgtatcctaggttat
ctatgctgtctcaccatagagaatattacctatttcagaatgtatgtccatgattcgccgggtaaatacatataatacac
aaatctggcttaataaagtctataatatatctcataaagaagtgctaaattggctagtgctatatattttttaagaaaatt
tcttttgactaagtccatatcgactttgtaaaagttcactttagcatacatatattacacgagccagaaattgtaacttt
tgcctaaaatcacaaattgcaaaatttaattgcttgcaaaaggtcacatgcttataatcaactttttttaaaaatttaaaa
tactttttttatttttttatttttaaacataaatgaaataatttatttattgtttatgattaccgaaacataaaacctgctc
aagaaaaagaaactgttttgtccttggaaaaaaagcactacctaggagcggccaaaatgccgaggctttcatagcttaaa
ctctttacagaaaataggcattatagatcagttcgagttttcttattcttccttccggttttatcgtcacagttttacag
taaataagtatcacctcttagagttcgatgataagctgtcaaacatgagaattaattccacatgttaaaatagtgaagga
gcatgttcggcacacagtggaccgaacgtggggtaagtgcactagggtccggttaaacggatctcgcattgatgaggcaa
cgctaattatcaacatatagattgttatctatctgcatgaacacgaaatctttacttgacgacttgaggctgatggtgtt
tatgcaaagaaaccactgtgtttaatatgtgtcactgtttgatattactgtcagcgtagaagataatagtaaaagcggtt
aataagtgtatttgagataagtgtgataaagtttttacagcgaaaagacgataaatacaagaaaatgattacgaggatac
ggagagaggtatgtacatgtgtatttatatactaagctgccggcggttgtttgcaagaccgagaaaaggctagcaagaat
cgggtcattgtagcgtatgcgcctgtgaacattctcttcaacaagtttgattccattgcggtgaaatggtaaaagtcaac
cccctgcgatgtatatttcctgtacaatcaatcaaaaagccaaatgatttagcattatctttacatcttgttattttac
agattttatgtttagatcttttatgcttgcttttcaaaaggcttgcaggcaagtgcacaaacaatacttaaataaatact
actcagtaataacctaTTTCTTAGCATTTTTGACGAAATTTGCTATTTTGTTAGAGTCTTTTACACCATTTGTCTCCACA
CCTCCGCTTACATCAACACCAATAACGCCATTTAATCTAAGCGCATCACCAACATTTTCTGGCGTCAGTCCACCAGCTAA
CATAAAATGTAAGCTCTCGGGGCTCTCTTGCCTTCCAACCCAGTCAGAAATCGAGTTCCAATCCAAAAGTTCACCTGTCC
CACCTGCTTCTGAATCAAACAAGGGAATAAACGAATGAGGTTTCTGTGAAGCTGCACTGAGTAGTATGTTGCAGTCTTTT
GGAAATACGAGTCTTTTAATAACTGGCAAACCGAGGAACTCTTGGTATTCTTGCCACGACTCATCTCCATGCAGTTGGAC
GATATCAATGCCGTAATCATTGACCAGAGCCAAAACATCCTCCTTAGGTTGATTACGAAACACGCCAACCAAGTATTTCG
GAGTGCCTGAACTATTTTTATATGCTTTTACAAGACTTGAAATTTTCCTTGCAATAACCGGGTCAATTGTTCTCTTTCTA
TTGGGCACACATATAATACCCAGCAAGTCAGCATCGGAATCTAGTGCACATTCTGCGGCCTCTGTGCTCTGCAAGCCGCA
AACTTTCACCAATGGACCAGAACTACCTGTGAAATTAATAACAGACATactccaagctgcctttgtgtgcttaatcacgt
atactcacgtgctcaatagtcaccaatgccctccctcttggccctctccttttcttttttcgaccgaattaattcttgaa
gacgaaagggcctcgtgatacgcctatttttataggttaatgtcatgataataatggtttcttagacgtcaggtggcact
tttcggggaaatgtgcgcggaacccctatttgtttatttttctaaatacattcaaatatgtatccgctcatgagacaata
accctgataaatgcttcaataatattgaaaaaggaagagtATGAGTATTCAACATTTCCGTGTCGCCCTTATTCCCTTTT
TTGCGGCATTTTGCCTTCCTGTTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACCAAACG
ACGAGCGTGACACCACGATGCCTGTAGCAATGGCAACAACGTTGCGCAAACTATTAACTGGCGAACTACTTACTCTAGCT
TCCCGGCAACAATTAATAGACTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACTGGGGCCAGATGGTAAGCCCT
CCCGTATCGTAGTTATCTACACGACGGGGAGTCAGGCAACTATGGATGAACGAAATAGACAGATCGCTGAGATAGGTGCC
TCACTGATTAAGCATTGGtaactgtcagaccaagtttactcatatatactttagattgatttaaaacttcatttttaatt
taaaaggatctaggtgaagatcctttttgataatctcatgaccaaaatcccttaacgtgagttttcgttccactgagcgt
cagaccccgtagaaaagatcaaaggatcttcttgagatcctttttttctgcgcgtaatctgctgcttgcaaacaaaaaaa
ccaccgctaccagcggtggtttgtttgccggatcaagagctaccaactctttttccgaaggtaactggcttcagcagagc
gcagataccaaatactgtccttctagtgtagccgtagttaggccaccacttcaagaactctgtagcaccgcctacatacc
tcgctctgctaatcctgttaccagtggctgctgccagtggcgataagtcgtgtcttaccgggttggactcaagacgatag

FIG. 13 Cont.

ttaccggataaggcgcagcggtcgggctgaacggggggttcgtgcacacagcccagcttggagcgaacgacctacaccga
actgagatacctacagcgtgagctatgagaaagcgccacgcttcccgaagggagaaaggcggacaggtatccggtaagcg
gcagggtcggaacaggagagcgcacgagggagcttccagggggaaacgcctggtatctttatagtcctgtcgggtttcgc
cacctctgacttgagcgtcgatttttgtgatgctcgtcaggggggcggagcctatggaaaaacgccagcaacgcggcctt
tttacggttcctggccttttgctggccttttgctcacatgttctttcctgcgttatcccctgattctgtggataaccgta
ttaccgcctttgagtgagctgataccgctcgccgcagccgaacgaccgagcgcagcgagtcagtgagcgaggaagcggaa
gagcgcccaatacgcaaaccgcctctccccgcgcgttggccgattcattaatgcaggatccgggatcgaagaaatgatgg
taaatgaaataggaaatcaaggagcatgaaggcaaaagacaaatataagggtcgaacgaaaaataaagtgaaaagtgttg
atatgatgtatttggctttgcggcgccgaaaaaacgagtttacgcaattgcacaatcatgctgactctgtggcggacccg
cgctcttgccggcccggcgataacgctgggcgtgaggctgtgcccggcggagtttttgcgcctgcattttccaaggttt
accctgcgctaaggggcgagattggagaagcaataagaatgccggttggggttgcgatgatgacgaccacgacaactggt
gtcattatttaagttgccgaaagaacctgagtgcatttgcaacatgagtatactagaagaatgagccaagacttgcgaga
cgcgagtttgccggtggtgcgaacaatagagcgaccatgaccttgaaggtgagacgcgcataaccgctagagtactttga
agaggaaacagcaatagggttgctaccagtataaatagacaggtacatacaacactggaaatggttgtctgtttgagtac
gctttcaattcatttgggtgtgcactttattatgttacaatatggaagggaactttacacttctcctatgcacatatatt
aattaaagtccaatgctagtagagaagggggtaacacccctccgcgctcttttccgatttttttctaaaccgtggaata
tttcggatatccttttgttgtttccgggtgtacaatatggacttcctcttttctggcaaccaaacccatacatcgggatt
cctataataccttcgttggtctccctaacatgtaggtggcggaggggagatatacaatagaacagataccagacaagaca
taatgggctaaacaagactacaccaattacactgcctcattgatg
//

FIG. 13 Cont.

434-1963: Gal4 DBD-H4-Gcn5-HA
434-874: Gal4 DBD (amino acids 1-147)
947-1033: H4 (amino acids 1-29)
1112-1816: Gcn5 (amino acids 18-252)
1850-1939: trimeric HA
...-...: CEN/ARS
...-...: TRP1

Translation: Gal4 DBD-H4-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMSGRGKGGKGLGKGGAKRHRKILRDNIQGISGSPILGYWKGRRDHPPKSDLIEGRGDPEVKRVKLENNVE
EIQPEQAETNKQEGTDKENKGKFEKETERIGGSEVVTDVEKGIVKFEFDGVEYTFKERPSVVEENEGKIEFRVVNNDNTK
ENMMVLTGLKNIFQKQLPKMPKEYIARLVYDRSHLSMAVIRKPLTVVGGITYRPFDKREFAEIVFCAISSTEQVRGYGAH
LMNHLKDYVRNTSNIKYFLTYADNYAIGYFKKQGFTKEITLDKSIWMGYIKDYEGGTLMQCSMAIPGGGRIFYPYDVPDY
AGYPYDVPDYAGSYPYDVPDYAAQCGRSS ; DNA sequence PDG3 8189 b.p. complete sequence
;
gtggtacataacgaactaatactgtagccctagacttgatagccatcatcatatcgaagtttcactaccctttttccatt
tgccatctattgaagtaataataggcgcatgcaacttcttttcttttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGCTGACCACCATGTCCGGTAGAGGTAA
AGGTGGTAAAGGTCTAGGAAAAGGTGGTGCCAAGCGTCACAGAAAGATTCTAAGAGATAACATCCAAGGTATTTCCgggt
cccctatactaggttattggaaaggtcgacgcgaccatcctccaaaatcggatctgatcgaaggtcgtggaGATCCCGAA
GTTAAACGGGTAAAATTAGAAAACAACGTTGAAGAAATACAACCTGAGCAGGCTGAGACCAATAAACAAGAGGGCACCGA
TAAAGAGAATAAAGGAAAGTTCGAGAAAGAAACTGAGAGAATAGGAGGATCTGAAGTGGTTACAGATGTGGAAAAAGGAA
TTGTCAAATTTGAATTTGATGGTGTTGAATACACATTCAAAGAGAGACCCAGTGTCGTAGAGGAAAATGAAGGTAAAATT
GAGTTTAGGGTGGTGAATAATGATAATACTAAAGAAAACATGATGGTCCTAACTGGATTAAAAAACATTTTTCAAAAGCA
ATTACCAAAAATGCCCAAAGAATACATTGCCAGGTTAGTCTATGATCGAAGTCATCTTTCCATGGCTGTCATTAGGAAGC
CATTGACTGTCGTAGGTGGCATAACATATCGACCTTTCGATAAGAGAGAATTCGCAGAAATTGTTTTCTGTGCCATCAGT
TCGACGGAACAGGTACGCGGTTATGGTGCGCATCTAATGAATCACTTAAAAGACTATGTTAGAAATACCTCGAACATAAA
ATATTTTTTGACATATGCAGATAATTACGCTATTGGATACTTTAAAAAGCAAGGCTTTACTAAAGAAATCACGTTGGATA
AAAGTATATGGATGGGATATATTAAAGATTATGAAGGTGGTACGCTGATGCAATGTTCCATGGCAATTCCCGGtggcggc
cgcatcttttacccatacgatgttcctgactatgcgggctatccctatgacgtcccggactatgcaggatcctatccata
tgacgttccagattacgctgctcagtgcggccgctctagctagaactagtggatcccccGATACCGTCGACCTGCAGAGA
TCTAtgaatcgtagatactgaaaaaccccgcaagttcacttcaactgtgcatcgtgcaccatctcaatttctttcattta
tacatcgttttgccttcttttatgtaactatactcctctaagtttcaatcttggccatgtaacctctgatctatagaatt
ttttaaatgactagaattaatgcccatcttttttttggacctaaattcttcatgaaaatatattacgagggcttattcag
aagctttggacttcttcgccagaggtttggtcaagtctccaatcaaggttgtcggcttgtctaccttgccagaaatttac
gaaaagatggaaaagggtcaaatcgttggtagatacgttgttgacacttctaaataagcgaatttcttatgatttatgat

FIG. 14 ttttattattaaataagttataaaaaaaataagtgtatacaaattttaaagtgactcttaggttttaaaacgaaattct
tattcttgagtaactctttcctgtaggtcaggttgctttctcaggtatagcatgaggtcgctcttattgaccacacctct
accggcatgccgagcaaatgcctgcaaatcgctccccatttcacccaattgtagatatgctaactccagcaatgagttga
tgaatctcggtgtgtattttatgtcctcagaggacaacacctgttgtaatcgttcttccacacggatcctggcgtaatag
cgaagaggcccgcaccgatcgcccttcccaacagttgcgcagcctgaatggcgaatggcgcctgatgcggtattttctcc
ttacgcatctgtgcggtatttcacaccgcatatatcgctgggccattctcatgaagaatatcttgaatttattgtcatat
tactagttggtgtggaagtccatatatcggtgatcaatatagtggttgacatgctggctagtcaacattgagccttttga
tcatgcaaatatattacggtattttacaatcaaatatcaaacttaactattgactttataacttatttaggtggtaacat
tcttataaaaagaaaaaaattactgcaaaacagtactagcttttaacttgtatcctaggttatctatgctgtctcacca
tagagaatattacctatttcagaatgtatgtccatgattcgccgggtaaatacatataatacacaaatctggcttaataa
agtctataatatatctcataaagaagtgctaaattggctagtgctatatattttaagaaaatttcttttgactaagtcc
atatcgactttgtaaaagttcactttagcatacatatattacacgagccagaaattgtaacttttgcctaaaatcacaaa
ttgcaaatttaattgcttgcaaaaggtcacatgcttataatcaactttttaaaatttaaaatactttttatttttt
atttttaaacataaatgaaataatttatttattgtttatgattaccgaaacataaaacctgctcaagaaaaagaaactgt
tttgtccttggaaaaaaagcactacctaggagcggccaaaatgccgaggctttcatagcttaaactctttacagaaaata
ggcattatagatcagttcgagttttcttattcttccttccggttttatcgtcacagttttacagtaaataagtatcacct
cttagagttcgatgataagctgtcaaacatgagaattaattccacatgttaaaatagtgaaggagcatgttcggcacaca
gtggaccgaacgtggggtaagtgcactagggtccggttaaacggatctcgcattgatgaggcaacgctaattatcaacat
atagattgttatctatctgcatgaacacgaaatctttacttgacgacttgaggctgatggtgtttatgcaaagaaaccac
tgtgtttaatatgtgtcactgtttgatattactgtcagcgtagaagataatagtaaaagcggttaataagtgtatttgag
ataagtgtgataaagtttttacagcgaaaagacgataaatacaagaaaatgattacgaggatacggagagaggtatgtac
atgtgtatttatatactaagctgccggcggttgtttgcaagaccgagaaaaggctagcaagaatcgggtcattgtagcgt
atgcgcctgtgaacattctcttcaacaagtttgattccattgcggtgaaatggtaaaagtcaacccccctgcgatgtatat
tttcctgtacaatcaatcaaaaagccaaatgatttagcattatctttacatcttgttattttacagattttatgtttaga
tcttttatgcttgcttttcaaaaggcttgcaggcaagtgcacaaacaatacttaaataaatactactcagtaataaccta
TTTCTTAGCATTTTTGACGAAATTTGCTATTTTGTTAGAGTCTTTTACACCATTTGTCTCCACACCTCCGCTTACATCAA
CACCAATAACGCCATTTAATCTAAGCGCATCACCAACATTTTCTGGCGTCAGTCCACCAGCTAACATAAAATGTAAGCTC
TCGGGGCTCTCTTGCCTTCCAACCCAGTCAGAAATCGAGTTCCAATCCAAAAGTTCACCTGTCCCACCTGCTTCTGAATC
AAACAAGGGAATAAACGAATGAGGTTTCTGTGAAGCTGCACTGAGTAGTATGTTGCAGTCTTTTGGAAATACGAGTCTTT
TAATAACTGGCAAACCGAGGAACTCTTGGTATTCTTGCCACGACTCATCTCCATGCAGTTGGACGATATCAATGCCGTAA
TCATTGACCAGAGCCAAAACATCCTCCTTAGGTTGATTACGAAACACGCCAACCAAGTATTTCGGAGTGCCTGAACTATT
TTTATATGCTTTTACAAGACTTGAAATTTTCCTTGCAATAACCGGGTCAATTGTTCTCTTTCTATTGGGCACACATATAA
TACCCAGCAAGTCAGCATCGGAATCTAGTGCACATTCTGCGGCCTCTGTGCTCTGCAAGCCGCAAACTTTCACCAATGGA
CCAGAACTACCTGTGAAATTAATAACAGACATactccaagctgcctttgtgtgcttaatcacgtatactcacgtgctcaa
tagtcaccaatgccctccctcttggccctctcctttttcttttttcgaccgaattaattcttgaagacgaaagggcctcgt
gatacgcctatttttataggttaatgtcatgataataatggtttcttagacgtcaggtggcacttttcggggaaatgtgc
gcggaacccctatttgtttatttttctaaatacattcaaatatgtatccgctcatgagacaataaccctgataaatgctt
caataatattgaaaaaggaagagtATGAGTATTCAACATTTCCGTGTCGCCCTTATTCCCTTTTTTGCGGCATTTTGCCT
TCCTGTTTTTGCTCACCCAGAAACGCTGGTGAAAGTAAAAGATGCTGAAGATCAGTTGGGTGCACGAGTGGGTTACATCG
AACTGGATCTCAACAGCGGTAAGATCCTTGAGAGTTTTCGCCCCGAAGAACGTTTTCCAATGATGAGCACTTTTAAAGTT
CTGCTATGTGGCGCGGTATTATCCCGTATTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGTAAGAGAATTATGCAGTGCTGCCATAA
CCATGAGTGATAACACTGCGGCCAACTTACTTCTGACAACGATCGGAGGACCGAAGGAGCTAACCGCTTTTTTGCACAAC
ATGGGGGATCATGTAACTCGCCTTGATCGTTGGGAACCGGAGCTGAATGAAGCCATACCAAACGACGAGCGTGACACCAC
GATGCCTGTAGCAATGGCAACAACGTTGCGCAAACTATTAACTGGCGAACTACTTACTCTAGCTTCCCGGCAACAATTAA
TAGACTGGATGGAGGCGGATAAAGTTGCAGGACCACTTCTGCGCTCGGCCCTTCCGGCTGGCTGGTTTATTGCTGATAAA
TCTGGAGCCGGTGAGCGTGGGTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGGTGCCTCACTGATTAAGCATT
GGtaactgtcagaccaagtttactcatatatactttagattgatttaaaacttcatttttaatttaaaaggatctaggtg
aagatcctttttgataatctcatgaccaaaatcccttaacgtgagttttcgttccactgagcgtcagaccccgtagaaaa
gatcaaaggatcttcttgagatcctttttttctgcgcgtaatctgctgcttgcaaacaaaaaaaccaccgctaccagcgg
tggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcct
gttaccagtggctgctgccagtggcgataagtcgtgtcttaccgggttggactcaagacgatagttaccggataaggcgc

FIG. 14 Cont.

agcggtcgggctgaacggggggttcgtgcacacagcccagcttggagcgaacgacctacaccgaactgagatacctacag
cgtgagctatgagaaagcgccacgcttcccgaagggagaaaggcggacaggtatccggtaagcggcagggtcggaacagg
agagcgcacgagggagcttccagggggaaacgcctggtatctttatagtcctgtcgggtttcgccacctctgacttgagc
gtcgatttttgtgatgctcgtcaggggggcggagcctatggaaaaacgccagcaacgcggcctttttacggttcctggcc
ttttgctggccttttgctcacatgttctttcctgcgttatcccctgattctgtggataaccgtattaccgcctttgagtg
agctgataccgctcgccgcagccgaacgaccgagcgcagcgagtcagtgagcgaggaagcggaagagcgcccaatacgca
aaccgcctctccccgcgcgttggccgattcattaatgcaggatccgggatcgaagaaatgatggtaaatgaaataggaaa
tcaaggagcatgaaggcaaaagacaaatataagggtcgaacgaaaaataaagtgaaaagtgttgatatgatgtatttggc
tttgcggcgccgaaaaaacgagtttacgcaattgcacaatcatgctgactctgtggcggacccgcgctcttgccggcccg
gcgataacgctgggcgtgaggctgtgcccggcggagtttttgcgcctgcattttccaaggtttaccctgcgctaagggg
cgagattggagaagcaataagaatgccggttggggttgcgatgatgacgaccacgacaactggtgtcattatttaagttg
ccgaaagaacctgagtgcatttgcaacatgagtatactagaagaatgagccaagacttgcgagacgcgagtttgccggtg
gtgcgaacaatagagcgaccatgaccttgaaggtgagacgcgcataaccgctagagtactttgaagaggaaacagcaata
gggttgctaccagtataaatagacaggtacatacaacactggaaatggttgtctgtttgagtacgctttcaattcatttg
ggtgtgcactttattatgttacaatatggaagggaactttacacttctcctatgcacatatattaattaaagtccaatgc
tagtagagaagggggtaacacccctccgcgctcttttccgatttttttctaaaccgtggaatatttcggatatcctttt
gttgtttccgggtgtacaatatggacttcctcttttctggcaaccaaacccatacatcgggattcctataataccttcgt
tggtctccctaacatgtaggtggcggaggggagatatacaatagaacagataccagacaagacataatgggctaaacaag
actacaccaattacactgcctcattgatg
//

FIG. 14 Cont.

434-1963: Gal4 DBD-H4-Gcn5-HA
434-874: Gal4 DBD (amino acids 1-147)
947-1033: H4 (amino acids 1-29)
1112-1816: Gcn5 (amino acids 18-252)
1721-1723: F221A point mutation
1850-1939: trimeric HA
...-...: CEN/ARS
...-...: TRP1

Translation: Gal4 DBD-H4-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMSGRGKGGKGLGKGGAKRHRKILRDNIQGISGSPILGYWKGRRDHPPKSDLIEGRGDPEVKRVKLENNVE
EIQPEQAETNKQEGTDKENKGKFEKETERIGGSEVVTDVEKGIVKFEFDGVEYTFKERPSVVEENEGKIEFRVVNNDNTK
ENMMVLTGLKNIFQKQLPKMPKEYIARLVYDRSHLSMAVIRKPLTVVGGITYRPFDKREFAEIVFCAISSTEQVRGYGAH
LMNHLKDYVRNTSNIKYFLTYADNYAIGYAKKQGFTKEITLDKSIWMGYIKDYEGGTLMQCSMAIPGGGRIFYPYDVPDY
AGYPYDVPDYAGSYPYDVPDYAAQCGRSS ; DNA sequence PDG3 8189 b.p. complete sequence
;
gtggtacataacgaactaatactgtagccctagacttgatagccatcatcatatcgaagtttcactacccttttccatt
tgccatctattgaagtaataataggcgcatgcaacttcttttcttttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGCTGACCACCATGTCCGGTAGAGGTAA
AGGTGGTAAAGGTCTAGGAAAAGGTGGTGCCAAGCGTCACAGAAAGATTCTAAGAGATAACATCCAAGGTATTTCCgggt
cccctatactaggttattggaaaggtcgacgcgaccatcctccaaaatcggatctgatcgaaggtcgtggaGATCCCGAA
GTTAAACGGGTAAAATTAGAAAACAACGTTGAAGAAATACAACCTGAGCAGGCTGAGACCAATAAACAAGAGGGCACCGA
TAAAGAGAATAAAGGAAAGTTCGAGAAAGAAACTGAGAGAATAGGAGGATCTGAAGTGGTTACAGATGTGGAAAAAGGAA
TTGTCAAATTTGAATTTGATGGTGTTGAATACACATTCAAAGAGAGACCCAGTGTCGTAGAGGAAAATGAAGGTAAAATT
GAGTTTAGGGTGGTGAATAATGATAATACTAAAGAAAACATGATGGTCCTAACTGGATTAAAAAACATTTTTCAAAAGCA
ATTACCAAAAATGCCCAAAGAATACATTGCCAGGTTAGTCTATGATCGAAGTCATCTTTCCATGGCTGTCATTAGGAAGC
CATTGACTGTCGTAGGTGGCATAACATATCGACCTTTCGATAAGAGAGAATTCGCAGAAATTGTTTTCTGTGCCATCAGT
TCGACGGAACAGGTACGCGGTTATGGTGCGCATCTAATGAATCACTTAAAAGACTATGTTAGAAATACCTCGAACATAAA
ATATTTTTTGACATATGCAGATAATTACGCTATTGGATACTTTAAAAAGCAAGGCTTTACTAAAGAAATCACGTTGGATA
AAAGTATATGGATGGGATATATTAAAGATTATGAAGGTGGTACGCTGATGCAATGTTCCATGGCAATTCCCGGtggcggc
cgcatcttttacccatacgatgttcctgactatgcgggctatccctatgacgtcccggactatgcaggatcctatccata
tgacgttccagattacgctgctcagtgcggccgctctagctagaactagtggatcccccGATACCGTCGACCTGCAGAGA
TCTAtgaatcgtagatactgaaaaaccccgcaagttcacttcaactgtgcatcgtgcaccatctcaatttctttcattta
tacatcgttttgccttcttttatgtaactatactcctctaagtttcaatcttggccatgtaacctctgatctatagaatt
ttttaaatgactagaattaatgcccatcttttttttggacctaaattcttcatgaaaatatattacgagggcttattcag

FIG. 15 aagctttggacttcttcgccagaggtttggtcaagtctccaatcaaggttgtcggcttgtctaccttgccagaaatttac
gaaaagatggaaaagggtcaaatcgttggtagatacgttgttgacacttctaaataagcgaatttcttatgatttatgat
ttttattattaaataagttataaaaaaaataagtgtatacaaattttaaagtgactcttaggttttaaaacgaaaattct
tattcttgagtaactctttcctgtaggtcaggttgctttctcaggtatagcatgaggtcgctcttattgaccacacctct
accggcatgccgagcaaatgcctgcaaatcgctccccatttcacccaattgtagatatgctaactccagcaatgagttga
tgaatctcggtgtgtattttatgtcctcagaggacaacacctgttgtaatcgttcttccacacggatcctggcgtaatag
cgaagaggcccgcaccgatcgcccttcccaacagttgcgcagcctgaatggcgaatggcgcctgatgcggtattttctcc
ttacgcatctgtgcggtatttcacaccgcatatatcgctgggccattctcatgaagaatatcttgaatttattgtcatat
tactagttggtgtggaagtccatatatcggtgatcaatatagtggttgacatgctggctagtcaacattgagccttttga
tcatgcaaatatattacggtattttacaatcaaatatcaaacttaactattgactttataacttatttaggtggtaacat
tcttataaaaaagaaaaaaattactgcaaaacagtactagcttttaacttgtatcctaggttatctatgctgtctcacca
tagagaatattacctatttcagaatgtatgtccatgattcgccgggtaaatacatataatacacaaatctggcttaataa
agtctataatatatctcataaagaagtgctaaattggctagtgctatatatttttaagaaaatttcttttgactaagtcc
atatcgactttgtaaaagttcactttagcatacatatattacacgagccagaaattgtaacttttgcctaaaatcacaaa
ttgcaaaatttaattgcttgcaaaaggtcacatgcttataatcaactttttaaaaatttaaaatactttttttattttt
atttttaaacataaatgaaataatttatttattgtttatgattaccgaaacataaaacctgctcaagaaaaagaaactgt
tttgtccttggaaaaaaagcactacctaggagcggccaaaatgccgaggctttcatagcttaaactctttacagaaaata
ggcattatagatcagttcgagttttcttattcttccttccggttttatcgtcacagttttacagtaaataagtatcacct
cttagagttcgatgataagctgtcaaacatgagaattaattccacatgttaaaatagtgaaggagcatgttcggcacaca
gtggaccgaacgtggggtaagtgcactagggtccggttaaacggatctcgcattgatgaggcaacgctaattatcaacat
atagattgttatctatctgcatgaacacgaaatctttacttgacgacttgaggctgatggtgtttatgcaaagaaaccac
tgtgtttaatatgtgtcactgtttgatattactgtcagcgtagaagataatagtaaaagcggttaataagtgtatttgag
ataagtgtgataaagtttttacagcgaaaagacgataaatacaagaaaatgattacgaggatacggagagaggtatgtac
atgtgtatttatatactaagctgccggcggttgtttgcaagaccgagaaaaggctagcaagaatcgggtcattgtagcgt
atgcgcctgtgaacattctcttcaacaagtttgattccattgcggtgaaatggtaaaagtcaacccccctgcgatgtatat
tttcctgtacaatcaatcaaaaagccaaatgatttagcattatctttacatcttgttattttacagattttatgtttaga
tcttttatgcttgcttttcaaaaggcttgcaggcaagtgcacaaacaatacttaaataaatactactcagtaataaccta
TTTCTTAGCATTTTTGACGAAATTTGCTATTTTGTTAGAGTCTTTTACACCATTTGTCTCCACACCTCCGCTTACATCAA
CACCAATAACGCCATTTAATCTAAGCGCATCACCAACATTTTCTGGCGTCAGTCCACCAGCTAACATAAAATGTAAGCTC
TCGGGGCTCTCTTGCCTTCCAACCCAGTCAGAAATCGAGTTCCAATCCAAAAGTTCACCTGTCCCACCTGCTTCTGAATC
AAACAAGGGAATAAACGAATGAGGTTTCTGTGAAGCTGCACTGAGTAGTATGTTGCAGTCTTTTGGAAATACGAGTCTTT
TAATAACTGGCAAACCGAGGAACTCTTGGTATTCTTGCCACGACTCATCTCCATGCAGTTGGACGATATCAATGCCGTAA
TCATTGACCAGAGCCAAAACATCCTCCTTAGGTTGATTACGAAACACGCCAACCAAGTATTTCGGAGTGCCTGAACTATT
TTTATATGCTTTTACAAGACTTGAAATTTTCCTTGCAATAACCGGGTCAATTGTTCTCTTTCTATTGGGCACACATATAA
TACCCAGCAAGTCAGCATCGGAATCTAGTGCACATTCTGCGGCCTCTGTGCTCTGCAAGCCGCAAACTTTCACCAATGGA
CCAGAACTACCTGTGAAATTAATAACAGACATactccaagctgcctttgtgtgcttaatcacgtatactcacgtgctcaa
tagtcaccaatgccctccctcttggccctctcctttcttttttcgaccgaattaattcttgaagacgaaagggcctcgt
gatacgcctatttttataggttaatgtcatgataataatggtttcttagacgtcaggtggcacttttcggggaaatgtgc
gcggaacccctatttgtttatttttctaaatacattcaaatatgtatccgctcatgagacaataaccctgataaatgctt
caataatattgaaaaaggaagagtATGAGTATTCAACATTTCCGTGTCGCCCTTATTCCCTTTTTTGCGGCATTTTGCCT
TCCTGTTTTTGCTCACCCAGAAACGCTGGTGAAAGTAAAAGATGCTGAAGATCAGTTGGGTGCACGAGTGGGTTACATCG
AACTGGATCTCAACAGCGGTAAGATCCTTGAGAGTTTTCGCCCCGAAGAACGTTTTCCAATGATGAGCACTTTTAAAGTT
CTGCTATGTGGCGCGGTATTATCCCGTATTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGTAAGAGAATTATGCAGTGCTGCCATAA
CCATGAGTGATAACACTGCGGCCAACTTACTTCTGACAACGATCGGAGGACCGAAGGAGCTAACCGCTTTTTTGCACAAC
ATGGGGGATCATGTAACTCGCCTTGATCGTTGGGAACCGGAGCTGAATGAAGCCATACCAAACGACGAGCGTGACACCAC
GATGCCTGTAGCAATGGCAACAACGTTGCGCAAACTATTAACTGGCGAACTACTTACTCTAGCTTCCCGGCAACAATTAA
TAGACTGGATGGAGGCGGATAAAGTTGCAGGACCACTTCTGCGCTCGGCCCTTCCGGCTGGCTGGTTTATTGCTGATAAA
TCTGGAGCCGGTGAGCGTGGGTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGGTGCCTCACTGATTAAGCATT
GGtaactgtcagaccaagtttactcatatatactttagattgatttaaaacttcatttttaatttaaaaggatctaggtg
aagatcctttttgataatctcatgaccaaaatcccttaacgtgagttttcgttccactgagcgtcagaccccgtagaaaa
gatcaaaggatcttcttgagatcctttttttctgcgcgtaatctgctgcttgcaaacaaaaaaaccaccgctaccagcgg
tggtttgtttgccggatcaagagctaccaactctttttccgaaggtaactggcttcagcagagcgcagataccaaatact

FIG. 15 Cont.

gtccttctagtgtagccgtagttaggccaccacttcaagaactctgtagcaccgcctacatacctcgctctgctaatcct
gttaccagtggctgctgccagtggcgataagtcgtgtcttaccgggttggactcaagacgatagttaccggataaggcgc
agcggtcgggctgaacggggggttcgtgcacacagcccagcttggagcgaacgacctacaccgaactgagatacctacag
cgtgagctatgagaaagcgccacgcttcccgaagggagaaaggcggacaggtatccggtaagcggcagggtcggaacagg
agagcgcacgagggagcttccagggggaaacgcctggtatctttatagtcctgtcgggtttcgccacctctgacttgagc
gtcgatttttgtgatgctcgtcaggggggcggagcctatggaaaaacgccagcaacgcggcctttttacggttcctggcc
ttttgctggccttttgctcacatgttctttcctgcgttatcccctgattctgtggataaccgtattaccgcctttgagtg
agctgataccgctcgccgcagccgaacgaccgagcgcagcgagtcagtgagcgaggaagcggaagagcgcccaatacgca
aaccgcctctccccgcgcgttggccgattcattaatgcaggatccgggatcgaagaaatgatggtaaatgaaataggaaa
tcaaggagcatgaaggcaaaagacaaatataagggtcgaacgaaaaataaagtgaaaagtgttgatatgatgtatttggc
tttgcggcgccgaaaaaacgagtttacgcaattgcacaatcatgctgactctgtggcggacccgcgctcttgccggcccg
gcgataacgctgggcgtgaggctgtgcccggcggagtttttgcgcctgcattttccaaggtttaccctgcgctaagggg
cgagattggagaagcaataagaatgccggttggggttgcgatgatgacgaccacgacaactggtgtcattatttaagttg
ccgaaagaacctgagtgcatttgcaacatgagtatactagaagaatgagccaagacttgcgagacgcgagtttgccggtg
gtgcgaacaatagagcgaccatgaccttgaaggtgagacgcgcataaccgctagagtactttgaagaggaaacagcaata
gggttgctaccagtataaatagacaggtacatacaacactggaaatggttgtctgtttgagtacgctttcaattcatttg
ggtgtgcactttattatgttacaatatggaagggaactttacacttctcctatgcacatatattaattaaagtccaatgc
tagtagagaagggggggtaacacccctccgcgctcttttccgatttttttctaaaccgtggaatatttcggatatcctttt
gttgtttccgggtgtacaatatggacttcctcttttctggcaaccaaacccatacatcgggattcctataataccttcgt
tggtctccctaacatgtaggtggcggaggggagatatacaatagaacagataccagacaagacataatgggctaaacaag
actacaccaattacactgcctcattgatg
//

FIG. 15 Cont.

5988-7613: Gal4 DBD-H3-Gcn5-HA
5988-6428: Gal4 DBD (amino acids 1-147)
6507-6683: H3 (amino acids 1-59)
6762-7466: Gcn5 (amino acids 18-252)
7500-7589: trimeric HA
...-...: 2μ
...-...: LEU2

Translation: Gal4-DBD-H3-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMFMARTKQTARKSTGGKAPRKQLASKAARKSAPSTGGVKKPHRYKPGTVALREIRRFQKSTEPGSPILGY
WKGRRDHPPKSDLIEGRGDPEVKRVKLENNVEEIQPEQAETNKQEGTDKENKGKFEKETERIGGSEVVTDVEKGIVKFEF
DGVEYTFKERPSVVEENEGKIEFRVVNNDNTKENMMVLTGLKNIFQKQLPKMPKEYIARLVYDRSHLSMAVIRKPLTVVG
GITYRPFDKREFAEIVFCAISSTEQVRGYGAHLMNHLKDYVRNTSNIKYFLTYADNYAIGYFKKQGFTKEITLDKSIWMG
YIKDYEGGTLMQCNMAIPGGGRIFYPYDVPDYAGYPYDVPDYAGSYPYDVPDYAAQCGRSS ; ### from DNA Strider Saturday, March 22, 2003 1:27:34 PM
; DNA sequence pdg5 7891 b.p. complete sequence
;
TCTTCCGCTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACTTTAAAAGTGC
TCATCATTGGAAAACGTTCTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATCAGG
GTTATTGTCTCATGAGCGGATACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGGCGTATCACGAGGCCCTTTCG
TCTTCAAGAATTAACTGTGGGAATACTCAGGTATCGTAAGATGCAAGAGTTCGAATCTCTTAGCAACCATTATTTTTTTC
CTCAACATAACGAGAACACACAGGGGCGCTATCGCACAGACAAATTCGATGACTGGAAATTTTTTGTTAATTTCAGAGGT
CGCCGCGCATATACCTTTTTCAACTGAAAAATTGGGAGAAAAAGGAAAGGTGAGAGGCCGGAACCGGCTTTTCATATAGA
ATAGAGAAGCGTTCATGACTAAATGCTTGCATCACAATACTTGAAGTTGACAATATTATTTAAGGACCTATTGTTTTTTC

FIG. 16

CAATAGGTGGTTAGCAATCGTCTTATTCTAACTTTTCTTACCTTTTACATTTCAGCAATATATATATATATATTTCAAGGAT
ATACATTCTAATGTCTGCCCCTATGTCTGCCCCTAAGAAGATCGTCGTTTTGCCAGGTGACCACGTTGGTCAAGATCACA
GCCGAAGCCATTAAGGTTCTTAAAGCTATTTCTGATGTTCGTTCCAATGTCAAGTTCGATTTCGAAAATCATTTAATTGG
TGGTGCTGCTATCGATGCTACAGGTGTCCCACTTCCAGATGAGGCGCTGGAAGCCTCCAAGAAGGTTGATGCCGTTTTGT
TAGGTGCTGTGGGTGGTCCTAAATGGGGTACAGGTAGTGTTAGACCTGAACAAGGTTTACTAAAAATCCGTAAAGAACTT
CAATTGTACGCCAACTTAAGACCATGTAACTTTGCATCCGACTCTCTTTTAGACTTATCTCCAATCAAGCCACAATTTGC
TAAAGGTACTGACTTCGTTGTTGTCAGAGAATTAGTGGGAGGTATTTACTTTGGTAAGAGAAAGGAAGACGATGGTGATG
GTGTCGCTTGGGATAGTGAACAATACACCGTTCCAGAAGTGCAAAGAATCACAAGAATGGCCGCTTTCATGGCCCTACAA
CATGAGCCACCATTGCCTATTTGGTCCTTGGATAAAGCTAATGTTTTGGCCTCTTCAAGATTATGGAGAAAAACTGTGGA
GGAAACCATCAAGAACGAATTTCCTACATTGAAGGTTCAACATCAATTGATTGATTCTGCCGCCATGATCCTAGTTAAGA
ACCCAACCCACCTAAATGGTATTATAATCACCAGCAACATGTTTGGTGATATCATCTCCGATGAAGCCTCCGTTATCCCA
GGTTCCTTGGGTTTGTTGCCATCTGCGTCCTTGGCCTCTTTGCCAGACAAGAACACCGCATTTGGTTTGTACGAACCATG
CCACGGTTCTGCTCCAGATTTGCCAAAGAATAAGGTTGACCCTATCGCCACTATCTTGTCTGCTGCAATGATGTTGAAAT
TGTCATTGAACTTGCCTGAAGAAGGTAAGGCCATTGAAGATGCAGTTAAAAAGGTTTTGGATGCAGGTATCAGAACTGGT
GATTTAGGTGGTTCCAACAGTACCACCGAAGTCGGTGATGCTGTCGCCGAAGAAGTTAAGAAAATCCTTGCTTAAAAAGA
TTCTCTTTTTTTATGATATTTGTACATAAACTTTATAAATGAAATTCATAATAGAAACGACACGAAATTACAAAATGGAA
TATGTTCATAGGGTAGAATTAATTCTCATGTTTGACAGCTTATCATCGGATCGATCCAATATCAAAGGAAATGATAGCAT
TGAAGGATGAGACTAATCCAATTGAGGAGTGGCAGCATATAGAACAGCTAAAGGGTAGTGCTGAAGGAAGCATACGATAC
CCCGCATGGAATGGGATAATATCACAGGAGGTACTAGACTACCTTTCATCCTACATAAATAGACGCATATAAGTACGCAT
TTAAGCATAAACACGCACTATGCCGTTCTTCTCATGTATATATATATACAGGCAACACGCAGATATAGGTGCGACGTGAA
CAGTGAGCTGTATGTGCGCAGCTCGCGTTGCATTTTCGGAAGCGCTCGTTTTCGGAAACGCTTTGAAGTTCCTATTCCGA
AGTTCCTATTCTCTAGCTAGAAAGTATAGGAACTTCAGAGCGCTTTTGAAAACCAAAAGCGCTCTGAAGACGCACTTTCA
AAAAACCAAAAACGCACCGGACTGTAACGAGCTACTAAAATATTGCGAATACCGCTTCCACAAACATTGCTCAAAAGTAT
CTCTTTGCTATATATCTCTGTGCTATATCCCTATATAACCTACCCATCCACCTTTCGCTCCTTGAACTTGCATCTAAACT
CGACCTCTACATTTTTTATGTTTATCTCTAGTATTACTCTTTAGACAAAAAAATTGTAGTAAGAACTATTCATAGAGTGA
ATCGAAAACAATACGAAAATGTAAACATTTCCTATACGTAGTATATAGAGACAAAATAGAAGAAACCGTTCATAATTTTC
TGACCAATGAAGAATCATCAACGCTATCACTTTCTGTTCACAAAGTATGCGCAATCCACATCGGTATAGAATATAATCGG
GGATGCCTTTATCTTGAAAAAATGCACCCGCAGCTTCGCTAGTAATCAGTAAACGCGGGAAGTGGAGTCAGGCTTTTTTT
ATGGAAGAGAAAATAGACACCAAAGTAGCCTTCTTCTAACCTTAACGGACCTACAGTGCAAAAAGTTATCAAGAGACTGC
ATTATAGAGCGCACAAAGGAGAAAAAAAGTAATCTAAGATGCTTTGTTAGAAAAATAGCGCTCTCGGGATGCATTTTTGT
AGAACAAAAAAGAAGTATAGATTCTTTGTTGGTAAAATAGCGCTCTCGCGTTGCATTTCTGTTCTGTAAAAATGCAGCTC
AGATTCTTTGTTTGAAAAATTAGCGCTCTCGCGTTGCATTTTTGTTTTACAAAAATGAAGCACAGATTCTTCGTTGGTAA
AATAGCGCTTTCGCGTTGCATTTCTGTTCTGTAAAAATGCAGCTCAGATTCTTTGTTTGAAAAATTAGCGCTCTCGCGTT
GCATTTTTGTTCTACAAAATGAAGCACAGATGCTTCGTTAACAAAGATATGCTATTGAAGTGCAAGATGGAAACGCAGAA
AATGAACCGGGGATGCGACGTGCAAGATTACCTATGCAATAGATGCAATAGTTTCTCCAGGAACCGAAATACATACATTG
TCTTCCGTAAAGCGCTAGACTATATATTATTATACAGGTTCAAATATACTATCTGTTTCAGGGAAAACTCCCAGGTTCGG
ATGTTCAAAATTCAATGATGGGTAACAAGTACGATCCGATATATGCGGTGTGAAATACCGCACAGATGCGTAAGGAGAAA
ATACCGCATCAGGCGCCATTCGCCATTCAGGCTGCGCAACTGTTGGGAAGGGCGATCGGTGCGGGCCTCTTCGCTATTAC
GCCAGCTGGCGAAAGGGGGATGTGCTGCAAGGCGATTAAGTTGGGTAACGCCAGGGTTTTCCCAGTCACGACGTTGTAAA
ACGACGGCCAGTGAATTcatgtaggtggcggaggggagatatacaatagaacagataccagacaagacataatgggctaa
acaagactacaccaattacactgcctcattgatggtggtacataacgaactaatactgtagccctagacttgatagccat
catcatatcgaagtttcactaccctttttccatttgccatctattgaagtaataataggcgcatgcaacttcttttcttt
tttttcttttctctctcccccgttgttgtctcaccatatccgcaatgacaaaaaaatgatggaagacactaaaggaaaa
aattaacgacaaagacagcaccaacagatgtcgttgttccagagctgatgaggggtatctcgaagcacacgaaactttt
ccttccttcattgacctgcaattattaatcttttgtttcctcgtcattgttctcgttccctttcttccttgtttcttttt
ctgcacaatatttcaagctataccaagcatacaatcaactccaagcttgaagcaagcctcctgaaagATGAAGCTACTGT
CTTCTATCGAACAAGCATGCGATATTTGCCGACTTAAAAAGCTCAAGTGCTCCAAAGAAAAACCGAAGTGCGCCAAGTGT
CTGAAGAACAACTGGGAGTGTCGCTACTCTCCCAAAACCAAAAGGTCTCCGCTGACTAGGGCACATCTGACAGAAGTGGA
ATCAAGGCTAGAAAGACTGGAACAGCTATTTCTACTGATTTTTCCTCGAGAAGACCTTGACATGATTTTGAAAATGGATT
CTTTACAGGATATAAAAGCATTGTTAACAGGATTATTTGTACAAGATAATGTGAATAAAGATGCCGTCACAGATAGATTG
GCTTCAGTGGAGACTGATATGCCTCTAACATTGAGACAGCATAGAATAAGTGCGACATCATCATCGGAAGAGAGTAGTAA
CAAAGGTCAAAGACAGTTGACTGTATCGAACTATCTATTCGATGATGAAGATACCCCACCAAACCCAAAAAAAGAGATCG
AATTCCAGCTGACCACCATGTTTatggccagaacaaagcaaacagcaagaaagtccactggtggtaaggccccaagaaag
caattagcttctaaggctgccagaaaatccgccccatctaccggtggtgttaagaagcctcacagatataagccaggtac

FIG. 16 Cont.

tgttgctttgagagaaatcagaagattccaaaaatctactgaaCCCgggtcccctatactaggttattggaaaggtcgac
gcgaccatcctccaaaatcggatctgatcgaaggtcgtggaGATCCCGAAGTTAAACGGGTAAAATTAGAAAACAACGTT
GAAGAAATACAACCTGAGCAGGCTGAGACCAATAAACAAGAGGGCACCGATAAAGAGAATAAAGGAAAGTTCGAGAAAGA
AACTGAGAGAATAGGAGGATCTGAAGTGGTTACAGATGTGGAAAAAGGAATTGTCAAATTTGAATTTGATGGTGTTGAAT
ACACATTCAAAGAGAGACCCAGTGTCGTAGAGGAAAATGAAGGTAAAATTGAGTTTAGGGTGGTGAATAATGATAATACT
AAAGAAAACATGATGGTCCTAACTGGATTAAAAAACATTTTTCAAAAGCAATTACCAAAAATGCCCAAAGAATACATTGC
CAGGTTAGTCTATGATCGAAGTCATCTTTCCATGGCTGTCATTAGGAAGCCATTGACTGTCGTAGGTGGCATAACATATC
GACCTTTCGATAAGAGAGAATTCGCAGAAATTGTTTTCTGTGCCATCAGTTCGACGGAACAGGTACGCGGTTATGGTGCG
CATCTAATGAATCACTTAAAAGACTATGTTAGAAATACCTCGAACATAAAATATTTTTTGACATATGCAGATAATTACGC
TATTGGATACTTTAAAAAGCAAGGCTTTACTAAAGAAATCACGTTGGATAAAAGTATATGGATGGGATATATTAAAGATT
ATGAAGGTGGTACGCTGATGCAATGTAACATGGCAATTCCCGGtggcggccgcatcttttacccatacgatgttcctgac
tatgcgggctatccctatgacgtcccggactatgcaggatcctatccatatgacgttccagattacgctgctcagtgcgg
ccgctctagctagaactagtggatcccccGATACCGTCGACCTGCAGGCATGCAAGCTTGGCGTAATCATGGTCATAGCT
GTTTCCTGTGTGAAATTGTTATCCGCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCCAGTCGGGAAACCTGTCGTGCCAGCTG
CATTAATGAATCGGCCAACGCGCGGGGAGAGGCGGTTTGCGTATTGGGCGC
//

FIG. 16 Cont.

5988-7613: Gal4 DBD-H3-Gcn5(F221A)-HA
5988-6428: Gal4 DBD (amino acids 1-147)
6507-6683: H3 (amino acids 1-59)
6762-7466: Gcn5 (amino acids 18-252)
7371-7373: F221A
7500-7589: trimeric HA
...-...: 2μ
...-...: LEU2

Translation: Gal4-DBD-H3-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMFMARTKQTARKSTGGKAPRKQLASKAARKSAPSTGGVKKPHRYKPGTVALREIRRFQKSTEPGSPILGY
WKGRRDHPPKSDLIEGRGDPEVKRVKLENNVEEIQPEQAETNKQEGTDKENKGKFEKETERIGGSEVVTDVEKGIVKFEF
DGVEYTFKERPSVVEENEGKIEFRVVNNDNTKENMMVLTGLKNIFQKQLPKMPKEYIARLVYDRSHLSMAVIRKPLTVVG
GITYRPFDKREFAEIVFCAISSTEQVRGYGAHLMNHLKDYVRNTSNIKYFLTYADNYAIGYAKKQGFTKEITLDKSIWMG
YIKDYEGGTLMQCNMAIPGGGRIFYPYDVPDYAGYPYDVPDYAGSYPYDVPDYAAQCGRSS ; DNA sequence pdg6 7891 b.p. complete sequence
;
TCTTCCGCTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACTTTAAAAGTGC
TCATCATTGGAAAACGTTCTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATCAGG
GTTATTGTCTCATGAGCGGATACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGGCGTATCACGAGGCCCTTTCG
TCTTCAAGAATTAACTGTGGGAATACTCAGGTATCGTAAGATGCAAGAGTTCGAATCTCTTAGCAACCATTATTTTTTTC
CTCAACATAACGAGAACACACAGGGGCGCTATCGCACAGACAAATTCGATGACTGGAAATTTTTTGTTAATTTCAGAGGT
CGCCGCGCATATACCTTTTTCAACTGAAAAATTGGAGAAAAAGGAAAGGTGAGAGGCCGGAACCGGCTTTTCATATAGA

FIG. 17

ATAGAGAAGCGTTCATGACTAAATGCTTGCATCACAATACTTGAAGTTGACAATATTATTTAAGGACCTATTGTTTTTTC
CAATAGGTGGTTAGCAATCGTCTTATTCTAACTTTTCTTACCTTTTACATTTCAGCAATATATATATATATTTCAAGGAT
ATACATTCTAATGTCTGCCCCTATGTCTGCCCCTAAGAAGATCGTCGTTTTGCCAGGTGACCACGTTGGTCAAGATCACA
GCCGAAGCCATTAAGGTTCTTAAAGCTATTTCTGATGTTCGTTCCAATGTCAAGTTCGATTTCGAAAATCATTTAATTGG
TGGTGCTGCTATCGATGCTACAGGTGTCCCACTTCCAGATGAGGCGCTGGAAGCCTCCAAGAAGGTTGATGCCGTTTTGT
TAGGTGCTGTGGGTGGTCCTAAATGGGGTACAGGTAGTGTTAGACCTGAACAAGGTTTACTAAAAATCCGTAAAGAACTT
CAATTGTACGCCAACTTAAGACCATGTAACTTTGCATCCGACTCTCTTTTAGACTTATCTCCAATCAAGCCACAATTTGC
TAAAGGTACTGACTTCGTTGTTGTCAGAGAATTAGTGGGAGGTATTTACTTTGGTAAGAGAAAGGAAGACGATGGTGATG
GTGTCGCTTGGGATAGTGAACAATACACCGTTCCAGAAGTGCAAAGAATCACAAGAATGGCCGCTTTCATGGCCCTACAA
CATGAGCCACCATTGCCTATTTGGTCCTTGGATAAAGCTAATGTTTTGGCCTCTTCAAGATTATGGAGAAAAACTGTGGA
GGAAACCATCAAGAACGAATTTCCTACATTGAAGGTTCAACATCAATTGATTGATTCTGCCGCCATGATCCTAGTTAAGA
ACCCAACCCACCTAAATGGTATTATAATCACCAGCAACATGTTTGGTGATATCATCTCCGATGAAGCCTCCGTTATCCCA
GGTTCCTTGGGTTTGTTGCCATCTGCGTCCTTGGCCTCTTTGCCAGACAAGAACACCGCATTTGGTTTGTACGAACCATG
CCACGGTTCTGCTCCAGATTTGCCAAAGAATAAGGTTGACCCTATCGCCACTATCTTGTCTGCTGCAATGATGTTGAAAT
TGTCATTGAACTTGCCTGAAGAAGGTAAGGCCATTGAAGATGCAGTTAAAAAGGTTTTGGATGCAGGTATCAGAACTGGT
GATTTAGGTGGTTCCAACAGTACCACCGAAGTCGGTGATGCTGTCGCCGAAGAAGTTAAGAAAATCCTTGCTTAAAAAGA
TTCTCTTTTTTTATGATATTTGTACATAAACTTTATAAATGAAATTCATAATAGAAACGACACGAAATTACAAAATGGAA
TATGTTCATAGGGTAGAATTAATTCTCATGTTTGACAGCTTATCATCGGATCGATCCAATATCAAAGGAAATGATAGCAT
TGAAGGATGAGACTAATCCAATTGAGGAGTGGCAGCATATAGAACAGCTAAAGGGTAGTGCTGAAGGAAGCATACGATAC
CCCGCATGGAATGGGATAATATCACAGGAGGTACTAGACTACCTTTCATCCTACATAAATAGACGCATATAAGTACGCAT
TTAAGCATAAACACGCACTATGCCGTTCTTCTCATGTATATATATATACAGGCAACACGCAGATATAGGTGCGACGTGAA
CAGTGAGCTGTATGTGCGCAGCTCGCGTTGCATTTTCGGAAGCGCTCGTTTTCGGAAACGCTTTGAAGTTCCTATTCCGA
AGTTCCTATTCTCTAGCTAGAAAGTATAGGAACTTCAGAGCGCTTTTGAAAACCAAAAGCGCTCTGAAGACGCACTTTCA
AAAAACCAAAAACGCACCGGACTGTAACGAGCTACTAAAATATTGCGAATACCGCTTCCACAAACATTGCTCAAAAGTAT
CTCTTTGCTATATATCTCTGTGCTATATCCCTATATAACCTACCCATCCACCTTTCGCTCCTTGAACTTGCATCTAAACT
CGACCTCTACATTTTTTATGTTTATCTCTAGTATTACTCTTTAGACAAAAAAATTGTAGTAAGAACTATTCATAGAGTGA
ATCGAAAACAATACGAAAATGTAAACATTTCCTATACGTAGTATATAGAGACAAAATAGAAGAAACCGTTCATAATTTTC
TGACCAATGAAGAATCATCAACGCTATCACTTTCTGTTCACAAAGTATGCGCAATCCACATCGGTATAGAATATAATCGG
GGATGCCTTTATCTTGAAAAAATGCACCCGCAGCTTCGCTAGTAATCAGTAAACGCGGGAAGTGGAGTCAGGCTTTTTTT
ATGGAAGAGAAAATAGACACCAAAGTAGCCTTCTTCTAACCTTAACGGACCTACAGTGCAAAAAGTTATCAAGAGACTGC
ATTATAGAGCGCACAAAGGAGAAAAAAAGTAATCTAAGATGCTTTGTTAGAAAAATAGCGCTCTCGGGATGCATTTTTGT
AGAACAAAAAAGAAGTATAGATTCTTTGTTGGTAAAATAGCGCTCTCGCGTTGCATTTCTGTTCTGTAAAAATGCAGCTC
AGATTCTTTGTTTGAAAAATTAGCGCTCTCGCGTTGCATTTTTGTTTTACAAAAATGAAGCACAGATTCTTCGTTGGTAA
AATAGCGCTTTCGCGTTGCATTTCTGTTCTGTAAAAATGCAGCTCAGATTCTTTGTTTGAAAAATTAGCGCTCTCGCGTT
GCATTTTTGTTCTACAAAATGAAGCACAGATGCTTCGTTAACAAAGATATGCTATTGAAGTGCAAGATGGAAACGCAGAA
AATGAACCGGGGATGCGACGTGCAAGATTACCTATGCAATAGATGCAATAGTTTCTCCAGGAACCGAAATACATACATTG
TCTTCCGTAAAGCGCTAGACTATATATTATTATACAGGTTCAAATATACTATCTGTTTCAGGGAAAACTCCCAGGTTCGG
ATGTTCAAAATTCAATGATGGGTAACAAGTACGATCCGATATATGCGGTGTGAAATACCGCACAGATGCGTAAGGAGAAA
ATACCGCATCAGGCGCCATTCGCCATTCAGGCTGCGCAACTGTTGGGAAGGGCGATCGGTGCGGGCCTCTTCGCTATTAC
GCCAGCTGGCGAAAGGGGGATGTGCTGCAAGGCGATTAAGTTGGGTAACGCCAGGGTTTTCCCAGTCACGACGTTGTAAA
ACGACGGCCAGTGAATTcatgtaggtggcggaggggagatatacaatagaacagataccagacaagacataatgggctaa
acaagactacaccaattacactgcctcattgatggtggtacataacgaactaatactgtagccctagacttgatagccat
catcatatcgaagtttcactaccctttttccatttgccatctattgaagtaataataggcgcatgcaacttcttttcttt
ttttttcttttctctctcccccgttgttgtctcaccatatccgcaatgacaaaaaaatgatggaagacactaaaggaaaa
aattaacgacaaagacagcaccaacagatgtcgttgttccagagctgatgaggggtatctcgaagcacacgaaactttt
ccttccttcattgacctgcaattattaatcttttgtttcctcgtcattgttctcgttccctttcttccttgtttcttttt
ctgcacaatatttcaagctataccaagcatacaatcaactccaagcttgaagcaagcctcctgaaagATGAAGCTACTGT
CTTCTATCGAACAAGCATGCGATATTTGCCGACTTAAAAAGCTCAAGTGCTCCAAAGAAAAACCGAAGTGCGCCAAGTGT
CTGAAGAACAACTGGGAGTGTCGCTACTCTCCCAAAACCAAAAGGTCTCCGCTGACTAGGGCACATCTGACAGAAGTGGA
ATCAAGGCTAGAAAGACTGGAACAGCTATTTCTACTGATTTTTCCTCGAGAAGACCTTGACATGATTTTGAAAATGGATT
CTTTACAGGATATAAAAGCATTGTTAACAGGATTATTTGTACAAGATAATGTGAATAAAGATGCCGTCACAGATAGATTG
GCTTCAGTGGAGACTGATATGCCTCTAACATTGAGACAGCATAGAATAAGTGCGACATCATCATCGGAAGAGAGTAGTAA
CAAAGGTCAAAGACAGTTGACTGTATCGAACTATCTATTCGATGATGAAGATACCCCACCAAACCCAAAAAAAGAGATCG
AATTCCAGCTGACCACCATGTTTatggccagaacaaagcaaacagcaagaaagtccactggtggtaaggccccaagaaag

FIG. 17 Cont.

caattagcttctaaggctgccagaaaatccgccccatctaccggtggtgttaagaagcctcacagatataagccaggtac
tgttgctttgagagaaatcagaagattccaaaaatctactgaaCCCgggtcccctatactaggttattggaaaggtcgac
gcgaccatcctccaaaatcggatctgatcgaaggtcgtggaGATCCCGAAGTTAAACGGGTAAAATTAGAAAACAACGTT
GAAGAAATACAACCTGAGCAGGCTGAGACCAATAAACAAGAGGGCACCGATAAAGAGAATAAAGGAAAGTTCGAGAAAGA
AACTGAGAGAATAGGAGGATCTGAAGTGGTTACAGATGTGGAAAAAGGAATTGTCAAATTTGAATTTGATGGTGTTGAAT
ACACATTCAAAGAGAGACCCAGTGTCGTAGAGGAAAATGAAGGTAAAATTGAGTTTAGGGTGGTGAATAATGATAATACT
AAAGAAAACATGATGGTCCTAACTGGATTAAAAAACATTTTTCAAAAGCAATTACCAAAAATGCCCAAAGAATACATTGC
CAGGTTAGTCTATGATCGAAGTCATCTTTCCATGGCTGTCATTAGGAAGCCATTGACTGTCGTAGGTGGCATAACATATC
GACCTTTCGATAAGAGAGAATTCGCAGAAATTGTTTTCTGTGCCATCAGTTCGACGGAACAGGTACGCGGTTATGGTGCG
CATCTAATGAATCACTTAAAAGACTATGTTAGAAATACCTCGAACATAAAATATTTTTTGACATATGCAGATAATTACGC
TATTGGATACgctAAAAAGCAAGGCTTCACTAAAGAAATCACGTTGGATAAAAGTATATGGATGGGATATATTAAAGATT
ATGAAGGTGGTACGCTGATGCAATGTAACATGGCAATTCCCGGtggcggccgcatcttttacccatacgatgttcctgac
tatgcgggctatccctatgacgtcccggactatgcaggatcctatccatatgacgttccagattacgctgctcagtgcgg
ccgctctagctagaactagtggatcccccGATACCGTCGACCTGCAGGCATGCAAGCTTGGCGTAATCATGGTCATAGCT
GTTTCCTGTGTGAAATTGTTATCCGCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCCAGTCGGGAAACCTGTCGTGCCAGCTG
CATTAATGAATCGGCCAACGCGCGGGGAGAGGCGGTTTGCGTATTGGGCGC
//

FIG. 17 Cont.

5988-7517: Gal4 DBD-H3-Gcn5-HA
5988-6428: Gal4 DBD (amino acids 1-147)
6501-6587: H4 (amino acids 1-29)
6666-7370: Gcn5 (amino acids 18-252)
7404-7493: trimeric HA
...-...: 2μ
...-...: LEU2

Translation: Gal4 DBD-H4-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMSGRGKGGKGLGKGGAKRHRKILRDNIQGISGSPILGYWKGRRDHPPKSDLIEGRGDPEVKRVKLENNVE
EIQPEQAETNKQEGTDKENKGKFEKETERIGGSEVVTDVEKGIVKFEFDGVEYTFKERPSVVEENEGKIEFRVVNNDNTK
ENMMVLTGLKNIFQKQLPKMPKEYIARLVYDRSHLSMAVIRKPLTVVGGITYRPFDKREFAEIVFCAISSTEQVRGYGAH
LMNHLKDYVRNTSNIKYFLTYADNYAIGYFKKQGFTKEITLDKSIWMGYIKDYEGGTLMQCSMAIPGGGRIFYPYDVPDY
AGYPYDVPDYAGSYPYDVPDYAAQCGRSS DNA sequence pdg7 7795 b.p. complete sequence TCTTCCGCTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACTTTAAAAGTGC
TCATCATTGGAAAACGTTCTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATCAGG
GTTATTGTCTCATGAGCGGATACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGGCGTATCACGAGGCCCTTTCG
TCTTCAAGAATTAACTGTGGGAATACTCAGGTATCGTAAGATGCAAGAGTTCGAATCTCTTAGCAACCATTATTTTTTTC
CTCAACATAACGAGAACACACAGGGGCGCTATCGCACAGACAAATTCGATGACTGGAAATTTTTTGTTAATTTCAGAGGT
CGCCGCGCATATACCTTTTTCAACTGAAAAATTGGGAGAAAAAGGAAAGGTGAGAGGCCGGAACCGGCTTTTCATATAGA
ATAGAGAAGCGTTCATGACTAAATGCTTGCATCACAATACTTGAAGTTGACAATATTATTTAAGGACCTATTGTTTTTTC

FIG. 18

CAATAGGTGGTTAGCAATCGTCTTATTCTAACTTTTCTTACCTTTTACATTTCAGCAATATATATATATATATTTCAAGGAT
ATACATTCTAATGTCTGCCCCTATGTCTGCCCCTAAGAAGATCGTCGTTTTGCCAGGTGACCACGTTGGTCAAGATCACA
GCCGAAGCCATTAAGGTTCTTAAAGCTATTTCTGATGTTCGTTCCAATGTCAAGTTCGATTTCGAAAATCATTTAATTGG
TGGTGCTGCTATCGATGCTACAGGTGTCCCACTTCCAGATGAGGCGCTGGAAGCCTCCAAGAAGGTTGATGCCGTTTTGT
TAGGTGCTGTGGGTGGTCCTAAATGGGGTACAGGTAGTGTTAGACCTGAACAAGGTTTACTAAAAATCCGTAAAGAACTT
CAATTGTACGCCAACTTAAGACCATGTAACTTTGCATCCGACTCTCTTTTAGACTTATCTCCAATCAAGCCACAATTTGC
TAAAGGTACTGACTTCGTTGTTGTCAGAGAATTAGTGGGAGGTATTTACTTTGGTAAGAGAAAGGAAGACGATGGTGATG
GTGTCGCTTGGGATAGTGAACAATACACCGTTCCAGAAGTGCAAAGAATCACAAGAATGGCCGCTTTCATGGCCCTACAA
CATGAGCCACCATTGCCTATTTGGTCCTTGGATAAAGCTAATGTTTTGGCCTCTTCAAGATTATGGAGAAAAACTGTGGA
GGAAACCATCAAGAACGAATTTCCTACATTGAAGGTTCAACATCAATTGATTGATTCTGCCGCCATGATCCTAGTTAAGA
ACCCAACCCACCTAAATGGTATTATAATCACCAGCAACATGTTTGGTGATATCATCTCCGATGAAGCCTCCGTTATCCCA
GGTTCCTTGGGTTTGTTGCCATCTGCGTCCTTGGCCTCTTTGCCAGACAAGAACACCGCATTTGGTTTGTACGAACCATG
CCACGGTTCTGCTCCAGATTTGCCAAAGAATAAGGTTGACCCTATCGCCACTATCTTGTCTGCTGCAATGATGTTGAAAT
TGTCATTGAACTTGCCTGAAGAAGGTAAGGCCATTGAAGATGCAGTTAAAAAGGTTTTGGATGCAGGTATCAGAACTGGT
GATTTAGGTGGTTCCAACAGTACCACCGAAGTCGGTGATGCTGTCGCCGAAGAAGTTAAGAAAATCCTTGCTTAAAAAGA
TTCTCTTTTTTTATGATATTTGTACATAAACTTTATAAATGAAATTCATAATAGAAACGACACGAAATTACAAAATGGAA
TATGTTCATAGGGTAGAATTAATTCTCATGTTTGACAGCTTATCATCGGATCGATCCAATATCAAAGGAAATGATAGCAT
TGAAGGATGAGACTAATCCAATTGAGGAGTGGCAGCATATAGAACAGCTAAAGGGTAGTGCTGAAGGAAGCATACGATAC
CCCGCATGGAATGGGATAATATCACAGGAGGTACTAGACTACCTTTCATCCTACATAAATAGACGCATATAAGTACGCAT
TTAAGCATAAACACGCACTATGCCGTTCTTCTCATGTATATATATATACAGGCAACACGCAGATATAGGTGCGACGTGAA
CAGTGAGCTGTATGTGCGCAGCTCGCGTTGCATTTTCGGAAGCGCTCGTTTTCGGAAACGCTTTGAAGTTCCTATTCCGA
AGTTCCTATTCTCTAGCTAGAAAGTATAGGAACTTCAGAGCGCTTTTGAAAACCAAAAGCGCTCTGAAGACGCACTTTCA
AAAAACCAAAAACGCACCGGACTGTAACGAGCTACTAAAATATTGCGAATACCGCTTCCACAAACATTGCTCAAAAGTAT
CTCTTTGCTATATATCTCTGTGCTATATCCCTATATAACCTACCCATCCACCTTTCGCTCCTTGAACTTGCATCTAAACT
CGACCTCTACATTTTTTATGTTTATCTCTAGTATTACTCTTTAGACAAAAAAATTGTAGTAAGAACTATTCATAGAGTGA
ATCGAAAACAATACGAAAATGTAAACATTTCCTATACGTAGTATATAGAGACAAAATAGAAGAAACCGTTCATAATTTTC
TGACCAATGAAGAATCATCAACGCTATCACTTTCTGTTCACAAAGTATGCGCAATCCACATCGGTATAGAATATAATCGG
GGATGCCTTTATCTTGAAAAAATGCACCCGCAGCTTCGCTAGTAATCAGTAAACGCGGGAAGTGGAGTCAGGCTTTTTTT
ATGGAAGAGAAAATAGACACCAAAGTAGCCTTCTTCTAACCTTAACGGACCTACAGTGCAAAAAGTTATCAAGAGACTGC
ATTATAGAGCGCACAAAGGAGAAAAAAAGTAATCTAAGATGCTTTGTTAGAAAAATAGCGCTCTCGGGATGCATTTTTGT
AGAACAAAAAAGAAGTATAGATTCTTTGTTGGTAAAATAGCGCTCTCGCGTTGCATTTCTGTTCTGTAAAAATGCAGCTC
AGATTCTTTGTTTGAAAAATTAGCGCTCTCGCGTTGCATTTTTGTTTTACAAAAATGAAGCACAGATTCTTCGTTGGTAA
AATAGCGCTTTCGCGTTGCATTTCTGTTCTGTAAAAATGCAGCTCAGATTCTTTGTTTGAAAAATTAGCGCTCTCGCGTT
GCATTTTTGTTCTACAAAATGAAGCACAGATGCTTCGTTAACAAAGATATGCTATTGAAGTGCAAGATGGAAACGCAGAA
AATGAACCGGGGATGCGACGTGCAAGATTACCTATGCAATAGATGCAATAGTTTCTCCAGGAACCGAAATACATACATTG
TCTTCCGTAAAGCGCTAGACTATATATTATTATACAGGTTCAAATATACTATCTGTTTCAGGGAAAACTCCCAGGTTCGG
ATGTTCAAAATTCAATGATGGGTAACAAGTACGATCCGATATATGCGGTGTGAAATACCGCACAGATGCGTAAGGAGAAA
ATACCGCATCAGGCGCCATTCGCCATTCAGGCTGCGCAACTGTTGGGAAGGGCGATCGGTGCGGGCCTCTTCGCTATTAC
GCCAGCTGGCGAAAGGGGGATGTGCTGCAAGGCGATTAAGTTGGGTAACGCCAGGGTTTTCCCAGTCACGACGTTGTAAA
ACGACGGCCAGTGAATTcatgtaggtggcggaggggagatatacaatagaacagataccagacaagacataatgggctaa
acaagactacaccaattacactgcctcattgatggtggtacataacgaactaatactgtagccctagacttgatagccat
catcatatcgaagtttcactacccttttccatttgccatctattgaagtaataataggcgcatgcaacttcttttcttt
tttttcttttctctctccccgttgttgtctcaccatatccgcaatgacaaaaaaatgatggaagacactaaaggaaaa
aattaacgacaaagacagcaccaacagatgtcgttgttccagagctgatgaggggtatctcgaagcacacgaaactttt
ccttccttcattgacctgcaattattaatcttttgtttcctcgtcattgttctcgttccctttcttccttgtttcttttt
ctgcacaatatttcaagctataccaagcatacaatcaactccaagcttgaagcaagcctcctgaaagATGAAGCTACTGT
CTTCTATCGAACAAGCATGCGATATTTGCCGACTTAAAAAGCTCAAGTGCTCCAAAGAAAAACCGAAGTGCGCCAAGTGT
CTGAAGAACAACTGGGAGTGTCGCTACTCTCCCAAAACCAAAAGGTCTCCGCTGACTAGGGCACATCTGACAGAAGTGGA
ATCAAGGCTAGAAAGACTGGAACAGCTATTTCTACTGATTTTTCCTCGAGAAGACCTTGACATGATTTTGAAAATGGATT
CTTTACAGGATATAAAAGCATTGTTAACAGGATTATTTGTACAAGATAATGTGAATAAAGATGCCGTCACAGATAGATTG
GCTTCAGTGGAGACTGATATGCCTCTAACATTGAGACAGCATAGAATAAGTGCGACATCATCATCGGAAGAGAGTAGTAA
CAAAGGTCAAAGACAGTTGACTGTATCGAACTATCTATTCGATGATGAAGATACCCCACCAAACCCAAAAAAAGAGATCG
AATTCCAGCTGACCACCATGTCCGGTAGAGGTAAAGGTGGTAAAGGTCTAGGAAAAGGTGGTGCCAAGCGTCACAGAAAG
ATTCTAAGAGATAACATCCAAGGTATTTCCgggtcccctatactaggttattggaaaggtcgacgcgaccatcctccaaa

FIG. 18 Cont.

atcggatctgatcgaaggtcgtggaGATCCCGAAGTTAAACGGGTAAAATTAGAAAACAACGTTGAAGAAATACAACCTG
AGCAGGCTGAGACCAATAAACAAGAGGGCACCGATAAAGAGAATAAAGGAAAGTTCGAGAAAGAAACTGAGAGAATAGGA
GGATCTGAAGTGGTTACAGATGTGGAAAAAGGAATTGTCAAATTTGAATTTGATGGTGTTGAATACACATTCAAAGAGAG
ACCCAGTGTCGTAGAGGAAAATGAAGGTAAAATTGAGTTTAGGGTGGTGAATAATGATAATACTAAAGAAAACATGATGG
TCCTAACTGGATTAAAAAACATTTTTCAAAAGCAATTACCAAAAATGCCCAAAGAATACATTGCCAGGTTAGTCTATGAT
CGAAGTCATCTTTCCATGGCTGTCATTAGGAAGCCATTGACTGTCGTAGGTGGCATAACATATCGACCTTTCGATAAGAG
AGAATTCGCAGAAATTGTTTTCTGTGCCATCAGTTCGACGGAACAGGTACGCGGTTATGGTGCGCATCTAATGAATCACT
TAAAAGACTATGTTAGAAATACCTCGAACATAAAATATTTTTTGACATATGCAGATAATTACGCTATTGGATACTTTAAA
AAGCAAGGCTTCACTAAAGAAATCACGTTGGATAAAAGTATATGGATGGGATATATTAAAGATTATGAAGGTGGTACGCT
GATGCAATGTtccATGGCAATTCCCGGtggcggccgcatcttttacccatacgatgttcctgactatgcgggctatccct
atgacgtcccggactatgcaggatcctatccatatgacgttccagattacgctgctcagtgcggccgctctagctagaac
tagtggatcccccGATACCGTCGACCTGCAGGCATGCAAGCTTGGCGTAATCATGGTCATAGCTGTTTCCTGTGTGAAAT
TGTTATCCGCTCACAATTCCACACAACATACGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACCTGTCGTGCCAGCTGCATTAATGAATCGGCC
AACGCGCGGGGAGAGGCGGTTTGCGTATTGGGCGC
//

FIG. 18 Cont.

5988-7517: Gal4 DBD-H3-Gcn5-HA
5988-6428: Gal4 DBD (amino acids 1-147)
6501-6587: H4 (amino acids 1-29)
6666-7370: Gcn5 (amino acids 18-252)
7275-7277: F221A
7404-7493: trimeric HA
...-...: 2μ
...-...: LEU2

Translation: Gal4 DBD-H4-Gcn5 F221A-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLTTMSGRGKGGKGLGKGGAKRHRKILRDNIQGISGSPILGYWKGRRDHPPKSDLIEGRGDPEVKRVKLENNVE
EIQPEQAETNKQEGTDKENKGKFEKETERIGGSEVVTDVEKGIVKFEFDGVEYTFKERPSVVEENEGKIEFRVVNNDNTK
ENMMVLTGLKNIFQKQLPKMPKEYIARLVYDRSHLSMAVIRKPLTVVGGITYRPFDKREFAEIVFCAISSTEQVRGYGAH
LMNHLKDYVRNTSNIKYFLTYADNYAIGYAKKQGFTKEITLDKSIWMGYIKDYEGGTLMQCSMAIPGGGRIFYPYDVPDY
AGYPYDVPDYAGSYPYDVPDYAAQCGRSS ; DNA sequence pdg7 7795 b.p. complete sequence
;
TCTTCCGCTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACTTTAAAAGTGC
TCATCATTGGAAAACGTTCTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATCAGG
GTTATTGTCTCATGAGCGGATACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGGCGTATCACGAGGCCCTTTCG
TCTTCAAGAATTAACTGTGGGAATACTCAGGTATCGTAAGATGCAAGAGTTCGAATCTCTTAGCAACCATTATTTTTTTC
CTCAACATAACGAGAACACACAGGGGCGCTATCGCACAGACAAATTCGATGACTGGAAATTTTTTGTTAATTTCAGAGGT

FIG. 19

CGCCGCGCATATACCTTTTTCAACTGAAAAATTGGGAGAAAAAGGAAAGGTGAGAGGCCGGAACCGGCTTTTCATATAGA
ATAGAGAAGCGTTCATGACTAAATGCTTGCATCACAATACTTGAAGTTGACAATATTATTTAAGGACCTATTGTTTTTTC
CAATAGGTGGTTAGCAATCGTCTTATTCTAACTTTTCTTACCTTTTACATTTCAGCAATATATATATATATATTTCAAGGAT
ATACATTCTAATGTCTGCCCCTATGTCTGCCCCTAAGAAGATCGTCGTTTTGCCAGGTGACCACGTTGGTCAAGATCACA
GCCGAAGCCATTAAGGTTCTTAAAGCTATTTCTGATGTTCGTTCCAATGTCAAGTTCGATTTCGAAAATCATTTAATTGG
TGGTGCTGCTATCGATGCTACAGGTGTCCCACTTCCAGATGAGGCGCTGGAAGCCTCCAAGAAGGTTGATGCCGTTTTGT
TAGGTGCTGTGGGTGGTCCTAAATGGGGTACAGGTAGTGTTAGACCTGAACAAGGTTTACTAAAAATCCGTAAAGAACTT
CAATTGTACGCCAACTTAAGACCATGTAACTTTGCATCCGACTCTCTTTTAGACTTATCTCCAATCAAGCCACAATTTGC
TAAAGGTACTGACTTCGTTGTTGTCAGAGAATTAGTGGGAGGTATTTACTTTGGTAAGAGAAAGGAAGACGATGGTGATG
GTGTCGCTTGGGATAGTGAACAATACACCGTTCCAGAAGTGCAAAGAATCACAAGAATGGCCGCTTTCATGGCCCTACAA
CATGAGCCACCATTGCCTATTTGGTCCTTGGATAAAGCTAATGTTTTGGCCTCTTCAAGATTATGGAGAAAAACTGTGGA
GGAAACCATCAAGAACGAATTTCCTACATTGAAGGTTCAACATCAATTGATTGATTCTGCCGCCATGATCCTAGTTAAGA
ACCCAACCCACCTAAATGGTATTATAATCACCAGCAACATGTTTGGTGATATCATCTCCGATGAAGCCTCCGTTATCCCA
GGTTCCTTGGGTTTGTTGCCATCTGCGTCCTTGGCCTCTTTGCCAGACAAGAACACCGCATTTGGTTTGTACGAACCATG
CCACGGTTCTGCTCCAGATTTGCCAAAGAATAAGGTTGACCCTATCGCCACTATCTTGTCTGCTGCAATGATGTTGAAAT
TGTCATTGAACTTGCCTGAAGAAGGTAAGGCCATTGAAGATGCAGTTAAAAAGGTTTTGGATGCAGGTATCAGAACTGGT
GATTTAGGTGGTTCCAACAGTACCACCGAAGTCGGTGATGCTGTCGCCGAAGAAGTTAAGAAAATCCTTGCTTAAAAAGA
TTCTCTTTTTTTATGATATTTGTACATAAACTTTATAAATGAAATTCATAATAGAAACGACACGAAATTACAAAATGGAA
TATGTTCATAGGGTAGAATTAATTCTCATGTTTGACAGCTTATCATCGGATCGATCCAATATCAAAGGAAATGATAGCAT
TGAAGGATGAGACTAATCCAATTGAGGAGTGGCAGCATATAGAACAGCTAAAGGGTAGTGCTGAAGGAAGCATACGATAC
CCCGCATGGAATGGGATAATATCACAGGAGGTACTAGACTACCTTTCATCCTACATAAATAGACGCATATAAGTACGCAT
TTAAGCATAAACACGCACTATGCCGTTCTTCTCATGTATATATATATACAGGCAACACGCAGATATAGGTGCGACGTGAA
CAGTGAGCTGTATGTGCGCAGCTCGCGTTGCATTTTCGGAAGCGCTCGTTTTCGGAAACGCTTTGAAGTTCCTATTCCGA
AGTTCCTATTCTCTAGCTAGAAAGTATAGGAACTTCAGAGCGCTTTTGAAAACCAAAAGCGCTCTGAAGACGCACTTTCA
AAAAACCAAAAACGCACCGGACTGTAACGAGCTACTAAAATATTGCGAATACCGCTTCCACAAACATTGCTCAAAAGTAT
CTCTTTGCTATATATCTCTGTGCTATATCCCTATATAACCTACCCATCCACCTTTCGCTCCTTGAACTTGCATCTAAACT
CGACCTCTACATTTTTTATGTTTATCTCTAGTATTACTCTTTAGACAAAAAAATTGTAGTAAGAACTATTCATAGAGTGA
ATCGAAAACAATACGAAAATGTAAACATTTCCTATACGTAGTATATAGAGACAAAATAGAAGAAACCGTTCATAATTTTC
TGACCAATGAAGAATCATCAACGCTATCACTTTCTGTTCACAAAGTATGCGCAATCCACATCGGTATAGAATATAATCGG
GGATGCCTTTATCTTGAAAAAATGCACCCGCAGCTTCGCTAGTAATCAGTAAACGCGGGAAGTGGAGTCAGGCTTTTTTT
ATGGAAGAGAAAATAGACACCAAAGTAGCCTTCTTCTAACCTTAACGGACCTACAGTGCAAAAAGTTATCAAGAGACTGC
ATTATAGAGCGCACAAAGGAGAAAAAAAGTAATCTAAGATGCTTTGTTAGAAAAATAGCGCTCTCGGGATGCATTTTTGT
AGAACAAAAAAGAAGTATAGATTCTTTGTTGGTAAAATAGCGCTCTCGCGTTGCATTTCTGTTCTGTAAAAATGCAGCTC
AGATTCTTTGTTTGAAAAATTAGCGCTCTCGCGTTGCATTTTTGTTTTACAAAAATGAAGCACAGATTCTTCGTTGGTAA
AATAGCGCTTTCGCGTTGCATTTCTGTTCTGTAAAAATGCAGCTCAGATTCTTTGTTTGAAAAATTAGCGCTCTCGCGTT
GCATTTTTGTTCTACAAAATGAAGCACAGATGCTTCGTTAACAAAGATATGCTATTGAAGTGCAAGATGGAAACGCAGAA
AATGAACCGGGGATGCGACGTGCAAGATTACCTATGCAATAGATGCAATAGTTTCTCCAGGAACCGAAATACATACATTG
TCTTCCGTAAAGCGCTAGACTATATATTATTATACAGGTTCAAATATACTATCTGTTTCAGGGAAAACTCCCAGGTTCGG
ATGTTCAAAATTCAATGATGGGTAACAAGTACGATCCGATATATGCGGTGTGAAATACCGCACAGATGCGTAAGGAGAAA
ATACCGCATCAGGCGCCATTCGCCATTCAGGCTGCGCAACTGTTGGGAAGGGCGATCGGTGCGGGCCTCTTCGCTATTAC
GCCAGCTGGCGAAAGGGGGATGTGCTGCAAGGCGATTAAGTTGGGTAACGCCAGGGTTTTCCCAGTCACGACGTTGTAAA
ACGACGGCCAGTGAATTcatgtaggtggcggaggggagatatacaatagaacagataccagacaagacataatgggctaa
acaagactacaccaattacactgcctcattgatggtggtacataacgaactaatactgtagccctagacttgatagccat
catcatatcgaagtttcactacccttttccatttgccatctattgaagtaataataggcgcatgcaacttcttttcttt
ttttttcttttctctctcccccgttgttgtctcaccatatccgcaatgacaaaaaaatgatggaagacactaaaggaaaa
aattaacgacaaagacagcaccaacagatgtcgttgttccagagctgatgaggggtatctcgaagcacacgaaactttt
ccttccttcattgacctgcaattattaatcttttgtttcctcgtcattgttctcgttccctttcttccttgtttcttttt
ctgcacaatatttcaagctataccaagcatacaatcaactccaagcttgaagcaagcctcctgaaagATGAAGCTACTGT
CTTCTATCGAACAAGCATGCGATATTTGCCGACTTAAAAAGCTCAAGTGCTCCAAAGAAAAACCGAAGTGCGCCAAGTGT
CTGAAGAACAACTGGGAGTGTCGCTACTCTCCCAAAACCAAAAGGTCTCCGCTGACTAGGGCACATCTGACAGAAGTGGA
ATCAAGGCTAGAAAGACTGGAACAGCTATTTCTACTGATTTTTCCTCGAGAAGACCTTGACATGATTTTGAAAATGGATT
CTTTACAGGATATAAAAGCATTGTTAACAGGATTATTTGTACAAGATAATGTGAATAAAGATGCCGTCACAGATAGATTG
GCTTCAGTGGAGACTGATATGCCTCTAACATTGAGACAGCATAGAATAAGTGCGACATCATCATCGGAAGAGAGTAGTAA
CAAAGGTCAAAGACAGTTGACTGTATCGAACTATCTATTCGATGATGAAGATACCCCACCAAACCCAAAAAAAGAGATCG

FIG. 19 Cont.

AATTCCAGCTGACCACCATGTCCGGTAGAGGTAAAGGTGGTAAAGGTCTAGGAAAAGGTGGTGCCAAGCGTCACAGAAAG
ATTCTAAGAGATAACATCCAAGGTATTTCCgggtcccctatactaggttattggaaaggtcgacgcgaccatcctccaaa
atcggatctgatcgaaggtcgtggaGATCCCGAAGTTAAACGGGTAAAATTAGAAAACAACGTTGAAGAAATACAACCTG
AGCAGGCTGAGACCAATAAACAAGAGGGCACCGATAAAGAGAATAAAGGAAAGTTCGAGAAAGAAACTGAGAGAATAGGA
GGATCTGAAGTGGTTACAGATGTGGAAAAAGGAATTGTCAAATTTGAATTTGATGGTGTTGAATACACATTCAAAGAGAG
ACCCAGTGTCGTAGAGGAAAATGAAGGTAAAATTGAGTTTAGGGTGGTGAATAATGATAATACTAAAGAAAACATGATGG
TCCTAACTGGATTAAAAAACATTTTTCAAAAGCAATTACCAAAAATGCCCAAAGAATACATTGCCAGGTTAGTCTATGAT
CGAAGTCATCTTTCCATGGCTGTCATTAGGAAGCCATTGACTGTCGTAGGTGGCATAACATATCGACCTTTCGATAAGAG
AGAATTCGCAGAAATTGTTTTCTGTGCCATCAGTTCGACGGAACAGGTACGCGGTTATGGTGCGCATCTAATGAATCACT
TAAAAGACTATGTTAGAAATACCTCGAACATAAAATATTTTTTGACATATGCAGATAATTACGCTATTGGATACGCTAAA
AAGCAAGGCTTCACTAAAGAAATCACGTTGGATAAAAGTATATGGATGGGATATATTAAAGATTATGAAGGTGGTACGCT
GATGCAATGTtccATGGCAATTCCCGGtggcggccgcatcttttacccatacgatgttcctgactatgcgggctatccct
atgacgtcccggactatgcaggatcctatccatatgacgttccagattacgctgctcagtgcggccgctctagctagaac
tagtggatcccccGATACCGTCGACCTGCAGGCATGCAAGCTTGGCGTAATCATGGTCATAGCTGTTTCCTGTGTGAAAT
TGTTATCCGCTCACAATTCCACACAACATACGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACCTGTCGTGCCAGCTGCATTAATGAATCGGCC
AACGCGCGGGGAGAGGCGGTTTGCGTATTGGGCGC
//

FIG. 19 Cont.

434-1861: Gal4 DBD-H3-Gcn5-HA
434-874: Gal4 DBD (amino acids 1-147)
1010-1714: Gcn5 (amino acids 18-252)
1748-1837: trimeric HA
...-...: CEN/ARS
...-...: TRP1

Translation: Gal4-DBD-Gcn5-HA
```
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQGSPILGYWKGRRDHPPKSDLIEGRGDPEVKRVKLENNVEEIQPEQAETNKQEGTDKENKGKFEKETERIGGSE
VVTDVEKGIVKFEFDGVEYTFKERPSVVEENEGKIEFRVVNNDNTKENMMVLTGLKNIFQKQLPKMPKEYIARLVYDRSH
LSMAVIRKPLTVVGGITYRPFDKREFAEIVFCAISSTEQVRGYGAHLMNHLKDYVRNTSNIKYFLTYADNYAIGYFKKQG
FTKEITLDKSIWMGYIKDYEGGTLMQCNMAIPGGGRIFYPYDVPDYAGYPYDVPDYAGSYPYDVPDYAAQCGRSS
```

```
; DNA sequence  PDG28   8087  b.p. complete sequence
;
gtggtacataacgaactaatactgtagccctagacttgatagccatcatcatatcgaagtttcactaccctttttccatt
tgccatctattgaagtaataataggcgcatgcaacttcttttcttttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGgggtcccctatactaggttattggaa
aggtcgacgcgaccatcctccaaaatcggatctgatcgaaggtcgtggaGATCCCGAAGTTAAACGGGTAAAATTAGAAA
ACAACGTTGAAGAAATACAACCTGAGCAGGCTGAGACCAATAAACAAGAGGGCACCGATAAAGAGAATAAAGGAAAGTTC
GAGAAAGAAACTGAGAGAATAGGAGGATCTGAAGTGGTTACAGATGTGGAAAAAGGAATTGTCAAATTTGAATTTGATGG
TGTTGAATACACATTCAAAGAGAGACCCAGTGTCGTAGAGGAAAATGAAGGTAAAATTGAGTTTAGGGTGGTGAATAATG
ATAATACTAAAGAAAACATGATGGTCCTAACTGGATTAAAAAACATTTTTCAAAAGCAATTACCAAAAATGCCCAAAGAA
TACATTGCCAGGTTAGTCTATGATCGAAGTCATCTTTCCATGGCTGTCATTAGGAAGCCATTGACTGTCGTAGGTGGCAT
AACATATCGACCTTTCGATAAGAGAGAATTCGCAGAAATTGTTTTCTGTGCCATCAGTTCGACGGAACAGGTACGCGGTT
ATGGTGCGCATCTAATGAATCACTTAAAAGACTATGTTAGAAATACCTCGAACATAAAATATTTTTTGACATATGCAGAT
AATTACGCTATTGGATACTTTAAAAAGCAAGGCTTTACTAAAGAAATCACGTTGGATAAAAGTATATGGATGGGATATAT
TAAAGATTATGAAGGTGGTACGCTGATGCAATGTAACATGGCAATTCCCGGtggcggccgcatcttttacccatacgatg
ttcctgactatgcgggctatccctatgacgtcccggactatgcaggatcctatccatatgacgttccagattacgctgct
cagtgcggccgctctagctagaactagtggatcccccGATACCGTCGACCTGCAGAGATCTAtgaatcgtagatactgaa
aaaccccgcaagttcacttcaactgtgcatcgtgcaccatctcaatttctttcatttatacatcgttttgccttcttta
tgtaactatactcctctaagtttcaatcttggccatgtaacctctgatctatagaatttttaaatgactagaattaatg
cccatcttttttttggacctaaattcttcatgaaaatatattacgagggcttattcagaagctttggacttcttcgccag
aggtttggtcaagtctccaatcaaggttgtcggcttgtctaccttgccagaaatttacgaaaagatggaaaagggtcaaa
tcgttggtagatacgttgttgacacttctaaataagcgaatttcttatgatttatgatttttattattaaataagttata
aaaaaaataagtgtatacaaattttaaagtgactcttaggttttaaaacgaaaattcttattcttgagtaactctttcct
gtaggtcaggttgctttctcaggtatagcatgaggtcgctcttattgaccacacctctaccggcatgccgagcaaatgcc
```

FIG. 20 tgcaaatcgctccccatttcacccaattgtagatatgctaactccagcaatgagttgatgaatctcggtgtgtattttat
gtcctcagaggacaacacctgttgtaatcgttcttccacacggatcctggcgtaatagcgaagaggcccgcaccgatcgc
ccttcccaacagttgcgcagcctgaatggcgaatggcgcctgatgcggtattttctccttacgcatctgtgcggtatttc
acaccgcatatatcgctgggccattctcatgaagaatatcttgaatttattgtcatattactagttggtgtggaagtcca
tatatcggtgatcaatatagtggttgacatgctggctagtcaacattgagccttttgatcatgcaaatatattacggtat
tttacaatcaaatatcaaacttaactattgactttataacttatttaggtggtaacattcttataaaaagaaaaaaatt
actgcaaaacagtactagcttttaacttgtatcctaggttatctatgctgtctcaccatagagaatattacctatttcag
aatgtatgtccatgattcgccgggtaaatacatataatacacaaatctggcttaataaagtctataatatatctcataaa
gaagtgctaaattggctagtgctatatattttaagaaaatttcttttgactaagtccatatcgactttgtaaaagttca
ctttagcatacatatattacacgagccagaaattgtaacttttgcctaaaatcacaaattgcaaatttaattgcttgca
aaaggtcacatgcttataatcaactttttaaaatttaaaatactttttatttttatttttaaacataaatgaaata
atttatttattgtttatgattaccgaaacataaaacctgctcaagaaaaagaaactgttttgtccttggaaaaaaagcac
tacctaggagcggccaaaatgccgaggctttcatagcttaaactctttacagaaaataggcattatagatcagttcgagt
tttcttattcttccttccggttttatcgtcacagttttacagtaaataagtatcacctcttagagttcgatgataagctg
tcaaacatgagaattaattccacatgttaaaatagtgaaggagcatgttcggcacacagtggaccgaacgtggggtaagt
gcactagggtccggttaaacggatctcgcattgatgaggcaacgctaattatcaacatatagattgttatctatctgcat
gaacacgaaatctttacttgacgacttgaggctgatggtgtttatgcaaagaaaccactgtgtttaatatgtgtcactgt
ttgatattactgtcagcgtagaagataatagtaaaagcggttaataagtgtatttgagataagtgtgataaagtttttac
agcgaaaagacgataaatacaagaaaatgattacgaggatacggagagaggtatgtacatgtgtatttatatactaagct
gccggcggttgtttgcaagaccgagaaaaggctagcaagaatcgggtcattgtagcgtatgcgcctgtgaacattctctt
caacaagtttgattccattgcggtgaaatggtaaaagtcaacccccctgcgatgtatattttcctgtacaatcaatcaaaa
agccaaatgatttagcattatctttacatcttgttattttacagattttatgtttagatcttttatgcttgcttttcaaa
aggcttgcaggcaagtgcacaaacaatacttaaataaatactactcagtaataacctaTTTCTTAGCATTTTTGACGAAA
TTTGCTATTTTGTTAGAGTCTTTTACACCATTTGTCTCCACACCTCCGCTTACATCAACACCAATAACGCCATTTAATCT
AAGCGCATCACCAACATTTTCTGGCGTCAGTCCACCAGCTAACATAAAATGTAAGCTCTCGGGGCTCTCTTGCCTTCCAA
CCCAGTCAGAAATCGAGTTCCAATCCAAAAGTTCACCTGTCCCACCTGCTTCTGAATCAAACAAGGGAATAAACGAATGA
GGTTTCTGTGAAGCTGCACTGAGTAGTATGTTGCAGTCTTTTGGAAATACGAGTCTTTTAATAACTGGCAAACCGAGGAA
CTCTTGGTATTCTTGCCACGACTCATCTCCATGCAGTTGGACGATATCAATGCCGTAATCATTGACCAGAGCCAAAACAT
CCTCCTTAGGTTGATTACGAAACACGCCAACCAAGTATTTCGGAGTGCCTGAACTATTTTTATATGCTTTTACAAGACTT
GAAATTTTCCTTGCAATAACCGGGTCAATTGTTCTCTTTCTATTGGGCACACATATAATACCCAGCAAGTCAGCATCGGA
ATCTAGTGCACATTCTGCGGCCTCTGTGCTCTGCAAGCCGCAAACTTTCACCAATGGACCAGAACTACCTGTGAAATTAA
TAACAGACATactccaagctgcctttgtgtgcttaatcacgtatactcacgtgctcaatagtcaccaatgccctccctct
tggccctctcctttctttttcgaccgaattaattcttgaagacgaaagggcctcgtgatacgcctatttttataggtt
aatgtcatgataataatggtttcttagacgtcaggtggcacttttcggggaaatgtgcgcggaacccctatttgtttatt
tttctaaatacattcaaatatgtatccgctcatgagacaataaccctgataaatgcttcaataatattgaaaaaggaaga
gtATGAGTATTCAACATTTCCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAACTGGATCTCAACAGCGGTAA
GATCCTTGAGAGTTTTCGCCCCGAAGAACGTTTTCCAATGATGAGCACTTTTAAAGTTCTGCTATGTGGCGCGGTATTAT
CCCGTATTGACGCCGGGCAAGAGCAACTCGGTCGCCGCATACACTATTCTCAGAATGACTTGGTTGAGTACTCACCAGTC
ACAGAAAAGCATCTTACGGATGGCATGACAGTAAGAGAATTATGCAGTGCTGCCATAACCATGAGTGATAACACTGCGGC
CAACTTACTTCTGACAACGATCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTGGtaactgtcagaccaagttta
ctcatatatactttagattgatttaaaacttcatttttaatttaaaaggatctaggtgaagatcctttttgataatctca
tgaccaaaatcccttaacgtgagttttcgttccactgagcgtcagaccccgtagaaaagatcaaaggatcttcttgagat
cctttttttctgcgcgtaatctgctgcttgcaaacaaaaaaaccaccgctaccagcggtggtttgtttgccggatcaaga
gctaccaactctttttccgaaggtaactggcttcagcagagcgcagataccaaatactgtccttctagtgtagccgtagt
taggccaccacttcaagaactctgtagcaccgcctacatacctcgctctgctaatcctgttaccagtggctgctgccagt
ggcgataagtcgtgtcttaccgggttggactcaagacgatagttaccggataaggcgcagcggtcgggctgaacgggggg
ttcgtgcacacagcccagcttggagcgaacgacctacaccgaactgagatacctacagcgtgagctatgagaaagcgcca
cgcttcccgaagggagaaaggcggacaggtatccggtaagcggcagggtcggaacaggagagcgcacgagggagcttcca

FIG. 20 Cont.

gggggaaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggccttttgctcaca
tgttctttcctgcgttatcccctgattctgtggataaccgtattaccgcctttgagtgagctgataccgctcgccgcagc
cgaacgaccgagcgcagcgagtcagtgagcgaggaagcggaagagcgcccaatacgcaaaccgcctctccccgcgcgttg
gccgattcattaatgcaggatccgggatcgaagaaatgatggtaaatgaaataggaaatcaaggagcatgaaggcaaaag
acaaatataagggtcgaacgaaaaataaagtgaaaagtgttgatatgatgtatttggctttgcggcgccgaaaaaacgag
tttacgcaattgcacaatcatgctgactctgtggcggacccgcgctcttgccggcccggcgataacgctgggcgtgaggc
tgtgcccggcggagtttttgcgcctgcattttccaaggtttaccctgcgctaaggggcgagattggagaagcaataaga
atgccggttggggttgcgatgatgacgaccacgacaactggtgtcattatttaagttgccgaaagaacctgagtgcattt
gcaacatgagtatactagaagaatgagccaagacttgcgagacgcgagtttgccggtggtgcgaacaatagagcgaccat
gaccttgaaggtgagacgcgcataaccgctagagtactttgaagaggaaacagcaatagggttgctaccagtataaatag
acaggtacatacaacactggaaatggttgtctgtttgagtacgctttcaattcatttgggtgtgcactttattatgttac
aatatggaagggaactttacacttctcctatgcacatatattaattaaagtccaatgctagtagagaagggggtaacac
ccctccgcgctcttttccgatttttttctaaaccgtggaatatttcggatatccttttgttgtttccgggtgtacaatat
ggacttcctcttttctggcaaccaaacccatacatcgggattcctataataccttcgttggtctccctaacatgtaggtg
gcggaggggagatatacaatagaacagataccagacaagacataatgggctaaacaagactacaccaattacactgcctc
attgatg
//

FIG. 20 Cont.

434-1861: Gal4 DBD-H3-Gcn5-HA
434-874: Gal4 DBD (amino acids 1-147)
1010-1714: Gcn5 (amino acids 18-252)
1619-1621: F221A mutation
1748-1837: trimeric HA
...-...: CEN/ARS
...-...: TRP1

Translation: Gal4-DBD-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQGSPILGYWKGRRDHPPKSDLIEGRGDPEVKRVKLENNVEEIQPEQAETNKQEGTDKENKGKFEKETERIGGSE
VVTDVEKGIVKFEFDGVEYTFKERPSVVEENEGKIEFRVVNNDNTKENMMVLTGLKNIFQKQLPKMPKEYIARLVYDRSH
LSMAVIRKPLTVVGGITYRPFDKREFAEIVFCAISSTEQVRGYGAHLMNHLKDYVRNTSNIKYFLTYADNYAIGYAKKQG
FTKEITLDKSIWMGYIKDYEGGTLMQCNMAIPGGGRIFYPYDVPDYAGYPYDVPDYAGSYPYDVPDYAAQCGRSS ; DNA sequence PDG28 8087 b.p. complete sequence
;
gtggtacataacgaactaatactgtagccctagacttgatagccatcatcatatcgaagtttcactacccttttttccatt
tgccatctattgaagtaataataggcgcatgcaacttcttttctttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGgggtcccctatactaggttattggaa
aggtcgacgcgaccatcctccaaaatcggatctgatcgaaggtcgtggaGATCCCGAAGTTAAACGGGTAAAATTAGAAA
ACAACGTTGAAGAAATACAACCTGAGCAGGCTGAGACCAATAAACAAGAGGGCACCGATAAAGAGAATAAAGGAAAGTTC
GAGAAAGAAACTGAGAGAATAGGAGGATCTGAAGTGGTTACAGATGTGGAAAAAGGAATTGTCAAATTTGAATTTGATGG
TGTTGAATACACATTCAAAGAGAGACCCAGTGTCGTAGAGGAAAATGAAGGTAAAATTGAGTTTAGGGTGGTGAATAATG
ATAATACTAAAGAAAACATGATGGTCCTAACTGGATTAAAAAACATTTTTCAAAAGCAATTACCAAAAATGCCCAAAGAA
TACATTGCCAGGTTAGTCTATGATCGAAGTCATCTTTCCATGGCTGTCATTAGGAAGCCATTGACTGTCGTAGGTGGCAT
AACATATCGACCTTTCGATAAGAGAGAATTCGCAGAAATTGTTTTCTGTGCCATCAGTTCGACGGAACAGGTACGCGGTT
ATGGTGCGCATCTAATGAATCACTTAAAAGACTATGTTAGAAATACCTCGAACATAAAATATTTTTTGACATATGCAGAT
AATTACGCTATTGGATACGCTAAAAAGCAAGGCTTTACTAAAGAAATCACGTTGGATAAAAGTATATGGATGGGATATAT
TAAAGATTATGAAGGTGGTACGCTGATGCAATGTAACATGGCAATTCCCGGtggcggccgcatcttttacccatacgatg
ttcctgactatgcgggctatccctatgacgtcccggactatgcaggatcctatccatatgacgttccagattacgctgct
cagtgcggccgctctagctagaactagtggatcccccGATACCGTCGACCTGCAGAGATCTAtgaatcgtagatactgaa
aaaccccgcaagttcacttcaactgtgcatcgtgcaccatctcaatttctttcatttatacatcgttttgccttctttta
tgtaactatactcctctaagtttcaatcttggccatgtaacctctgatctatagaattttttaaatgactagaattaatg
cccatcttttttttggacctaaattcttcatgaaaatatattacgagggcttattcagaagctttggacttcttcgccag
aggtttggtcaagtctccaatcaaggttgtcggcttgtctaccttgccagaaatttacgaaaagatggaaaagggtcaaa
tcgttggtagatacgttgttgacacttctaaataagcgaatttcttatgatttatgatttttattattaaataagttata
aaaaaaataagtgtatacaaattttaaagtgactcttaggttttaaaacgaaaattcttattcttgagtaactctttcct

FIG. 21 gtaggtcaggttgctttctcaggtatagcatgaggtcgctcttattgaccacacctctaccggcatgccgagcaaatgcc
tgcaaatcgctccccatttcacccaattgtagatatgctaactccagcaatgagttgatgaatctcggtgtgtattttat
gtcctcagaggacaacacctgttgtaatcgttcttccacacggatcctggcgtaatagcgaagaggcccgcaccgatcgc
ccttcccaacagttgcgcagcctgaatggcgaatggcgcctgatgcggtattttctccttacgcatctgtgcggtatttc
acaccgcatatatcgctgggccattctcatgaagaatatcttgaatttattgtcatattactagttggtgtggaagtcca
tatatcggtgatcaatatagtggttgacatgctggctagtcaacattgagccttttgatcatgcaaatatattacggtat
tttacaatcaaatatcaaacttaactattgactttataacttatttaggtggtaacattcttataaaaagaaaaaatt
actgcaaaacagtactagcttttaacttgtatcctaggttatctatgctgtctcaccatagagaatattacctatttcag
aatgtatgtccatgattcgccgggtaaatacatataatacacaaatctggcttaataaagtctataatatatctcataaa
gaagtgctaaattggctagtgctatatattttaagaaaatttcttttgactaagtccatatcgactttgtaaaagttca
ctttagcatacatatattacacgagccagaaattgtaacttttgcctaaaatcacaaattgcaaaatttaattgcttgca
aaaggtcacatgcttataatcaactttttaaaaatttaaaatactttttatttttttatttttaaacataaatgaaata
atttatttattgtttatgattaccgaaacataaaacctgctcaagaaaaagaaactgttttgtccttggaaaaaaagcac
tacctaggagcggccaaaatgccgaggctttcatagcttaaactctttacagaaaataggcattatagatcagttcgagt
tttcttattcttccttccggttttatcgtcacagttttacagtaaataagtatcacctcttagagttcgatgataagctg
tcaaacatgagaattaattccacatgttaaaatagtgaaggagcatgttcggcacacagtggaccgaacgtggggtaagt
gcactagggtccggttaaacggatctcgcattgatgaggcaacgctaattatcaacatatagattgttatctatctgcat
gaacacgaaatctttacttgacgacttgaggctgatggtgtttatgcaaagaaaccactgtgtttaatatgtgtcactgt
ttgatattactgtcagcgtagaagataatagtaaaagcggttaataagtgtatttgagataagtgtgataaagtttttac
agcgaaaagacgataaatacaagaaaatgattacgaggatacggagagaggtatgtacatgtgtatttatatactaagct
gccggcggttgtttgcaagaccgagaaaaggctagcaagaatcgggtcattgtagcgtatgcgcctgtgaacattctctt
caacaagtttgattccattgcggtgaaatggtaaaagtcaacccccctgcgatgtatatttcctgtacaatcaatcaaaa
agccaaatgatttagcattatctttacatcttgttattttacagattttatgtttagatcttttatgcttgcttttcaaa
aggcttgcaggcaagtgcacaaacaatacttaaataaatactactcagtaataacctaTTTCTTAGCATTTTTGACGAAA
TTTGCTATTTTGTTAGAGTCTTTTACACCATTTGTCTCCACACCTCCGCTTACATCAACACCAATAACGCCATTTAATCT
AAGCGCATCACCAACATTTTCTGGCGTCAGTCCACCAGCTAACATAAAATGTAAGCTCTCGGGGCTCTCTTGCCTTCCAA
CCCAGTCAGAAATCGAGTTCCAATCCAAAAGTTCACCTGTCCCACCTGCTTCTGAATCAAACAAGGGAATAAACGAATGA
GGTTTCTGTGAAGCTGCACTGAGTAGTATGTTGCAGTCTTTTGGAAATACGAGTCTTTTAATAACTGGCAAACCGAGGAA
CTCTTGGTATTCTTGCCACGACTCATCTCCATGCAGTTGGACGATATCAATGCCGTAATCATTGACCAGAGCCAAAACAT
CCTCCTTAGGTTGATTACGAAACACGCCAACCAAGTATTTCGGAGTGCCTGAACTATTTTTATATGCTTTTACAAGACTT
GAAATTTTCCTTGCAATAACCGGGTCAATTGTTCTCTTTCTATTGGGCACACATATAATACCCAGCAAGTCAGCATCGGA
ATCTAGTGCACATTCTGCGGCCTCTGTGCTCTGCAAGCCGCAAACTTTCACCAATGGACCAGAACTACCTGTGAAATTAA
TAACAGACATactccaagctgcctttgtgtgcttaatcacgtatactcacgtgctcaatagtcaccaatgccctccctct
tggccctctccttttctttttcgaccgaattaattcttgaagacgaaagggcctcgtgatacgcctatttttataggtt
aatgtcatgataataatggtttcttagacgtcaggtggcacttttcggggaaatgtgcgcggaacccctatttgtttatt
tttctaaatacattcaaatatgtatccgctcatgagacaataaccctgataaatgcttcaataatattgaaaaaggaaga
gtATGAGTATTCAACATTTCCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAACTGGATCTCAACAGCGGTAA
GATCCTTGAGAGTTTTCGCCCCGAAGAACGTTTTCCAATGATGAGCACTTTTAAAGTTCTGCTATGTGGCGCGGTATTAT
CCCGTATTGACGCCGGGCAAGAGCAACTCGGTCGCCGCATACACTATTCTCAGAATGACTTGGTTGAGTACTCACCAGTC
ACAGAAAAGCATCTTACGGATGGCATGACAGTAAGAGAATTATGCAGTGCTGCCATAACCATGAGTGATAACACTGCGGC
CAACTTACTTCTGACAACGATCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTGGtaactgtcagaccaagttta
ctcatatatactttagattgatttaaaacttcatttttaatttaaaaggatctaggtgaagatcctttttgataatctca
tgaccaaaatcccttaacgtgagttttcgttccactgagcgtcagaccccgtagaaaagatcaaaggatcttcttgagat
cctttttttctgcgcgtaatctgctgcttgcaaacaaaaaaaccaccgctaccagcggtggtttgtttgccggatcaaga
gctaccaactctttttccgaaggtaactggcttcagcagagcgcagataccaaatactgtccttctagtgtagccgtagt
taggccaccacttcaagaactctgtagcaccgcctacatacctcgctctgctaatcctgttaccagtggctgctgccagt
ggcgataagtcgtgtcttaccgggttggactcaagacgatagttaccggataaggcgcagcggtcgggctgaacgggggg
ttcgtgcacacagcccagcttggagcgaacgacctacaccgaactgagatacctacagcgtgagctatgagaaagcgcca

FIG. 21 Cont.

cgcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggccttttgctcaca
tgttctttcctgcgttatcccctgattctgtggataaccgtattaccgcctttgagtgagctgataccgctcgccgcagc
cgaacgaccgagcgcagcgagtcagtgagcgaggaagcggaagagcgcccaatacgcaaaccgcctctccccgcgcgttg
gccgattcattaatgcaggatccgggatcgaagaaatgatggtaaatgaaataggaaatcaaggagcatgaaggcaaaag
acaaatataagggtcgaacgaaaaataaagtgaaaagtgttgatatgatgtatttggctttgcggcgccgaaaaaacgag
tttacgcaattgcacaatcatgctgactctgtggcggacccgcgctcttgccggcccggcgataacgctgggcgtgaggc
tgtgcccggcggagtttttttgcgcctgcattttccaaggtttaccctgcgctaaggggcgagattggagaagcaataaga
atgccggttggggttgcgatgatgacgaccacgacaactggtgtcattatttaagttgccgaaagaacctgagtgcattt
gcaacatgagtatactagaagaatgagccaagacttgcgagacgcgagtttgccggtggtgcgaacaatagagcgaccat
gaccttgaaggtgagacgcgcataaccgctagagtactttgaagaggaaacagcaatagggttgctaccagtataaatag
acaggtacatacaacactggaaatggttgtctgtttgagtacgctttcaattcatttgggtgtgcactttattatgttac
aatatggaagggaactttacacttctcctatgcacatatattaattaaagtccaatgctagtagagaaggggggtaacac
ccctccgcgctcttttccgatttttttctaaaccgtggaatatttcggatatccttttgttgtttccgggtgtacaatat
ggacttcctcttttctggcaaccaaacccatacatcgggattcctataataccttcgttggtctccctaacatgtaggtg
gcggaggggagatatacaatagaacagataccagacaagacataatgggctaaacaagactacaccaattacactgcctc
attgatg
//

FIG. 21 Cont.

```
434-1894: Gal4 DBD-MCS-Gcn5(wt)-HA
926-970: multicloning sequence
1043-1747: Gcn5 (aa18-252)
1781-1871: trimeric HA

Translation: GDBD-MCS-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQGTMHELPRLEPGSPILGYWKGRRDHPPKSDLIEGRGDPEVKRVKLENNVEEIQPEQAETNKQEGTDKENKGKF
EKETERIGGSEVVTDVEKGIVKFEFDGVEYTFKERPSVVEENEGKIEFRVVNNDNTKENMMVLTGLKNIFQKQLPKMPKE
YIARLVYDRSHLSMAVIRKPLTVVGGITYRPFDKREFAEIVFCAISSTEQVRGYGAHLMNHLKDYVRNTSNIKYFLTYAD
NYAIGYFKKQGFTKEITLDKSIWMGYIKDYEGGTLMQCNMAIPGGGRIFYPYDVPDYAGYPYDVPDYAGSYPYDVPDYAA
QCGRSS


; ### from DNA Strider  Wednesday, March 26, 2003   1:40:57 PM
; DNA sequence  pDG30   8120  b.p. complete sequence
;
gtggtacataacgaactaatactgtagccctagacttgatagccatcatcatatcgaagtttcactacccttttttccatt
tgccatctattgaagtaataataggcgcatgcaacttcttttcttttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGGGTACCATGCATGAGCTCCCGCGGCT
CGAGCCCgggtcccctatactaggttattggaaaggtcgacgcgaccatcctccaaaatcggatctgatcgaaggtcgtg
gaGATCCCGAAGTTAAACGGGTAAAATTAGAAAACAACGTTGAAGAAATACAACCTGAGCAGGCTGAGACCAATAAACAA
GAGGGCACCGATAAAGAGAATAAAGGAAAGTTCGAGAAAGAAACTGAGAGAATAGGAGGATCTGAAGTGGTTACAGATGT
GGAAAAAGGAATTGTCAAATTTGAATTTGATGGTGTTGAATACACATTCAAAGAGAGACCCAGTGTCGTAGAGGAAAATG
AAGGTAAAATTGAGTTTAGGGTGGTGAATAATGATAATACTAAAGAAAACATGATGGTCCTAACTGGATTAAAAAACATT
TTTCAAAAGCAATTACCAAAAATGCCCAAAGAATACATTGCCAGGTTAGTCTATGATCGAAGTCATCTTTCCATGGCTGT
CATTAGGAAGCCATTGACTGTCGTAGGTGGCATAACATATCGACCTTTCGATAAGAGAGAATTCGCAGAAATTGTTTTCT
GTGCCATCAGTTCGACGGAACAGGTACGCGGTTATGGTGCGCATCTAATGAATCACTTAAAAGACTATGTTAGAAATACC
TCGAACATAAAATATTTTTTGACATATGCAGATAATTACGCTATTGGATACTTTAAAAAGCAAGGCTTTACTAAAGAAAT
CACGTTGGATAAAAGTATATGGATGGGATATATTAAAGATTATGAAGGTGGTACGCTGATGCAATGTAACATGGCAATTC
CCGGtggcggccgcatcttttacccatacgatgttcctgactatgcgggctatccctatgacgtcccggactatgcagga
tcctatccatatgacgttccagattacgctgctcagtgcggccgctctagctagaactagtggatcccccGATACCGTCG
ACCTGCAGAGATCTAtgaatcgtagatactgaaaaccccgcaagttcacttcaactgtgcatcgtgcaccatctcaatt
tctttcatttatacatcgttttgccttcttttatgtaactatactcctctaagtttcaatcttggccatgtaacctctga
tctatagaatttttaaatgactagaattaatgcccatcttttttttggacctaaattcttcatgaaaatatattacgag
ggcttattcagaagctttggacttcttcgccagaggtttggtcaagtctccaatcaaggttgtcggcttgtctaccttgc
cagaaatttacgaaaagatggaaaagggtcaaatcgttggtagatacgttgttgacacttctaaataagcgaatttctta
tgatttatgatttttattattaaataagttataaaaaaaataagtgtatacaaattttaaagtgactcttaggttttaaa
acgaaaattcttattcttgagtaactctttcctgtaggtcaggttgctttctcaggtatagcatgaggtcgctcttattg
accacacctctaccggcatgccgagcaaatgcctgcaaatcgctccccatttcacccaattgtagatatgctaactccag
caatgagttgatgaatctcggtgtgtattttatgtcctcagaggacaacacctgttgtaatcgttcttccacacggatcc
tggcgtaatagcgaagaggcccgcaccgatcgcccttcccaacagttgcgcagcctgaatggcgaatggcgcctgatgcg
gtattttctccttacgcatctgtgcggtatttcacaccgcatatatcgctgggccattctcatgaagaatatcttgaatt
tattgtcatattactagttggtgtggaagtccatatatcggtgatcaatatagtggttgacatgctggctagtcaacatt
```

FIG. 22 gagccttttgatcatgcaaatatattacggtatttacaatcaaatatcaaacttaactattgactttataacttattta
ggtggtaacattcttataaaaaagaaaaaattactgcaaaacagtactagcttttaacttgtatcctaggttatctatg
ctgtctcaccatagagaatattacctatttcagaatgtatgtccatgattcgccgggtaaatacatataatacacaaatc
tggcttaataaagtctataatatatctcataaagaagtgctaaattggctagtgctatatatttttaagaaaatttcttt
tgactaagtccatatcgactttgtaaaagttcactttagcatacatatattacacgagccagaaattgtaacttttgcct
aaaatcacaaattgcaaaatttaattgcttgcaaaaggtcacatgcttataatcaactttttttaaaaatttaaaatactt
ttttattttttattttaaacataaatgaaataatttatttattgtttatgattaccgaaacataaaacctgctcaagaa
aaagaaactgttttgtccttggaaaaaaagcactacctaggagcggccaaaatgccgaggctttcatagcttaaactctt
tacagaaaataggcattatagatcagttcgagttttcttattcttccttccggttttatcgtcacagttttacagtaaat
aagtatcacctcttagagttcgatgataagctgtcaaacatgagaattaattccacatgttaaaatagtgaaggagcatg
ttcggcacacagtggaccgaacgtggggtaagtgcactagggtccggttaaacggatctcgcattgatgaggcaacgcta
attatcaacatatagattgttatctatctgcatgaacacgaaatctttacttgacgacttgaggctgatggtgtttatgc
aaagaaaccactgtgtttaatatgtgtcactgtttgatattactgtcagcgtagaagataatagtaaaagcggttaataa
gtgtatttgagataagtgtgataaagtttttacagcgaaaagacgataaatacaagaaaatgattacgaggatacggaga
gaggtatgtacatgtgtatttatatactaagctgccggcggttgtttgcaagaccgagaaaaggctagcaagaatcgggt
cattgtagcgtatgcgcctgtgaacattctcttcaacaagtttgattccattgcggtgaaatggtaaaagtcaacccccct
gcgatgtatattttcctgtacaatcaatcaaaaagccaaatgatttagcattatctttacatcttgttattttacagatt
ttatgtttagatcttttatgcttgcttttcaaaaggcttgcaggcaagtgcacaaacaatacttaaataaatactactca
gtaataacctaTTTCTTAGCATTTTTGACGAAATTTGCTATTTTGTTAGAGTCTTTTACACCATTTGTCTCCACACCTCC
GCTTACATCAACACCAATAACGCCATTTAATCTAAGCGCATCACCAACATTTTCTGGCGTCAGTCCACCAGCTAACATAA
AATGTAAGCTCTCGGGGCTCTCTTGCCTTCCAACCCAGTCAGAAATCGAGTTCCAATCCAAAAGTTCACCTGTCCCACCT
GCTTCTGAATCAAACAAGGGAATAAACGAATGAGGTTTCTGTGAAGCTGCACTGAGTAGTATGTTGCAGTCTTTTGGAAA
TACGAGTCTTTTAATAACTGGCAAACCGAGGAACTCTTGGTATTCTTGCCACGACTCATCTCCATGCAGTTGGACGATAT
CAATGCCGTAATCATTGACCAGAGCCAAAACATCCTCCTTAGGTTGATTACGAAACACGCCAACCAAGTATTTCGGAGTG
CCTGAACTATTTTTATATGCTTTTACAAGACTTGAAATTTTCCTTGCAATAACCGGGTCAATTGTTCTCTTTCTATTGGG
CACACATATAATACCCAGCAAGTCAGCATCGGAATCTAGTGCACATTCTGCGGCCTCTGTGCTCTGCAAGCCGCAAACTT
TCACCAATGGACCAGAACTACCTGTGAAATTAATAACAGACATactccaagctgcctttgtgtgcttaatcacgtatact
cacgtgctcaatagtcaccaatgccctccctcttggccctctccttttctttttttcgaccgaattaattcttgaagacga
aagggcctcgtgatacgcctatttttataggttaatgtcatgataataatggtttcttagacgtcaggtggcacttttcg
gggaaatgtgcgcggaacccctatttgtttatttttctaaatacattcaaatatgtatccgctcatgagacaataaccct
gataaatgcttcaataatattgaaaaaggaagagtATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCCCCGAAGAACGTTTTCCAATGATGAGCA
CTTTTAAAGTTCTGCTATGTGGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAACCGCTT
TTTTGCACAACATGGGGGATCATGTAACTCGCCTTGATCGTTGGGAACCGGAGCTGAATGAAGCCATACCAAACGACGAG
CGTGACACCACGATGCCTGTAGCAATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCTCGGCCCTTCCGGCTGGCTGGTTTA
TTGCTGATAAATCTGGAGCCGGTGAGCGTGGGTCTCGCGGTATCATTGCAGCACTGGGGCCAGATGGTAAGCCCTCCCGT
ATCGTAGTTATCTACACGACGGGGAGTCAGGCAACTATGGATGAACGAAATAGACAGATCGCTGAGATAGGTGCCTCACT
GATTAAGCATTGGtaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagac
cccgtagaaaagatcaaaggatcttcttgagatcctttttttctgcgcgtaatctgctgcttgcaaacaaaaaaaccacc
gctaccagcggtggtttgtttgccggatcaagagctaccaactctttttccgaaggtaactggcttcagcagagcgcaga
taccaaatactgtccttctagtgtagccgtagttaggccaccacttcaagaactctgtagcaccgcctacatacctcgct
ctgctaatcctgttaccagtggctgctgccagtggcgataagtcgtgtcttaccgggttggactcaagacgatagttacc
ggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcagg
gtcggaacaggagagcgcacgagggagcttccagggggaaacgcctggtatctttatagtcctgtcgggtttcgccacct
ctgacttgagcgtcgatttttgtgatgctcgtcaggggggcggagcctatggaaaaacgccagcaacgcggcctttttac
ggttcctggccttttgctggccttttgctcacatgttctttcctgcgttatcccctgattctgtggataaccgtattacc
gcctttgagtgagctgataccgctcgccgcagccgaacgaccgagcgcagcgagtcagtgagcgaggaagcggaagagcg
cccaatacgcaaaccgcctctccccgcgcgttggccgattcattaatgcaggatccgggatcgaagaaatgatggtaaat
gaaataggaaatcaaggagcatgaaggcaaaagacaaatataagggtcgaacgaaaaataaagtgaaaagtgttgatatg
atgtatttggctttgcggcgccgaaaaaacgagtttacgcaattgcacaatcatgctgactctgtggcggacccgcgctc
ttgccggcccggcgataacgctgggcgtgaggctgtgcccggcggagtttttttgcgcctgcatttccaaggtttaccct
gcgctaaggggcgagattggagaagcaataagaatgccggttggggttgcgatgatgacgaccacgacaactggtgtcat

FIG. 22 Cont.

tatttaagttgccgaaagaacctgagtgcatttgcaacatgagtatactagaagaatgagccaagacttgcgagacgcga
gtttgccggtggtgcgaacaatagagcgaccatgaccttgaaggtgagacgcgcataaccgctagagtactttgaagagg
aaacagcaatagggttgctaccagtataaatagacaggtacatacaacactggaaatggttgtctgtttgagtacgcttt
caattcatttgggtgtgcactttattatgttacaatatggaagggaactttacacttctcctatgcacatatattaatta
aagtccaatgctagtagagaagggggtaacacccctccgcgctcttttccgatttttttctaaaccgtggaatatttcg
gatatccttttgttgtttccgggtgtacaatatggacttcctcttttctggcaaccaaacccatacatcgggattcctat
aataccttcgttggtctccctaacatgtaggtggcggaggggagatatacaatagaacagataccagacaagacataatg
ggctaaacaagactacaccaattacactgcctcattgatg
//

FIG. 22 Cont.

```
434-1894: Gal4 DBD-MCS-Gcn5(wt)-HA
926-970: multicloning sequence
1043-1747: Gcn5 (F221A) (aa18-252)
1781-1871: trimeric HA

Translation: GDBD-MCS-Gcn5(F221A)-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQGTMHELPRLEPGSPILGYWKGRRDHPPKSDLIEGRGDPEVKRVKLENNVEEIQPEQAETNKQEGTDKENKGKF
EKETERIGGSEVVTDVEKGIVKFEFDGVEYTFKERPSVVEENEGKIEFRVVNNDNTKENMMVLTGLKNIFQKQLPKMPKE
YIARLVYDRSHLSMAVIRKPLTVVGGITYRPFDKREFAEIVFCAISSTEQVRGYGAHLMNHLKDYVRNTSNIKYFLTYAD
NYAIGYAKKQGFTKEITLDKSIWMGYIKDYEGGTLMQCNMAIPGGGRIFYPYDVPDYAGYPYDVPDYAGSYPYDVPDYAA
QCGRSS


; ### from DNA Strider  Wednesday, March 26, 2003   1:41:20 PM
; DNA sequence  pDG31   8120  b.p. complete sequence
;
gtggtacataacgaactaatactgtagccctagacttgatagccatcatcatatcgaagtttcactaccctttttccatt
tgccatctattgaagtaataataggcgcatgcaacttctttctttttttttctttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGGGTACCATGCATGAGCTCCCGCGGCT
CGAGCCCgggtcccctatactaggttattggaaaggtcgacgcgaccatcctccaaaatcggatctgatcgaaggtcgtg
gaGATCCCGAAGTTAAACGGGTAAAATTAGAAAACAACGTTGAAGAAATACAACCTGAGCAGGCTGAGACCAATAAACAA
GAGGGCACCGATAAAGAGAATAAAGGAAAGTTCGAGAAAGAAACTGAGAGAATAGGAGGATCTGAAGTGGTTACAGATGT
GGAAAAAGGAATTGTCAAATTTGAATTTGATGGTGTTGAATACACATTCAAAGAGAGACCCAGTGTCGTAGAGGAAAATG
AAGGTAAAATTGAGTTTAGGGTGGTGAATAATGATAATACTAAAGAAAACATGATGGTCCTAACTGGATTAAAAAACATT
TTTCAAAAGCAATTACCAAAAATGCCCAAAGAATACATTGCCAGGTTAGTCTATGATCGAAGTCATCTTTCCATGGCTGT
CATTAGGAAGCCATTGACTGTCGTAGGTGGCATAACATATCGACCTTTCGATAAGAGAGAATTCGCAGAAATTGTTTTCT
GTGCCATCAGTTCGACGGAACAGGTACGCGGTTATGGTGCGCATCTAATGAATCACTTAAAAGACTATGTTAGAAATACC
TCGAACATAAAATATTTTTTGACATATGCAGATAATTACGCTATTGGATACgctAAAAAGCAAGGCTTTACTAAAGAAAT
CACGTTGGATAAAAGTATATGGATGGGATATATTAAAGATTATGAAGGTGGTACGCTGATGCAATGTAACATGGCAATTC
CCGGtggcggccgcatcttttacccatacgatgttcctgactatgcgggctatccctatgacgtcccggactatgcagga
tcctatccatatgacgttccagattacgctgctcagtgcggccgctctagctagaactagtggatcccccGATACCGTCG
ACCTGCAGAGATCTAtgaatcgtagatactgaaaaaccccgcaagttcacttcaactgtgcatcgtgcaccatctcaatt
tctttcatttatacatcgttttgccttcttttatgtaactatactcctctaagtttcaatcttggccatgtaacctctga
tctatagaatttttaaatgactagaattaatgcccatctttttttggacctaaattcttcatgaaaatatattacgag
ggcttattcagaagctttggacttcttcgccagaggtttggtcaagtctccaatcaaggttgtcggcttgtctaccttgc
cagaaatttacgaaaagatggaaaagggtcaaatcgttggtagatacgttgttgacacttctaaataagcgaatttctta
tgatttatgatttttattattaaataagttataaaaaaaataagtgtatacaaattttaaagtgactcttaggttttaaa
acgaaaattcttattcttgagtaactctttcctgtaggtcaggttgctttctcaggtatagcatgaggtcgctcttattg
accacacctctaccggcatgccgagcaaatgcctgcaaatcgctccccatttcacccaattgtagatatgctaactccag
caatgagttgatgaatctcggtgtgtattttatgtcctcagaggacaacacctgttgtaatcgttcttccacacggatcc
tggcgtaatagcgaagaggcccgcaccgatcgcccttcccaacagttgcgcagcctgaatggcgaatggcgcctgatgcg
gtattttctccttacgcatctgtgcggtatttcacaccgcatatatcgctgggccattctcatgaagaatatcttgaatt
tattgtcatattactagttggtgtggaagtccatatatcggtgatcaatatagtggttgacatgctggctagtcaacatt
gagccttttgatcatgcaaatatattacggtattttacaatcaaatatcaaacttaactattgactttataacttattta
ggtggtaacattcttataaaaagaaaaaaattactgcaaaacagtactagcttttaacttgtatcctaggttatctatg
```

FIG. 23 ctgtctcaccatagagaatattacctatttcagaatgtatgtccatgattcgccgggtaaatacatataatacacaaatc
tggcttaataaagtctataatatatctcataaagaagtgctaaattggctagtgctatatattttaagaaaatttcttt
tgactaagtccatatcgactttgtaaaagttcactttagcatacatatattacacgagccagaaattgtaacttttgcct
aaaatcacaaattgcaaaatttaattgcttgcaaaaggtcacatgcttataatcaactttttaaaaatttaaaatactt
ttttatttttattttaaacataaatgaaataatttatttattgtttatgattaccgaaacataaaacctgctcaagaa
aaagaaactgttttgtccttggaaaaaaagcactacctaggagcggccaaaatgccgaggctttcatagcttaaactctt
tacagaaaataggcattatagatcagttcgagttttcttattcttccttccggttttatcgtcacagttttacagtaaat
aagtatcacctcttagagttcgatgataagctgtcaaacatgagaattaattccacatgttaaaatagtgaaggagcatg
ttcggcacacagtggaccgaacgtggggtaagtgcactagggtccggttaaacggatctcgcattgatgaggcaacgcta
attatcaacatatagattgttatctatctgcatgaacacgaaatctttacttgacgacttgaggctgatggtgtttatgc
aaagaaaccactgtgtttaatatgtgtcactgtttgatattactgtcagcgtagaagataatagtaaaagcggttaataa
gtgtatttgagataagtgtgataaagtttttacagcgaaaagacgataaatacaagaaaatgattacgaggatacggaga
gaggtatgtacatgtgtatttatatactaagctgccggcggttgtttgcaagaccgagaaaaggctagcaagaatcgggt
cattgtagcgtatgcgcctgtgaacattctcttcaacaagtttgattccattgcggtgaaatggtaaaagtcaacccccct
gcgatgtatatttcctgtacaatcaatcaaaaagccaaatgatttagcattatctttacatcttgttattttacagatt
ttatgtttagatcttttatgcttgcttttcaaaaggcttgcaggcaagtgcacaaacaatacttaaataaatactactca
gtaataacctaTTTCTTAGCATTTTTGACGAAATTTGCTATTTTGTTAGAGTCTTTTACACCATTTGTCTCCACACCTCC
GCTTACATCAACACCAATAACGCCATTTAATCTAAGCGCATCACCAACATTTTCTGGCGTCAGTCCACCAGCTAACATAA
AATGTAAGCTCTCGGGGCTCTCTTGCCTTCCAACCCAGTCAGAAATCGAGTTCCAATCCAAAAGTTCACCTGTCCCACCT
GCTTCTGAATCAAACAAGGGAATAAACGAATGAGGTTTCTGTGAAGCTGCACTGAGTAGTATGTTGCAGTCTTTTGGAAA
TACGAGTCTTTTAATAACTGGCAAACCGAGGAACTCTTGGTATTCTTGCCACGACTCATCTCCATGCAGTTGGACGATAT
CAATGCCGTAATCATTGACCAGAGCCAAAACATCCTCCTTAGGTTGATTACGAAACACGCCAACCAAGTATTTCGGAGTG
CCTGAACTATTTTTATATGCTTTTACAAGACTTGAAATTTTCCTTGCAATAACCGGGTCAATTGTTCTCTTTCTATTGGG
CACACATATAATACCCAGCAAGTCAGCATCGGAATCTAGTGCACATTCTGCGGCCTCTGTGCTCTGCAAGCCGCAAACTT
TCACCAATGGACCAGAACTACCTGTGAAATTAATAACAGACATactccaagctgcctttgtgtgcttaatcacgtatact
cacgtgctcaatagtcaccaatgccctccctcttggccctctcctttctttttcgaccgaattaattcttgaagacga
aagggcctcgtgatacgcctatttttataggttaatgtcatgataataatggtttcttagacgtcaggtggcacttttcg
gggaaatgtgcgcggaacccctatttgtttatttttctaaatacattcaaatatgtatccgctcatgagacaataaccct
gataaatgcttcaataatattgaaaaaggaagagtATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCCCCGAAGAACGTTTTCCAATGATGAGCA
CTTTTAAAGTTCTGCTATGTGGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAACCGCTT
TTTTGCACAACATGGGGGATCATGTAACTCGCCTTGATCGTTGGGAACCGGAGCTGAATGAAGCCATACCAAACGACGAG
CGTGACACCACGATGCCTGTAGCAATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCTCGGCCCTTCCGGCTGGCTGGTTTA
TTGCTGATAAATCTGGAGCCGGTGAGCGTGGGTCTCGCGGTATCATTGCAGCACTGGGGCCAGATGGTAAGCCCTCCCGT
ATCGTAGTTATCTACACGACGGGGAGTCAGGCAACTATGGATGAACGAAATAGACAGATCGCTGAGATAGGTGCCTCACT
GATTAAGCATTGGtaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagac
cccgtagaaaagatcaaaggatcttcttgagatcctttttttctgcgcgtaatctgctgcttgcaaacaaaaaaaccacc
gctaccagcggtggtttgtttgccggatcaagagctaccaactctttttccgaaggtaactggcttcagcagagcgcaga
taccaaatactgtccttctagtgtagccgtagttaggccaccacttcaagaactctgtagcaccgcctacatacctcgct
ctgctaatcctgttaccagtggctgctgccagtggcgataagtcgtgtcttaccgggttggactcaagacgatagttacc
ggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcagg
gtcggaacaggagagcgcacgagggagcttccagggggaaacgcctggtatctttatagtcctgtcgggtttcgccacct
ctgacttgagcgtcgatttttgtgatgctcgtcaggggggcggagcctatggaaaaacgccagcaacgcggcctttttac
ggttcctggccttttgctggccttttgctcacatgttctttcctgcgttatcccctgattctgtggataaccgtattacc
gcctttgagtgagctgataccgctcgccgcagccgaacgaccgagcgcagcgagtcagtgagcgaggaagcggaagagcg
cccaatacgcaaaccgcctctccccgcgcgttggccgattcattaatgcaggatccgggatcgaagaaatgatggtaaat
gaaataggaaatcaaggagcatgaaggcaaaagacaaatataagggtcgaacgaaaaataaagtgaaaagtgttgatatg
atgtatttggctttgcggcgccgaaaaaacgagtttacgcaattgcacaatcatgctgactctgtggcggacccgcgctc
ttgccggcccggcgataacgctgggcgtgaggctgtgcccggcggagtttttgcgcctgcattttccaaggtttaccct
gcgctaagggggcgagattggagaagcaataagaatgccggttggggttgcgatgatgacgaccacgacaactggtgtcat
tatttaagttgccgaaagaacctgagtgcatttgcaacatgagtatactagaagaatgagccaagacttgcgagacgcga
gtttgccggtggtgcgaacaatagagcgaccatgaccttgaaggtgagacgcgcataaccgctagagtactttgaagagg

FIG. 23 Cont.

aaacagcaatagggttgctaccagtataaatagacaggtacatacaacactggaaatggttgtctgtttgagtacgcttt
caattcatttgggtgtgcactttattatgttacaatatggaagggaactttacacttctcctatgcacatatattaatta
aagtccaatgctagtagagaagggggtaacacccctccgcgctcttttccgatttttttctaaaccgtggaatatttcg
gatatccttttgttgtttccgggtgtacaatatggacttcctcttttctggcaaccaaacccatacatcgggattcctat
aataccttcgttggtctccctaacatgtaggtggcggaggggagatatacaatagaacagataccagacaagacataatg
ggctaaacaagactacaccaattacactgcctcattgatg
//

FIG. 23 Cont.

434-2146: Gal4 DBD-p53-Gcn5-HA
434-874: Gal4 DBD (amino acids 1-147)
938-1216: p53 (amino acids 300-393)
1295-1999: Gcn5 (amino acids 18-252)
2033-2119: trimeric HA Translation: Gal4-DBD-p53(300-393)-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLPGSTKRALPNNTSSSPQPKKKPLDGEYFTLQIRGRERFEMFRELNEALELKDAQAGKEPGGSRAHSSHLKSK
KGQSTSRHKKLMFKTEGPDSDPGSPILGYWKGRRDHPPKSDLIEGRGDPEVKRVKLENNVEEIQPEQAETNKQEGTDKEN
KGKFEKETERIGGSEVVTDVEKGIVKFEFDGVEYTFKERPSVVEENEGKIEFRVVNNDNTKENMMVLTGLKNIFQKQLPK
MPKEYIARLVYDRSHLSMAVIRKPLTVVGGITYRPFDKREFAEIVFCAISSTEQVRGYGAHLMNHLKDYVRNTSNIKYFL
TYADNYAIGYFKKQGFTKEITLDKSIWMGYIKDYEGGTLMQCNMAIPGGGRIFYPYDVPDYAGYPYDVPDYAGSYPYDVP
DYAAQCGRSS ; ### from DNA Strider Saturday, April 19, 2003 3:19:24 PM
; DNA sequence pMK485 8372 b.p. complete sequence
;
gtggtacataacgaactaatactgtagccctagacttgatagccatcatcatatcgaagtttcactaccctttttccatt
tgccatctattgaagtaataataggcgcatgcaacttcttttcttttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGCTGccagggagcactaagcgagcact
gcccaacaacaccagctcctctccccagccaaagaagaaaccactggatggagaatatttcacccttcagatccgtgggc
gtgagcgcttcgagatgttccgagagctgaatgaggccttggaactcaaggatgcccaggctgggaaggagccaggggg
agcagggctcactccagccacctgaagtccaaaaagggtcagtctacctcccgccataaaaactcatgttcaagacaga
agggcctgactcagacCCCgggtcccctatactaggttattggaaaggtcgacgcgaccatcctccaaaatcggatctga
tcgaaggtcgtggaGATCCCGAAGTTAAACGGGTAAAATTAGAAAACAACGTTGAAGAAATACAACCTGAGCAGGCTGAG
ACCAATAAACAAGAGGGCACCGATAAAGAGAATAAAGGAAAGTTCGAGAAAGAAACTGAGAGAATAGGAGGATCTGAAGT
GGTTACAGATGTGGAAAAAGGAATTGTCAAATTTGAATTTGATGGTGTTGAATACACATTCAAAGAGAGACCCAGTGTCG
TAGAGGAAAATGAAGGTAAAATTGAGTTTAGGGTGGTGAATAATGATAATACTAAAGAAAACATGATGGTCCTAACTGGA
TTAAAAAACATTTTTCAAAAGCAATTACCAAAAATGCCCAAAGAATACATTGCCAGGTTAGTCTATGATCGAAGTCATCT
TTCCATGGCTGTCATTAGGAAGCCATTGACTGTCGTAGGTGGCATAACATATCGACCTTTCGATAAGAGAGAATTCGCAG
AAATTGTTTTCTGTGCCATCAGTTCGACGGAACAGGTACGCGGTTATGGTGCGCATCTAATGAATCACTTAAAAGACTAT
GTTAGAAATACCTCGAACATAAAATATTTTTTGACATATGCAGATAATTACGCTATTGGATACTTTAAAAAGCAAGGCTT
TACTAAAGAAATCACGTTGGATAAAAGTATATGGATGGGATATATTAAAGATTATGAAGGTGGTACGCTGATGCAATGTA
ACATGGCAATTCCCGGtggcggccgcatcttttacccatacgatgttcctgactatgcgggctatccctatgacgtcccg
gactatgcaggatcctatccatatgacgttccagattacgctgctcagtgcggccgctctagctagaactagtggatccc

FIG. 24 ccGATACCGTCGACCTGCAGAGATCTAtgaatcgtagatactgaaaaaccccgcaagttcacttcaactgtgcatcgtgc
accatctcaatttctttcatttatacatcgttttgccttcttttatgtaactatactcctctaagtttcaatcttggcca
tgtaacctctgatctatagaatttttaaatgactagaattaatgcccatcttttttttggacctaaattcttcatgaaa
atatattacgagggcttattcagaagctttggacttcttcgccagaggtttggtcaagtctccaatcaaggttgtcggct
tgtctaccttgccagaaatttacgaaaagatggaaaagggtcaaatcgttggtagatacgttgttgacacttctaaataa
gcgaatttcttatgatttatgatttttattattaaataagttataaaaaaaataagtgtatacaaattttaaagtgactc
ttaggttttaaaacgaaaattcttattcttgagtaactctttcctgtaggtcaggttgctttctcaggtatagcatgagg
tcgctcttattgaccacacctctaccggcatgccgagcaaatgcctgcaaatcgctccccatttcacccaattgtagata
tgctaactccagcaatgagttgatgaatctcggtgtgtattttatgtcctcagaggacaacacctgttgtaatcgttctt
ccacacggatcctggcgtaatagcgaagaggcccgcaccgatcgcccttcccaacagttgcgcagcctgaatggcgaatg
gcgcctgatgcggtatttctccttacgcatctgtgcggtatttcacaccgcatatatcgctgggccattctcatgaaga
atatcttgaatttattgtcatattactagttggtgtggaagtccatatatcggtgatcaatatagtggttgacatgctgg
ctagtcaacattgagccttttgatcatgcaaatatattacggtattttacaatcaaatatcaaacttaactattgacttt
ataacttatttaggtggtaacattcttataaaaaagaaaaaattactgcaaaacagtactagcttttaacttgtatcct
aggttatctatgctgtctcaccatagagaatattacctatttcagaatgtatgtccatgattcgccgggtaaatacatat
aatacacaaatctggcttaataaagtctataatatatctcataaagaagtgctaaattggctagtgctatatattttaa
gaaaatttcttttgactaagtccatatcgactttgtaaaagttcactttagcatacatatattacacgagccagaaattg
taacttttgcctaaaatcacaaattgcaaaatttaattgcttgcaaaaggtcacatgcttataatcaacttttttaaaaa
tttaaaatactttttttatttttttatttttaaacataaatgaaataatttatttattgtttatgattaccgaaacataaaa
cctgctcaagaaaaagaaactgttttgtccttggaaaaaaagcactacctaggagcggccaaaatgccgaggctttcata
gcttaaactctttacagaaaataggcattatagatcagttcgagttttcttattcttccttccggttttatcgtcacagt
tttacagtaaataagtatcacctcttagagttcgatgataagctgtcaaacatgagaattaattccacatgttaaaatag
tgaaggagcatgttcggcacacagtggaccgaacgtggggtaagtgcactagggtccggttaaacggatctcgcattgat
gaggcaacgctaattatcaacatatagattgttatctatctgcatgaacacgaaatctttacttgacgacttgaggctga
tggtgtttatgcaaagaaaccactgtgtttaatatgtgtcactgtttgatattactgtcagcgtagaagataatagtaaa
agcggttaataagtgtatttgagataagtgtgataaagtttttacagcgaaaagacgataaatacaagaaaatgattacg
aggatacggagagaggtatgtacatgtgtatttatatactaagctgccggcggttgtttgcaagaccgagaaaaggctag
caagaatcgggtcattgtagcgtatgcgcctgtgaacattctcttcaacaagtttgattccattgcggtgaaatggtaaa
agtcaacccccctgcgatgtatattttcctgtacaatcaatcaaaaagccaaatgatttagcattatctttacatcttgtt
attttacagattttatgtttagatcttttatgcttgcttttcaaaaggcttgcaggcaagtgcacaaacaatacttaaat
aaatactactcagtaataacctaTTTCTTAGCATTTTTGACGAAATTTGCTATTTTGTTAGAGTCTTTTACACCATTTGT
CTCCACACCTCCGCTTACATCAACACCAATAACGCCATTTAATCTAAGCGCATCACCAACATTTTCTGGCGTCAGTCCAC
CAGCTAACATAAAATGTAAGCTCTCGGGGCTCTCTTGCCTTCCAACCCAGTCAGAAATCGAGTTCCAATCCAAAAGTTCA
CCTGTCCCACCTGCTTCTGAATCAAACAAGGGAATAAACGAATGAGGTTTCTGTGAAGCTGCACTGAGTAGTATGTTGCA
GTCTTTTGGAAATACGAGTCTTTTAATAACTGGCAAACCGAGGAACTCTTGGTATTCTTGCCACGACTCATCTCCATGCA
GTTGGACGATATCAATGCCGTAATCATTGACCAGAGCCAAAACATCCTCCTTAGGTTGATTACGAAACACGCCAACCAAG
TATTTCGGAGTGCCTGAACTATTTTTATATGCTTTTACAAGACTTGAAATTTTCCTTGCAATAACCGGGTCAATTGTTCT
CTTTCTATTGGGCACACATATAATACCCAGCAAGTCAGCATCGGAATCTAGTGCACATTCTGCGGCCTCTGTGCTCTGCA
AGCCGCAAACTTTCACCAATGGACCAGAACTACCTGTGAAATTAATAACAGACATactccaagctgcctttgtgtgctta
atcacgtatactcacgtgctcaatagtcaccaatgccctccctcttggccctctcctttttctttttttcgaccgaattaat
tcttgaagacgaaagggcctcgtgatacgcctatttttataggttaatgtcatgataataatggtttcttagacgtcagg
tggcacttttcggggaaatgtgcgcggaacccctatttgtttatttttctaaatacattcaaatatgtatccgctcatga
gacaataaccctgataaatgcttcaataatattgaaaaaggaagagtATGAGTATTCAACATTTCCGTGTCGCCCTTATT
CCCTTTTTTGCGGCATTTTGCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTATTGACGCCGGGCAAGAGCAACTCGGTCGC
CGCATACACTATTCTCAGAATGACTTGGTTGAGTACTCACCAGTCACAGAAAAGCATCTTACGGATGGCATGACAGTAAG
AGAATTATGCAGTGCTGCCATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAGGACCACTTCTGCGCTCGGCCCTTCCGG
CTGGCTGGTTTATTGCTGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATAGACAGATCGCTGAGAT
AGGTGCCTCACTGATTAAGCATTGGtaactgtcagaccaagtttactcatatatactttagattgatttaaaacttcatt

FIG. 24 Cont.

tttaatttaaaaggatctaggtgaagatcctttttgataatctcatgaccaaaatcccttaacgtgagttttcgttccac
tgagcgtcagaccccgtagaaaagatcaaaggatcttcttgagatcctttttttctgcgcgtaatctgctgcttgcaaac
aaaaaaaccaccgctaccagcggtggtttgtttgccggatcaagagctaccaactctttttccgaaggtaactggcttca
gcagagcgcagataccaaatactgtccttctagtgtagccgtagttaggccaccacttcaagaactctgtagcaccgcct
acatacctcgctctgctaatcctgttaccagtggctgctgccagtggcgataagtcgtgtcttaccgggttggactcaag
acgatagttaccggataaggcgcagcggtcgggctgaacggggggttcgtgcacacagcccagcttggagcgaacgacct
acaccgaactgagatacctacagcgtgagctatgagaaagcgccacgcttcccgaagggagaaaggcggacaggtatccg
gtaagcggcagggtcggaacaggagagcgcacgagggagcttccagggggaaacgcctggtatctttatagtcctgtcgg
gtttcgccacctctgacttgagcgtcgatttttgtgatgctcgtcaggggggcggagcctatggaaaaacgccagcaacg
cggcctttttacggttcctggccttttgctggccttttgctcacatgttctttcctgcgttatcccctgattctgtggat
aaccgtattaccgcctttgagtgagctgataccgctcgccgcagccgaacgaccgagcgcagcgagtcagtgagcgagga
agcggaagagcgcccaatacgcaaaccgcctctccccgcgcgttggccgattcattaatgcaggatccgggatcgaagaa
atgatggtaaatgaaataggaaatcaaggagcatgaaggcaaaagacaaatataagggtcgaacgaaaaataaagtgaaa
agtgttgatatgatgtatttggctttgcggcgccgaaaaaacgagtttacgcaattgcacaatcatgctgactctgtggc
ggacccgcgctcttgccggcccggcgataacgctgggcgtgaggctgtgcccggcggagtttttgcgcctgcattttcc
aaggtttaccctgcgctaaggggcgagattggagaagcaataagaatgccggttggggttgcgatgatgacgaccacgac
aactggtgtcattatttaagttgccgaaagaacctgagtgcatttgcaacatgagtatactagaagaatgagccaagact
tgcgagacgcgagtttgccggtggtgcgaacaatagagcgaccatgaccttgaaggtgagacgcgcataaccgctagagt
actttgaagaggaaacagcaatagggttgctaccagtataaatagacaggtacatacaacactggaaatggttgtctgtt
tgagtacgctttcaattcatttgggtgtgcactttattatgttacaatatggaagggaactttacacttctcctatgcac
atatattaattaaagtccaatgctagtagagaagggggggtaacacccctccgcgctcttttccgatttttttctaaaccg
tggaatatttcggatatccttttgttgtttccgggtgtacaatatggacttcctcttttctggcaaccaaacccatacat
cgggattcctataataccttcgttggtctccctaacatgtaggtggcggaggggagatatacaatagaacagataccaga
caagacataatgggctaaacaagactacaccaattacactgcctcattgatg
//

FIG. 24 Cont.

434-2146: Gal4 DBD-p53-Gcn5-HA
434-874: Gal4 DBD (amino acids 1-147)
938-1216: p53 (amino acids 300-393)
1295-1999: Gcn5 (amino acids 18-252) with Phe221 changed to Ala
2033-2119: trimeric HA Translation: Gal4-DBD-p53(300-393)-Gcn5-HA
MKLLSSIEQACDICRLKKLKCSKEKPKCAKCLKNNWECRYSPKTKRSPLTRAHLTEVESRLERLEQLFLLIFPREDLDMI
LKMDSLQDIKALLTGLFVQDNVNKDAVTDRLASVETDMPLTLRQHRISATSSSEESSNKGQRQLTVSNYLFDDEDTPPNP
KKEIEFQLPGSTKRALPNNTSSSPQPKKKPLDGEYFTLQIRGRERFEMFRELNEALELKDAQAGKEPGGSRAHSSHLKSK
KGQSTSRHKKLMFKTEGPDSDPGSPILGYWKGRRDHPPKSDLIEGRGDPEVKRVKLENNVEEIQPEQAETNKQEGTDKEN
KGKFEKETERIGGSEVVTDVEKGIVKFEFDGVEYTFKERPSVVEENEGKIEFRVVNNDNTKENMMVLTGLKNIFQKQLPK
MPKEYIARLVYDRSHLSMAVIRKPLTVVGGITYRPFDKREFAEIVFCAISSTEQVRGYGAHLMNHLKDYVRNTSNIKYFL
TYADNYAIGYAKKQGFTKEITLDKSIWMGYIKDYEGGTLMQCNMAIPGGGRIFYPYDVPDYAGYPYDVPDYAGSYPYDVP
DYAAQCGRSS ; ### from DNA Strider Saturday, April 19, 2003 3:19:24 PM
; DNA sequence pMK486 8372 b.p. complete sequence
;
gtggtacataacgaactaatactgtagccctagacttgatagccatcatcatatcgaagtttcactaccctttttccatt
tgccatctattgaagtaataataggcgcatgcaacttcttttctttttttttcttttctctctcccccgttgttgtctca
ccatatccgcaatgacaaaaaaatgatggaagacactaaaggaaaaaattaacgacaaagacagcaccaacagatgtcgt
tgttccagagctgatgaggggtatctcgaagcacacgaaactttttccttccttcattgacctgcaattattaatctttt
gtttcctcgtcattgttctcgttccctttcttccttgtttctttttctgcacaatatttcaagctataccaagcatacaa
tcaactccaagcttgaagcaagcctcctgaaagATGAAGCTACTGTCTTCTATCGAACAAGCATGCGATATTTGCCGACT
TAAAAAGCTCAAGTGCTCCAAAGAAAAACCGAAGTGCGCCAAGTGTCTGAAGAACAACTGGGAGTGTCGCTACTCTCCCA
AAACCAAAAGGTCTCCGCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAGCATTGTTAACAGGATT
ATTTGTACAAGATAATGTGAATAAAGATGCCGTCACAGATAGATTGGCTTCAGTGGAGACTGATATGCCTCTAACATTGA
GACAGCATAGAATAAGTGCGACATCATCATCGGAAGAGAGTAGTAACAAAGGTCAAAGACAGTTGACTGTATCGAACTAT
CTATTCGATGATGAAGATACCCCACCAAACCCAAAAAAAGAGATCGAATTCCAGCTGccagggagcactaagcgagcact
gcccaacaacaccagctcctctccccagccaaagaagaaaccactggatggagaatatttcaccccttcagatccgtgggc
gtgagcgcttcgagatgttccgagagctgaatgaggccttggaactcaaggatgcccaggctgggaaggagccagggggg
agcagggctcactccagccacctgaagtccaaaaagggtcagtctacctcccgccataaaaaactcatgttcaagacaga
agggcctgactcagacCCCgggtcccctatactaggttattggaaaggtcgacgcgaccatcctccaaaatcggatctga
tcgaaggtcgtggaGATCCCGAAGTTAAACGGGTAAAATTAGAAAACAACGTTGAAGAAATACAACCTGAGCAGGCTGAG
ACCAATAAACAAGAGGGCACCGATAAAGAGAATAAAGGAAAGTTCGAGAAAGAAACTGAGAGAATAGGAGGATCTGAAGT
GGTTACAGATGTGGAAAAAGGAATTGTCAAATTTGAATTTGATGGTGTTGAATACACATTCAAAGAGAGACCCAGTGTCG
TAGAGGAAAATGAAGGTAAAATTGAGTTTAGGGTGGTGAATAATGATAATACTAAAGAAAACATGATGGTCCTAACTGGA
TTAAAAAACATTTTTCAAAAGCAATTACCAAAAATGCCCAAAGAATACATTGCCAGGTTAGTCTATGATCGAAGTCATCT
TTCCATGGCTGTCATTAGGAAGCCATTGACTGTCGTAGGTGGCATAACATATCGACCTTTCGATAAGAGAGAATTCGCAG
AAATTGTTTTCTGTGCCATCAGTTCGACGGAACAGGTACGCGGTTATGGTGCGCATCTAATGAATCACTTAAAAGACTAT
GTTAGAAATACCTCGAACATAAAATATTTTTTGACATATGCAGATAATTACGCTATTGGATACGCTAAAAAGCAAGGCTT
TACTAAAGAAATCACGTTGGATAAAAGTATATGGATGGGATATATTAAAGATTATGAAGGTGGTACGCTGATGCAATGTA
ACATGGCAATTCCCGGtggcggccgcatcttttacccatacgatgttcctgactatgcgggctatccctatgacgtcccg
gactatgcaggatcctatccatatgacgttccagattacgctgctcagtgcggccgctctagctagaactagtggatccc

FIG. 25 ccGATACCGTCGACCTGCAGAGATCTAtgaatcgtagatactgaaaaaccccgcaagttcacttcaactgtgcatcgtgc
accatctcaatttctttcatttatacatcgttttgccttcttttatgtaactatactcctctaagtttcaatcttggcca
tgtaacctctgatctatagaatttttaaatgactagaattaatgcccatcttttttttggacctaaattcttcatgaaa
atatattacgagggcttattcagaagctttggacttcttcgccagaggtttggtcaagtctccaatcaaggttgtcggct
tgtctaccttgccagaaatttacgaaaagatggaaaagggtcaaatcgttggtagatacgttgttgacacttctaaataa
gcgaatttcttatgatttatgatttttattattaaataagttataaaaaaaataagtgtatacaaattttaaagtgactc
ttaggttttaaaacgaaaattcttattcttgagtaactctttcctgtaggtcaggttgctttctcaggtatagcatgagg
tcgctcttattgaccacacctctaccggcatgccgagcaaatgcctgcaaatcgctccccatttcacccaattgtagata
tgctaactccagcaatgagttgatgaatctcggtgtgtattttatgtcctcagaggacaacacctgttgtaatcgttctt
ccacacggatcctggcgtaatagcgaagaggcccgcaccgatcgcccttcccaacagttgcgcagcctgaatggcgaatg
gcgcctgatgcggtattttctccttacgcatctgtgcggtatttcacaccgcatatatcgctggccattctcatgaaga
atatcttgaatttattgtcatattactagttggtgtggaagtccatatatcggtgatcaatatagtggttgacatgctgg
ctagtcaacattgagccttttgatcatgcaaatatattacggtattttacaatcaaatatcaaacttaactattgacttt
ataacttatttaggtggtaacattcttataaaaagaaaaaaattactgcaaaacagtactagcttttaacttgtatcct
aggttatctatgctgtctcaccatagagaatattacctatttcagaatgtatgtccatgattcgccgggtaaatacatat
aatacacaaatctggcttaataaagtctataatatatctcataaagaagtgctaaattggctagtgctatatatttttaa
gaaaatttcttttgactaagtccatatcgactttgtaaaagttcactttagcatacatatattacacgagccagaaattg
taacttttgcctaaaatcacaaattgcaaaatttaattgcttgcaaaaggtcacatgcttataatcaacttttttaaaaa
tttaaaatactttttttatttttttatttttaaacataaatgaataatttatttattgtttatgattaccgaaacataaaa
cctgctcaagaaaaagaaactgttttgtccttggaaaaaaagcactacctaggagcggccaaaatgccgaggctttcata
gcttaaactctttacagaaaataggcattatagatcagttcgagttttcttattcttccttccggttttatcgtcacagt
tttacagtaaataagtatcacctcttagagttcgatgataagctgtcaaacatgagaattaattccacatgttaaaatag
tgaaggagcatgttcggcacacagtggaccgaacgtggggtaagtgcactagggtccggttaaacggatctcgcattgat
gaggcaacgctaattatcaacatatagattgttatctatctgcatgaacacgaaatctttacttgacgacttgaggctga
tggtgtttatgcaaagaaaccactgtgtttaatatgtgtcactgtttgatattactgtcagcgtagaagataatagtaaa
agcggttaataagtgtatttgagataagtgtgataaagtttttacagcgaaaagacgataaatacaagaaaatgattacg
aggatacggagagaggtatgtacatgtgtatttatatactaagctgccggcggttgtttgcaagaccgagaaaaggctag
caagaatcgggtcattgtagcgtatgcgcctgtgaacattctcttcaacaagtttgattccattgcggtgaaatggtaaa
agtcaacccccctgcgatgtatatttcctgtacaatcaatcaaaaagccaaatgatttagcattatctttacatcttgtt
attttacagattttatgtttagatcttttatgcttgcttttcaaaaggcttgcaggcaagtgcacaaacaatacttaaat
aaatactactcagtaataacctaTTTCTTAGCATTTTTGACGAAATTTGCTATTTTGTTAGAGTCTTTTACACCATTTGT
CTCCACACCTCCGCTTACATCAACACCAATAACGCCATTTAATCTAAGCGCATCACCAACATTTTCTGGCGTCAGTCCAC
CAGCTAACATAAAATGTAAGCTCTCGGGGCTCTCTTGCCTTCCAACCCAGTCAGAAATCGAGTTCCAATCCAAAAGTTCA
CCTGTCCCACCTGCTTCTGAATCAAACAAGGGAATAAACGAATGAGGTTTCTGTGAAGCTGCACTGAGTAGTATGTTGCA
GTCTTTTGGAAATACGAGTCTTTTAATAACTGGCAAACCGAGGAACTCTTGGTATTCTTGCCACGACTCATCTCCATGCA
GTTGGACGATATCAATGCCGTAATCATTGACCAGAGCCAAAACATCCTCCTTAGGTTGATTACGAAACACGCCAACCAAG
TATTTCGGAGTGCCTGAACTATTTTTATATGCTTTTACAAGACTTGAAATTTTCCTTGCAATAACCGGGTCAATTGTTCT
CTTTCTATTGGGCACACATATAATACCCAGCAAGTCAGCATCGGAATCTAGTGCACATTCTGCGGCCTCTGTGCTCTGCA
AGCCGCAAACTTTCACCAATGGACCAGAACTACCTGTGAAATTAATAACAGACATactccaagctgcctttgtgtgctta
atcacgtatactcacgtgctcaatagtcaccaatgccctccctcttggccctctcctttttcttttttcgaccgaattaat
tcttgaagacgaaagggcctcgtgatacgcctatttttataggttaatgtcatgataataatggtttcttagacgtcagg
tggcacttttcggggaaatgtgcgcggaacccctatttgtttatttttctaaatacattcaaatatgtatccgctcatga
gacaataaccctgataaatgcttcaataatattgaaaaaggaagagtATGAGTATTCAACATTTCCGTGTCGCCCTTATT
CCCTTTTTTGCGGCATTTTGCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTATTGACGCCGGGCAAGAGCAACTCGGTCGC
CGCATACACTATTCTCAGAATGACTTGGTTGAGTACTCACCAGTCACAGAAAAGCATCTTACGGATGGCATGACAGTAAG
AGAATTATGCAGTGCTGCCATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAGGACCACTTCTGCGCTCGGCCCTTCCGG
CTGGCTGGTTTATTGCTGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATAGACAGATCGCTGAGAT
AGGTGCCTCACTGATTAAGCATTGGtaactgtcagaccaagtttactcatatatactttagattgatttaaaacttcatt

FIG. 25 Cont.

CTD-Kin28wt CTD-Kin28mut Kin28wt

Phosphorylated CTD-interacting proteins
1 = Fcp1
2 = Ssn8/Srb11
3= Tfb3
4 = Whi2
5 = YMR181c
6 = YPL229w
7 = YDR428C Kin28-interacting proteins
A = Ccl1
B = Pcl10
C = YDL100c Autophosphorylation of H3 at Ser10 by the tethered Ipl1 kinase Ab: Anti-HA Anti-H3.Pi Bait: H3-Ipl1 mutant, H3-Ipl1 wt, Blank vector, H3-Ipl1 mutant, H3-Ipl1 wt, Blank vector GST pulldown shows acetylation-stimulated interaction between p53 and PIASxα and acetylation-independent interaction between p53 and PIASxβ

434-2482: Gal4 DBD-H3-Ipl1-HA
434-874: Gal4 DBD (amino acids 1-147)
932-952: TEV cleavage sequence (ENLYFQG)
974-1153: H3 (amino acids 1-59)
1235-2332: Ipl1 ORF
2369-2458: HAx3

Translation: Gal4 DBD-H3-Ipl1-HAx3
MKLLSSIEQACDICRLKKLKCSKEKPKCAKCLKNNWECRYSPKTKRSPLTRAHLTEVESR
LERLEQLFLLIFPREDLDMILKMDSLQDIKALLTGLFVQDNVNKDAVTDRLASVETDMPL
TLRQHRISATSSSEESSNKGQRQLTVSNYLFDDEDTPPNPKKEIEFQENLYFQGLTTMFM
ARTKQTARKSTGGKAPRKQLASKAARKSAPSTGGVKKPHRYKPGTVALREIRRFQKSTEP
GSPILGYWKGRRDHPPKSDLIEGRGGPQRNSLVNIKLNANSPSKKTTTRPNTSRINKPWR
ISHSPQQRNPNSKIPSPVREKLNRLPVNNKKFLDMESSKIPSPIRKATSSKMIHENKKLP
KFKSLSLDDFELGKKLGKGKFGKVYCVRHRSTGYICALKVMEKEEIIKYNLQKQFRREVE
IQTSLNHPNLTKSYGYFHDEKRVYLLMEYLVNGEMYKLLRLHGPFNDILASDYIYQIANA
LDYMHKKNIIHRDIKPENILIGFNNVIKLTDFGWSIINPPENRRKTVCGTIDYLSPEMVE
SREYDHTIDAWALGVLAFELLTGAPPFEEEMKDTTYKRIAALDIKMPSNISQDAQDLILK
LLKYDPKDRMRLGDVKMHPWILRNKPFWENKRLELMAIPGGGRIFYPYDVPDYAGYPYDV
PDYAGSYPYDVPDYAAQCGRSS ; ### from DNA Strider Thursday, February 5, 2004 12:57:23 PM
; DNA sequence PDG64 8708 b.p. complete sequence
;
gtggtacataacgaactaatactgtagccctagacttgatagccatcatcatatcgaagtttca
ctacccttttccatttgccatctattgaagtaataataggcgcatgcaacttcttttcttttt
ttttcttttctctctcccccgttgttgtctcaccatatccgcaatgacaaaaaaatgatggaag
acactaaaggaaaaaattaacgacaaagacagcaccaacagatgtcgttgttccagagctgatg
aggggtatctcgaagcacacgaaactttttccttccttcattgacctgcaattattaatctttt
gtttcctcgtcattgttctcgttccctttcttccttgtttctttttctgcacaatatttcaagc
tataccaagcatacaatcaactccaagcttgaagcaagcctcctgaaagATGAAGCTACTGTCT
TCTATCGAACAAGCATGCGATATTTGCCGACTTAAAAAGCTCAAGTGCTCCAAAGAAAAACCGA
AGTGCGCCAAGTGTCTGAAGAACAACTGGGAGTGTCGCTACTCTCCCAAAACCAAAAGGTCTCC
GCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAG
CATTGTTAACAGGATTATTTGTACAAGATAATGTGAATAAAGATGCCGTCACAGATAGATTGGC
TTCAGTGGAGACTGATATGCCTCTAACATTGAGACAGCATAGAATAAGTGCGACATCATCATCG
GAAGAGAGTAGTAACAAAGGTCAAAGACAGTTGACTGTATCGAACTATCTATTCGATGATGAAG
ATACCCCACCAAACCCAAAAAAAGAGATCGAATTCCAGgagaatttgtattttcaaggtCTGAC
CACCATGTTTatggccagaacaaagcaaacagcaagaaagtccactggtggtaaggccccaaga
aagcaattagcttctaaggctgccagaaaatccgccccatctaccggtggtgttaagaagcctc
acagatataagccaggtactgttgctttgagagaaatcagaagattccaaaaatctactgaaCC
Cgggtcccctatactaggttattggaaaggtcgacgcgaccatcctccaaaatcggatctgatc
gaaggtcgtggaGGGCCCCAACGCAATAGTTTAGTAAATATCAAACTAAACGCTAATTCGCCAT

FIG. 30

CGAAAAAGACCACAACAAGACCAAATACGTCCAGGATCAATAAACCATGGAGAATATCCCATTC
GCCGCAGCAAAGAAACCCGAATTCAAAAATACCTTCACCTGTAAGAGAAAAATTGAACAGATTA
CCTGTAAACAATAAGAAGTTTTTGGATATGGAAAGCTCCAAAATTCCATCACCTATAAGGAAAG
CGACTTCTTCCAAAATGATACACGAAAATAAGAAGCTACCTAAATTTAAATCCCTATCACTCGA
TGACTTTGAACTGGGGAAGAAATTAGGAAAGGGTAAATTCGGTAAAGTTTATTGCGTTCGGCAC
AGGAGTACAGGATATATTTGCGCACTGAAAGTAATGGAGAAGGAAGAAATAATAAAGTATAATT
TACAGAAACAATTCAGAAGGGAGGTAGAAATACAAACATCGCTAAATCATCCGAATCTAACTAA
ATCATACGGCTATTTTCATGATGAAAAAAGAGTGTACCTGCTAATGGAATACTTAGTCAATGGG
GAAATGTATAAACTATTGAGGTTACACGGACCCTTCAACGATATTTTAGCATCAGATTATATTT
ATCAAATTGCCAATGCCCTAGATTATATGCATAAAAAGAATATTATTCATAGAGATATTAAACC
TGAAAATATACTAATAGGGTTCAATAATGTCATTAAGTTAACGGACTTCGGATGGAGTATAATA
AATCCGCCAGAAAATAGAAGGAAAACTGTCTGTGGGACAATTGACTACCTTTCTCCAGAAATGG
TGGAGTCAAGGGAATATGATCACACTATAGATGCATGGGCTCTTGGCGTCCTGGCGTTTGAACT
ACTGACCGGTGCCCCTCCGTTCGAAGAAGAAATGAAAGATACTACATATAAAAGGATAGCAGCA
CTGGATATCAAAATGCCCAGTAACATTTCTCAGGATGCGCAAGATTTAATACTTAAACTACTAA
AATACGACCCCAAAGATAGAATGCGCCTTGGAGACGTAAAAATGCATCCTTGGATACTAAGAAA
CAAGCCCTTTTGGGAAAATAAGCGGTTAGAGCTCATGGCAATTCCCGGtggcggccgcatcttt
tacccatacgatgttcctgactatgcgggctatccctatgacgtcccggactatgcaggatcct
atccatatgacgttccagattacgctgctcagtgcggccgctctagctagaactagtggatccc
ccGATACCGTCGACCTGCAGAGATCTAtgaatcgtagatactgaaaaaccccgcaagttcactt
caactgtgcatcgtgcaccatctcaatttctttcatttatacatcgttttgccttcttttatgt
aactatactcctctaagtttcaatcttggccatgtaacctctgatctatagaatttttttaaatg
actagaattaatgcccatcttttttttggacctaaattcttcatgaaaatatattacgagggct
tattcagaagctttggacttcttcgccagaggtttggtcaagtctccaatcaaggttgtcggct
tgtctaccttgccagaaatttacgaaaagatggaaaagggtcaaatcgttggtagatacgttgt
tgacacttctaaataagcgaatttcttatgatttatgatttttattattaaataagttataaaa
aaaataagtgtatacaaattttaaagtgactcttaggttttaaaacgaaaattcttattcttga
gtaactctttcctgtaggtcaggttgctttctcaggtatagcatgaggtcgctcttattgacca
cacctctaccggcatgccgagcaaatgcctgcaaatcgctccccatttcacccaattgtagata
tgctaactccagcaatgagttgatgaatctcggtgtgtattttatgtcctcagaggacaacacc
tgttgtaatcgttcttccacacggatcctggcgtaatagcgaagaggcccgcaccgatcgccct
tcccaacagttgcgcagcctgaatggcgaatggcgcctgatgcggtattttctccttacgcatc
tgtgcggtatttcacaccgcatatatcgctgggccattctcatgaagaatatcttgaatttatt
gtcatattactagttggtgtggaagtccatatatcggtgatcaatatagtggttgacatgctgg
ctagtcaacattgagccttttgatcatgcaaatatattacggtattttacaatcaaatatcaaa
cttaactattgactttataacttatttaggtggtaacattcttataaaaaagaaaaaaattact
gcaaaacagtactagcttttaacttgtatcctaggttatctatgctgtctcaccatagagaata
ttacctatttcagaatgtatgtccatgattcgccgggtaaatacatataatacacaaatctggc
ttaataaagtctataatatatctcataaagaagtgctaaattggctagtgctatatattttttaa
gaaaatttcttttgactaagtccatatcgactttgtaaaagttcactttagcatacatatatta
cacgagccagaaattgtaacttttgcctaaaatcacaaattgcaaaatttaattgcttgcaaaa
ggtcacatgcttataatcaactttttttaaaaatttaaaatactttttttatttttttattttttaaa
cataaatgaaataatttatttattgtttatgattaccgaaacataaaacctgctcaagaaaaag
aaactgttttgtccttggaaaaaaagcactacctaggagcggccaaaatgccgaggctttcata
gcttaaactctttacagaaaataggcattatagatcagttcgagttttcttattcttccttccg
gttttatcgtcacagttttacagtaaataagtatcacctcttagagttcgatgataagctgtca
aacatgagaattaattccacatgttaaaatagtgaaggagcatgttcggcacacagtggaccga

FIG. 30 Cont.

acgtggggtaagtgcactagggtccggttaaacggatctcgcattgatgaggcaacgctaatta
tcaacatatagattgttatctatctgcatgaacacgaaatctttacttgacgacttgaggctga
tggtgtttatgcaaagaaaccactgtgtttaatatgtgtcactgtttgatattactgtcagcgt
agaagataatagtaaaagcggttaataagtgtatttgagataagtgtgataaagtttttacagc
gaaaagacgataaatacaagaaaatgattacgaggatacggagagaggtatgtacatgtgtatt
tatatactaagctgccggcggttgtttgcaagaccgagaaaaggctagcaagaatcgggtcatt
gtagcgtatgcgcctgtgaacattctcttcaacaagtttgattccattgcggtgaaatggtaaa
agtcaacccccctgcgatgtatatttttcctgtacaatcaatcaaaaagccaaatgatttagcatt
atctttacatcttgttattttacagattttatgtttagatcttttatgcttgcttttcaaaagg
cttgcaggcaagtgcacaaacaatacttaaataaatactactcagtaataacctaTTTCTTAGC
ATTTTTGACGAAATTTGCTATTTTGTTAGAGTCTTTTACACCATTTGTCTCCACACCTCCGCTT
ACATCAACACCAATAACGCCATTTAATCTAAGCGCATCACCAACATTTTCTGGCGTCAGTCCAC
CAGCTAACATAAAATGTAAGCTCTCGGGGCTCTCTTGCCTTCCAACCCAGTCAGAAATCGAGTT
CCAATCCAAAAGTTCACCTGTCCCACCTGCTTCTGAATCAAACAAGGGAATAAACGAATGAGGT
TTCTGTGAAGCTGCACTGAGTAGTATGTTGCAGTCTTTTGGAAATACGAGTCTTTTAATAACTG
GCAAACCGAGGAACTCTTGGTATTCTTGCCACGACTCATCTCCATGCAGTTGGACGATATCAAT
GCCGTAATCATTGACCAGAGCCAAAACATCCTCCTTAGGTTGATTACGAAACACGCCAACCAAG
TATTTCGGAGTGCCTGAACTATTTTTATATGCTTTTACAAGACTTGAAATTTTCCTTGCAATAA
CCGGGTCAATTGTTCTCTTTCTATTGGGCACACATATAATACCCAGCAAGTCAGCATCGGAATC
TAGTGCACATTCTGCGGCCTCTGTGCTCTGCAAGCCGCAAACTTTCACCAATGGACCAGAACTA
CCTGTGAAATTAATAACAGACATactccaagctgcctttgtgtgcttaatcacgtatactcacg
tgctcaatagtcaccaatgccctccctcttggccctctccttttctttttcgaccgaattaat
tcttgaagacgaaagggcctcgtgatacgcctatttttataggttaatgtcatgataataatgg
tttcttagacgtcaggtggcacttttcggggaaatgtgcgcggaacccctatttgtttattttt
ctaaatacattcaaatatgtatccgctcatgagacaataaccctgataaatgcttcaataatat
tgaaaaaggaagagtATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATGACTTGGTTGA
GTACTCACCAGTCACAGAAAAGCATCTTACGGATGGCATGACAGTAAGAGAATTATGCAGTGCT
GCCATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCGGA
GCTGAATGAAGCCATACCAAACGACGAGCGTGACACCACGATGCCTGTAGCAATGGCAACAACG
TTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATA
GACAGATCGCTGAGATAGGTGCCTCACTGATTAAGCATTGGtaactgtcagaccaagtttactc
atatatactttagattgatttaaaacttcatttttaatttaaaaggatctaggtgaagatcctt
tttgataatctcatgaccaaaatcccttaacgtgagttttcgttccactgagcgtcagaccccg
tagaaaagatcaaaggatcttcttgagatcctttttttctgcgcgtaatctgctgcttgcaaac
aaaaaaaccaccgctaccagcggtggtttgtttgccggatcaagagctaccaactctttttccg
aaggtaactggcttcagcagagcgcagataccaaatactgtccttctagtgtagccgtagttag
gccaccacttcaagaactctgtagcaccgcctacatacctcgctctgctaatcctgttaccagt
ggctgctgccagtggcgataagtcgtgtcttaccgggttggactcaagacgatagttaccggat
aaggcgcagcggtcgggctgaacgggggggttcgtgcacacagcccagcttggagcgaacgacct

FIG. 30 Cont.

acaccgaactgagatacctacagcgtgagctatgagaaagcgccacgcttcccgaagggagaaa
ggcggacaggtatccggtaagcggcagggtcggaacaggagagcgcacgagggagcttccaggg
ggaaacgcctggtatctttatagtcctgtcgggtttcgccacctctgacttgagcgtcgatttt
tgtgatgctcgtcaggggggcggagcctatggaaaaacgccagcaacgcggcctttttacggtt
cctggccttttgctggccttttgctcacatgttctttcctgcgttatcccctgattctgtggat
aaccgtattaccgcctttgagtgagctgataccgctcgccgcagccgaacgaccgagcgcagcg
agtcagtgagcgaggaagcggaagagcgcccaatacgcaaaccgcctctccccgcgcgttggcc
gattcattaatgcaggatccgggatcgaagaaatgatggtaaatgaaataggaaatcaaggagc
atgaaggcaaaagacaaatataagggtcgaacgaaaaataaagtgaaaagtgttgatatgatgt
atttggctttgcggcgccgaaaaaacgagtttacgcaattgcacaatcatgctgactctgtggc
ggacccgcgctcttgccggcccggcgataacgctgggcgtgaggctgtgcccggcggagttttt
tgcgcctgcattttccaaggtttaccctgcgctaaggggcgagattggagaagcaataagaatg
ccggttggggttgcgatgatgacgaccacgacaactggtgtcattatttaagttgccgaaagaa
cctgagtgcatttgcaacatgagtatactagaagaatgagccaagacttgcgagacgcgagttt
gccggtggtgcgaacaatagagcgaccatgaccttgaaggtgagacgcgcataaccgctagagt
actttgaagaggaaacagcaatagggttgctaccagtataaatagacaggtacatacaacactg
gaaatggttgtctgtttgagtacgctttcaattcatttgggtgtgcactttattatgttacaat
atggaagggaactttacacttctcctatgcacatatattaattaaagtccaatgctagtagaga
agggggtaacacccctccgcgctcttttccgatttttttctaaaccgtggaatatttcggata
tcctttgttgtttccgggtgtacaatatggacttcctcttttctggcaaccaaacccatacat
cgggattcctataataccttcgttggtctccctaacatgtaggtggcggaggggagatatacaa
tagaacagataccagacaagacataatgggctaaacaagactacaccaattacactgcctcatt
gatg
//

FIG. 30 Cont.

434-2482: Gal4 DBD-H3-Ipl1-HA
434-874: Gal4 DBD (amino acids 1-147)
932-952: TEV cleavage sequence (ENLYFQG)
974-1153: H3 (amino acids 1-59)
1235-2332: Ipl1 ORF with E152Q V153L double mutations
2369-2458: HAx3

Translation: Gal4 DBD-H3-Ipl1-HAx3
MKLLSSIEQACDICRLKKLKCSKEKPKCAKCLKNNWECRYSPKTKRSPLTRAHLTEVESR
LERLEQLFLLIFPREDLDMILKMDSLQDIKALLTGLFVQDNVNKDAVTDRLASVETDMPL
TLRQHRISATSSSEESSNKGQRQLTVSNYLFDDEDTPPNPKKEIEFQENLYFQGLTTMFM
ARTKQTARKSTGGKAPRKQLASKAARKSAPSTGGVKKPHRYKPGTVALREIRRFQKSTEP
GSPILGYWKGRRDHPPKSDLIEGRGGPQRNSLVNIKLNANSPSKKTTTRPNTSRINKPWR
ISHSPQQRNPNSKIPSPVREKLNRLPVNNKKFLDMESSKIPSPIRKATSSKMIHENKKLP
KFKSLSLDDFELGKKLGKGKFGKVYCVRHRSTGYICALKVMEKEEIIKYNLQKQFRRQLE
IQTSLNHPNLTKSYGYFHDEKRVYLLMEYLVNGEMYKLLRLHGPFNDILASDYIYQIANA
LDYMHKKNIIHRDIKPENILIGFNNVIKLTDFGWSIINPPENRRKTVCGTIDYLSPEMVE
SREYDHTIDAWALGVLAFELLTGAPPFEEEMKDTTYKRIAALDIKMPSNISQDAQDLILK
LLKYDPKDRMRLGDVKMHPWILRNKPFWENKRLELMAIPGGGRIFYPYDVPDYAGYPYDV
PDYAGSYPYDVPDYAAQCGRSS ; ### from DNA Strider Thursday, February 5, 2004 12:57:23 PM
; DNA sequence PDG65 8708 b.p. complete sequence
;
gtggtacataacgaactaatactgtagccctagacttgatagccatcatcatatcgaagtttca
ctacccttttccatttgccatctattgaagtaataataggcgcatgcaacttcttttctttt
ttttcttttctctctcccccgttgttgtctcaccatatccgcaatgacaaaaaaatgatggaag
acactaaaggaaaaaattaacgacaaagacagcaccaacagatgtcgttgttccagagctgatg
aggggtatctcgaagcacacgaaactttttccttccttcattgacctgcaattattaatctttt
gtttcctcgtcattgttctcgttccctttcttccttgtttctttttctgcacaatatttcaagc
tataccaagcatacaatcaactccaagcttgaagcaagcctcctgaaagATGAAGCTACTGTCT
TCTATCGAACAAGCATGCGATATTTGCCGACTTAAAAAGCTCAAGTGCTCCAAAGAAAAACCGA
AGTGCGCCAAGTGTCTGAAGAACAACTGGGAGTGTCGCTACTCTCCCAAAACCAAAAGGTCTCC
GCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAG
CATTGTTAACAGGATTATTTGTACAAGATAATGTGAATAAAGATGCCGTCACAGATAGATTGGC
TTCAGTGGAGACTGATATGCCTCTAACATTGAGACAGCATAGAATAAGTGCGACATCATCATCG
GAAGAGAGTAGTAACAAAGGTCAAAGACAGTTGACTGTATCGAACTATCTATTCGATGATGAAG
ATACCCCACCAAACCCAAAAAAAGAGATCGAATTCCAGgagaatttgtattttcaaggtCTGAC
CACCATGTTTatggccagaacaaagcaaacagcaagaaagtccactggtggtaaggccccaaga
aagcaattagcttctaaggctgccagaaaatccgccccatctaccggtggtgttaagaagcctc
acagatataagccaggtactgttgctttgagagaaatcagaagattccaaaaatctactgaaCC
Cgggtcccctatactaggttattggaaaggtcgacgcgaccatcctccaaaatcggatctgatc
gaaggtcgtggaGGGCCCCAACGCAATAGTTTAGTAAATATCAAACTAAACGCTAATTCGCCAT

FIG. 31

CGAAAAAGACCACAACAAGACCAAATACGTCCAGGATCAATAAACCATGGAGAATATCCCATTC
GCCGCAGCAAAGAAACCCGAATTCAAAAATACCTTCACCTGTAAGAGAAAAATTGAACAGATTA
CCTGTAAACAATAAGAAGTTTTTGGATATGGAAAGCTCCAAAATTCCATCACCTATAAGGAAAG
CGACTTCTTCCAAAATGATACACGAAAATAAGAAGCTACCTAAATTTAAATCCCTATCACTCGA
TGACTTTGAACTGGGGAAGAAATTAGGAAAGGGTAAATTCGGTAAAGTTTATTGCGTTCGGCAC
AGGAGTACAGGATATATTTGCGCACTGAAAGTAATGGAGAAGGAAGAAATAATAAAGTATAATT
TACAGAAACAATTCAGAAGGCAGCTGGAAATACAAACATCGCTAAATCATCCGAATCTAACTAA
ATCATACGGCTATTTTCATGATGAAAAAAGAGTGTACCTGCTAATGGAATACTTAGTCAATGGG
GAAATGTATAAACTATTGAGGTTACACGGACCCTTCAACGATATTTTAGCATCAGATTATATTT
ATCAAATTGCCAATGCCCTAGATTATATGCATAAAAAGAATATTATTCATAGAGATATTAAACC
TGAAAATATACTAATAGGGTTCAATAATGTCATTAAGTTAACGGACTTCGGATGGAGTATAATA
AATCCGCCAGAAAATAGAAGGAAAACTGTCTGTGGGACAATTGACTACCTTTCTCCAGAAATGG
TGGAGTCAAGGGAATATGATCACACTATAGATGCATGGGCTCTTGGCGTCCTGGCGTTTGAACT
ACTGACCGGTGCCCCTCCGTTCGAAGAAGAAATGAAAGATACTACATATAAAAGGATAGCAGCA
CTGGATATCAAAATGCCCAGTAACATTTCTCAGGATGCGCAAGATTTAATACTTAAACTACTAA
AATACGACCCCAAAGATAGAATGCGCCTTGGAGACGTAAAAATGCATCCTTGGATACTAAGAAA
CAAGCCCTTTTGGGAAAATAAGCGGTTAGAGCTCATGGCAATTCCCGGtggcggccgcatcttt
tacccatacgatgttcctgactatgcgggctatccctatgacgtcccggactatgcaggatcct
atccatatgacgttccagattacgctgctcagtgcggccgctctagctagaactagtggatccc
ccGATACCGTCGACCTGCAGAGATCTAtgaatcgtagatactgaaaaaccccgcaagttcactt
caactgtgcatcgtgcaccatctcaatttctttcatttatacatcgttttgccttcttttatgt
aactatactcctctaagtttcaatcttggccatgtaacctctgatctatagaatttttaaatg
actagaattaatgcccatcttttttttggacctaaattcttcatgaaaatatattacgagggct
tattcagaagctttggacttcttcgccagaggtttggtcaagtctccaatcaaggttgtcggct
tgtctaccttgccagaaatttacgaaaagatggaaaagggtcaaatcgttggtagatacgttgt
tgacacttctaaataagcgaatttcttatgatttatgattttattattaaataagttataaaa
aaaataagtgtatacaaattttaaagtgactcttaggttttaaaacgaaaattcttattcttga
gtaactctttcctgtaggtcaggttgctttctcaggtatagcatgaggtcgctcttattgacca
cacctctaccggcatgccgagcaaatgcctgcaaatcgctccccatttcacccaattgtagata
tgctaactccagcaatgagttgatgaatctcggtgtgtattttatgtcctcagaggacaacacc
tgttgtaatcgttcttccacacggatcctggcgtaatagcgaagaggcccgcaccgatcgccct
tcccaacagttgcgcagcctgaatggcgaatggcgcctgatgcggtattttctccttacgcatc
tgtgcggtatttcacaccgcatatatcgctgggccattctcatgaagaatatcttgaatttatt
gtcatattactagttggtgtggaagtccatatatcggtgatcaatatagtggttgacatgctgg
ctagtcaacattgagccttttgatcatgcaaatatattacggtattttacaatcaaatatcaaa
cttaactattgactttataacttatttaggtggtaacattcttataaaaaagaaaaaaattact
gcaaaacagtactagcttttaacttgtatcctaggttatctatgctgtctcaccatagagaata
ttacctatttcagaatgtatgtccatgattcgccgggtaaatacatataatacacaaatctggc
ttaataaagtctataatatatctcataaagaagtgctaaattggctagtgctatatatttttaa
gaaaatttcttttgactaagtccatatcgactttgtaaaagttcactttagcatacatatatta
cacgagccagaaattgtaacttttgcctaaaatcacaaattgcaaaatttaattgcttgcaaaa
ggtcacatgcttataatcaactttttaaaaatttaaaatactttttttatttttttatttttaaa
cataaatgaaataatttatttattgtttatgattaccgaaacataaaacctgctcaagaaaaag
aaactgttttgtccttggaaaaaaagcactacctaggagcggccaaaatgccgaggctttcata
gcttaaactctttacagaaaataggcattatagatcagttcgagttttcttattcttccttccg
gttttatcgtcacagttttacagtaaataagtatcacctcttagagttcgatgataagctgtca
aacatgagaattaattccacatgttaaaatagtgaaggagcatgttcggcacacagtggaccga

FIG. 31 Cont.

acgtggggtaagtgcactagggtccggttaaacggatctcgcattgatgaggcaacgctaatta
tcaacatatagattgttatctatctgcatgaacacgaaatctttacttgacgacttgaggctga
tggtgtttatgcaaagaaaccactgtgtttaatatgtgtcactgtttgatattactgtcagcgt
agaagataatagtaaaagcggttaataagtgtatttgagataagtgtgataaagtttttacagc
gaaaagacgataaatacaagaaaatgattacgaggatacggagagaggtatgtacatgtgtatt
tatatactaagctgccggcggttgtttgcaagaccgagaaaaggctagcaagaatcgggtcatt
gtagcgtatgcgcctgtgaacattctcttcaacaagtttgattccattgcggtgaaatggtaaa
agtcaacccccctgcgatgtatatttcctgtacaatcaatcaaaaagccaaatgatttagcatt
atctttacatcttgttattttacagattttatgtttagatcttttatgcttgcttttcaaaagg
cttgcaggcaagtgcacaaacaatacttaaataaatactactcagtaataacctaTTTCTTAGC
ATTTTTGACGAAATTTGCTATTTTGTTAGAGTCTTTTACACCATTTGTCTCCACACCTCCGCTT
ACATCAACACCAATAACGCCATTTAATCTAAGCGCATCACCAACATTTTCTGGCGTCAGTCCAC
CAGCTAACATAAAATGTAAGCTCTCGGGGCTCTCTTGCCTTCCAACCCAGTCAGAAATCGAGTT
CCAATCCAAAAGTTCACCTGTCCCACCTGCTTCTGAATCAAACAAGGGAATAAACGAATGAGGT
TTCTGTGAAGCTGCACTGAGTAGTATGTTGCAGTCTTTTGGAAATACGAGTCTTTTAATAACTG
GCAAACCGAGGAACTCTTGGTATTCTTGCCACGACTCATCTCCATGCAGTTGGACGATATCAAT
GCCGTAATCATTGACCAGAGCCAAAACATCCTCCTTAGGTTGATTACGAAACACGCCAACCAAG
TATTTCGGAGTGCCTGAACTATTTTTATATGCTTTTACAAGACTTGAAATTTTCCTTGCAATAA
CCGGGTCAATTGTTCTCTTTCTATTGGGCACACATATAATACCCAGCAAGTCAGCATCGGAATC
TAGTGCACATTCTGCGGCCTCTGTGCTCTGCAAGCCGCAAACTTTCACCAATGGACCAGAACTA
CCTGTGAAATTAATAACAGACATactccaagctgcctttgtgtgcttaatcacgtatactcacg
tgctcaatagtcaccaatgccctccctcttggccctctccttttcttttttcgaccgaattaat
tcttgaagacgaaagggcctcgtgatacgcctatttttataggttaatgtcatgataataatgg
tttcttagacgtcaggtggcacttttcggggaaatgtgcgcggaacccctatttgtttattttt
ctaaatacattcaaatatgtatccgctcatgagacaataaccctgataaatgcttcaataatat
tgaaaaaggaagagtATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATGACTTGGTTGA
GTACTCACCAGTCACAGAAAAGCATCTTACGGATGGCATGACAGTAAGAGAATTATGCAGTGCT
GCCATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCGGA
GCTGAATGAAGCCATACCAAACGACGAGCGTGACACCACGATGCCTGTAGCAATGGCAACAACG
TTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATA
GACAGATCGCTGAGATAGGTGCCTCACTGATTAAGCATTGGtaactgtcagaccaagtttactc
atatatactttagattgatttaaaacttcatttttaatttaaaaggatctaggtgaagatcctt
tttgataatctcatgaccaaaatcccttaacgtgagttttcgttccactgagcgtcagaccccg
tagaaaagatcaaaggatcttcttgagatcctttttttctgcgcgtaatctgctgcttgcaaac
aaaaaaaccaccgctaccagcggtggtttgtttgccggatcaagagctaccaactctttttccg
aaggtaactggcttcagcagagcgcagataccaaatactgtccttctagtgtagccgtagttag
gccaccacttcaagaactctgtagcaccgcctacatacctcgctctgctaatcctgttaccagt
ggctgctgccagtggcgataagtcgtgtcttaccgggttggactcaagacgatagttaccggat
aaggcgcagcggtcgggctgaacggggggttcgtgcacacagcccagcttggagcgaacgacct

FIG. 31 Cont.

```
acaccgaactgagatacctacagcgtgagctatgagaaagcgccacgcttcccgaagggagaaa
ggcggacaggtatccggtaagcggcagggtcggaacaggagagcgcacgagggagcttccaggg
ggaaacgcctggtatctttatagtcctgtcgggtttcgccacctctgacttgagcgtcgatttt
tgtgatgctcgtcaggggggcggagcctatggaaaaacgccagcaacgcggcctttttacggtt
cctggccttttgctggccttttgctcacatgttctttcctgcgttatcccctgattctgtggat
aaccgtattaccgcctttgagtgagctgataccgctcgccgcagccgaacgaccgagcgcagcg
agtcagtgagcgaggaagcggaagagcgcccaatacgcaaaccgcctctccccgcgcgttggcc
gattcattaatgcaggatccgggatcgaagaaatgatggtaaatgaaataggaaatcaaggagc
atgaaggcaaaagacaaatataagggtcgaacgaaaaataaagtgaaaagtgttgatatgatgt
atttggctttgcggcgccgaaaaaacgagtttacgcaattgcacaatcatgctgactctgtggc
ggacccgcgctcttgccggcccggcgataacgctgggcgtgaggctgtgcccggcggagttttt
tgcgcctgcattttccaaggtttaccctgcgctaagggcgagattggagaagcaataagaatg
ccggttggggttgcgatgatgacgaccacgacaactggtgtcattatttaagttgccgaaagaa
cctgagtgcatttgcaacatgagtatactagaagaatgagccaagacttgcgagacgcgagttt
gccggtggtgcgaacaatagagcgaccatgaccttgaaggtgagacgcgcataaccgctagagt
actttgaagaggaaacagcaatagggttgctaccagtataaatagacaggtacatacaacactg
gaaatggttgtctgtttgagtacgctttcaattcatttgggtgtgcactttattatgttacaat
atggaagggaactttacacttctcctatgcacatatattaattaaagtccaatgctagtagaga
agggggtaacacccctccgcgctcttttccgatttttttctaaaccgtggaatatttcggata
tccttttgttgtttccgggtgtacaatatggacttcctcttttctggcaaccaaacccatacat
cgggattcctataataccttcgttggtctccctaacatgtaggtggcggaggggagatatacaa
tagaacagataccagacaagacataatgggctaaacaagactacaccaattacactgcctcatt
gatg
//
```

FIG. 31 Cont.

434-2041: Gal4 DBD-TEV-Kin28-HAx3
434-874: Gal4 DBD (amino acids 1-147)
932-952: TEV cleavage sequence (ENLYFQG)
953-958: EcoRI
959-964: PuvII
969-974: NcoI
977-1894: Kin28 (cDNA)
1991-2080: trimeric HA Translation: Gal4 DBD-CTDx3-TEV-Kin28-HAx3
MKLLSSIEQACDICRLKKLKCSKEKPKCAKCLKNNWECRYSPKTKRSPLTRAHLTEVESR
LERLEQLFLLIFPREDLDMILKMDSLQDIKALLTGLFVQDNVNKDAVTDRLASVETDMPL
TLRQHRISATSSSEESSNKGQRQLTVSNYLFDDEDTPPNPKKEIELENLYFQGEFQLTTMA
MKVNMEYTKEKKVGEGTYAVVYLGCQHSTGRKIAIKEIKTSEFKDGLDMSAIREVKYLQE
MQHPNVIELIDIFMAYDNLNLVLEFLPTDLEVVIKDKSILFTPADIKAWMLMTLRGVYHC
HRNFILHRDLKPNNLLFSPDGQIKVADFGLARAIPAPHEILTSNVVTRWYRAPELLFGAK
HYTSAIDIWSVGVIFAELMLRIPYLPGQNDVDQMEVTFRALGTPTDRDWPEVSSFMTYNK
LQIYPPPSRDELRKRFIAASEYALDFMCGMLTMNPQKRWTAVQCLESDYFKELPPPSDPS
SIKIRNVMAIPGGGRIFYPYDVPDYAGYPYDVPDYAGSYPYDVPDYAAQCGRSS-N-WIP
RYRRPAEIYES-ILKNPASSLQLCIVHHLNFFHLYIVLPSFM-LYSSKFQSWPCNL-SIE
FFK-LELMPIFFLDLNS ; DNA sequence    pMK498 w/ TEV    8264   b.p.  complete sequence
;
gtggtacataacgaactaatactgtagccctagacttgatagccatcatcatatcgaagtttca
ctaccttttttccatttgccatctattgaagtaataataggcgcatgcaacttcttttcttttt
ttttcttttctctctccccgttgttgtctcaccatatccgcaatgacaaaaaaatgatggaag
acactaaaggaaaaaattaacgacaaagacagcaccaacagatgtcgttgttccagagctgatg
aggggtatctcgaagcacacgaaactttttccttccttcattgacctgcaattattaatctttt
gtttcctcgtcattgttctcgttccctttcttccttgtttctttttctgcacaatatttcaagc
tataccaagcatacaatcaactccaagcttgaagcaagcctcctgaaagATGAAGCTACTGTCT
TCTATCGAACAAGCATGCGATATTTGCCGACTTAAAAAGCTCAAGTGCTCCAAAGAAAAACCGA
AGTGCGCCAAGTGTCTGAAGAACAACTGGGAGTGTCGCTACTCTCCCAAAACCAAAAGGTCTCC
GCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAG
CATTGTTAACAGGATTATTTGTACAAGATAATGTGAATAAAGATGCCGTCACAGATAGATTGGC
TTCAGTGGAGACTGATATGCCTCTAACATTGAGACAGCATAGAATAAGTGCGACATCATCATCG
GAAGAGAGTAGTAACAAAGGTCAAAGACAGTTGACTGTATCGAACTATCTATTCGATGATGAAG
ATACCCCACCAAACCCAAAAAAAGAGATCGAATTggagaatttgtattttcagggcgaattcCA
GCTGACCACCATGGCAATGAAAGTGAATATGGAGTACACAAAGGAAAAGAAAGTTGGTGAGGGT
ACTTATGCGGTTGTTTACTTGGGTTGTCAACACTCTACTGGAAGAAAGATTGCTATTAAGGAGA
TCAAAACATCCGAATTTAAAGATGGTTTAGATATGTCAGCTATCCGTGAAGTTAAGTACCTCCA
AGAAATGCAGCATCCGAACGTCATAGAACTAATAGACATATTTATGGCTTATGATAATTTAAAT
CTCGTTCTGGAGTTCCTACCAACTGATCTAGAGGTGGTAATAAAAGACAAATCAATACTGTTTA
CACCAGCAGATATTAAGGCATGGATGCTTATGACTTTGAGGGGCGTGTATCATTGCCACAGAAA
TTTCATTTTGCACAGGGATCTGAAACCAAACAATTTATTATTTTCACCTGATGGCCAGATAAAA

FIG. 32

GTAGCAGATTTCGGTCTAGCAAGGGCGATACCGGCCCCACATGAGATACTGACAAGTAACGTCG
TAACAAGATGGTATAGAGCGCCAGAATTGTTGTTTGGAGCTAAACATTACACATCGGCTATTGA
TATCTGGTCAGTAGGCGTTATATTCGCGGAATTAATGCTAAGGATACCTTATTTACCAGGACAG
AATGATGTCGATCAAATGGAAGTAACGTTCAGGGCCTTAGGGACACCTACAGATAGAGATTGGC
CCGAAGTTTCTTCCTTTATGACGTATAACAAGTTACAAATATATCCGCCCCCTTCAAGAGATGA
ATTGAGGAAAAGGTTCATTGCTGCTAGCGAATACGCCTTAGATTTTATGTGTGGAATGCTAACG
ATGAACCCACAAAAGAGGTGGACCGCTGTTCAGTGTTTAGAAAGTGATTATTTCAAAGAATTAC
CACCACCAAGTGACCCGTCTTCAATAAAAATACGTAACgtcatggCAATTCCCGGtggcggccg
catcttttacccatacgatgttcctgactatgcgggctatccctatgacgtcccggactatgca
ggatcctatccatatgacgttccagattacgctgctcagtgcggccgctctagctagaactagt
ggatcccccgataCCGTCGACCTGCAGAGATCTAtgaatcgtagatactgaaaaaccccgcaag
ttcacttcaactgtgcatcgtgcaccatctcaatttctttcatttatacatcgttttgccttct
tttatgtaactatactcctctaagtttcaatcttggccatgtaacctctgatctatagaatttt
ttaaatgactagaattaatgcccatctttttttggacctaaattcttcatgaaaatatattac
gagggcttattcagaagctttggacttcttcgccagaggtttggtcaagtctccaatcaaggtt
gtcggcttgtctaccttgccagaaatttacgaaaagatggaaaagggtcaaatcgttggtagat
acgttgttgacacttctaaataagcgaatttcttatgatttatgatttttattattaaataagt
tataaaaaaaataagtgtatacaaattttaaagtgactcttaggttttaaaacgaaaattctta
ttcttgagtaactctttcctgtaggtcaggttgctttctcaggtatagcatgaggtcgctctta
ttgaccacacctctaccggcatgccgagcaaatgcctgcaaatcgctccccatttcacccaatt
gtagatatgctaactccagcaatgagttgatgaatctcggtgtgtattttatgtcctcagagga
caacacctgttgtaatcgttcttccacacggatcctggcgtaatagcgaagaggcccgcaccga
tcgcccttcccaacagttgcgcagcctgaatggcgaatggcgcctgatgcggtattttctcctt
acgcatctgtgcggtatttcacaccgcatatatcgctgggccattctcatgaagaatatcttga
atttattgtcatattactagttggtgtggaagtccatatatcggtgatcaatatagtggttgac
atgctggctagtcaacattgagccttttgatcatgcaaatatattacggtattttacaatcaaa
tatcaaacttaactattgactttataacttatttaggtggtaacattcttataaaaaagaaaaa
aattactgcaaaacagtactagcttttaacttgtatcctaggttatctatgctgtctcaccata
gagaatattacctatttcagaatgtatgtccatgattcgccgggtaaatacatataatacacaa
atctggcttaataaagtctataatatatctcataaagaagtgctaaattggctagtgctatata
tttttaagaaaatttcttttgactaagtccatatcgactttgtaaaagttcactttagcataca
tatattacacgagccagaaattgtaacttttgcctaaaatcacaaattgcaaaatttaattgct
tgcaaaaggtcacatgcttataatcaactttttttaaaaatttaaaatactttttttatttttttat
ttttaaacataaatgaaataatttatttattgtttatgattaccgaaacataaaacctgctcaa
gaaaaagaaactgttttgtccttggaaaaaaagcactacctaggagcggccaaaatgccgaggc
tttcatagcttaaactctttacagaaaataggcattatagatcagttcgagttttcttattctt
ccttccggttttatcgtcacagttttacagtaaataagtatcacctcttagagttcgatgataa
gctgtcaaacatgagaattaattccacatgttaaaatagtgaaggagcatgttcggcacacagt
ggaccgaacgtggggtaagtgcactagggtccggttaaacggatctcgcattgatgaggcaacg
ctaattatcaacatatagattgttatctatctgcatgaacacgaaatctttacttgacgacttg
aggctgatggtgtttatgcaaagaaaccactgtgtttaatatgtgtcactgtttgatattactg
tcagcgtagaagataatagtaaaagcggttaataagtgtatttgagataagtgtgataaagttt
ttacagcgaaaagacgataaatacaagaaaatgattacgaggatacggagagaggtatgtacat
gtgtatttatatactaagctgccggcggttgtttgcaagaccgagaaaaggctagcaagaatcg
ggtcattgtagcgtatgcgcctgtgaacattctcttcaacaagtttgattccattgcggtgaaa
tggtaaaagtcaaccccctgcgatgtatatttcctgtacaatcaatcaaaaagccaaatgatt
tagcattatctttacatcttgttattttacagattttatgtttagatcttttatgcttgctttt

FIG. 32 Cont.

caaaaggcttgcaggcaagtgcacaaacaatacttaaataaatactactcagtaataacctaTT
TCTTAGCATTTTTGACGAAATTTGCTATTTTGTTAGAGTCTTTTACACCATTTGTCTCCACACC
TCCGCTTACATCAACACCAATAACGCCATTTAATCTAAGCGCATCACCAACATTTTCTGGCGTC
AGTCCACCAGCTAACATAAAATGTAAGCTCTCGGGGCTCTCTTGCCTTCCAACCCAGTCAGAAA
TCGAGTTCCAATCCAAAAGTTCACCTGTCCCACCTGCTTCTGAATCAAACAAGGGAATAAACGA
ATGAGGTTTCTGTGAAGCTGCACTGAGTAGTATGTTGCAGTCTTTTGGAAATACGAGTCTTTTA
ATAACTGGCAAACCGAGGAACTCTTGGTATTCTTGCCACGACTCATCTCCATGCAGTTGGACGA
TATCAATGCCGTAATCATTGACCAGAGCCAAAACATCCTCCTTAGGTTGATTACGAAACACGCC
AACCAAGTATTTCGGAGTGCCTGAACTATTTTTATATGCTTTTACAAGACTTGAAATTTTCCTT
GCAATAACCGGGTCAATTGTTCTCTTTCTATTGGGCACACATATAATACCCAGCAAGTCAGCAT
CGGAATCTAGTGCACATTCTGCGGCCTCTGTGCTCTGCAAGCCGCAAACTTTCACCAATGGACC
AGAACTACCTGTGAAATTAATAACAGACATactccaagctgcctttgtgtgcttaatcacgtat
actcacgtgctcaatagtcaccaatgccctccctcttggccctctccttttcttttttcgaccg
aattaattcttgaagacgaaagggcctcgtgatacgcctatttttataggttaatgtcatgata
ataatggtttcttagacgtcaggtggcacttttcggggaaatgtgcgcggaacccctatttgtt
tatttttctaaatacattcaaatatgtatccgctcatgagacaataaccctgataaatgcttca
ataatattgaaaaaggaagagtATGAGTATTCAACATTTCCGTGTCGCCCTTATTCCCTTTTTT
GCGGCATTTTGCCTTCCTGTTTTTGCTCACCCAGAAACGCTGGTGAAAGTAAAAGATGCTGAAG
ATCAGTTGGGTGCACGAGTGGGTTACATCGAACTGGATCTCAACAGCGGTAAGATCCTTGAGAG
TTTTCGCCCCGAAGAACGTTTTCCAATGATGAGCACTTTTAAAGTTCTGCTATGTGGCGCGGTA
TTATCCCGTATTGACGCCGGGCAAGAGCAACTCGGTCGCCGCATACACTATTCTCAGAATGACT
TGGTTGAGTACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGATCGGAGGA
CCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGTAGCAATGGC
AACAACGTTGCGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGGCTGGT
TTATTGCTGATAAATCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGtaactgtcagaccaag
tttactcatatatactttagattgatttaaaacttcatttttaatttaaaaggatctaggtgaa
gatcctttttgataatctcatgaccaaaatcccttaacgtgagttttcgttccactgagcgtca
gaccccgtagaaaagatcaaaggatcttcttgagatcctttttttctgcgcgtaatctgctgct
tgcaaacaaaaaaaccaccgctaccagcggtggtttgtttgccggatcaagagctaccaactct
ttttccgaaggtaactggcttcagcagagcgcagataccaaatactgtccttctagtgtagccg
tagttaggccaccacttcaagaactctgtagcaccgcctacatacctcgctctgctaatcctgt
taccagtggctgctgccagtggcgataagtcgtgtcttaccgggttggactcaagacgatagtt
accggataaggcgcagcggtcgggctgaacggggggttcgtgcacacagcccagcttggagcga
acgacctacaccgaactgagatacctacagcgtgagctatgagaaagcgccacgcttcccgaag
ggagaaaggcggacaggtatccggtaagcggcagggtcggaacaggagagcgcacgagggagct
tccagggggaaacgcctggtatctttatagtcctgtcgggtttcgccacctctgacttgagcgt
cgatttttgtgatgctcgtcaggggggcggagcctatggaaaaacgccagcaacgcggcctttt
tacggttcctggccttttgctggccttttgctcacatgttctttcctgcgttatcccctgattc
tgtggataaccgtattaccgcctttgagtgagctgataccgctcgccgcagccgaacgaccgag
cgcagcgagtcagtgagcgaggaagcggaagagcgcccaatacgcaaaccgcctctccccgcgc
gttggccgattcattaatgcaggatccgggatcgaagaaatgatggtaaatgaaataggaaatc
aaggagcatgaaggcaaaagacaaatataagggtcgaacgaaaaataaagtgaaaagtgttgat

FIG. 32 Cont.

atgatgtatttggctttgcggcgccgaaaaaacgagtttacgcaattgcacaatcatgctgact
ctgtggcggacccgcgctcttgccggcccggcgataacgctgggcgtgaggctgtgcccggcgg
agtttttgcgcctgcattttccaaggtttaccctgcgctaaggggcgagattggagaagcaat
aagaatgccggttggggttgcgatgatgacgaccacgacaactggtgtcattatttaagttgcc
gaaagaacctgagtgcatttgcaacatgagtatactagaagaatgagccaagacttgcgagacg
cgagtttgccggtggtgcgaacaatagagcgaccatgaccttgaaggtgagacgcgcataaccg
ctagagtactttgaagaggaaacagcaatagggttgctaccagtataaatagacaggtacatac
aacactggaaatggttgtctgtttgagtacgctttcaattcatttgggtgtgcactttattatg
ttacaatatggaagggaactttacacttctcctatgcacatatattaattaaagtccaatgcta
gtagagaagggggggtaacacccctccgcgctcttttccgatttttttctaaaccgtggaatatt
tcggatatcctttttgttgtttccgggtgtacaatatggacttcctcttttctggcaaccaaacc
catacatcgggattcctataataccttcgttggtctccctaacatgtaggtggcggaggggaga
tatacaatagaacagataccagacaagacataatgggctaaacaagactacaccaattacactg
cctcattgatg
//

FIG. 32 Cont.

434-2104: Gal4 DBD-TEV-CTDx3-Kin28-HAx3
434-874: Gal4 DBD (amino acids 1-147)
932-952: TEV cleavage sequence (ENLYFQG)
962-1024: CTD (three tandem repeats of YSTPSPS)
1040-1957: Kin28 (cDNA)
1991-2080: trimeric HA Translation: Gal4 DBD-CTDx3-TEV-Kin28-HAx3
MKLLSSIEQACDICRLKKLKCSKEKPKCAKCLKNNWECRYSPKTKRSPLTRAHLTEVESRLERL
EQLFLLIFPREDLDMILKMDSLQDIKALLTGLFVQDNVNKDAVTDRLASVETDMPLTLRQHRIS
ATSSSEESSNKGQRQLTVSNYLFDDEDTPPNPKKEIELENLYFQGEFQYSPTSPSYSLTSPSYS
PTSPSLTTMAMKVNMEYTKEKKVGEGTYAVVYLGCQHSTGRKIAIKEIKTSEFKDGLDMSAIRE
VKYLQEMQHPNVIELIDIFMAYDNLNLVLEFLPTDLEVVIKDKSILFTPADIKAWMLMTLRGVY
HCHRNFILHRDLKPNNLLFSPDGQIKVADFGLARAIPAPHEILTSNVVTRWYRAPELLFGAKHY
TSAIDIWSVGVIFAELMLRIPYLPGQNDVDQMEVTFRALGTPTDRDWPEVSSFMTYNKLQIYPP
PSRDELRKRFIAASEYALDFMCGMLTMNPQKRWTAVQCLESDYFKELPPPSDPSSIKIRNVMAI
PGGGRIFYPYDVPDYAGYPYDVPDYAGSYPYDVPDYAAQCGRSS ; ### from DNA Strider Thursday, February 5, 2004 12:10:50 PM
; DNA sequence pMK500 w/ TEV 8330 b.p. complete sequence
;
gtggtacataacgaactaatactgtagccctagacttgatagccatcatcatatcgaagtttca
ctacccttttccatttgccatctattgaagtaataataggcgcatgcaacttcttttctttttt
ttttcttttctctctcccccgttgttgtctcaccatatccgcaatgacaaaaaatgatggaag
acactaaaggaaaaaattaacgacaaagacagcaccaacagatgtcgttgttccagagctgatg
aggggtatctcgaagcacacgaaactttttccttccttcattgacctgcaattattaatctttt
gtttcctcgtcattgttctcgttccctttcttccttgtttctttttctgcacaatatttcaagc
tataccaagcatacaatcaactccaagcttgaagcaagcctcctgaaagATGAAGCTACTGTCT
TCTATCGAACAAGCATGCGATATTTGCCGACTTAAAAAGCTCAAGTGCTCCAAAGAAAAACCGA
AGTGCGCCAAGTGTCTGAAGAACAACTGGGAGTGTCGCTACTCTCCCAAAACCAAAAGGTCTCC
GCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAG
CATTGTTAACAGGATTATTTGTACAAGATAATGTGAATAAAGATGCCGTCACAGATAGATTGGC
TTCAGTGGAGACTGATATGCCTCTAACATTGAGACAGCATAGAATAAGTGCGACATCATCATCG
GAAGAGAGTAGTAACAAAGGTCAAAGACAGTTGACTGTATCGAACTATCTATTCGATGATGAAG
ATACCCCACCAAACCCAAAAAAAGAGATCGAATTggagaatttgtattttcagggtGAATTCCA
Gtattcgccaactagtccttcgtattcgccaactagtccttcgtattcgccaactagtccttcg
CTGACCACCATGGCAATGAAAGTGAATATGGAGTACACAAAGGAAAAGAAAGTTGGTGAGGGTA
CTTATGCGGTTGTTTACTTGGGTTGTCAACACTCTACTGGAAGAAAGATTGCTATTAAGGAGAT
CAAAACATCCGAATTTAAAGATGGTTTAGATATGTCAGCTATCCGTGAAGTTAAGTACCTCCAA
GAAATGCAGCATCCGAACGTCATAGAACTAATAGACATATTTATGGCTTATGATAATTTAAATC
TCGTTCTGGAGTTCCTACCAACTGATCTAGAGGTGGTAATAAAAGACAAATCAATACTGTTTAC
ACCAGCAGATATTAAGGCATGGATGCTTATGACTTTGAGGGGCGTGTATCATTGCCACAGAAAT
TTCATTTTGCACAGGGATCTGAAACCAAACAATTTATTATTTTCACCTGATGGCCAGATAAAAG
TAGCAGATTTCGGTCTAGCAAGGGCGATACCGGCCCCACATGAGATACTGACAAGTAACGTCGT
AACAAGATGGTATAGAGCGCCAGAATTGTTGTTTGGAGCTAAACATTACACATCGGCTATTGAT
ATCTGGTCAGTAGGCGTTATATTCGCGGAATTAATGCTAAGGATACCTTATTTACCAGGACAGA

FIG. 33

ATGATGTCGATCAAATGGAAGTAACGTTCAGGGCCTTAGGGACACCTACAGATAGAGATTGGCC
CGAAGTTTCTTCCTTTATGACGTATAACAAGTTACAAATATATCCGCCCCCTTCAAGAGATGAA
TTGAGGAAAAGGTTCATTGCTGCTAGCGAATACGCCTTAGATTTTATGTGTGGAATGCTAACGA
TGAACCCACAAAAGAGGTGGACCGCTGTTCAGTGTTTAGAAAGTGATTATTTCAAAGAATTACC
ACCACCAAGTGACCCGTCTTCAATAAAAATACGTAACgtcatggCAATTCCCGGtggcggccgc
atcttttacccatacgatgttcctgactatgcgggctatccctatgacgtcccggactatgcag
gatcctatccatatgacgttccagattacgctgctcagtgcggccgctctagctagaactagtg
gatcccccgataCCGTCGACCTGCAGAGATCTAtgaatcgtagatactgaaaaaccccgcaagt
tcacttcaactgtgcatcgtgcaccatctcaatttctttcatttatacatcgttttgccttctt
ttatgtaactatactcctctaagtttcaatcttggccatgtaacctctgatctatagaatttt
taaatgactagaattaatgcccatctttttttggacctaaattcttcatgaaaatatattacg
agggcttattcagaagctttggacttcttcgccagaggtttggtcaagtctccaatcaaggttg
tcggcttgtctaccttgccagaaatttacgaaaagatggaaaagggtcaaatcgttggtagata
cgttgttgacacttctaaataagcgaatttcttatgatttatgattttattattaaataagtt
ataaaaaaaataagtgtatacaaattttaaagtgactcttaggttttaaaacgaaaattcttat
tcttgagtaactctttcctgtaggtcaggttgctttctcaggtatagcatgaggtcgctcttat
tgaccacacctctaccggcatgccgagcaaatgcctgcaaatcgctccccatttcacccaattg
tagatatgctaactccagcaatgagttgatgaatctcggtgtgtattttatgtcctcagaggac
aacacctgttgtaatcgttcttccacacggatcctggcgtaatagcgaagaggcccgcaccgat
cgcccttcccaacagttgcgcagcctgaatggcgaatggcgcctgatgcggtattttctcctta
cgcatctgtgcggtatttcacaccgcatatatcgctgggccattctcatgaagaatatcttgaa
tttattgtcatattactagttggtgtggaagtccatatatcggtgatcaatatagtggttgaca
tgctggctagtcaacattgagccttttgatcatgcaaatatattacggtattttacaatcaaat
atcaaacttaactattgactttataacttatttaggtggtaacattcttataaaaagaaaaaa
attactgcaaaacagtactagcttttaacttgtatcctaggttatctatgctgtctcaccatag
agaatattacctatttcagaatgtatgtccatgattcgccgggtaaatacatataatacacaaa
tctggcttaataaagtctataatatatctcataaagaagtgctaaattggctagtgctatatat
ttttaagaaaatttcttttgactaagtccatatcgactttgtaaaagttcactttagcatacat
atattacacgagccagaaattgtaactttgcctaaaatcacaaattgcaaaatttaattgctt
gcaaaaggtcacatgcttataatcaactttttaaaaatttaaaatactttttatttttatt
tttaaacataaatgaaataatttatttattgtttatgattaccgaaacataaaacctgctcaag
aaaaagaaactgttttgtccttggaaaaaaagcactacctaggagcggccaaaatgccgaggct
ttcatagcttaaactctttacagaaaataggcattatagatcagttcgagttttcttattcttc
cttccggttttatcgtcacagttttacagtaaataagtatcacctcttagagttcgatgataag
ctgtcaaacatgagaattaattccacatgttaaaatagtgaaggagcatgttcggcacacagtg
gaccgaacgtggggtaagtgcactagggtccggttaaacggatctcgcattgatgaggcaacgc
taattatcaacatatagattgttatctatctgcatgaacacgaaatctttacttgacgacttga
ggctgatggtgtttatgcaaagaaaccactgtgtttaatatgtgtcactgtttgatattactgt
cagcgtagaagataatagtaaaagcggttaataagtgtatttgagataagtgtgataaagtttt
tacagcgaaaagacgataaatacaagaaaatgattacgaggatacggagagaggtatgtacatg
tgtatttatatactaagctgccggcggttgtttgcaagaccgagaaaaggctagcaagaatcgg
gtcattgtagcgtatgcgcctgtgaacattctcttcaacaagtttgattccattgcggtgaaat
ggtaaaagtcaacccccctgcgatgtatatttcctgtacaatcaatcaaaaagccaaatgattt
agcattatctttacatcttgttattttacagattttatgtttagatcttttatgcttgctttc
aaaaggcttgcaggcaagtgcacaaacaatacttaaataaatactactcagtaataacctaTTT
CTTAGCATTTTTGACGAAATTTGCTATTTTGTTAGAGTCTTTTACACCATTTGTCTCCACACCT
CCGCTTACATCAACACCAATAACGCCATTTAATCTAAGCGCATCACCAACATTTTCTGGCGTCA

FIG. 33 Cont.

GTCCACCAGCTAACATAAAATGTAAGCTCTCGGGGCTCTCTTGCCTTCCAACCCAGTCAGAAAT
CGAGTTCCAATCCAAAAGTTCACCTGTCCCACCTGCTTCTGAATCAAACAAGGGAATAAACGAA
TGAGGTTTCTGTGAAGCTGCACTGAGTAGTATGTTGCAGTCTTTTGGAAATACGAGTCTTTTAA
TAACTGGCAAACCGAGGAACTCTTGGTATTCTTGCCACGACTCATCTCCATGCAGTTGGACGAT
ATCAATGCCGTAATCATTGACCAGAGCCAAAACATCCTCCTTAGGTTGATTACGAAACACGCCA
ACCAAGTATTTCGGAGTGCCTGAACTATTTTTATATGCTTTTACAAGACTTGAAATTTTCCTTG
CAATAACCGGGTCAATTGTTCTCTTTCTATTGGGCACACATATAATACCCAGCAAGTCAGCATC
GGAATCTAGTGCACATTCTGCGGCCTCTGTGCTCTGCAAGCCGCAAACTTTCACCAATGGACCA
GAACTACCTGTGAAATTAATAACAGACATactccaagctgcctttgtgtgcttaatcacgtata
ctcacgtgctcaatagtcaccaatgccctccctcttggccctctcctttttcttttttcgaccga
attaattcttgaagacgaaagggcctcgtgatacgcctatttttataggttaatgtcatgataa
taatggtttcttagacgtcaggtggcacttttcggggaaatgtgcgcggaacccctatttgttt
atttttctaaatacattcaaatatgtatccgctcatgagacaataaccctgataaatgcttcaa
taatattgaaaaaggaagagtATGAGTATTCAACATTTCCGTGTCGCCCTTATTCCCTTTTTTG
CGGCATTTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGAGAGT
TTTCGCCCCGAAGAACGTTTTCCAATGATGAGCACTTTTAAAGTTCTGCTATGTGGCGCGGTAT
TATCCCGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTTGGGA
ACCGGAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTAATAG
ACTGGATGGAGGCGGATAAAGTTGCAGGACCACTTCTGCGCTCGGCCCTTCCGGCTGGCTGGTT
TATTGCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGATGAAC
GAAATAGACAGATCGCTGAGATAGGTGCCTCACTGATTAAGCATTGGtaactgtcagaccaagt
ttactcatatatactttagattgatttaaaacttcatttttaatttaaaaggatctaggtgaag
atcctttttgataatctcatgaccaaaatcccttaacgtgagttttcgttccactgagcgtcag
accccgtagaaaagatcaaaggatcttcttgagatcctttttttctgcgcgtaatctgctgctt
gcaaacaaaaaaaccaccgctaccagcggtggtttgtttgccggatcaagagctaccaactctt
tttccgaaggtaactggcttcagcagagcgcagataccaaatactgtccttctagtgtagccgt
agttaggccaccacttcaagaactctgtagcaccgcctacatacctcgctctgctaatcctgtt
accagtggctgctgccagtggcgataagtcgtgtcttaccgggttggactcaagacgatagtta
ccggataaggcgcagcggtcgggctgaacggggggttcgtgcacacagcccagcttggagcgaa
cgacctacaccgaactgagatacctacagcgtgagctatgagaaagcgccacgcttcccgaagg
gagaaaggcggacaggtatccggtaagcggcagggtcggaacaggagagcgcacgagggagctt
ccagggggaaacgcctggtatctttatagtcctgtcgggtttcgccacctctgacttgagcgtc
gatttttgtgatgctcgtcaggggggcggagcctatggaaaaacgccagcaacgcggcctttttt
acggttcctggccttttgctggccttttgctcacatgttctttcctgcgttatcccctgattct
gtggataaccgtattaccgcctttgagtgagctgataccgctcgccgcagccgaacgaccgagc
gcagcgagtcagtgagcgaggaagcggaagagcgcccaatacgcaaaccgcctctccccgcgcg
ttggccgattcattaatgcaggatccgggatcgaagaaatgatggtaaatgaaataggaaatca
aggagcatgaaggcaaaagacaaatataagggtcgaacgaaaaataaagtgaaaagtgttgata
tgatgtatttggctttgcggcgccgaaaaaacgagtttacgcaattgcacaatcatgctgactc
tgtggcggacccgcgctcttgccggcccggcgataacgctgggcgtgaggctgtgcccggcgga
gtttttgcgcctgcattttccaaggtttaccctgcgctaaggggcgagattggagaagcaata

FIG. 33 Cont.

agaatgccggttggggttgcgatgatgacgaccacgacaactggtgtcattatttaagttgccg
aaagaacctgagtgcatttgcaacatgagtatactagaagaatgagccaagacttgcgagacgc
gagtttgccggtggtgcgaacaatagagcgaccatgaccttgaaggtgagacgcgcataaccgc
tagagtactttgaagaggaaacagcaatagggttgctaccagtataaatagacaggtacataca
acactggaaatggttgtctgtttgagtacgctttcaattcatttgggtgtgcactttattatgt
tacaatatggaagggaactttacacttctcctatgcacatatattaattaaagtccaatgctag
tagagaagggggtaacacccctccgcgctcttttccgatttttttctaaaccgtggaatattt
cggatatccttttgttgtttccgggtgtacaatatggacttcctcttttctggcaaccaaaccc
atacatcgggattcctataataccttcgttggtctccctaacatgtaggtggcggaggggagat
atacaatagaacagataccagacaagacataatgggctaaacaagactacaccaattacactgc
ctcattgatg
//

FIG. 33 Cont.

434-2104: Gal4 DBD-TEV-CTDx3-Kin28-HAx3
434-874: Gal4 DBD (amino acids 1-147)
932-952: TEV cleavage sequence (ENLYFQG)
962-1024: CTD (three tandem repeats of YSTPSPS)
1040-1957: Kin28 (cDNA) with E54Q mutation
1991-2080: trimeric HA Translation: Gal4 DBD-CTDx3-TEV-Kin28-HAx3
MKLLSSIEQACDICRLKKLKCSKEKPKCAKCLKNNWECRYSPKTKRSPLTRAHLTEVESRLERL
EQLFLLIFPREDLDMILKMDSLQDIKALLTGLFVQDNVNKDAVTDRLASVETDMPLTLRQHRIS
ATSSSEESSNKGQRQLTVSNYLFDDEDTPPNPKKEIELENLYFQGEFQYSPTSPSYSLTSPSYS
PTSPSLTTMAMKVNMEYTKEKKVGEGTYAVVYLGCQHSTGRKIAIKEIKTSEFKDGLDMSAIRQ
VKYLQEMQHPNVIELIDIFMAYDNLNLVLEFLPTDLEVVIKDKSILFTPADIKAWMLMTLRGVY
HCHRNFILHRDLKPNNLLFSPDGQIKVADFGLARAIPAPHEILTSNVVTRWYRAPELLFGAKHY
TSAIDIWSVGVIFAELMLRIPYLPGQNDVDQMEVTFRALGTPTDRDWPEVSSFMTYNKLQIYPP
PSRDELRKRFIAASEYALDFMCGMLTMNPQKRWTAVQCLESDYFKELPPPSDPSSIKIRNVMAI
PGGGRIFYPYDVPDYAGYPYDVPDYAGSYPYDVPDYAAQCGRSS ; ### from DNA Strider Thursday, February 5, 2004 12:10:50 PM
; DNA sequence pMK502 w/ TEV 8330 b.p. complete sequence
;
gtggtacataacgaactaatactgtagccctagacttgatagccatcatcatatcgaagtttca
ctacccttttccatttgccatctattgaagtaataataggcgcatgcaacttcttttcttttt
ttttctttctctctcccccgttgttgtctcaccatatccgcaatgacaaaaaaatgatggaag
acactaaaggaaaaaattaacgacaaagacagcaccaacagatgtcgttgttccagagctgatg
aggggtatctcgaagcacacgaaactttttccttccttcattgacctgcaattattaatctttt
gtttcctcgtcattgttctcgttccctttcttccttgtttctttttctgcacaatatttcaagc
tataccaagcatacaatcaactccaagcttgaagcaagcctcctgaaagATGAAGCTACTGTCT
TCTATCGAACAAGCATGCGATATTTGCCGACTTAAAAAGCTCAAGTGCTCCAAAGAAAAACCGA
AGTGCGCCAAGTGTCTGAAGAACAACTGGGAGTGTCGCTACTCTCCCAAAACCAAAAGGTCTCC
GCTGACTAGGGCACATCTGACAGAAGTGGAATCAAGGCTAGAAAGACTGGAACAGCTATTTCTA
CTGATTTTTCCTCGAGAAGACCTTGACATGATTTTGAAAATGGATTCTTTACAGGATATAAAAG
CATTGTTAACAGGATTATTTGTACAAGATAATGTGAATAAAGATGCCGTCACAGATAGATTGGC
TTCAGTGGAGACTGATATGCCTCTAACATTGAGACAGCATAGAATAAGTGCGACATCATCATCG
GAAGAGAGTAGTAACAAAGGTCAAAGACAGTTGACTGTATCGAACTATCTATTCGATGATGAAG
ATACCCCACCAAACCCAAAAAAAGAGATCGAATTggagaatttgtattttcagggtGAATTCCA
Gtattcgccaactagtccttcgtattcgccaactagtccttcgtattcgccaactagtccttcg
CTGACCACCATGGCAATGAAAGTGAATATGGAGTACACAAAGGAAAAGAAAGTTGGTGAGGGTA
CTTATGCGGTTGTTTACTTGGGTTGTCAACACTCTACTGGAAGAAAGATTGCTATTAAGGAGAT
CAAAACATCCGAATTTAAAGATGGTTTAGATATGTCAGCTATCCGTCAACTTAAGTACCTCCAA
GAAATGCAGCATCCGAACGTCATAGAACTAATAGACATATTTATGGCTTATGATAATTTAAATC
TCGTTCTGGAGTTCCTACCAACTGATCTAGAGGTGGTAATAAAAGACAAATCAATACTGTTTAC
ACCAGCAGATATTAAGGCATGGATGCTTATGACTTTGAGGGGCGTGTATCATTGCCACAGAAAT
TTCATTTTGCACAGGGATCTGAAACCAAACAATTTATTATTTTCACCTGATGGCCAGATAAAAG
TAGCAGATTTCGGTCTAGCAAGGGCGATACCGGCCCCACATGAGATACTGACAAGTAACGTCGT

FIG. 34

AACAAGATGGTATAGAGCGCCAGAATTGTTGTTTGGAGCTAAACATTACACATCGGCTATTGAT
ATCTGGTCAGTAGGCGTTATATTCGCGGAATTAATGCTAAGGATACCTTATTTACCAGGACAGA
ATGATGTCGATCAAATGGAAGTAACGTTCAGGGCCTTAGGGACACCTACAGATAGAGATTGGCC
CGAAGTTTCTTCCTTTATGACGTATAACAAGTTACAAATATATCCGCCCCCTTCAAGAGATGAA
TTGAGGAAAAGGTTCATTGCTGCTAGCGAATACGCCTTAGATTTTATGTGTGGAATGCTAACGA
TGAACCCACAAAAGAGGTGGACCGCTGTTCAGTGTTTAGAAAGTGATTATTTCAAAGAATTACC
ACCACCAAGTGACCCGTCTTCAATAAAAATACGTAACgtcatggCAATTCCCGGtggcggccgc
atcttttacccatacgatgttcctgactatgcgggctatccctatgacgtcccggactatgcag
gatcctatccatatgacgttccagattacgctgctcagtgcggccgctctagctagaactagtg
gatcccccgataCCGTCGACCTGCAGAGATCTAtgaatcgtagatactgaaaaaccccgcaagt
tcacttcaactgtgcatcgtgcaccatctcaatttctttcatttatacatcgttttgccttctt
ttatgtaactatactcctctaagtttcaatcttggccatgtaacctctgatctatagaatttttt
taaatgactagaattaatgcccatcttttttttggacctaaattcttcatgaaaatatattacg
agggcttattcagaagctttggacttcttcgccagaggtttggtcaagtctccaatcaaggttg
tcggcttgtctaccttgccagaaatttacgaaaagatggaaaagggtcaaatcgttggtagata
cgttgttgacacttctaaataagcgaatttcttatgatttatgatttttattattaaataagtt
ataaaaaaaataagtgtatacaaattttaaagtgactcttaggttttaaaacgaaaattcttat
tcttgagtaactctttcctgtaggtcaggttgctttctcaggtatagcatgaggtcgctcttat
tgaccacacctctaccggcatgccgagcaaatgcctgcaaatcgctccccatttcacccaattg
tagatatgctaactccagcaatgagttgatgaatctcggtgtgtattttatgtcctcagaggac
aacacctgttgtaatcgttcttccacacggatcctggcgtaatagcgaagaggcccgcaccgat
cgcccttcccaacagttgcgcagcctgaatggcgaatggcgcctgatgcggtattttctcctta
cgcatctgtgcggtatttcacaccgcatatatcgctgggccattctcatgaagaatatcttgaa
tttattgtcatattactagttggtgtggaagtccatatatcggtgatcaatatagtggttgaca
tgctggctagtcaacattgagcctttttgatcatgcaaatatattacggtattttacaatcaaat
atcaaacttaactattgactttataacttatttaggtggtaacattcttataaaaaagaaaaaa
attactgcaaaacagtactagcttttaacttgtatcctaggttatctatgctgtctcaccatag
agaatattacctatttcagaatgtatgtccatgattcgccgggtaaatacatataatacacaaa
tctggcttaataaagtctataatatatctcataaagaagtgctaaattggctagtgctatatat
ttttaagaaaatttcttttgactaagtccatatcgactttgtaaaagttcactttagcatacat
atattacacgagccagaaattgtaactttgcctaaaatcacaaattgcaaaatttaattgctt
gcaaaaggtcacatgcttataatcaactttttttaaaatttaaaatactttttttatttttttatt
tttaaacataaatgaaataatttatttattgtttatgattaccgaaacataaaacctgctcaag
aaaaagaaactgttttgtccttggaaaaaaagcactacctaggagcggccaaaatgccgaggct
ttcatagcttaaactctttacagaaaataggcattatagatcagttcgagtttttcttattcttc
cttccggttttatcgtcacagttttacagtaaataagtatcacctcttagagttcgatgataag
ctgtcaaacatgagaattaattccacatgttaaaatagtgaaggagcatgttcggcacacagtg
gaccgaacgtggggtaagtgcactagggtccggttaaacggatctcgcattgatgaggcaacgc
taattatcaacatatagattgttatctatctgcatgaacacgaaatctttacttgacgacttga
ggctgatggtgtttatgcaaagaaaccactgtgtttaatatgtgtcactgtttgatattactgt
cagcgtagaagataatagtaaaagcggttaataagtgtatttgagataagtgtgataaagtttt
tacagcgaaaagacgataaatacaagaaaatgattacgaggatacggagagaggtatgtacatg
tgtatttatatactaagctgccggcggttgtttgcaagaccgagaaaaggctagcaagaatcgg
gtcattgtagcgtatgcgcctgtgaacattctcttcaacaagtttgattccattgcggtgaaat
ggtaaaagtcaaccccctgcgatgtatatttcctgtacaatcaatcaaaaagccaaatgattt
agcattatctttacatcttgttattttacagattttatgtttagatcttttatgcttgctttttc
aaaaggcttgcaggcaagtgcacaaacaatacttaaataaatactactcagtaataacctaTTT

FIG. 34 Cont.

tgtggcggacccgcgctcttgccggcccggcgataacgctgggcgtgaggctgtgcccggcgga
gtttttgcgcctgcattttccaaggtttaccctgcgctaaggggcgagattggagaagcaata
agaatgccggttggggttgcgatgatgacgaccacgacaactggtgtcattatttaagttgccg
aaagaacctgagtgcatttgcaacatgagtatactagaagaatgagccaagacttgcgagacgc
gagtttgccggtggtgcgaacaatagagcgaccatgaccttgaaggtgagacgcgcataaccgc
tagagtactttgaagaggaaacagcaatagggttgctaccagtataaatagacaggtacataca
acactggaaatggttgtctgtttgagtacgctttcaattcatttgggtgtgcactttattatgt
tacaatatggaagggaactttacacttctcctatgcacatatattaattaaagtccaatgctag
tagagaagggggtaacacccctccgcgctcttttccgatttttttctaaaccgtggaatattt
cggatatccttttgttgtttccgggtgtacaatatggacttcctcttttctggcaaccaaaccc
atacatcgggattcctataataccttcgttggtctccctaacatgtaggtggcggaggggagat
atacaatagaacagataccagacaagacataatgggctaaacaagactacaccaattacactgc
ctcattgatg
//

FIG. 34 Cont.

AUTOCATALYSIS/YEAST TWO-HYBRID ASSAY

This application for patent under 35 U.S.C. § 111(a) claims priority to Provisional Applications Ser. Nos. 60/482,188 filed on Jun. 24, 2003 and 60/448,068 filed on Feb. 18, 2003 under 35 U.S.C. § 111(b).

This invention was funded in part by a grant from the National Institutes of Heath, grant number NIH-RO1 GM62282 to M-H Kuo. The Government may have certain rights in this invention.

FIELD OF THE INVENTION

The present invention is related to an improved assay system wherein protein-protein interactions that require specific post-translational modifications, or are inhibited by specific post-translational modifications of the relevant proteins can be detected.

BACKGROUND

Protein-protein interactions are fundamental to proteomics (proteomics can be defined as the qualitative and quantitative studies of the proteome, the protein products of a species genome). Proteins are the most abundant and versatile macromolecules in living systems and serve crucial functions in essentially all biological processes. Proteins may perform structural, transport, protective, catalytic, sensory, neuro-transmitting, regulatory and many other functions. Though versatile as they are, considering the complexity of even the simplest life form, it is not surprising that proteins rarely function by themselves. Rather, they interact with other proteins and molecules. In the proteomic and genomic era, it has become clear to researchers that what constitutes a cell is the collective effort of these proteins whose functions are key to normal development and differentiation. Protein-protein interactions are fundamental to the understanding of biology, disease and even life itself.

In order to understand the normal biological processes and the diseases resulting from breakdown of normal functioning of proteins, it is important to study protein interactions. In the last twenty years science has made significant progress in the study of protein-protein interactions. The techniques developed include protein precipitation, transfection of suspected interacting proteins into host cells, in vitro biochemical analyses and yeast two-hybrid screening.

Thus far, the most versatile genetic system for screening and testing protein-protein interactions is the yeast two-hybrid (Y2H) system (Fields, S., and O. Song, "A novel genetic system to detect protein-protein interactions" *Nature* 340:245-246, 1989; U.S. Pat. Nos. 5,283,273, 5,468,614 and 5,667,973). Currently, it is estimated that there are at least 10,000 interactions among the 6,000 proteins in yeast (Uetz, P., "Two-hybrid arrays" *Curr Opin Chem Biol* 6:57-62, 2002). The actual number of protein-protein interactions is probably much higher, because the two proteins, bait and prey, studied by the Y2H method are not designed to be modified (see below) in any way. Thus, protein-protein interactions that require either interacting protein to be chemically modified will escape the detection by the Y2H method.

Post-translational modifications, or PTMs, refer to the specific chemical moieties added to target amino acid residues of proteins after the latter are synthesized (translated). Numerous proteins contain specific PTMs that are critical for their functions. PTMs may activate or inactivate the recipient proteins. Certain PTMs may flag the modified proteins for degradation or transport to selective intra- or extra-cellular destiny. Many more PTMs perform yet to be identified functions. Common PTMs include acetylation, phosphorylation, methylation, ubiquitylation, glycosylation, etc. Frequently, these PTMs are indispensable for the functions of the recipient proteins. However, in most cases, it is not known exactly what these PTMs do at a molecular level. One well-thought idea is that specific PTMs create new interface for protein-protein interactions. Some of these interactions may occur only after one of the two interacting partners is modified at a particular amino acid residue(s). For example, the well-conserved Phospho Tyrosine Binding (PTB) motif interacts with proteins that are phosphorylated at various tyrosine residues. The bromodomain that is shared by many transcriptional activators binds histones that are acetylated (Dhalluin, C., et al., "Structure and ligand of a histone acetyltransferase bromodomain" *Nature* 399:491-496, 1999; Jacobson, R. H., et al., "Structure and function of a human TAFII250 double bromodomain module" *Science* 288:1422-1425, 2000). In contrast, it is equally possible that existing protein-protein interactions may be inhibited if one of the two interacting proteins receives a particular modification. For example, the Silent Information Regulator protein Sir3 binds only to unacetylated histones for transcriptional repression (Edmondson, D. G., M. M. Smith, and S. Y. Roth, "Repression domain of the yeast global repressor Tup1 interacts directly with histones H3 and H4" *Genes Dev* 10:1247-1259). Acetylation of the histones antagonizes the function of Sir3 and leads to transcriptional de-silencing of the underlying genes (Carmen, et al., "Acetylation of the yeast histone H4 N terminus regulates its binding to heterochromatin protein SIR3" *J Biol Chem* 277:4778-81, 2002). These biochemical data support the idea that PTMs may positively or negatively regulate protein-protein interactions. However, these reports only represent sporadic examples of such regulation. In other words, to understand how PTMs regulate protein-protein interactions at a global and proteomic scale, a non-biased genetic method is needed.

In light of the primal importance of the possible effects of PTMs on protein-protein interactions, several groups independently reported a common strategy with which these authors were able to detect protein-protein interactions induced by specific phosphorylation (Cao, H., W. E. Courchesne, and C. C. Mastick, "A phosphotyrosine-dependent protein interaction screen reveals a role for phosphorylation of caveolin-1 on tyrosine 14: recruitment of C-terminal Src kinase" *J Biol Chem* 277:8771-8774, 2002; Shaywitz, A. J., S. L. Dove, M. E. Greenberg, and A. Hochschild, "Analysis of phosphorylation-dependent protein-protein interactions using a bacterial two-hybrid system" *Sci STKE* 2002:L11, 2002; Yamada, M., et al., "Analysis of tyrosine phosphorylation-dependent protein-protein interactions in TrkB-mediated intracellular signaling using modified yeast two-hybrid system" *J Biochem* (Tokyo) 130:157-65, 2001). In each case, kinases were expressed in the two-hybrid reporter cells that normally lack such enzyme systems. The bait proteins produced in these cells are thus modified by the foreign enzymes. For example, a tyrosine kinase and a serine/threonine kinase were expressed in yeast Shaywitz, A. J., S. L. Dove, M. E. Greenberg, and A. Hochschild, "Analysis of phosphorylation-dependent protein-protein interactions using a bacterial two-hybrid system" *Sci STKE* 2002:L11, 2002; Yamada, M., et al., "Analysis of tyrosine phosphorylation-dependent protein-protein interactions in TrkB-mediated intracellular signaling using modified yeast two-hybrid system" *J Biochem* (Tokyo)

130:157-65, 2001) and *E. coli* (Cao, H., W. E. Courchesne, and C. C. Mastick, "A phosphotyrosine-dependent protein interaction screen reveals a role for phosphorylation of caveolin-1 on tyrosine 14: recruitment of C-terminal Src kinase" *J Biol Chem* 277:8771-8774, 2002), respectively. The substrate proteins, existing in the form of two-hybrid baits, were shown to be phosphorylated in vivo and consequently allowed the detection of interactions involving protein phosphorylation Yamada, M., et al., "Analysis of tyrosine phosphorylation-dependent protein-protein interactions in TrkB-mediated intracellular signaling using modified yeast two-hybrid system" *J Biochem* (Tokyo) 130:157-65, 2001).

The above methods rely on the typical enzyme-substrate reactions occurring in trans (i.e., between two distinct proteins) to create the baits for genetic selection. Therefore, one concern is whether the efficiency of the bait modification would be sufficient to surpass the level of the unmodified bait, permitting a high signal-to-noise ratio in the genetic screen. To avoid this potential problem, one may choose to over-produce the foreign enzyme. However, such treatment may result in uncontrolled enzymatic action on host proteins, leading to cellular toxicity.

Unfortunately, there is not any method that enables researchers to screen for such interactions in a global, non-biased manner. Therefore, what is needed is an assay system that enables researchers to detect protein-protein interactions that are dependent upon or inhibited by post-translational modifications.

SUMMARY OF THE INVENTION

The AC/Y2H system of the present invention offers two major advantages over present technologies. In one embodiment the enzyme is expressed in its natural host where the opposing enzymes (i.e., HDACs) are present. Pleiotropic effect is less likely. On the other hand, the desired catalysis is most likely carried out in cis, and is dominant over the endogenous HDAC trans-activity, leading to a constitutive modification of the bait. Moreover, the use of the catalytically inactivated enzyme in a parallel, counter screen will allow fast identification of protein interactions disrupted by selective PTMs. A reversal in the genetic screening criteria can reveal protein interactions that are perturbed by a specific PTM.

A simple modification of the current AC/Y2H constructs may identify other proteins that recognize different histone modifications or different modifications of other proteins. For example, in one embodiment, a substitution of the HAT with other histone modifying enzymes such as, for example, kinases (see, for example, Table 2) will create AC baits containing the corresponding modifications. AC/Y2H can thus be used to identify the cognate binding factors. It this way, it is contemplated that the present invention can detect the PTMs of other proteins that may be subjected to similar studies.

In one embodiment, the present invention contemplates a compound, comprising a) a first amino acid sequence comprising at least a portion of a histone amino terminal tail, said first amino acid sequence linked to b) a second amino acid sequence comprising at least a portion of a histone acetyltransferase. In another embodiment, the present invention contemplates that the second amino acid sequence comprises the active catalytic domain of Gcn5 (see, for example, FIG. 20, [SEQ ID NO: 23] from plasmid pDG28 [SEQ ID NO: 9] and FIG. 22, [SEQ ID NO: 25] from plasmid pDG30 [SEQ ID NO: 11]). In yet another embodiment, the present invention contemplates that the second amino acid sequence comprises a catalytically inactive portion of Gcn5 (see, for example, FIG. 21, [SEQ ID NO: 24] from plasmid pDG29 [SEQ ID NO: 10] and FIG. 23, [SEQ ID NO: 26] from plasmid pDG31 [SEQ ID NO: 12]). In still yet another embodiment, the present invention contemplates that the first amino acid sequence comprises the histone H3 tail (see, for example, FIG. 12, pDG1 [SEQ ID NO: 15]; FIG. 13, pDG2 [SEQ ID NO: 16]; FIG. 16, pDG5 [SEQ ID NO: 19] and; FIG. 17, pDG6 [SEQ ID NO: 20]). In still yet another embodiment, the present invention contemplates that the first amino acid sequence comprises the histone H4 tail (amino acids 1-29) (see, for example, FIG. 14, pDG3 [SEQ ID NO: 17]; FIG. 15, pDG4 [SEQ ID NO: 18]; FIG. 18, pDG7 [SEQ ID NO: 21] and; FIG. 19, pDG8 [SEQ ID NO: 22]). In still yet another embodiment, the present invention contemplates that the compound comprises a fusion protein. In still yet another embodiment, the present invention contemplates that the compound exhibits autoacetylation. In still yet another embodiment, the present invention contemplates that the compound further comprises a DNA binding moiety. In still yet another embodiment, the present invention contemplates that the DNA binding moiety is linked to said first amino acid sequence. In still yet another embodiment, the present invention contemplates that the DNA binding moiety comprises the Gal4 DNA binding domain. In still yet another embodiment, the present invention contemplates that the compound further comprises a detectable moiety linked to said second amino acid sequence. In still yet another embodiment, the present invention contemplates that the detectable moiety comprises an epitope.

In one embodiment, the present invention contemplates a nucleic acid encoding the fusion protein of the present invention. In another embodiment, the present invention contemplates an expression vector comprising the nucleic acid. In yet another embodiment, the present invention contemplates yeast transformed with the expression vector. In still yet another embodiment, the present invention contemplates a whole cell extract of the yeast.

In one embodiment, the present invention contemplates a method for detecting protein-protein interactions, said interactions requiring a post translational modification of one of the said proteins, said method comprising: (a) providing a host cell comprising a detectable gene wherein the detectable gene expresses a detectable protein when the detectable gene is activated by an amino acid sequence including a transcriptional activation domain when the transcriptional activation domain is in sufficient proximity to the detectable gene; (b) providing a first chimeric gene that is capable of being expressed in the host cell, the first chimeric gene comprising a DNA sequence that encodes a first hybrid protein, the first hybrid protein comprising: (i) a DNA-binding moiety that recognizes a binding site on the detectable gene in the host cell; (ii) a first test protein or fragment thereof, comprising a reactive moiety capable of being modified through catalysis, that is to be tested for interaction with at least one second test protein or fragment thereof; and (iii) a catalytic moiety that is capable of catalyzing said first test protein; (c) providing a second chimeric gene that is capable of being expressed in the host cell, the second chimeric gene comprising a DNA sequence that encodes a second hybrid protein, the second hybrid protein comprising: (i) the transcriptional activation domain; and (ii) a second test protein or fragment thereof that is to be tested for interaction with the first test protein or fragment thereof when said first test protein has been modified by the catalysis of said reactive moiety to create a modified first test protein;

wherein interaction between the first modified test protein and the second test protein in the host cell causes the transcriptional activation domain to activate transcription of the detectable gene; (d) introducing the first chimeric gene and the second chimeric gene into the host cell; (e) subjecting the host cell to conditions under which the first hybrid protein and the second hybrid protein are expressed in sufficient quantity for the detectable gene to be activated; and (f) determining whether the detectable gene has been expressed to a degree greater than expression in the absence of an interaction between the first test protein and the second test protein.

In another embodiment, the present invention contemplates a method, wherein said binding DNA-moiety comprises GDBD; said catalytic moiety comprises the catalytic domain of Gcn5 and; said reactive moiety comprises a histone amino terminal tail capable of being acetylated by Gcn5. In yet another embodiment, the present invention contemplates a method, wherein said first test protein and said second test protein are encoded on a library of plasmids containing DNA inserts, derived from the group consisting of genomic DNA, cDNA and synthetically generated DNA. In still yet another embodiment, the present invention contemplates a method, wherein first test protein and said second test protein are derived from derived from the group consisting of bacterial protein, viral protein, oncogene-encoded protein, mammalian protein, fungal protein and plant protein.

In one embodiment, the present invention contemplates that the a compound, comprising a) a first amino acid sequence comprising at least a portion of a histone amino terminal tail, said first amino acid sequence linked to b) a second amino acid sequence comprising at least a portion of a histone modifying enzyme. In another embodiment, the present invention contemplates a compound, wherein said histone modifying enzyme comprises at least a portion of a acetyltransferase. In yet another embodiment, the present invention contemplates a compound, wherein said portion comprises an active catalytic domain of an acetyltransferase.

One embodiment of the design of the AC/2H system is illustrated in FIG. 1. The present invention is not limited to this embodiment. Other embodiments are also contemplated and contained herein. Other the two-hybrid interactions and their dependence on the modification of the protein of interest (A) are in Table 1. This embodiment of the system is composed of the following elements:

In one embodiment, the protein A that is known or suspected to be the substrate of protein B (e.g., an enzyme) for a post-translational modification is physically fused to the enzyme B. This fusion is achieved by ligating in-frame the DNA fragments encoding A and B. The A-B fusion is expressed in bacterial or yeast cells (alone or within the context of two-hybrid baits, see below), the protein B is able to affect (e.g., catalyze) modification of the linked protein A resulting in the "autocatalysis" of the A-B hybrid protein.

In one embodiment, the A-B DNA fusion is further ligated in-frame to another DNA fragment which encodes a protein module C that, e.g., constitutes the bait or the prey hybrid protein in the two-hybrid system. For example, in the Yeast Two-Hybrid system (U.S. Pat. Nos. 5,283,273, 5,468,614 and 5,667,973), the module would be, for example, the DNA binding domain of Gal4 or LexA, or the activation domain of a transcriptional activator, whereas in the Spit-Ubiquitin system (U.S. Pat. Nos. 5,503,977 and 5,585,245), module C would be, for example, the NubG or Cub (Johnsson, et al., "Split ubiquitin as a sensor of protein interactions in vivo" *Proc. Natl. Acad. Sci. USA* 91:10340-10344, 1994).

In one embodiment, the C-A-B hybrid DNA fragment is further ligated in-frame to module D which encodes a peptide used as an epitope tag that can be detected and quantified by immunochemical means.

In one embodiment, an otherwise identical C-A-B'-D hybrid DNA is created in the same manner as the C-A-B-D hybrid. The B' fragment encodes a catalytically inactive form of the enzyme B which is created by site-directed mutagenesis to ablate the catalytic power of the enzyme B. Therefore, while the C-A-B-D chimera contains a constitutive modification within the A module, the C-A-B'-D mutant enzyme fusion fails to do so due to the mutation(s) (e.g., point mutation(s)) that abolishes the catalytic power of the enzyme B.

In one embodiment, the C-A-B-D and C-A-B'-D chimeric DNA fragments are each ligated to a plasmid vector designed for the corresponding two-hybrid system.

In one embodiment, in addition to the C-A-B-D and C-A-B'-D chimera, two additional control hybrids are created: C-B-D and C-B'-D.

In one embodiment, the final two-hybrid plasmids bearing the in-frame fusion of C-A-B-D, C-A-B'-D, C-B-D, or C-B'-D hybrid are delivered (transformed) to the corresponding two-hybrid host cells, and the quantity of the four hybrids and the modification status of protein A in both cases are characterized by appropriate means, such as immunochemical analyses using antibodies specific for D, and antibodies specific for A that is modified by the enzyme B.

Although the present invention is not limited to any particular protein-protein interaction, as summarized in Table 1, protein-protein interactions that are detected by the set of autocatalysis baits can be one of four classes: Positive interactions with only the C-A-B-D chimera, but not C-A-B'-D, C-B-D, or C-B'-D, are triggered by the modification of A.; interactions that are detected by the C-A-B'-D hybrid, but not C-A-B-D, C-B-D, or C-B'-D are specific for the unmodified A (i.e., inhibited by A modification by the enzyme B). Therefore, the AC/2H method is capable of detecting protein-protein interactions that are either induced or inhibited by a specific post-translational modification.

In one embodiment, the present invention contemplates a compound, comprising a) a first amino acid sequence comprising at least a portion of a histone amino terminal tail, said first amino acid sequence linked to b) a second amino acid sequence comprising at least a portion of a histone acetyltransferase. In another embodiment, the present invention contemplates that the second amino acid sequence comprises the active catalytic domain of Gcn5. In yet another embodiment, the present invention contemplates that the second amino acid sequence comprises a catalytically inactive portion of Gcn5. In still yet another embodiment, the present invention contemplates that the first amino acid sequence comprises the histone H3 tail. In still yet another embodiment, the present invention contemplates that the first amino acid sequence comprises the histone H4 tail. In still yet another embodiment, the present invention contemplates that the compound comprises a fusion protein. In still yet another embodiment, the present invention contemplates that the compound exhibits autoacetylation. In still yet another embodiment, the present invention contemplates that the compound further comprises a DNA binding moiety. In still yet another embodiment, the present invention contemplates that the compound comprising the DNA binding moiety is linked to said first amino acid sequence. In still yet another embodiment, the present invention contemplates that the DNA binding moiety comprises the Gal4 DNA binding domain. In still yet another embodiment, the present invention contemplates that the DNA binding moiety comprises the Gal4 DNA binding domain further comprises a detectable moiety linked to said second amino acid sequence. In still yet another embodiment, the present invention contemplates that the detectable moiety comprises an epitope. In still yet another embodiment, the present invention contemplates the nucleic acid encoding the compounds of the present invention. In still yet another embodiment, the present invention contemplates an expression vector encoding the compounds of the present invention. In still yet another embodiment, the present invention contemplates yeast transformed with the expression vector. In still yet another embodiment, the present invention contemplates a whole cell extract of the yeast transfected with the expression vectors of the present invention.

In one embodiment, the present invention contemplates a method for detecting protein-protein interactions, said interactions requiring a post translational modification of one of the said proteins, said method comprising: (a) providing a host cell comprising a detectable gene wherein the detectable gene expresses a detectable protein when the detectable gene is activated by an amino acid sequence including a transcriptional activation domain when the transcriptional activation domain is in sufficient proximity to the detectable gene; (b) providing a first chimeric gene that is capable of being expressed in the host cell, the first chimeric gene comprising a DNA sequence that encodes a first hybrid protein, the first hybrid protein comprising: (i) a DNA-binding moiety that recognizes a binding site on the detectable gene in the host cell; (ii) a first test protein or fragment thereof, comprising a reactive moiety capable of being modified through catalysis, that is to be tested for interaction with at least one second test protein or fragment thereof; and (iii) a catalytic moiety that is capable of catalyzing said first test protein; (c) providing a second chimeric gene that is capable of being expressed in the host cell, the second chimeric gene comprising a DNA sequence that encodes a second hybrid protein, the second hybrid protein comprising: (i) the transcriptional activation domain; and (ii) a second test protein or fragment thereof that is to be tested for interaction with the first test protein or fragment thereof when said first test protein has been modified by the catalysis of said reactive moiety to create a modified first test protein; wherein interaction between the first modified test protein and the second test protein in the host cell causes the transcriptional activation domain to activate transcription of the detectable gene; (d) introducing the first chimeric gene and the second chimeric gene into the host cell; (e) subjecting the host cell to conditions under which the first hybrid protein and the second hybrid protein are expressed in sufficient quantity for the detectable gene to be activated; and (f) determining whether the detectable gene has been expressed to a degree greater than expression in the absence of an interaction between the first test protein and the second test protein.

In another embodiment, the present invention contemplates that the binding DNA-moiety comprises GDBD; said catalytic moiety comprises the catalytic domain of Gcn5 and; said reactive moiety comprises a histone amino terminal tail capable of being acetylated by Gcn5. In yet another embodiment, the present invention contemplates that the first test protein and said second test protein are encoded on a library of plasmids containing DNA inserts, derived from the group consisting of genomic DNA, cDNA and synthetically generated DNA. In still yet another embodiment, the present invention contemplates that the first test protein and said second test protein are derived from derived from the group consisting of bacterial protein, viral protein, oncogene-encoded protein, mammalian protein, fungal protein and plant protein.

In one embodiment, the present invention contemplates a compound, comprising a) a first amino acid sequence comprising at least a portion of an enzyme substrate, said first amino acid sequence linked to b) a second amino acid sequence comprising at least a portion of an enzyme capable of enzymatically converting said first amino acid sequence.

In one embodiment, the present invention contemplates a method for detecting protein-protein interactions, comprising: (a) providing a host cell comprising a detectable gene, wherein the detectable gene expresses a detectable protein when the detectable gene is activated by an amino acid sequence comprising a transcriptional activation domain; (b) providing a first chimeric gene that is capable of being expressed in said host cell, the first chimeric gene comprising a DNA sequence that encodes a first hybrid protein, the first hybrid protein comprising: (i) a DNA-binding moiety that recognizes a binding site on the detectable gene in the host cell; (ii) a reactive moiety capable of being modified through catalysis; and (iii) a catalytic moiety that is capable of catalyzing said reactive moiety; (c) providing a second chimeric gene that is capable of being expressed in the host cell, the second chimeric gene comprising a DNA sequence that encodes a second hybrid protein, the second hybrid protein comprising a transcriptional activation domain; and (d) introducing the first chimeric gene and the second chimeric gene into the host cell under conditions wherein the first hybrid protein and the second hybrid protein are expressed.

In another embodiment, the present invention contemplates that the above method comprises determining whether the detectable gene has been expressed.

In one embodiment, the present invention contemplates a compound, comprising a) a first amino acid sequence comprising at least a portion of a histone amino terminal tail, said first amino acid sequence linked to b) a second amino acid sequence comprising at least a portion of a protein kinase. In another embodiment, the present invention contemplates that the second amino acid sequence comprises the active domain of IPL1 kinase. As with the compound embodied above, this embodiment of the present invention contemplates that, in certain embodiments, the second amino acid sequence may be catalytically inactive, that the first amino acid sequence comprises the histone H3 tail or the histone H4 tail, that the compound comprise a fusion protein, that the compound exhibits autophosphorylation, that the compound further comprises a DNA binding moiety, that the DNA binding moiety is bound to the first amino acid sequence, that the DNA binding moiety may comprise Gal4, that the second amino acid sequence comprises a detectable moiety and that said detectable moiety comprises an epitope. One embodiment of the present invention also contemplates the nucleic acid encoding the fusion protein above, an expression vector comprising that nucleic acid, a yeast transformed with that expression vector and the whole cell extract form that yeast.

In one embodiment, the present invention contemplates a compound, comprising a) a first amino acid sequence comprising at least a portion of a carboxy terminal domain, said first amino acid sequence linked to b) a second amino acid sequence comprising at least a portion of protein kinase. In another embodiment, the present invention contemplates that the second amino acid sequence comprises the active domain of KIN28 kinase. In another embodiment, the present invention contemplates that the second amino acid sequence comprises the active domain of KIN28 kinase. As with the compound embodied above this embodiment of the present invention contemplates that, if desired, the second amino acid sequence may be catalytically inactive, that the first amino acid sequence comprises a trimer of the carboxyl terminal domain, that the compound comprise a fusion protein, that the compound exhibits autophosphorylation, that the compound further comprises a DNA binding moiety, that the DNA binding moiety is bound to the first amino acid sequence, that the DNA binding moiety may comprise Gal4, that the second amino acid sequence comprises a detectable moiety and that said detectable moiety comprises an epitope. One embodiment of the present invention also contemplates the nucleic acid encoding the fusion protein above, an expression vector comprising that nucleic acid, a yeast transformed with that expression vector and the whole cell extract form that yeast.

One embodiment of the present invention also contemplates a compound comprising acetylated PIASxα bound to p53.

DEFINITIONS

In order to better understand the invention, the following definitions are provided.

The terms "protein," "peptide" and "polypeptide" refer to compounds comprising amino acids joined via peptide bonds and these terms are used interchangeably. A "protein," "peptide" or "polypeptide" encoded by a gene is not limited to the amino acid sequence encoded by the gene, but includes post-translational modifications of the protein. A "protein," "peptide" or "polypeptide" will also refer to a region or fragment of the named peptide.

Where the term "amino acid sequence" is recited herein to refer to an amino acid sequence of a protein molecule, "amino acid sequence" and like terms, such as "polypeptide," "peptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid. The term "portion" when used in reference to a nucleotide sequence (as in "a portion of a given nucleotide sequence") refers to fragments of that nucleotide sequence. The fragments may range in size from ten nucleotide residues to the entire nucleotide sequence minus one nucleotide.

"At least a portion of a histone amino terminal tail" shall be defined as a fragment of a histone amino acid tail of at least four amino acids.

"At least a portion of a histone acetyl transferase" shall be defined as a fragment of a histone acetyl transferase of at least four amino acids.

"Histone H3 tail" shall be defined as the N-terminal portion of the H3 peptide. The tail is approximately 10-20 amino acids in length. The histone tail is believed to be important in transcriptional regulation.

"Histone H4 tail" shall be defined as the N-terminal portion of the H4 peptide. The tail is approximately 10-20 amino acids in length. The histone tail is believed to be important in transcriptional regulation.

"Active domain" shall be defined as the portion of a molecule that has functional properties such as, but not limited to, catalytic and enzymatic properties.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms. Chimeric peptides are produced form "chimeric genes."

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations.

The term "gene" refers to a nucleic acid (e.g., DNA sequence, RNA sequence or nucleotide sequence) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. A "translation product" of a DNA sequence is the peptide sequence generated via from the mRNA encoded by the DNA.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous" when used in reference to a gene refers to a gene encoding a peptide that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide sequence" or "nucleic acid sequence" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a sequence or a variant nucleic acid sequence (e.g., mutation or polymorphism in a given allele of a particular gene or for detecting the presence or absence of a particular protein or the structure or activity or effect of a particular protein or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or MRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qb replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlain et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of MRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term “constitutive” when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, an “inducible” promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term “regulatory element” refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be “endogenous” or “exogenous” or “heterologous.” An “endogenous” enhancer or promoter is one that is naturally linked with a given gene in the genome. An “exogenous” or “heterologous” enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a “heterologous promoter” in operable combination with the second gene. A variety of such combinations are contemplated (e.g., the first and second genes can be from the same species, or from different species).

The term “naturally linked” or “naturally located” when used in reference to the relative positions of nucleic acid sequences means that the nucleic acid sequences exist in nature in the relative positions.

The presence of “splicing signals” on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term “poly(A) site” or “poly(A) sequence” as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be “heterologous” or “endogenous.” An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term “vector” refers to nucleic acid molecules that transfer DNA segment(s) from one cell to another. The term “vehicle” is sometimes used interchangeably with “vector.”

The terms “expression vector” or “expression cassette” refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term “transfection” refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term “stable transfection” or “stably transfected” refers to the introduction and integration of foreign DNA into the genome of the transfected cell. The term “stable transfectant” refers to a cell that has stably integrated foreign DNA into the genomic DNA.

The term “transient transfection” or “transiently transfected” refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term “transient transfectant” refers to cells that have taken up foreign DNA but have failed to integrate this DNA.

The term “stable expression” means the expression of an exogenous sequence wherein the transfected sequences has been integrated into the genome.

The term “transient expression” means the expression of an exogenous sequence wherein the transfected sequences has failed to integrate into the genome.

The term “calcium phosphate co-precipitation” refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms “infecting” and “infection” when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms “bombarding, “bombardment,” and “biolistic bombardment” refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven micro-projectile accelerator (PDS-1000/He, BioRad).

The term “transgene” refers to a foreign gene that is placed into an organism by the process of transfection. The term “foreign gene” refers to any nucleic acid (e.g., gene sequence) that is introduced into the genome of an organism by experimental manipulations and may include gene sequences found in that organism so long as the introduced gene does not reside in the same location as does the naturally-occurring gene.

The term “transgenic” when used in reference to a host cell or an organism refers to a host cell or an organism that contains at least one heterologous or foreign gene in the host cell or in one or more of cells of the organism.

The term “host cell” refers to any cell capable of replicating and/or transcribing and/or translating a heterologous gene. Thus, a “host cell” refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms “transformants” or “transformed cells” include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term “selectable marker” refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be “positive” or “negative.” Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term “reporter gene” refers to a gene encoding a protein that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term “overexpression” refers to the production of a gene product in transgenic organisms that exceeds levels of production in normal or non-transformed organisms. The term “cosuppression” refers to the expression of a foreign gene which has substantial homology to an endogenous gene resulting in the suppression of expression of both the foreign and the endogenous gene. As used herein, the term “altered levels” refers to the production of gene product(s) in transgenic organisms in amounts or proportions that differ from that of normal or non-transformed organisms.

The terms “Southern blot analysis” and “Southern blot” and “Southern” refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989*] Molecular Cloning: A Laboratory Manual*, Cold Spring Harbor Press, NY, pp 9.31-9.58).

The term “Northern blot analysis” and “Northern blot” and “Northern” refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39-7.52).

The terms “Western blot analysis” and “Western blot” and “Western” refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term “antigenic determinant” refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the “immunogen” used to elicit the immune response) for binding to an antibody.

The term “isolated” when used in relation to a nucleic acid, as in “an isolated oligonucleotide” refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. In one embodiment, polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The terms "sample" and "source" are used in their broadest sense. In one sense they can refer to a animal cell or tissue. In another sense, they is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "immunohistochemical assay" is defined as an assay that comprises peptides (e.g., antibodies) that recognized antigenic determinants (e.g., epitopes). The peptides are linked either directly or indirectly to other peptides or other compounds (e.g., fluorescent peptides or chemicals, enzymes and the like) that give a detectable signal in the given assay system. An example of an immunohistochemical assay would be an ELISA assay.

"Portion" of a peptide shall be defined as a sequence of at least 10 amino acids up to the total length of the peptide less one amino acid. In a preferred embodiment, portion shall include Lys9 and/or Lys14 amino acid of the histone H3 tail.

"Linked," in regards to the peptides of the present invention, shall be defined as peptides or peptide portions that are connected via peptide bonds or via chemical bonds.

"Autoacetylation" shall be defined an enzymatic compound (e.g., a protein or peptide) that has the ability to acetylate an amino acid residue on same compound. In other words, autoacetylation is a form of autocatalysis.

"DNA binding moiety" shall be defined as a portion of a molecule that has the ability to bind DNA. For example, the Gal4 DNA binding domain is a DNA binding moiety.

"Detectable moiety" shall be defined as a portion of a molecule that can be readably detected by standard biochemical means. The HA moiety used in the present invention is a example of a detectable moiety.

"Epitope" shall be defined as a site on a molecule against which an antibody will be produced and to which it will bind.

"Fragment" shall be defined as a portion of, for example, a peptide, protein or nucleic acid.

"Enzyme" shall be defined as a catalyst (e.g., a peptide or protein or fragment thereof) that catalyses reactions (e.g., chemical or biochemical reactions) of other substances (e.g., proteins, etc.) without itself being destroyed or altered upon completion of the reactions.

"Enzymatically converted" shall be defined as a substance that has been acted upon by a catalyst.

"Transcriptional activation domain" shall be defined as a nucleotide sequence that, when activated (for example, by a transcription factor) initiated the transcription of a sequence of DNA. For example, see U.S. Pat. Nos. 6,271,341; 6,133,027; 5,750,667 and 6,114,111 which are incorporated herein by reference.

"In sufficient proximity" shall be defined as, for example, being close enough to exert an effect on something else. For example, a transcription factor is "in sufficient proximity" to a transcriptional activation domain when it can initiate transcription. Additionally, "in sufficient proximity" as it relates to Yeast two-hybrid systems, is defined in U.S. Pat. Nos. 5,667,973; 5,468,614 and 5,283,173 which are incorporated herein by reference.

"Expressed to a degree greater than" shall be defined as expression (of, for example, a gene) to a level higher (e.g., by at least approximately 10 percent higher) than another gene or the same gene in another system. In other words, it shall mean that a difference in expression is detectable by at least approximately 10 percent over background and preferably over 20 percent of more.

DESCRIPTION OF FIGURES

FIG. 13, pDG2 [SEQ ID NOS: 2 and 16]; FIG. 16, pDG5 [SEQ ID NOS: 5 and 19] and; FIG. 17, pDG6 [SEQ ID NOS: 6 and 20]). The mutant Gcn5 F221A, marked by the "thunderbolt", fails to catalyze the histone acetylation (see, for example, FIG. 14, pDG3 [SEQ ID NOS: 3 and 17]; FIG. 15, pDG4 [SEQ ID NOS: 4 and 18]; FIG. 18, pDG7 [SEQ ID NOS: 7 and 21] and; FIG. 19, pDG8 [SEQ ID NOS: 8 and 22]). In the yeast strain where the GDBD-H3 or H4-Gcn5-HA is co-expressed with a corresponding acetylated histone binding protein that is fused to a transcriptional activation domain, the reporter gene under the control of the enhancer element UASgal will be activated due to the interaction between the autoacetylated histone bait and the specific prey protein. On the other hand, such interactions will not be seen if the mutant Gcn5 F221A is part of the autocatalytic bait fusion.

FIGS. 10A and B show the autoacetylation of p53 by Gcn5. (A) Schematic drawing of the p53 autoacetylation constructs. (B) p53 fusion proteins were expressed in yeast, immunoprecipitated by antibodies against HA or against acetylated Lys320 (K320.Ac), and then tested by western analyses to quantify the relative abundance and the status of K320 acetylation. It is clear that p53 is acetylated when fused to the wildtype Gcn5, but not by the mutant Gcn5 in the autocatalysis context. Two independent yeast colonies bearing these two autocatalysis baits were analyzed in parallel.

FIG. 12 shows the nucleotide sequence (SEQ ID NO: 1) and amino acid sequence (SEQ ID NO: 15) of the coding region of the plasmid pDG1. pDG1 is a low-copy TRP1 yeast vector (pODB2) containing Gal4 DNA binding domain, histone H3 (amino acids 1-59), Gcn5 (amino acids 18-252), and a trimeric HA epitope under the control of yeast ADH1 promoter and ADH1 terminator.

FIG. 13 shows the nucleotide sequence (SEQ ID NO: 2) and amino acid sequence (SEQ ID NO: 16) of the coding region of the plasmid pDG2. pDG2 is a low-copy TRP1 yeast vector (pODB2) containing Gal4 DNA binding domain, histone H3 (amino acids 1-59), Gcn5 F221A mutant allele (amino acids 18-252), and a trimeric HA epitope under the control of yeast ADH1 promoter and ADH1 terminator.

FIG. 14 shows the nucleotide sequence (SEQ ID NO: 3) and amino acid sequence (SEQ ID NO: 17) of the coding region of the plasmid pDG3. pDG3 is a low-copy TRP1 yeast vector (pODB2) containing Gal4 DNA binding domain, histone H4 (amino acids 1-29), Gcn5 (amino acids 18-252), and a trimeric HA epitope under the control of yeast ADH1 promoter and ADH1 terminator.

FIG. 15 shows the nucleotide sequence (SEQ ID NO: 4) and amino acid sequence (SEQ ID NO: 18) of the coding region of the plasmid pDG4. pDG4 is a low-copy TRP1 yeast vector (pODB2) containing Gal4 DNA binding domain, histone H4 (amino acids 1-29), Gcn5 F221A mutant allele (amino acids 18-252), and a trimeric HA epitope under the control of yeast ADH1 promoter and ADH1 terminator.

FIG. 16 shows the nucleotide sequence (SEQ ID NO: 5) and amino acid sequence (SEQ ID NO: 19) of the coding region of the plasmid pDG5. pDG5 is a high-copy LEU2 yeast vector (YEplac181) containing Gal4 DNA binding domain, histone H3 (amino acids 1-59), Gcn5 (amino acids 18-252), and a trimeric HA epitope under the control of yeast ADH1 promoter and ADH1 terminator.

FIG. 17 shows the nucleotide sequence (SEQ ID NO: 6) and amino acid sequence (SEQ ID NO: 20) of the coding region of the plasmid pDG6. pDG6 is a high-copy LEU2 yeast vector (YEplac181) containing Gal4 DNA binding domain, histone H3 (amino acids 1-59), Gcn5 F221A mutant allele (amino acids 18-252), and a trimeric HA epitope under the control of yeast ADH1 promoter and ADH1 terminator.

FIG. 18 shows the nucleotide sequence (SEQ ID NO: 7) and amino acid sequence (SEQ ID NO: 21) of the coding region of the plasmid pDG7. pDG7 is a high-copy LEU2 yeast vector (YEplac181) containing Gal4 DNA binding domain, histone H4 (amino acids 1-29), Gcn5 (amino acids 18-252), and a trimeric HA epitope under the control of yeast ADH1 promoter and ADH1 terminator.

FIG. 19 shows the nucleotide sequence (SEQ ID NO: 8) and amino acid sequence (SEQ ID NO: 22) of the coding region of the plasmid pDG8. pDG8 is a high-copy LEU2 yeast vector (YEplac181) containing Gal4 DNA binding domain, histone H4 (amino acids 1-29), Gcn5 F221A mutant allele (amino acids 18-252), and a trimeric HA epitope under the control of yeast ADH1 promoter and ADH1 terminator.

FIG. 20 shows the nucleotide sequence (SEQ ID NO: 9) and amino acid sequence (SEQ ID NO: 23) of the coding region of the plasmid pDG28. pDG28 is a low-copy TRP1 yeast vector (pODB2) containing Gal4 DNA binding domain, Gcn5 (amino acids 18-252), and a trimeric HA epitope under the control of yeast ADH1 promoter and ADH1 terminator.

FIG. 21 shows the nucleotide sequence (SEQ ID NO: 10) and amino acid sequence (SEQ ID NO: 24) of the coding region of the plasmid pDG29. pDG29 is a low-copy TRP1 yeast vector (pODB2) containing Gal4 DNA binding domain, Gcn5 F221A mutant allele (amino acids 18-252), and a trimeric HA epitope under the control of yeast ADH1 promoter and ADH1 terminator.

FIG. 22 shows the nucleotide sequence (SEQ ID NO: 11) and amino acid sequence (SEQ ID NO: 25) of the coding region of the plasmid pDG30. pDG30, based on pDG1, the H3 sequence is replaced with a multicloning sequence. The MSC allows insertion of known and putative substrates for Gcn5 in the tethered catalysis/yeast two-hybrid assays.

FIG. 23 shows the nucleotide sequence (SEQ ID NO: 12) and amino acid sequence (SEQ ID NO: 26) of the coding region of the plasmid pDG31. pDG31, based on pDG2, the H3 sequence is replaced with a multicloning sequence.

FIG. 24 shows the nucleotide sequence (SEQ ID NO: 13) and amino acid sequence (SEQ ID NO: 27) of the coding region of the plasmid pMK485. pMK485 is a low-copy TRP1 yeast vector (pODB2) containing Gal4 DNA binding domain, tumor suppressor protein p53 amino acids 300-393, Gcn5 (amino acids 18-252), and a trimeric HA epitope under the control of yeast ADH1 promoter and ADH1 terminator.

FIG. 25 shows the nucleotide sequence (SEQ ID NO: 14) and amino acid sequence (SEQ ID NO: 28) of the coding region of the plasmid pMK486. pMK486 is a low-copy TRP1 yeast vector (pODB2) containing Gal4 DNA binding domain, tumor suppressor protein p53 amino acids 300-393, Gcn5 (amino acids 18-252) with the F221A mutation, and a trimeric HA epitope under the control of yeast ADH1 promoter and ADH1 terminator.

FIG. 30 shows the nucleotide sequence (SEQ ID NO: 29) and amino acid sequence (SEQ ID NO: 30) of the coding region of the plasmid pDG64.

FIG. 31 shows the nucleotide sequence (SEQ ID NO: 31) and amino acid sequence (SEQ ID NO: 32) of the coding region of the plasmid pDG65.

FIG. 32 shows the nucleotide sequence (SEQ ID NO: 33) and amino acid sequence (SEQ ID NO: 34) of the coding region of the plasmid pMK498.

FIG. 33 shows the nucleotide sequence (SEQ ID NO: 35) and amino acid sequence (SEQ ID NO: 36) of the coding region of the plasmid pMK500.

FIG. 34 shows the nucleotide sequence (SEQ ID NO: 37) and amino acid sequence (SEQ ID NO: 38) of the coding region of the plasmid pDG502.

DESCRIPTION OF THE INVENTION AND PREFERRED EMBODIMENTS

Figure 1:
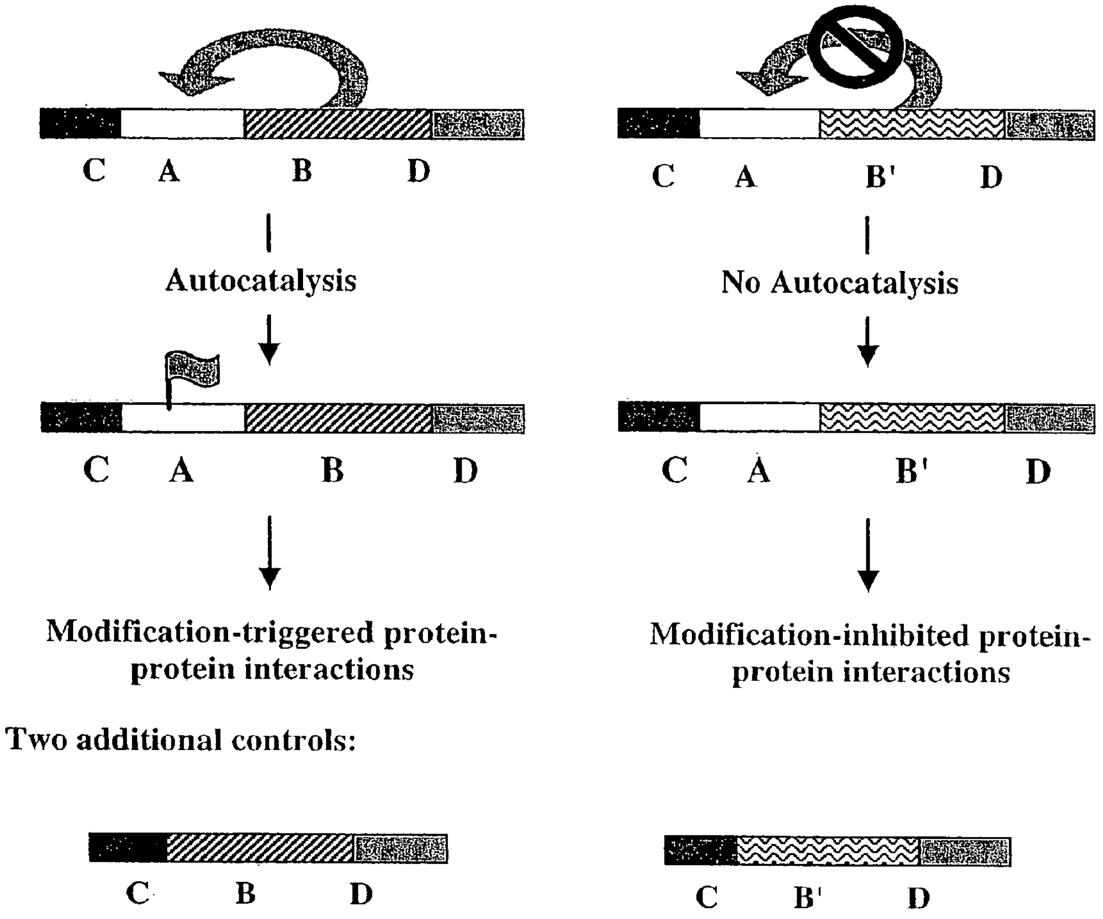
FIG. 1 shows the design of the AC/2H system. A protein (A) is fused to either an active protein-modifying enzyme (B) or a catalytically inactivated mutant form of B (B') to create an autocatalytic hybrid protein (the wildtype B fusion) or an otherwise identical but unmodified hybrid protein (i.e. the mutant B' fusion). The DNA fragments encoding the A-B and A-B' hybrids are ligated in-frame to module C for a two-hybrid bait, and module D for easy purification and characterization of the final autocatalytic hybrid proteins. Two more controls composed of C-B-D and C-B'-D are created similarly. The curved arrow indicates the autocatalysis of the enzyme-substrate fusion protein (denoted by the "flag" on the protein A).

Although the present invention is not limited by specific theories or mechanisms of action, it is believed that histones are the substrates of multiple PTMs that are critical for probably all DNA-templated processes. Additionally, for example, histone acetyltransfereases (HATs) are targets for oncogenesis. For example, two of the best known mammalian HATs, p300 and CBP, are targets of several oncoproteins, and translocation mutations of p300/CBP and other HATs have been found in certain cancers (Timmermann, S., et al., "Histone acetylation and disease" *Cell Mol Life Sci* 58:728-36, 2001). One normal function of p300/CBP is tied to a machinery controlling DNA damage repair (Rapic-Otrin, V., et al., "Sequential binding of UV DNA damage binding factor and degradation of the p48 subunit as early events after UV irradiation" *Nucleic Acids Res* 30:2588-98, 2002; Tini, M., et al., "Association of CBP/p300 acetylase and thymine DNA glycosylase links DNA repair and transcription" *Mol Cell* 9:265-77, 2002). Oncoproteins may also function through the recruitment of HDACs, leading to acute promyelocytic leukemia, lymphoid oncogenic transformation, and acute myeloid leukemia (Marks, P., et al., "Histone deacetylases and cancer: causes and therapies" *Nat Rev Cancer* 1:194-202, 2001). Therefore, mutations that influence the balance of histone acetylation may have significant roles in carcinogenesis. Currently, more than a dozen synthetic or natural HDAC inhibitors already show tumor inhibition activity in animal models, and at least six of them are being tested in Phase I and II clinical trials (Marks, P., et al., "Histone deacetylases and cancer: causes and therapies" *Nat Rev Cancer* 1:194-202, 2001). Identification and studies of AcBPs in yeast will undoubtedly help identify human oncoproteins and/or tumor suppressors displaying similar affinity. Therefore, one embodiment of the present invention contemplates novel cancer treatments and screening methods based on the compounds and methods of the present invention.

Chromatin Structure

Eukaryotic chromatin provides a structural basis for genomic DNA organization that is essential for packaging the entire genome into the nucleus and chromosome segregation during mitosis and meiosis. In contrast, all DNA-templated processes require appropriate access and even progressing through selective loci by large multi-subunit machineries under specified conditions. How chromatin structure is regulated to meet these two antagonistic needs is a critical question under very active investigation. Several conserved mechanisms control the dynamic characteristics of chromatin, including covalent modifications of histones, selective use of histone variants, and ATP hydrolysis-dependent chromatin remodeling activities (Hayes, J. J., and J. C. Hansen, "Nucleosomes and the chromatin fiber" *Curr Opin Genet Dev* 11:124-9, 2001; Wolffe, A, "Chromatin, structure and function" *Academic Press* 1998; Wolffe, A. P., and J. J. Hayes, "Chromatin disruption and modification" *Nucleic Acids Res* 27:711-20, 1999). Other mechanisms such as DNA methylation and special RNA molecules (e.g., the XIST and small interfering RNAs (siRNAs)), frequently impose more widespread and stable effects on chromatin (Hall, I. M., et al., "Establishment and maintenance of a heterochromatin domain" *Science* 297:2232-2237, 2002; Kelley, R. L., and M. I. Kuroda, "Noncoding RNA genes in dosage compensation and imprinting" *Cell* 103:9-12, 2000; Mlynarczyk, S. K., and B. Panning, "X inactivation: Tsix and Xist as yin and yang" *Curr Biol* 10:R899-903, 2000; Panning, B., and R. Jaenisch, "RNA and the epigenetic regulation of X chromosome inactivation" *Cell* 93:305-308, 1998; Reinhart, B. J., and D. P. Bartel, "Small RNAs correspond to centromere heterochromatic repeats" *Science* 297:1831, 1998; Volpe, T. A., et al., "Regulation of heterochromatic silencing and histone H3 lysine-9 methylation by RNAi" *Science* 297:1833-1837, 2002). Research in our laboratory revolves around the functional studies of covalent modifications of histones. It has been a challenge to establish the molecular mechanisms by which different histone modifications, or a single modification recurring at different residues of histones, may bring about different biological functions, such as transcriptional regulation of selective genes, DNA replication and chromatin assembly, recombination, and DNA damage repair. The "histone code" hypothesis (Strahl, B. D., and C. D. Allis, "The language of covalent histone modifications" *Nature* 403:41-45, 2000) suggests that histone modifications function as transducing signals to recruit certain proteins to the underlying loci for specific molecular functions. In this proposal, we use histone acetylation as the model to test this hypothesis. Specifically, we have developed a genetic system permitting non-biased screening for protein-protein interactions induced by histone modifications. Functional characterization of the acetylated histone binding proteins (AcBPs) is expected to shed light on the spectrum and the mechanisms of histone acetylation functions. Furthermore, based on the AcBP studies, our research has been extend to other modifications to obtain a panorama view of how chromatin dynamics may be determined by covalent modifications of histones.

Core histone N-terminal Tails are Covalently Modified

Core histones H2A, H2B, H3, and H4 are highly conserved proteins essential for chromatin organization. Two molecules of each of the core histones are wrapped around by about 150 basepairs of DNA to form a nucleosome (van Holde, K. E, "Chromatin" *Springer-Verlag* 1989; Wolffe, A., "Chromatin, structure and function" Academic Press 1998). Formation of nucleosomes requires extensive histone-histone and histone-DNA interactions occurring mainly within the central histone-fold domain of each core histone (Arents, G., R. W. Burlingame, et al., "The nucleosomal core histone octamer at 3.1 A resolution: a tripartite protein assembly and a left-handed superhelix" *Proc Natl Acad Sci USA* 88:10148-10152, 1991; Luger, K., A., et al. "Crystal structure of the nucleosome core particle at 2.8 Å resolution" *Nature* 389:251-260, 1997). Each core histone contains an amino-terminal tail and sometimes a carboxyl-terminal extension. Much of the histone tails protrude from the nucleosomal core particle. Crystal structures of nucleosomal core particles indicate that histone tails are not structured and some part of them may interact with adjacent nucleosomes (Hansen, J. C., C. Tse, and A. P. Wolffe, "Structure and function of the core histone N-termini: more than meets the eye" *Biochemistry* 37:17637-17641, 1998; Luger, K., et al., "Crystal structure of the nucleosome core particle at 2.8 Å resolution" *Nature* 389:251-260, 1997; White, C. L., R. K. Suto, and K. Luger, "Structure of the yeast nucleosome core particle reveals fundamental changes in internucleosome interactions" *Embo J* 20:5207-5218, 2001). Deleting the amino tail domains of histones H3 and H4, or of the H2A and H2B together causes yeast cell death (Ling, X., et al., "Yeast histone H3 and H4 amino termini are important for nucleosome assembly in vivo and in vitro: redundant and position-independent functions in assembly but not in gene regulation" *Genes Dev* 10:686-699, 1996). These results demonstrate the importance of histone tails in cell viability. However, the direct cause of the cell death remains unclear.

Histone tails are the targets for multiple post-translational modifications including acetylation, methylation, phosphorylation, ubiquitylation and several other less studied chemical changes (Spencer, V. A., and J. R. Davie, "Role of covalent modifications of histones in regulating gene expression" *Gene* 240:1-12, 1999; van Holde, K. E, "Chromatin" *Springer-Verlag* 1989; Wolffe, A "Chromatin, structure and function" *Academic Press*, 1998; Wolffe, A. P., and J. J. Hayes, "Chromatin disruption and modification" *Nucleic Acids Res* 27:711-720, 1999). Individual and combined actions of these covalent modifications may contribute significantly to the general functions of histone tails. Many of these modifications change the ionic charge of the highly basic histones. At the first approximation, alteration of the ionic state of histones can have substantial effects on the compact structure of chromatin which generally restricts the binding and progression of protein factors. For example, the Km of the interaction between a highly basic histone H4 tail peptide and double-stranded DNA is about 10-12 M, whereas acetylation of this peptide decreases the affinity by a factor of $10^6$ (Hong, L., et al., "Studies of the DNA binding properties of histone H4 amino terminus. Thermal denaturation studies reveal that acetylation markedly reduces the binding constant of the H4 "tail" to DNA" *J Biol Chem* 268:305-314, 1993). A weakened DNA-histone interaction may allow for better access of DNA binding and processing factors to find their cognate DNA elements (Tse, C., T. Sera, A. P. Wolffe, and J. C. Hansen, "Disruption of higher-order folding by core histone acetylation dramatically enhances transcription of nucleosomal arrays by RNA polymerase III" *Mol Cell Biol* 18:4629-4638, 1998; Vettese-Dadey, M., et al., "Acetylation of histone H4 plays a primary role in enhancing transcription factor binding to nucleosomal DNA in vitro" *Embo J* 15:2508-2518, 1996; Workman, J. L., and R. E. Kingston, "Alteration of nucleosome structure as a mechanism of transcriptional regulation" *Annu Rev Biochem* 67:545-579, 1998). On the other hand, the diversity of histone tail modifications also suggests that multiple mechanisms may be used by these covalent modifications in different chromatin-related functions (detailed below). In fact, probably all DNA-templated processes related to chromatin metabolism are influenced or accompanied by one or more of these modifications.

Many histone modifying enzymes have been identified. Histone acetyltransferases (HATs) and deacetylases (HDACs) are two families of opposing enzymes that acetylate and deacetylate histones, respectively (Kuo, M. H., and C. D. Allis, "Roles of histone acetyltransferases and deacetylases in gene regulation" *Bioessays* 20:615-626, 1998; Peterson, C. L., "HDAC's at work: everyone doing their part" *Mol Cell* 9:921-922, 2002, Roth, S. Y., J. M. Denu, and C. D. Allis, "Histone acetyltransferases" *Annu Rev Biochem* 70:81-120, 2001). Methylation of histones occurs at lysine and arginine residues (van Holde, K. E., "Chromatin" *Springer-Verlag* 1989). Arginine and lysine methyltransferases have been found in different organisms (Jenuwein, T., "Re-SET-ting heterochromatin by histone methyltransferases" *Trends Cell Biol* 11:266-273, 2001). Thus far, no known enzymes actively remove the methyl moiety from a methylated histone (Bannister, A. J., R. Schneider, and T. Kouzarides, "Histone methylation: dynamic or static?" *Cell* 109:801-806, 2002). Several kinases possess the histone phosphorylation activity (De Souza, C. P., et al., "Mitotic histone H3 phosphorylation by the NIMA kinase in *Aspergillus nidulans*" *Cell* 102:293-302, 2000; Hsu, J. Y., et al., "Mitotic phosphorylation of histone H3 is governed by Ip11/aurora kinase and Glc7/PP1 phosphatase in budding yeast and nematodes" *Cell* 102:279-291, 2000; Lo, W. S., et al., "Snf1—a histone kinase that works in concert with the histone acetyltransferase Gcn5 to regulate transcription" *Science* 293:1142-1146, 2001). Less is certain with regards to the histone phosphatases. Lastly, one histone H2B ubiquitin ligase has been found in the budding yeast (Robzyk, K., J. Recht, and M. A. Osley, "Rad6-dependent ubiquitination of histone H2B in yeast" *Science* 287:501-504, 2000); ubiquitylation of histones is a widely conserved events with functions outside protein degradation (Jason, L. J., et al., "Histone ubiquitination: a tagging tail unfolds?" *Bioessays* 24:166-174, 2002).

Considering the number of modifications each histone tail may have and the size of each histone tails (from around 20 to 60 amino acids), these modifications occur at a fairly high density. Also, lysine residues can be acetylated, methylated, and ubiquitylated. It is thus not surprising that these modifications may influence each other. For example, acetylation at lysine 14 of H3 can be facilitated by phosphorylation at serine 10 (Cheung, P., et al., "Synergistic coupling of histone H3 phosphorylation and acetylation in response to epidermal growth factor stimulation" *Mol Cell* 5:905-915, 2000; Lo, W. S., et al., "Phosphorylation of serine 10 in histone H3 is functionally linked in vitro and in vivo to Gcn5-mediated acetylation at lysine 14" *Mol Cell* 5:917-926, 2002), probably because of an increased affinity between the HATs and the phosphorylated H3 (Lo, W. S., et al., "Phosphorylation of serine 10 in histone H3 is functionally linked in vitro and in vivo to Gcn5-mediated acetylation at lysine 14" *Mol Cell* 5:917-926, 2002). Lysine methylation is found enriched in hyperacetylated loci and is tied to transcriptional activation (Strahl, B. D., et al., "Methylation of histone H4 at arginine 3 occurs in vivo and is mediated by the nuclear receptor coactivator PRMT1" *Curr Biol* 11:996-1000, 2001). The deacetylase complex, NuRD, is excluded from nucleosomes containing H3 methylated at lysine 4 (Zegerman, P., et al, "Histone H3 lysine 4 methylation disrupts binding of nucleosome remodeling and deacetylase (NuRD) repressor complex" *J Biol Chem* 277:11621-11624, 2002), partly explaining how histone acetylation and methylation may be enriched at the same region. Moreover, H3 K4 methylation is completely abolished in a yeast strain where the H2B ubiquitylation is prevented (Dover, J., et al., "Methylation of histone H3 by COMPASS requires ubiquitination of histone H2B by Rad6" *J Biol Chem* 277:28368-28371, 2002; Sun, Z. W., and C. D. Allis, "Ubiquitination of histone H2B regulates H3 methylation and gene silencing in yeast" *Nature* 418:104-108, 2002), strongly suggesting that different histone modifications may cross-talk and coordinate each other's action.

Histone Acetylation is Necessary for DNA-templated Nuclear Activities

Acetylation is one of the best studied histone modifications. Genetic and biochemical studies on HATs, HDACs, and on the acetylatable lysine residues have established the roles of histone acetylation in transcriptional regulation (Elgin, S. C. R., and J. L. Workman (ed.), "Chromatin structure and gene expression" *Oxford University Press*, 2000: Turner, B. M., "Chromatin and gene regulation" *Blackwell Science*, 2001). Hyper- and hypo-acetylated histones are generally associated with transcriptional activation and repression, respectively. In many cases, transcriptional activators first bind to their target DNA sequences and then recruit coactivators to the promoter (Agalioti, T., et al., "Ordered recruitment of chromatin modifying and general transcription factors to the IFN-beta promoter" *Cell* 103: 667-678, 2000; Cosma, M. P., T. Tanaka, and K. Nasmyth, "Ordered recruitment of transcription and chromatin remodeling factors to a cell cycle- and developmentally regulated promoter" *Cell* 97:299-311, 1999; Krebs, J. E., et al. "Cell cycle-regulated histone acetylation required for expression of the yeast HO gene" *Genes Dev* 13:1412-1421, 1999; Kuo, M. H., et al., "Gcn4 activator targets Gcn5 histone acetyltransferase to specific promoters independently of transcription" *Mol Cell* 6:1309-1320, 2000). Many of the transcriptional coactivators possess histone acetylation or chromatin remodeling activities. The HAT then acetylates nucleosomes at the promoter and activates transcription (Kuo, M. H., et al., "Gcn4 activator targets Gcn5 histone acetyltransferase to specific promoters independently of transcription" *Mol Cell* 6:1309-1320, 2000; Kuo, M. H.,et al., "Histone acetyltransferase activity of yeast Gcn5p is required for the activation of target genes in vivo" *Genes Dev* 12:627-639, 1998; Parekh, B. S., and T. Maniatis, "Virus infection leads to localized hyperacetylation of histones H3 and H4 at the IFN-beta promoter" *Mol Cell* 3:125-129, 1999). Transcriptional repressors and co-repressors, frequently containing the HDAC activity, function in a similar fashion (Narlikar, G. J., H. Y. Fan, and R. E. Kingston, "Cooperation between complexes that regulate chromatin structure and transcription" *Cell* 108:475-487, 2002). In some cases, acetylation may help other DNA binding factors bind their cognate elements (Krebs, J. E., et al., "Cell cycle-regulated histone acetylation required for expression of the yeast HO gene" *Genes Dev* 13:1412-1421, 1999; Vettese-Dadey, M., et al., "Acetylation of histone H4 plays a primary role in enhancing transcription factor binding to nucleosomal DNA in vitro" *Embo J* 15:2508-2518, 1996), or help chromatin remodeling complexes perform their functions (Barbaric, S., et al., "Increasing the rate of chromatin remodeling and gene activation—a novel role for the histone acetyltransferase Gcn5" *Embo J* 20:4944-4951, 2001). However, in most other cases, it is unknown which step(s) of transcriptional activation is directly affected by histone acetylation. Furthermore, deviation from this "acetylation=activation" dogma does exist. For example, mutations of certain HATs actually perturb transcriptional silencing (Sun, Z. W., and M. Hampsey, "A general requirement for the Sin3-Rpd3 histone deacetylase complex in regulating silencing in *Saccharomyces cerevisiae*" *Genetics* 152:921-932, 1999), suggesting that the transcriptional readout may not be the result of a simple acetyllysine counting mechanism.

Other nuclear activities are linked to acetylation as well. For example, the yeast and human Elongator complexes that are important for transcriptional elongation contain HAT components; the HAT activity is an integral and essential part of the complexes (Kim, J. H., W. S. Lane, and D. Reinberg., "Human Elongator facilitates RNA polymerase II transcription through chromatin" *Proc Natl Acad Sci USA* 99:1241-1246, 2002; Wittschieben, B. O., et al., "Overlapping roles for the histone acetyltransferase activities of SAGA and elongator in vivo" *Embo J* 19:3060-3068, 2000). The yeast NuA3 HAT complex (Sas3 is the catalytic subunit) interacts with Spt16 that is a component of yeast CP (Cdc68/Pob3) (Brewster, N. K., G. C. Johnston, and R. A. Singer, "A bipartite yeast SSRP1 analog comprised of Pob3 and Nhp6 proteins modulates transcription" *Mol Cell Biol* 21:3491-3502, 2001; Evans, D. R., et al., "The yeast protein complex containing cdc68 and pob3 mediates core-promoter repression through the cdc68 N-terminal domain" *Genetics* 150:1393-1405, 1998) and mammalian FACT (Facilitates chromatin transcription) complexes (John, S., et al., "The something about silencing protein, Sas3, is the catalytic subunit of NuA3, a yTAF(II)30-containing HAT complex that interacts with the Spt16 subunit of the yeast CP (Cdc68/Pob3)-FACT complex" *Genes Dev* 14:1196-1208, 2000). These two complexes also function in transcriptional elongation. V(D)J joining in immune cells has been suggested to be enhanced by histone hyperacetylation at the recombination signal sequences (McBlane, F., and J. Boyes, "Stimulation of V(D)J recombination by histone acetylation" *Curr Biol* 10:483-486, 2000; McMurry, M. T., and M. S. Krangel, "A role for histone acetylation in the developmental regulation of VDJ recombination" *Science* 287:495-498, 2000), although other data argue for a more important role played by promoter positioning (Sikes, M. L., et al., "Regulation of V(D)J recombination: A dominant role for promoter positioning in gene segment accessibility" *Proc Natl Acad Sci USA* 99:12309-12314, 2002). For DNA repair, one yeast HAT Gcn5 is important for photoreactivation and nucleotide excision repair of UV-induced cyclobutane pyrimidine dimers at certain loci (Teng, Y., Y. Yu, and R. Waters, "The *Saccharomyces cerevisiae* histone acetyltransferase Gcn5 has a role in the photoreactivation and nucleotide excision repair of UV-induced cyclobutane pyrimidine dimers in the MFA2 gene" *J Mol Biol* 316:489-499, 2002). Another yeast HAT, Esa1 complex, is recruited to the double-strand DNA breaks for both nonhomologous end joining repair and a new replication-coupled repair pathway (Bird, A. W., et al., "Acetylation of histone H4 by Esa1 is required for DNA double-strand break repair" *Nature* 419:411-415, 2002). The human p300/CBP acetyltransferase is found associated with the p127 subunit of the UV-damaged DNA binding protein complex (UV-DDB) that is implicated in global genomic nucleotide excision repair (Rapic-Otrin, V., et al., "Sequential binding of UV DNA damage binding factor and degradation of the p48 subunit as early events after UV irradiation" *Nucleic Acids Res* 30:2588-2598, 2002), as well as with the thymine DNA glycosylase that functions in repair of G/T and G/U mismatches (Tini, M., et al., "Association of CBP/p300 acetylase and thymine DNA glycosylase links DNA repair and transcription" *Mol Cell* 9:265-277, 2002).

Multiple HATs, Multiple Acetylation, and Multiple Functions

Multiple HATs and HDACs exist in probably all eukaryotes, in sync with the many functions linked to acetylation. These enzymes may display very different substrate specificities (Table 1).

TABLE 1

| | Predicted protein-protein interactions using the different Autocatalytic baits | | | | |
|---|---|---|---|---|---|
| | C-A-B-D | C-A-B'-D | C-B-D | C-B'-D | The detected interaction is: |
| 1 | + | − | − | − | induced by A modification |
| 2 | − | + | − | − | inhibited by A modification |
| 3 | + | + | − | − | independent of A modification |
| 4 | + | + | + | + | not specific for the protein A |

For example, even though Lys14 of H3 seems to be the favored acetylation target for many HATs, these enzymes may differ from each other in their ability to acetylate other lysines of H3 or other core histones (Sterner, D. E., and S. L. Berger, "Acetylation of histones and transcription-related factors" *Microbiol Mol Biol Rev* 64:435-459, 2000). The mammalian p300/CBP HATs acetylate multiple lysines of all four core histones (Ogryzko, V. V., et al., "The transcriptional coactivators p300 and CBP are histone acetyltransferases" *Cell* 87:953-959, 1996). Esa1 is an essential HAT which prefers H2A and H4 (Smith, E. R., et al., "ESA1 is a histone acetyltransferase that is essential for growth in yeast" *Proc Natl Acad Sci USA* 95:3561-3565, 1998). The catalytic subunit of the Elongator complex, Elp3, is able to acetylate all four core histones in an in-gel activity assay (Wittschieben, B. O., et al., "A novel histone acetyltransferase is an integral subunit of elongating RNA polymerase II holoenzyme" *Mol Cell* 4:123-128, 1999), whereas the isolated complex acetylates.K14 of H3 and K8 of H4 (Winkler, G. S., et al., "Elongator is a histone H3 and H4 acetyltransferase important for normal histone acetylation levels in vivo" *Proc Natl Acad Sci USA* 99:3517-3522, 2002). The significance of maintaining different acetylation patterns is exemplified by several reports that the global acetylation of H3 and H4 establishes a transcriptionally poised state (Hebbes, T. R., et al., "Core histone hyperacetylation co-maps with generalized DNase I sensitivity in the chicken beta-globin chromosomal domain" *Embo J* 13:1823-1830, 1994; Kuo, M. H., et al., "Gcn4 activator targets Gcn5 histone acetyltransferase to specific promoters independently of transcription" *Mol Cell* 6:1309-1320, 2000; Schubeler, D., et al., "Nuclear localization and histone acetylation: a pathway for chromatin opening and transcriptional activation of the human beta-globin locus" *Genes Dev* 14:940-950, 2000; Vogelauer, M., J. Wu, N. Suka, and M. Grunstein, "Global histone acetylation and deacetylation in yeast" *Nature* 408:495-498, 2000), whereas the promoter-specific hyperacetylation of H3 seems to be a more direct cause of transcriptional activation (Kuo, M. H., et al., "Gcn4 activator targets Gcn5 histone acetyltransferase to specific promoters independently of transcription" *Mol Cell* 6:1309-1320, 2000; Parekh, B. S., and T. Maniatis, "Virus infection leads to localized hyperacetylation of histones H3 and H4 at the IFN-beta promoter" *Mol Cell* 3:125-129, 1999). Similarly, different yeast HDACs not only show distinct preference on the target acetyllysines, but also differ in the genomic loci to which they are recruited and function (Kurdistani, S. K., et al., "Genome-wide binding map of the histone deacetylase Rpd3 in yeast" *Nat Genet* 31:248-254, 2002; Peterson, C. L., "HDAC's at work: everyone doing their part" *Mol Cell* 9:921-922, 2002; Robyr, D., et al., "Microarray deacetylation maps determine genome-wide functions for yeast histone deacetylases" *Cell* 109:437-446, 2002).

Compared with transcriptional regulation, less is known how other nuclear activities may be affected by different acetylation patterns. For example, Esa1 and Gcn5 are important for DNA damage repair via separate pathways (Bird, A. W., et al., "Acetylation of histone H4 by Esa1 is required for DNA double-strand break repair" *Nature* 419:411-415, 2002; Teng, Y., Y. Yu, and R. Waters,. "The *Saccharomyces cerevisiae* histone acetyltransferase Gcn5 has a role in the photoreactivation and nucleotide excision repair of UV-induced cyclobutane pyrimidine dimers in the MFA2 gene" *J Mol Biol* 316:489-499, 2002). Is this functional differentiation a result of the very different histone acetylation patterns generated by these two enzymes? When Gcn5 participates in UV damage repair, does it create an acetylation product identical to that generated during transcriptional activation? If so, how does one acetylation pattern specify different biological functions? If not, do these differences of the acetylation pattern have physiological significance? Furthermore, arginine mutations introduced at selective lysine residues of histone tails appear to cause dissimilar outcomes in gene activity and chromatin assembly (Braunstein, M., et al., "Efficient transcriptional silencing in *Saccharomyces cerevisiae* requires a heterochromatin histone acetylation pattern" *Mol Cell Biol* 16:4349-5436, 1996; Ma, X. J., et al., "Deposition-related sites K5/K12 in histone H4 are not required for nucleosome deposition in yeast" *Proc Natl Acad Sci USA* 95:6693-6698, 1998; Mann, R. K., and M. Grunstein, "Histone H3 N-terminal mutations allow hyperactivation of the yeast GAL1 gene in vivo" *Embo J* 11:3297-306., 1992; Zhang, W., et al., "Essential and redundant functions of histone acetylation revealed by mutation of target lysines and loss of the Gcn5p acetyltransferase" *Embo J* 17:3155-3167, 1998), indicating that each lysine residue, and likely the acetylation at these sites, may play different roles.

In short, how acetylation of histones controls selective, locus-specific functions remains a mystery. At a broader scale, much less is known as to how histone modifications exert their molecular functions. The present invention is ideal to find answers to this conundrum. We are particularly interested in using the present invention to test whether a histone/nucleosome bearing a particular acetylation pattern may perform specific nuclear functions, and if so, whether these functions are carried out by proteins with specific affinity toward this acetylation pattern. The present invention, a novel "autocatalysis/yeast two-hybrid" method, can identify proteins based on their ability to bind an acetylated histone in vivo. These proteins are known to perform distinct biological roles, and hence are likely to link histone acetylation to different chromatin functions. It is contemplated that the present invention can analyze these acetylated histone binding proteins (AcBPs) to see how one particular acetylated histone species may contribute to particular nuclear functions. Furthermore, the present invention can be used to identify other AcBPs that prefer different acetylated histone populations. Functional studies of these AcBPs will likely shed light on the wide spectrum of functions linked to histone acetylation and, importantly, how these functions are performed at a molecular level.

Post-translational Modifications

Proteins are the most versatile macromolecules in living systems and serve crucial functions in essentially all biological processes. Many proteins also function at the intersection between discrete cellular pathways, such as the communication between chromatin integrity surveillance (aka, checkpoint), cell cycle control, and programmed cell death pathways. The appropriate execution within a function and the coordination between different pathways require numerous interactions between proteins. Stable or transient interactions with selective protein partners are essential for the functions of most, if not all, proteins. Understanding protein-protein interaction at a proteomic scale is now an achievable goal which will ultimately reveal how normal cells function and how malignancies, for example, arise from misregulation of certain cellular activities.

Currently available data suggest that there are at least 10,000 protein-protein interactions among the 6,200 yeast proteins (Uetz, P., Curr Opin Chem Biol 6:57-62, 2002). Such estimation is mainly based on known protein-protein interactions carried out between the "native" or "unmodified" proteins. The total number of protein-protein interactions obviously increases when the genome size increases. That is, human proteins (30,000-60,000 are encoded by the human genome) perform a much greater number and combination of distinct protein-protein interactions. On the other hand, numerous proteins contained post-translational modifications (PTMs) in which selective chemical moieties are added to specific amino acid residues of the target proteins after these proteins are synthesized (see below). Evidence showed that PTMs may trigger or prevent protein-protein interactions. Few currently available methods are suitable for detecting such interactions at a global scale. Thus, our current knowledge on proteomic interactions is far from complete unless those interactions requiring specific PTMs are identified and investigated.

Chemical moieties that constitute post-translational modifications include, for example, the acetyl group (acetylation), the methyl group (methylation), the hydroxyl group (hydroxylation), simple and complex sugars (glycosylation), lipids (myristoylation, palmitoylation, etc), phosphate (phosphorylation), ubiquitin (ubiquitylation), etc. The biological significance of PTMs can be exemplified by phosphorylation: There are 120 kinases in yeast (total protein-encoding genes are around 6,000), and ~550 kinases in human (30,000 to 60,000 total genes). It is estimated that 30% of cellular proteins contain covalently bound phosphate (Cohen, P. 2000. Trends Biochem. Sci. 25:596-602). Given the wide variety of PTMs, it is quite possible that most, if not all, aspects of cellular functions require appropriate regulation of PTMs of specific proteins. The molecular consequences of PTMs vary significantly, including protein stability, intra- and extra-cellular localization, co-factor binding/removal, activation/inactivation of the enzymatic activities of the modified proteins, association/dissociation with other protein factors, and so on. Of these known functions, the potential of a given PTM to recruit or repel a specific protein partner(s) is one of the very important, yet least characterized. Local conformational changes resulted from the PTM, or the chemical moiety itself along with the nearby sequences may solicit protein-protein interactions that are specific for the modified state. Alternatively, an existing protein-protein interaction may be abolished by the PTM. An increasing amount of evidence, mostly obtained by sporadic analyses, supports this notion. However, the lack of an efficient, non-biased genetic method that allows genome-wide identification of such interactions thwarts our full exploration of this territory. In the following sections, a brief review of literature on the involvement of PTMs in protein-protein interactions is given, followed by a detailed description of the Autocatalysis/Two-Hybrid system that provides a versatile and novel solution to this problem.

Phosphorylation of a Tumor Suppressor Protein P53 Recruits Acetyltransferases

Mutations of a tumor suppressor protein p53 have been found in greater than 50% of cancer patients. When cells are exposed to UV, ionizing radiation, and other DNA damaging agents, p53 accumulates in the nucleus and regulates the expression of many genes to arrest the cell cycle so that DNA damages can be repaired. If the damage is too extensive to be repaired, p53 instead triggers apoptosis (programmed cell death) to wipe out the damaged cells so that the mutation will not be passed to progeny cells. A cascade of molecular events, including phosphorylation and acetylation, leads to the accumulation and activation of p53 in the nucleus. Though carried out by distinct enzymes, p53 phosphorylation and acetylation are intimately related to each other in that the phosphorylated p53 binds an acetyltransferase p300/CBP better than without the phosphorylation. p300/CBP then acetylates the carboxyl domain of p53. Meanwhile, p300/CBP recruits yet another acetyltransferase PCAF, which also acetylates p53 within its carboxyl domain. The heavily acetylated p53 further recruits transcriptional coactivators and activates certain genes for cell cycle arrest (Barlev, et al., *Mol. Cell* 8:1243-1252, 2001).

Histone Acetylation and Methylation Recruit Regulators for Transcriptional Control Histones are the basic protein constituents for eukaryotic genome organization, i.e., the chromatin. Histones serve two opposing functions for chromatin structures. On the one hand, histones condense the chromatin which nucleates the formation of mitotic chromosomes for equal distribution of the two sets of genome to the daughter cells during cell division. The rigid structure of chromosomes renders most genomic loci refractory for nuclear activities such as gene activation. On the other hand, histones undergo a variety of PTMs which control the biochemical and biophysical characteristics of histones and hence the dynamics of chromatin. Many of the histone modifications antagonize the condensing roles of histones so that selective loci are poised for gene activation, recombination, and other nuclear functions. Histone modifications include acetylation, methylation, phosphorylation, ubiquitylation, and some other less studied PTMs. Probably all nuclear DNA-templated processes (i.e. transcriptional regulation, DNA replication, chromatin assembly during cell division, DNA damage repair, and recombination) are affected by one or more histone modifications. The mechanisms by which histone PTMs regulate the underlying locus activity remain large unclear. The "histone code" hypothesis suggests that each specifically modified histone acts a transducing signal to recruit other proteins for different molecular functions. Indeed, the acetylated histones are bound by several transcriptional activators containing the bromodomain (see Example 2), whereas methylated histones are bound by several chromodomain-containing transcriptional repressors. The known functions of histone acetylation and methylation in gene regulation correlate well with the corresponding binding proteins.

Furthermore, the Silent Information Regulator protein Sir3 represses transcription by binding the unacetylated histones; acetylation of histones inhibits the binding of Sir3 protein and causes transcriptional de-silencing.

Autocatalysis/Two-Hybrid System to Identify Protein-Protein Interactions Involving PTMs The above examples clearly indicate that protein-protein interactions may be induced or inhibited by specific post-translational modifications. An efficient and non-biased method that allows for the identification of such interactions will be of immense importance for constructing the proteomic interactions database in any organism. The Autocatalysis/Two-Hybrid system (AC/2H) provides such a method.

The essence of any genetic method deriving from the Yeast Two-Hybrid system to identify protein-protein interactions involving PTMs is the effective creation of a specifically and constitutively modified bait. The current invention is novel in that it generates a specialized bait which has the unique ability to catalyze the desired covalent modification within itself at a specific amino acid residue(s). The presence of the covalent modification within the bait allows protein-protein interactions that is induced by this modification to be identified. Moreover, a counterscreen using an otherwise identical bait but lacks the specific PTM will sort out interactions that are independent of, or are inhibited by the covalent modification under investigation.

The detailed design of the AC/2H system is illustrated in FIG. 1. In nature, the protein of interest, A, can be modified by an enzyme, B, in a traditional trans-reaction. The rate of these two proteins to encounter and associate with each other in the environment dictates the efficiency of the catalysis. In contrast, in the AC/2H system, the enzyme and the substrate are encoded as a single protein (or fused to other modules for the purpose of two-hybrid screening, see below), therefore enzyme B catalyzes the modification of A while these two proteins are covalently linked to each other. In other words, for every molecule of the enzyme synthesized, there is a molecule of the substrate within its vicinity. The rate of catalysis can thus reach maximum (the maximal rate of an enzymatic action, Vmax, is defined as that when all enzyme molecules associate with the substrates). As a control, the substrate protein A is also fused to a mutant enzyme B which contains a pre-determined mutation that abolishes the catalytic power of the enzyme (the resulting mutant is denoted B'). The substrate A within the A-B' fusion thus remains unmodified within the substrate A. When A-B and A-B' are used in two parallel two-hybrid tests (after fusing these two to modules C and D, see legends of FIG. 1), proteins that require a modified A for the interaction will display positive reporter readout with the A-B but not the A-B' fusion. On the other hand, if a protein only interacts with the unmodified A, a positive interaction will then be detected by A-B' but not A-B fusion. Proteins that interact with A independently of the latter's modification status will be scored positive in both A-B and A-B'.

Exemplary Uses and of the AC/2H System

As summarized below and without limiting the present invention to any particular use, the power and some of the novel uses of the AC/2H system are several fold. These descriptions below are provided as exemplary only and do not limit the invention in any way.

In one embodiment, it is contemplated that the substrate and the enzyme used in the autocatalysis context can be any known reaction partners. As shown in the examples in the EXPERIMENTAL section, histones H3 and H4 were fused to a histone acetyltransferase Gcn5 which leads to auto-acetylation of both histones by the linked Gcn5. In one embodiment, a substitution of the histone acetyltransferase Gcn5 with other histone modifying enzymes such as Snf1, a known histone H3 kinase, will create an phosphorylated AC bait. Likewise, substituting the histone with other proteins, such as the tumor suppressor protein p53 that is known to be acetylated, phosphorylated, and ubiquitylated, one can identify proteins that interact only with the modified p53 protein. By selecting for those interactions that occur only when p53 is fused to an enzymatically inactivated, but not the wildtype enzyme, p53 interaction partners that are excluded by specific modification(s) of p53 can also be identified. It is thus contemplated that the present invention can detect protein-protein interactions induced or inhibited by a variety of post-translational modifications.

Figure 5A:
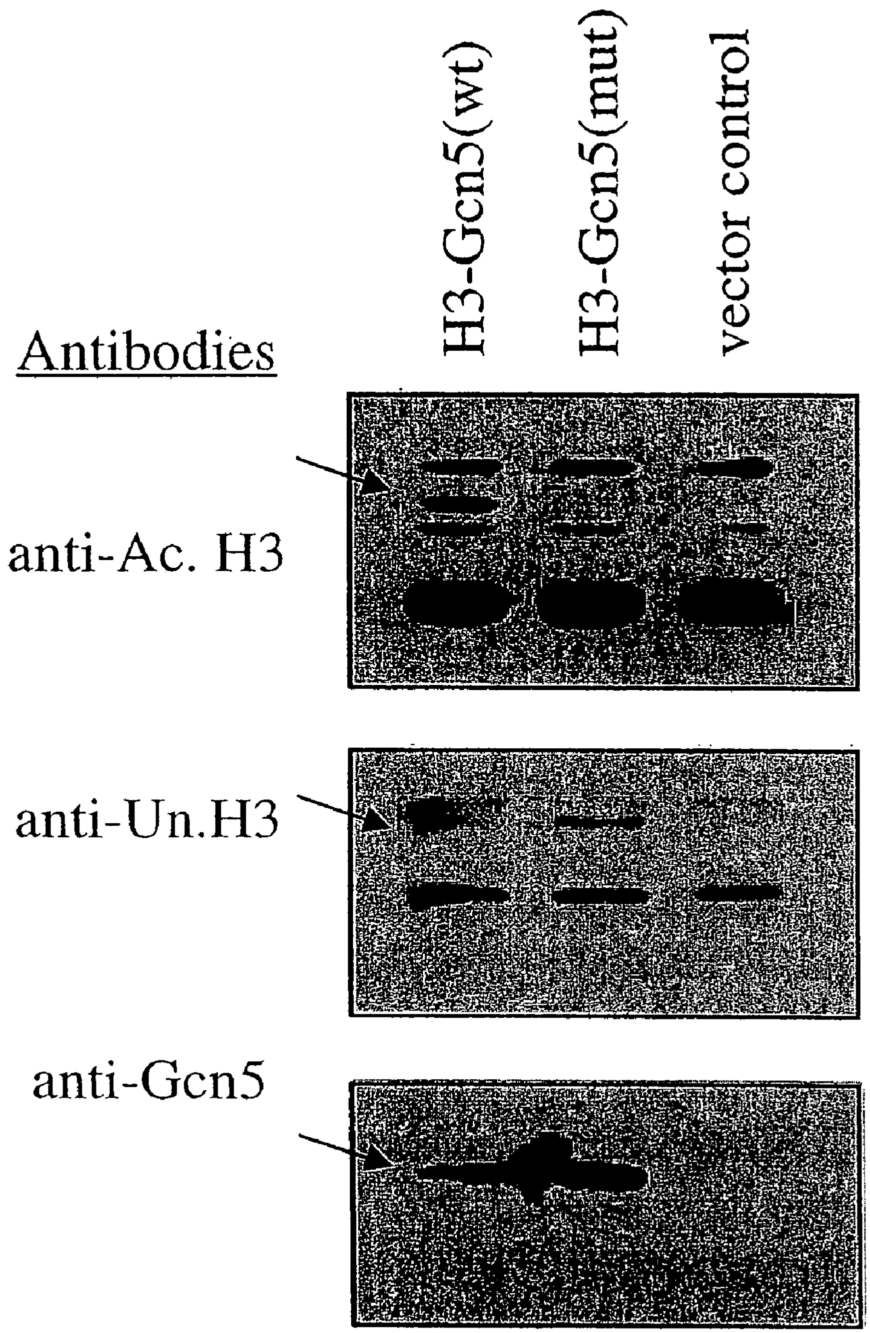
FIGS. 5A, B and C show autoacetylation of H3-Gcn5 and H4-Gcn5 within the context of the Ras Recruitment System. To test the feasibility of the autocatalysis in two-hybrid tests, the H3-Gcn5 (wildtype or F221A mutant) was fused in-frame to the glutathione (GST) and the Ras protein. The H3-GST-Gcn5-Ras fusion was expressed in bacteria (A) and yeast (B) prior to purification for western analyses. The purified fusion proteins were then resolved by SDS-PAGE and analyzed by an antibody specific for histone H3 acetylation. In addition, histone H4 was fused to Gcn5 in parallel experiments and were purified from yeast and probed with an antibody against acetylated H4 (C). In all cases, the wildtype Gcn5 fusion leads to autoacetylation of H3 and H4, in both bacteria and yeast host strains, whereas the mutant Gcn5 fusion failed to do so, providing an ideal negative control for acetylation-dependent protein-protein interactions. Furthermore, the H3-Gcn5 protein expressed and purified from bacteria was also subjected to western analyses using an antibody specific for unacetylated H3 (A, middle panel). The very weak signal seen associated with the wildtype Gcn5 fusion indicates that the autocatalysis is very efficient, such that the residual unacetylated H3 can not be detected effectively by this antibody.
Figure 5B:
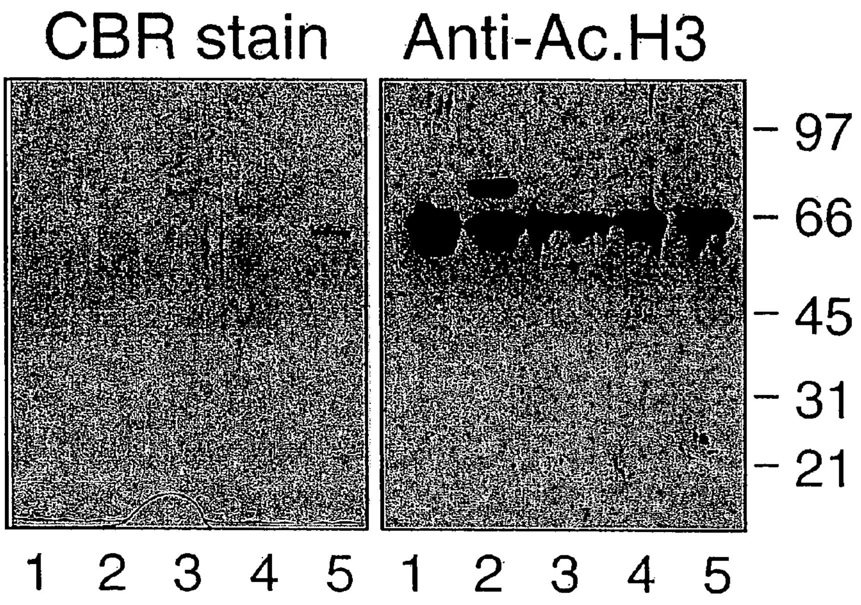
Figure 5C:
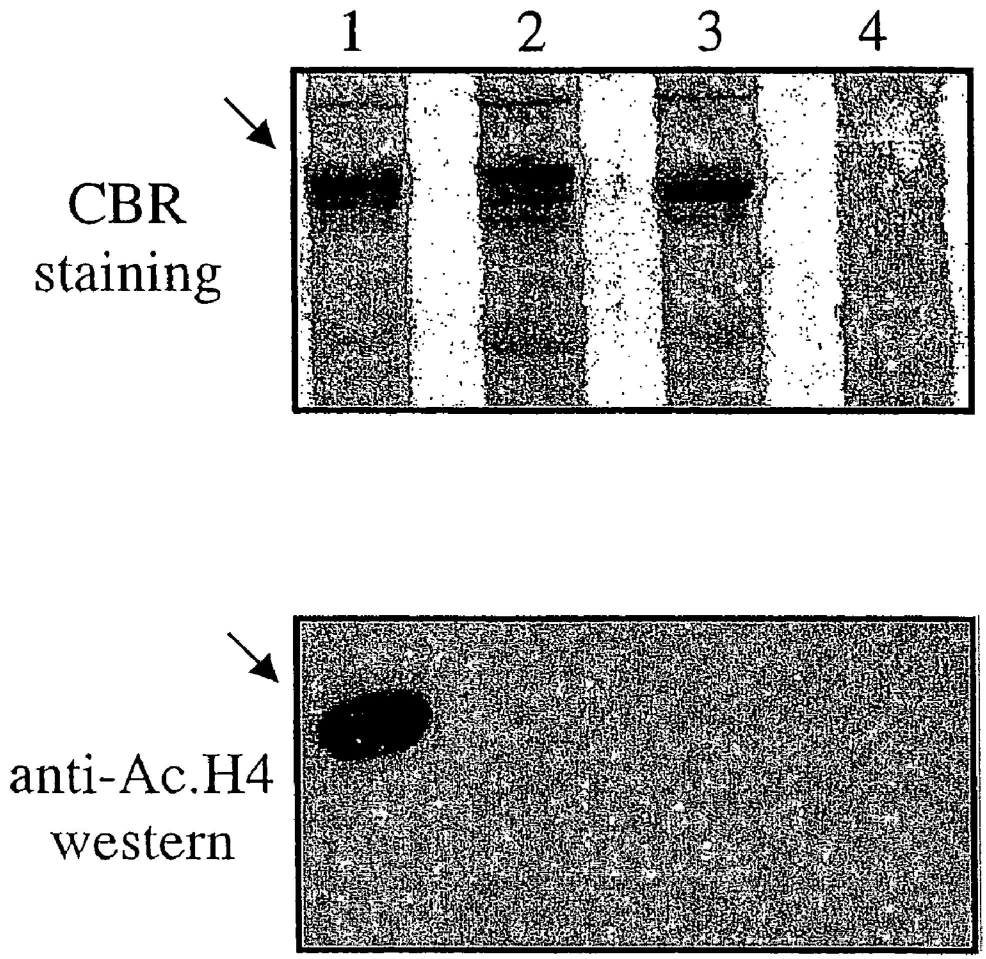
Figure 6:
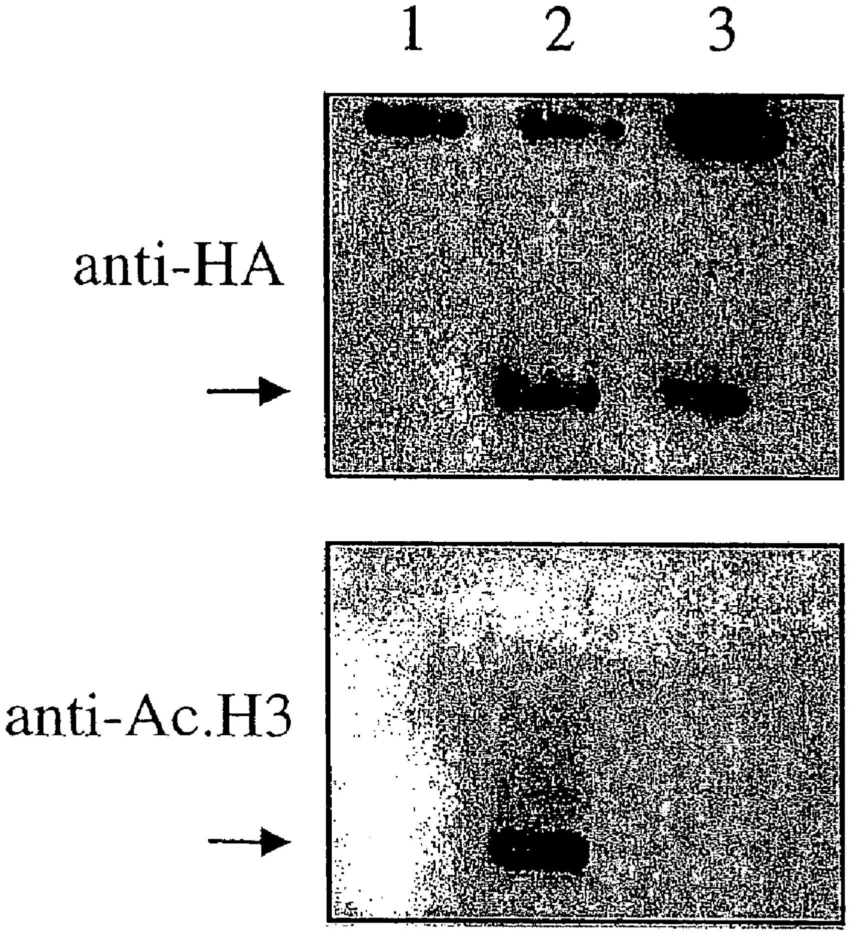
FIG. 6 shows the autoacetylation of H3-Gcn5 in the classical yeast two-hybrid setting. The design of the autocatalytic baits is shown in FIG. 4. The yeast proteins were immunoprecipitated by the anti-HA antibody, followed by SDS-PAGE and western analyses using antibodies against HA (as a loading control, left panel), and against the acetylated H3 (to see the acetylation status, right panel). The positions of the fusion proteins of interest are marked by the arrows.

The autocatalytic capacity of the enzyme-substrate fusion of the present invention is not affected by which two-hybrid system is chosen (see FIGS. 5 and 6). Presently, several methods complement the original Yeast Two-Hybrid system (U.S. Pat. Nos. 5,283,273, 5,468,614 and 5,667,973) in different ways. Some of these derivatives include the Split-Ubiquitin system (Johnsson, et al., "Split ubiquitin as a sensor of protein interactions in vivo" *Proc. Natl. Acad. Sci. USA* 91:10340-10344, 1994; U.S. Pat. Nos. 5,503,977 and 5,585,245), Bacterial Two-Hybrid and Multi-Hybrid systems (U.S. Pat. No. 6,333,154), and Sos and Ras Recruitment system (Aronheim, 2001, Methods Enzymol 332:260-70). Certain kinds of protein-proteins interactions are not likely to be detected by the Y2H (such as those occurring on or within the membrane), but can be detected by one or more of these derivatives. It is contemplated that the autocatalysis concept can be used in conjunction with these methods and hence maximize our ability to screen for PTM-triggered or perturbed protein-protein interactions (see Example 1). All U.S. Patents referred to in this document are incorporated herein by reference.

In one embodiment, it is contemplated that a substrate can be fused to more than one enzyme such that multiple post-translational modifications can be added to the substrate simultaneously. If certain protein-protein interactions require concomitant PTMs of one of the two interacting proteins, a tandem autocatalytic bait (i.e. a fusion composed of substrate A-enzyme B1-enzyme B2) can be created.

In one embodiment, it is also contemplated that two proteins may interact with each other only when both of them contain specific modifications. One can thus create autocatalytic bait and prey (i.e., substrate A1-enzyme B1 and substrate A2-enzyme B2) and fuse these hybrids to the appropriate two-hybrid modules to test the interaction.

Figure 2:
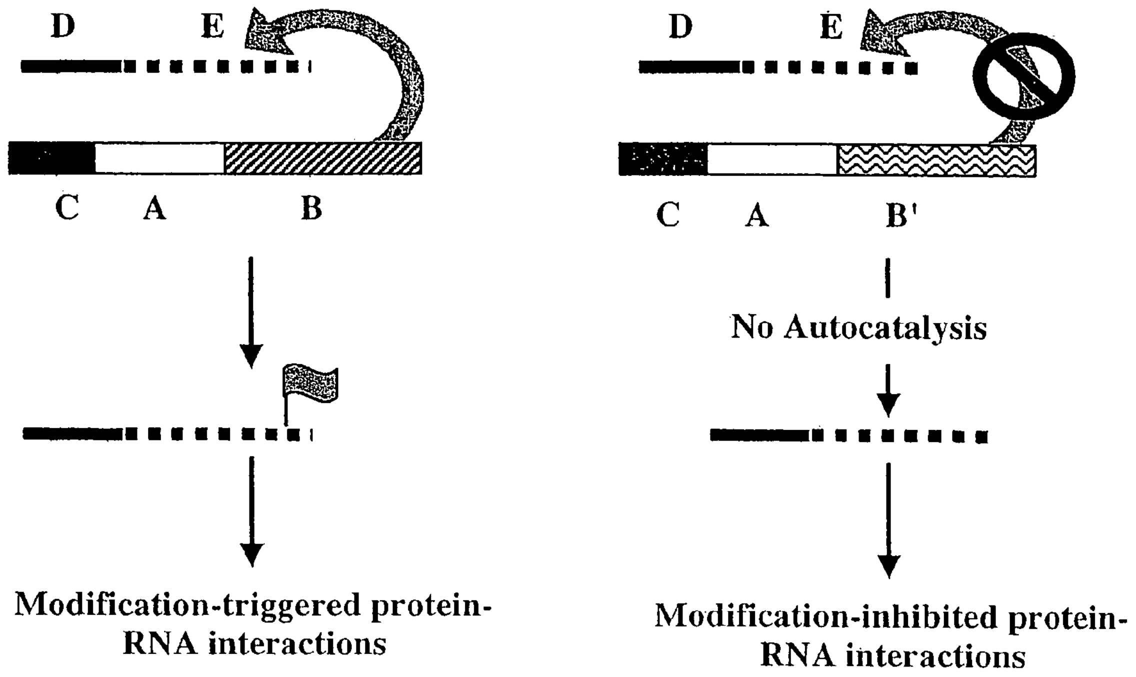
FIG. 2 shows the application of the concept of autocatalysis to the Three-Hybrid system to identify protein-RNA interactions that require a specific modification of the RNA molecule. The module A is a known RNA binding protein that binds module D. Module A is fused in-framed to the DNA binding module C and an RNA modifying enzyme B. The module D is the known interaction partner of protein A. The module E is the RNA molecule of interest that is modified by the enzyme B. When the C-A-B hybrid protein and the D-E hybrid RNA are expressed in the same cell, the C-A-B hybrid protein recruits the D-E hybrid RNA to the promoter region and the enzyme B is thus able to modify the target RNA module E (indicated by the "flag"). The presence of the modified E at the promoter will recruit its interaction proteins, when fused to the activation domain, and activates the transcription from the nearby reporter gene. In the control strain, the enzyme B is replaced with the catalytically inactive enzyme B' so that the modification of the RNA module E is no longer possible. The C-A-B' and D-E hybrids will be the negative control as used in FIG. 1. Hence, protein-RNA interactions that require the target RNA to be modified can be detected.

In another embodiment, a Modified RNA binding protein screening using the Autocatalysis concept is contemplated. The ability of certain proteins to interact with selective RNA molecules plays critical roles in a variety of biological functions, such as pre-mRNA splicing, telomerase activity, RNA transport, etc. The yeast Three-Hybrid System (Sen-Gupta, D.J. et al., "A three-hybrid system to detect RNA-protein interactions in vivo" *Proc Natl Acad Sci USA* 93:8496-501, 1996) is a derivative of the Y2H method to detect protein-RNA interactions. Many RNA molecules are known to be modified after synthesis (i.e., post-transcriptional modifications). If the responsible enzyme is known, the Autocatalysis concept can be applied to the Three-Hybrid system to screen for the proteins that interact with only the appropriately modified RNA molecules (FIG. 2).

For example, in the Three-Hybrid system, the bait is composed of two hybrid proteins: the first hybrid protein consists of a DNA binding motif and a known RNA-binding protein. The second hybrid, an RNA hybrid, is a fusion of two RNAs: one being the ligand for the RNA-binding protein within the first hybrid, and the second being the RNA of interest to which the interacting proteins are to be screened/tested. The third hybrid is the traditional activation domain fusion. To incorporate the Autocatalysis design to the Three-Hybrid method so that proteins that interact only with the modified RNA can be detected, the RNA modifying enzyme can be fused to the first (protein) hybrid. When the second (RNA) hybrid is recruited to the promoter via interaction with the RNA-binding protein within the first triple-hybrid protein, the fused RNA modifying enzyme can modify the bait RNA. If the third hybrid contains the cognate binding protein, positive interactions can then be detected. A parallel fusion with the mutant RNA modifying enzyme will yield a negative result on the interaction test.

Figure 3:
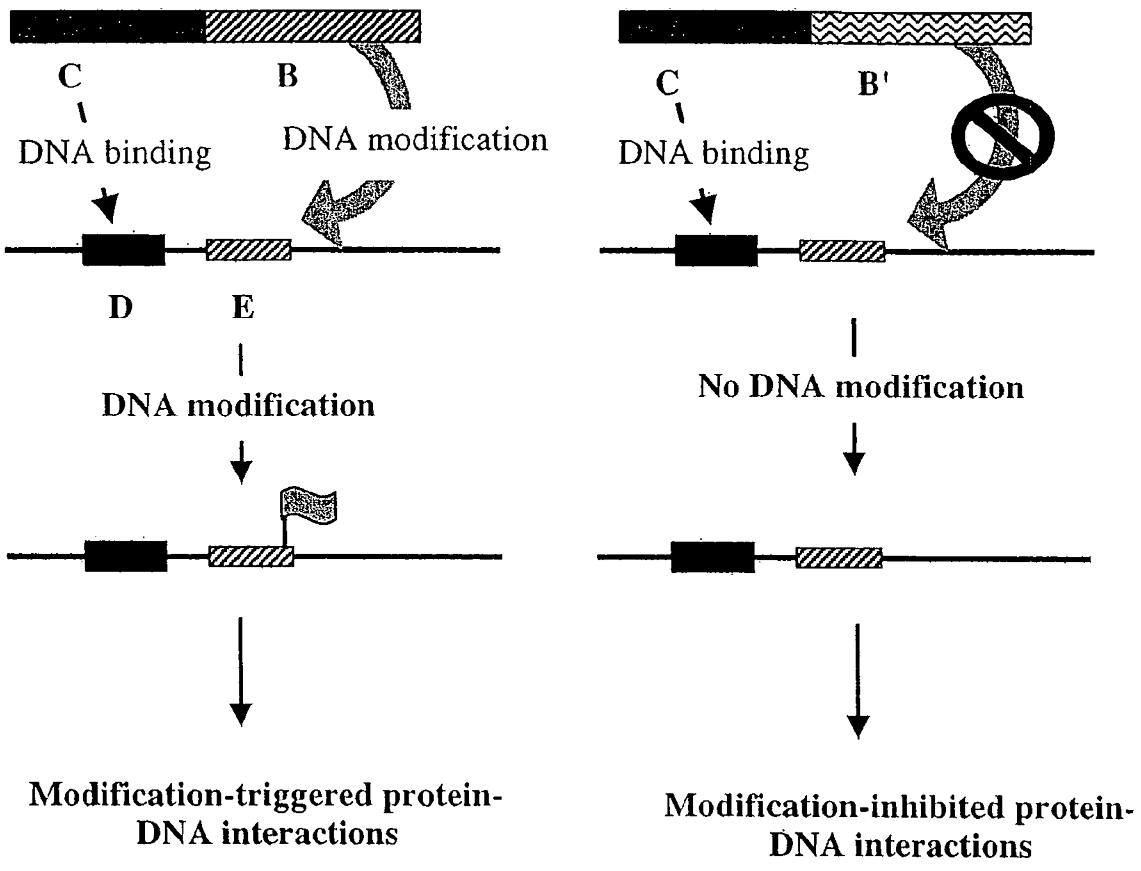
FIG. 3 shows the use of the autocatalysis design in identifying protein-DNA interactions that require a specific modification of the DNA element. The modules C is a sequence-specific DNA binding protein that binds the element D. The module B is a DNA modifying enzyme whereas the element E is a DNA sequence containing the modification target for the enzyme B. The D-E fusion is inserted in front of the reporter gene (not shown). When the C-B hybrid protein is expressed in the strain bearing D-E-reporter gene, the enzyme B is brought to the promoter via C-D interaction and modifies the E element. If a protein that is able to interact with the modified E element but not the unmodified E, expression from the reporter gene will be detected. On the other hand, if the enzyme B is substituted with the mutant B', no modification of E will be yielded; interactions involving the E element but do not require its modification by B can be sorted out by the B' control hybrid.

In one embodiment, it is contemplated that the DNA is known to be modified under certain conditions. For example, methylation of DNA is the basis for the prokaryotic restriction system. In eukaryotes, DNA methylation has been linked to gene regulation and developmental control. Methylated DNA recruits selective proteins that repress transcription. As shown in FIG. 3, the target DNA sequence is engineered to the proximity of the target sequence to which the bait protein binds (e.g., the UASgal that binds the GDBD). The DNA modifying enzyme is fused to the DNA binding module so that it will be brought to the target DNA element via the protein-DNA interaction between UASgal and GDBD. If the AD fusion contains a protein that binds the modified DNA element, transcriptional activation of the reporter gene will be detected. On the other hand, if the mutant DNA modifying enzyme is used, or if the modification target DNA in omitted, no interaction will be detected.

i) Autophosphorylation of CTD by Kin28 and Ctk1 Kinases.

Phosphorylation is the best known PTM. Protein-protein interactions triggered by phosphorylation of one of the two interacting partners have been reported in different systems, and it is very likely that many more such interactions exist in divergent cellular functions. It is well known that 14-3-3 proteins bind phosphoserine/phosphothreonine proteins, whereas SH2 and PTB proteins bind phosphotyrosine in a context-dependent manner. On the other hand, proteins lacking the 14-3-3, SH2, or PTB modules may be novel proteins that bind specifically phosphorylated protein targets. One example is the WW domain protein Ess1 that interacts with the phosphorylated Carboxyl Terminal Domain (CTD) of the largest subunit of the RNA polymerase II in eukaryotes (Myers, et al., "Phosphorylation of RNA polymerase II CTD fragments results in tight binding to the WW domain from the yeast prolyl isomerase Ess1" Biochemistry 40:8479-86, 2001). At least two other proteins also interact with the phosphorylated CTD (Ho, et al, "The guanylyltransferase domain of mammalian mRNA capping enzyme binds to the phosphorylated carboxyl-terminal domain of RNA polymerase II" J Biol Chem 273:9577-85, 1998; McCracken, et al, "5'-Capping enzymes are targeted to pre-mRNA by binding to the phosphorylated carboxy-terminal domain of RNA polymerase II" Genes Dev 11:3306-18, 1997). CTD phosphorylation is intimately associated with transcriptional elongation (Riedl, T., and J. M. Egly, "Phosphorylation in transcription: the CTD and more" Gene Expr 9:3-13, 2000). Several autoimmune diseases are associated with auto-antibodies against the CTD (Dahmus, M. E., "Phosphorylation of the C-terminal domain of RNA polymerase II" Biochim Biophys Acta 1261:171-82, 1995). Therefore, the phosphorylated CTD is an excellent model for search for proteins that bind phosphorylated proteins, with the known phosphoprotein-binding modules or not.

The CTD of the largest subunit of RNA polymerase II is composed of tandem repeats of a heptapeptide Tyr1-Ser2-Pro3-Thr4-Ser5-Pro6-Ser7. Different kinases phosphorylate different residues. For example, Ser2 is phosphorylated by Csk1, and Ser5 is the preferred target for Kin28 and several other protein kinases (Bensaude, et al, "Regulated phosphorylation of the RNA polymerase II C-terminal domain (CTD)" Biochem Cell Biol 77:249-55, 1999; Keogh, et al, "Kin28 is found within TFIIH and a Kin28-Ccl1-Tfb3 trimer complex with differential sensitivities to T-loop phosphorylation" Mol Cell Biol 22:1288-97, 2002; Murray, et al, "Phosphorylation of the RNA polymerase II carboxy-terminal domain by the Bur1 cyclin-dependent kinase" Mol Cell Biol 21:4089-96, 2001). In one embodiment, it is contemplated that CTD, phosphorylated at Ser2 or Ser5, acts as the target for protein-protein interactions. It is also contemplated that CTD-Csk1 and CTD-Kin28 are created and ligated in-frame to GDBD-HA construct to create autophosphorylation baits. Thus, the methodologies described in Examples 1-5 are employed to characterize the phosphorylation status of the fused CTD within the autocatalysis context. Additionally, it is contemplates that genetic screens are used to identify proteins that function as phosphorylated CTD-binding proteins.

ii) Automethylation of Histones H3 and H14.

Transcriptional activation is associated with histones H3 and H4 Arg3 methylation as well as H3 Lys4 methylation (Strahl, et al, "Methylation of histone H4 at arginine 3 occurs in vivo and is mediated by the nuclear receptor coactivator PRMT1" Curr Biol 11:996-1000, 2001; Wang, et al, "Methylation of histone H4 at arginine 3 facilitating transcriptional activation by nuclear hormone receptor" Science 293:853-7, 2001), whereas transcriptional repression and silencing are associated with histone H3 Lsy9 methylation (Lachner, et al, "Methylation of histone H3 lysine 9 creates a binding site for HP1 proteins" Nature 410:116-20, 2001; Nakayama, et al, "Role of histone H3 lysine 9 methylation in epigenetic control of heterochromatin assembly" Science 292:110-3, 2001). Lys9 methylation is known to recruit chromodomain-containing proteins (Lachner, et al, "Methylation of histone H3 lysine 9 creates a binding site for HP1 proteins" Nature 410:116-20, 2001). Although histones methylated at arginine residues have not been shown to bind other proteins, arginine methylation in SmD1 and SmD3 was shown to be recognized by the Survivor of Motor Neurons (SMN) protein (Friesen, et al, "SMN, the product of the spinal muscular atrophy gene, binds preferentially to dimethylarginine-containing protein targets" Mol Cell 7:1111-7, 2001). The search for extra proteins that interact specifically with methylated proteins is thus of high significance in both basic and clinical research. In the yeast *Saccharomyces cerevisiae*, at least three lysine methyltransferases modify histone H3: Set1 (Lys4) (Briggs, et al, "Histone H3 lysine 4 methylation is mediated by Set1 and required for cell growth and rDNA silencing in *Saccharomyces cerevisiae*" Genes Dev 15:3286-95, 2001; Bryk, et al, "Evidence that Set1, a factor required for methylation of histone H3, regulates rDNA silencing in *S. cerevisiae* by a Sir2-independent mechanism" Curr Biol 12:165-70, 2002), Set2 (Lys36) (Strahl, et al, "Set2 is a nucleosomal histone H3-selective methyltransferase that mediates transcriptional repression" Mol Cell Biol 22:1298-306, 2002), and Dot1 (Lys79) (Dlakic, M., "Chromatin silencing protein and pachytene checkpoint regulator Dot1p has a methyltransferase fold" Trends Biochem Sci 26:405-7, 2001; van Leeuwen, et al., "Dot1p modulates silencing in yeast by methylation of the nucleosome core" Cell 109:745-56, 2001). In addition, Arg3 of H4 is methylated by Rmt1 (Lacoste, et al., "Disruptor of Telomeric Silencing-1 Is a Chromatin-specific Histone H3 Methyltransferase" J Biol Chem 277:30421-4, 2002). In one embodiment of the present invention, it is contemplated that the collection of different methylated histone species provides an excellent model to screen for methylated histone binding proteins. Toward this end, we have constructed H3-Set1, H3-Set2, H3-Dot1, and H4-Rmt1 fusion constructs. In short, these fusion fragments can be inserted in-frame with GDBD-HA and expressed in yeast for immunochemical characterization for the desired modifications. Enzymatically inactive versions of each enzyme can be included in the counter-screening constructs as the negative control for subsequent genetic screening. When the automethylation is confirmed, genetic screening is carried out.

Advantages of the AC/2H System

The current invention offers several advantages over existing methods. In one embodiment, the enzyme catalyzes the substrate modification in cis (i.e., autocatalytically). Although the present invention is not limited to any particular theory, it is believed that the enzyme acts at its maximal rate and efficiency. This is clearly different and much more preferable than the typical, trans-reactions of most natural or artificial protein modifications. In another embodiment, the autocatalytic enzyme-substrate fusion can be expressed in its natural host where the opposing enzymes (e.g., deacetylases vs. acetyltransferases, phosphatases vs. kinases, etc.) are present. While pleiotropic effects are frequently seen when protein modifying enzymes are overexpressed (especially when the opposing enzyme is absent), the AC/2H system does not need to over- or ectopically express the enzyme. It is thus much less likely that adverse effects may result from the Autocatalysis setting. In yet another embodiment, the inclusion of the catalytically inactivated enzyme in a parallel chimeric protein fusion provides an ideal control for protein-protein interactions that do not require the modification of the bait protein. In yet another embodiment, the reversal in the genetic screening criteria can reveal protein interactions that are perturbed by a the bait modification. In yet another embodiment, the use of tandem array of different protein modifying enzymes in the autocatalytic baits may provide baits possessing multiple modifications. One single construct is thus sufficient for the bait creation and the target protein screening. In yet another embodiment, the bait bearing the specific chemical modification can be a protein (FIG. 1), an RNA (FIG. 2), and a DNA (FIG. 3).

Experimental

The following examples serve to demonstrate certain aspects of the present invention and do not limit it in any way.

EXAMPLE 1

Evidence of Autocatalysis in Two Different Two-Hybrid Systems and Two Different Organisms.

Figure 4:
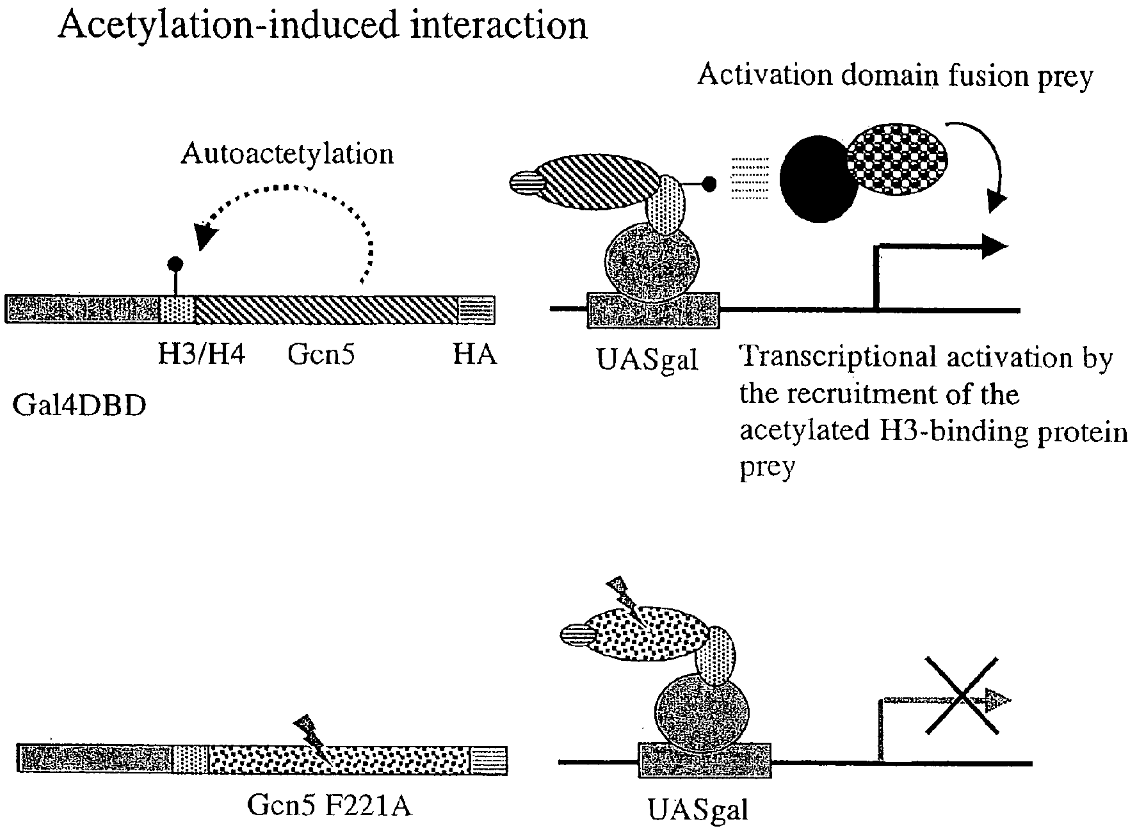
FIG. 4 shows the design of the autoacetylated H3/H4-Gcn5 baits for the Yeast Two-Hybrid screening. The histone tails H3 and H4 are individually fused to the catalytic domain of a histone acetyltransferase Gcn5, the Gal4 DNA binding domain (GDBD), and the HA epitope tag to create plasmid constructs pDG1-4 (low-copy yeast vectors) and pDG5-8 (high-copy yeast vectors). When wildtype Gcn5 is included in the fusion, autocatalysis results in the acetylation of the fused histone H3 or H4 (the "lollipop") (see, for example, FIG. 12, pDG1 [SEQ ID NOS: 1 and 15]

The concept and feasibility of Autocatalysis was tested using an array of fusion proteins composed of histones H3, H4 (as the substrates) and the prototypic histone acetyltransferase, Gcn5. The detailed overview of this system is shown in FIG. 4.

To first test if the autocatalysis actually is feasible, histone H3 (amino acids 2 to 60) was fused to Gcn5 (the catalytic domain, amino acids 1 to 252). In the first setting, H3 was fused to the glutathione S-transferase (GST), followed by the Gcn5 catalytic domain, and by the Ras protein. The Ras protein is a part of the bait used in the Ras Recruitment System, an alternative to Stanley Fields' Yeast Two-Hybrid system (Aronheim, A., *Methods Enzymol* 332:260-70, 2001) (U.S. Pat. No. 5,776,689). The GST is an epitope tag allowing efficient purification of the fusion protein. In addition, a point mutation of Gcn5, F221A (Kuo, M.-H., et al., "Histone acetyltransferase activity of yeast Gcn5p is required for the activation of target genes in vivo" Genes Dev 12:627-639, 1998) was also used to create parallel, catalytically inactive fusion proteins. The F221A significantly diminishes the enzymatic activity of Gcn5, and hence provides an un-acetylated histone H3 bait for counter-screening. In addition, the H3-GST-GCN5-Ras DNA construct was inserted in a bacterial expression vector and a yeast vector. Autocatalysis can thus be tested in proteins synthesized in either *E. coli* or yeast. The fusion proteins were synthesized and purified from *E. coli* or yeast, resolved by SDS-PAGE, and analyzed by western blots using two antibodies. The first antibody recognizes preferentially the acetylated histone H3, whereas the second antibody recognizes the unacetylated histones. As shown in FIG. 5A, the bacterial H3-Gcn5 fusion clearly demonstrates autoacetylation whereas the mutant Gcn5 function is not detectably acetylated under the same condition. FIG. 5B shows very similar results from fusion proteins derived from yeast. These results clearly indicate that the autocatalysis is not dependent on the host cells.

Furthermore, a fusion between Gcn5 and yet another histone, H4, was also created. The acetylation status of H4-GST-Gcn5-Ras, expressed and purified from yeast, is shown in FIG. 5C. Again, the western results clearly indicate the acetylation of H4 by the wildtype Gcn5 but not the F221A mutant.

FIG. 6 shows the autocatalysis when H3-Gcn5 was expressed within the prototypic Yeast Two-Hybrid system context. In this setting, H3-Gcn5 was inserted between the Gal4 DNA binding domain (GDBD) and the hemaglutinin (HA) epitope tag (FIG. 12, pDG1 [SEQ ID NOS: 1 and 15]; FIG. 13, pDG2 [SEQ ID NOS: 2 and 16]; FIG. 16, pDG5 [SEQ ID NOS: 5 and 19] and; FIG. 17, pDG6 [SEQ ID NOS: 6 and 20]) and expressed in yeast. Yeast proteins were prepared and immunoprecipitated by an antibody against the HA tag. The immunoprecipitated materials were thus subjected to western analyses using the acetylated H3-specific antibody mentioned above. The western blot results are very clear: when H3 was fused to the wildtype Gcn5, it was acetylated efficiently; however, when H3 was fused to the F221A mutant Gcn5 fragment, no acetylation was detected.

In short, autoacetylation is clearly achieved in two different two-hybrid systems and in two different organisms. In sharp contrast, the mutant Gcn5 fusion fails to catalyze the autoacetylation. Therefore, the concept of autocatalysis and the use of a catalytically inactive mutation to create the unmodified bait for counter-screening has been proved feasible.

EXAMPLE 2

Confirmation of An Interaction between Acetylated Histones and the Bromodomain of the PCAF Protein.

This Example is to show that AC/Y2H recapitulates bromodomain-acetylated histone interaction in vivo.

To further confirm that the AC/2H can identify protein-protein interactions that require specific PTMs, the GDBD-H3-Gcn5-HA constructs were used in the Yeast Two-Hybrid genetic tests. In the Y2H system, the expression of one of the three reporter genes reveals the protein-protein interactions (James, et al., *Genetics* 144:1425-1436, 1996). The first reporter is the bacterial lacZ gene under the control of GAL7 promoter. Positive interactions are indicated by elevated β-galactosidase activity. The second reporter is the HIS3 gene under the control of the GAL1 promoter. When HIS3 gene is upregulated by positive protein-protein interactions, yeast cells display significant resistance to the chemical 3-amino-1,2,4-triazole (3-AT) and survive in the absence of histidine (His). The third reporter construct is the ADE2 gene fused to the promoter of GAL2 gene. Yeast cells gain the ability to survive in the absence of adenine (Ade) when protein-protein interactions exist between the bait and the prey proteins.

Figure 7:
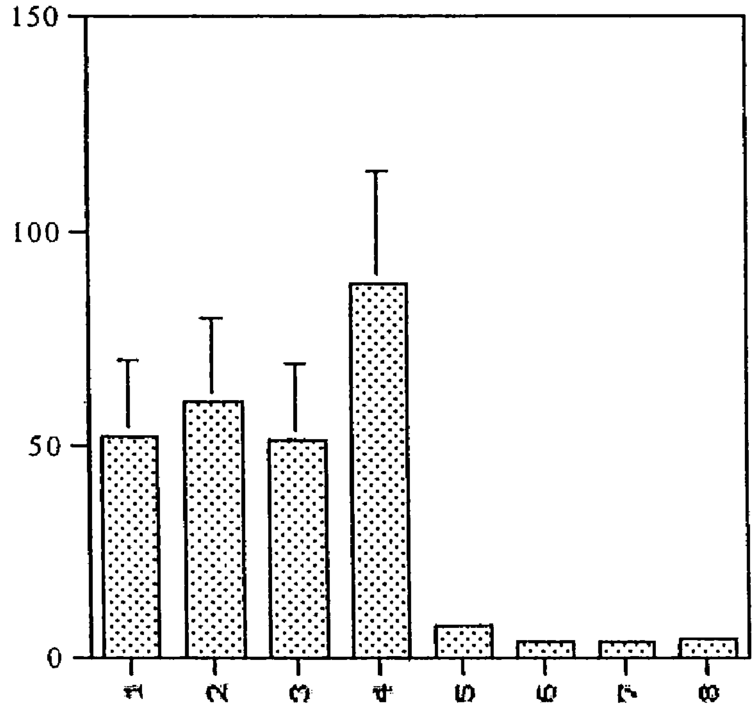
FIG. 7 shows a previously reported acetylated histone interaction can be detected by the AC/Y2H method. The bromodomain of PCAF was fused to the Gal4 activation domain (AD). The PCAF-AD and the AD-only vectors were transformed into the bait-containing yeast strains. The UAS-gal-lacZ reporter gene expression was assessed by measuring the b-galactosidase activity from log-phase cells (Y axis: units/mg protein/min). Stronger lacZ expression indicates protein-protein interactions.

In the first test of AC/Y2H, it was asked whether a previously reported interaction between acetylated histones and the PCAF bromodomain can be detected by our system. This interaction was identified by biochemical means (Dhalluin, C., et al., "Structure and ligand of a histone acetyltransferase bromodomain" *Nature* 399:491-496, 1999; Jacobson, R. H., et al., "Structure and function of a human TAFII250 double bromodomain module" *Science* 288:1422-1425, 2000). To test this in vivo with the AC/Y2H system, the bromodomain of the PCAF protein was fused to the Activation Domain (AD) of the Gal4 transcriptional activator. The AD-PCAF expression construct was transformed into different yeast strains bearing a variety of AC baits. The two-hybrid interaction was assessed by measuring the b-galactosidase activity. As shown in FIG. 7, the PCAF bromodomain interacts with H4-Gcn5 (wildtype, pDG3) fusion but not the mutant Gcn5 counterpart (pDG4). A weaker interaction was detected between the PCAF bromodomain and the H3-Gcn5 fusion (pDG1). Again, the mutant Gcn5 fusion (pDG2) showed a negligible level of lacZ expression. The activation of lacZ caused by GDBD-H3/H4-Gcn5(wt) alone (bars 1 and 3) is an anticipated background level of transcription. This is because tethering Gcn5, a transcriptional coactivator, to the promoter had been shown to induce modest transcription (Marcus, G. A., et al., "Functional similarity and physical association between GCN5 and ADA2: putative transcriptional adaptors" Embo J 13:4807-4815, 1994). In conclusion, the AC/2H system is able to detect a previously reported protein-protein interaction that requires a specific post-translational modification. Additionally, these data are the first in vivo evidence that the highly conserved bromodomain is indeed able to interact with specific acetylated histones.

EXAMPLE 3

Identification of Novel Acetylated Histone Binding Proteins Using the AC/Y2H Methodology.

This Example shows that AC/Y2H using a modified chromatin component (e.g., acetylated histone H3) identifies three chromatin-related proteins Cac1, Rmt1, and Rpm2.

To definitively test whether the AC/2H system is suitable for genetic screening, the GDBD-H3-Gcn5-HA (pDG1) was tested in two different formats of Y2H. The first approach uses a high-throughput screening method (Uetz, P., et al., "A comprehensive analysis of protein-protein interactions in *Saccharomyces cerevisiae" Nature* 403:623-7, 2000). In this approach, protein-protein interactions were tested in about 6,000 yeast strains simultaneously. Each of these 6,000 strains expresses a unique chimeric protein that contains the Gal4 activation domain (AD) and one of the about 6,000 open reading frames (ORFs). The high-throughput Y2H approach uses a robot to cross each of these AD-fusion yeast haploid strains to the one that contained either the GDBD-H3-Gcn5(wildtype)-HA (i.e., pDG1) or the GDBD-H3-Gcn5(F221A)-HA (i.e., pDG2) expression plasmid. The ability of each of the diploid strain after the crossing (now both the bait and one of the 6,000 prey proteins are present in the same diploid cell) to grow in a medium lacking histidine (−His) or adenine (−Ade) was assessed. Candidates that showed positive interactions with the wildtype Gcn5 fusion but not the mutant Gcn5 hybrid were sorted out and tested again for the growth in different media. As seen in FIG. 8A, Rmt1, Cac1 and Exo84 allowed yeast cells to grow in −His medium in the presence of the acetylated H3 bait (resulting from the H3-wildtype Gcn5 fusion), but not of the unacetylated H3 (i.e., the H3-Gcn5 F221A fusion). When these same cells were tested under a more stringent condition (-Ade medium), only Rmt1-AD fusion allows H3-wildtype Gcn5 bait-bearing cells to grow. These results indicate that Cac1, Exo84, and Rmt1 possess intrinsic affinity to acetylated histone H3, and that the Rmt1 may interact with the acetylated H3 at the highest affinity among the three.

Figure 8:
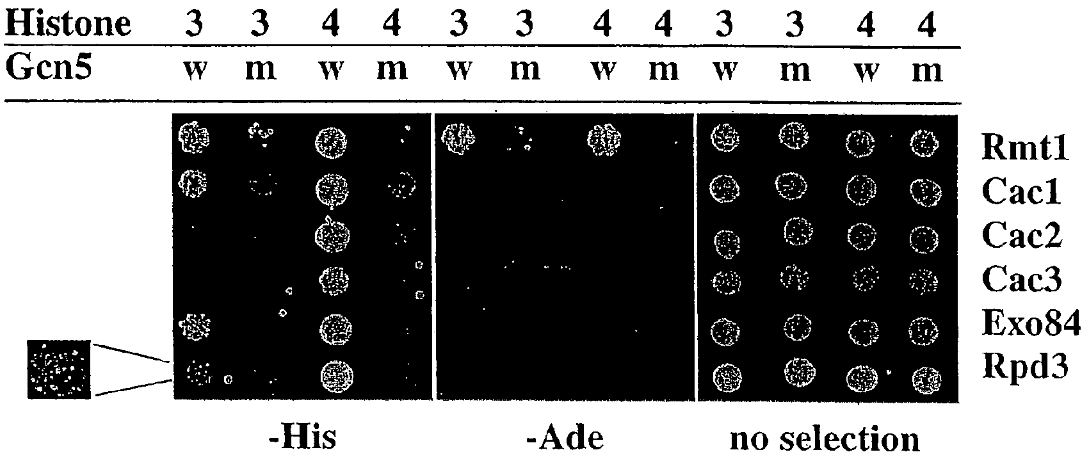
FIG. 8 show the identification of acetylated histone H3- and H4-binding proteins by the AC/2H system: high-throughput method. The composition of the baits are shown on the top (3, H3; 4, H4; w, wildtype Gcn5; m, F221A Gcn5); the AD fusion preys are listed on the right. Three media were used: −His medium is more sensitive and allows weaker interaction to be detected; −Ade plate reveals stronger interactions. The Rpd3+H3-Gcn5 (wt) is blown up to show the weak/transient interaction revealed by the −His medium. Note that the H4-Gcn5 bait activates moderate transcription so that all strains containing this bait are able to grow on −His plate. However, on −Ade plate, the H4-Gcn5 bait does not induce high enough ADE2 reporter expression. Therefore, strong Y2H interactions are detectable in this medium.

In addition, we also tested the interaction between Rpd3-AD fusion and H3-Gcn5 chimeric proteins. Rpd3 is a histone deacetylase (Rundlett, S. E., et al., *Proc Natl Acad Sci USA* 93:14503-14508, 1996; Taunton, et al., *Science* 272:408-411, 1996). HDACs are the most obvious AcBPs. The enlarged photo insert in FIG. 8 shows that a weak interaction can be detected between the acetylated H3 and Rpd3. This weak association is likely resulting from the constant turnover and transient nature of enzyme-substrate interactions.

Figure 9:
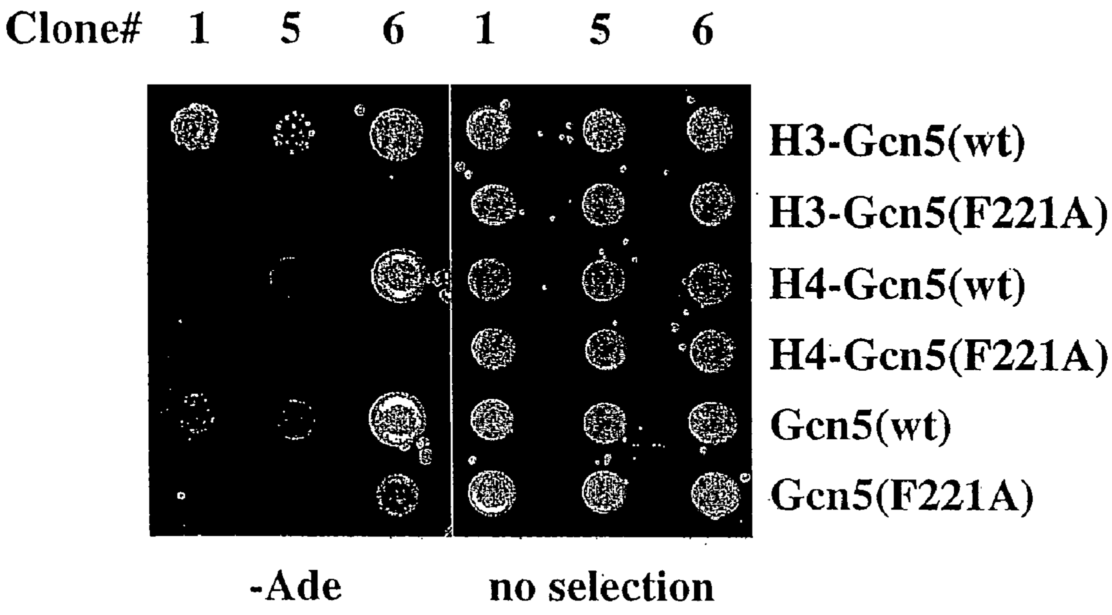
FIG. 9 shows the identification of acetylated histone H3- and H4-binding proteins by the AC/2H system: AD library screening. Two putative AHBPs (acetylated histone binding proteins) were identified by AD library screening using the GDBD-H3-Gcn5-HA bait. Different bait constructs are listed on the right (GDBD and HA are omitted from the legends). The growth on the -Ade plate (left) was assessed. Clone 5 and, to a lesser degree, clone 1 showed obvious growth on the -Ade plate only when the H3-Gcn5 (wt) bait was present, indicating the exclusive interaction with an acetylated H3. On the other hand, clone 6 caused robust growth whenever the wildtype Gcn5 was included in the bait, suggesting 1) that the wildtype Gcn5 interacts with this protein, or 2) that the autoacetylated H3 bait interacts with this prey, or 3) that the enzymatically active Gcn5, while tethered to the promoter region, acetylates nearby histones and/or other protein factors that act as the interacting partner for the prey. DNA sequencing analyses showed that these three candidates are a novel peptide (clone 5), Rpm2 (clone 1), and Cin8 (clone 6).

In the second test, a yeast genomic DNA library with AD fusion was used to screen for acetylated histone H3 binding proteins. This is the "traditional" type of Y2H screen that is being used in numerous labs nowadays. In this test, yeast cells were sequentially transformed with the GDBD-H3-Gcn5(wildtype)-HA construct and the AD-yeast DNA library. Yeast transformants were tested for their ability to grow in the absence of adenine for strong interactions solicited by the H3 acetylation. From this screen, another protein, Rpm2, was found to be a strong acetylated H3 interacting protein (FIG. 9).

Previously reported results indicate that the identification of Cac1, Rmt1, and Rpm2 as the novel acetylated histone binding protein is very significant:

CAC1/RLF2: Cac1 (Kaufman, et al., *Genes Dev* 11:345-357, 1997), or Rlf2 (Enomoto, et al., *Genes Dev* 11:358-370, 1997), is the largest subunit of the yeast chromatin assembly factor complex-I (CAF-I). The activity of CAF-I is conserved from yeast through human (Kaufman, et al., *Cell* 81:1105-1114, 1995; Kaufman, et al., *Genes Dev* 11:345-357, 1997). It is thought that CAF-I binds and delivers newly synthesized histones H3 and H4 to DNA replication forks for nucleosome assembly. Curiously, the human CAF-I interacts with H3/H4 in a tail independent manner Kaufman, et al., *Cell* 81:1105-1114, 1995; Verreault, et al., *Cell* 87:95-104, 1996). My AC/Y2H result thus shows an unsuspected, acetylation-dependent role played by CAF-I. Indeed, CAF-I also participates in (Enomoto, et al., *Genes Dev* 12:219-232, 1998; Monson et al., *Proc Natl Acad Sci USA* 94:13081-13086, 1997). The silencing functions are likely mediated through the Sas2-containing HAT complex, SAS-I (Meijsing, et al., *Genes Dev* 15:3169-3182, 2001). Further, H4 K16 mutation confers the same de-silencing phenotype caused by the sas2 null mutation (Meijsing, et al., *Genes Dev* 15:3169-3182, 2001), linking histone acetylation to Cac1 functions. Furthermore, deleting CAC1 causes defects in repairing UV-damaged DNA (Game, et al., *Genetics* 151:485-497, 1999). Recent data also showed that CAF-I and Hir proteins associate with the kinetochore and are important for centromere functions (Sharp, et al., *Genes Dev* 16:85-100, 2002).

RMT1/HMT1: Rmt1 (protein arginine methyltransferase), or Hmt1 (hnRNP methyltransferase 1) (Henry, et al., *Mol Cell Biol* 16:3668-3678, 1996), transfers the methyl moiety from S-adenosyl methionine to specific arginine residues of certain proteins. Known substrates for Rmt1 include Npl3 (Henry, et al., *Mol Cell Biol* 16:3668-3678, 1996) and Nab2 (Green, et al., *J Biol Chem* 277:7752-7760, 2002). Nab2 and Nlp3 function in splicing and mRNA transport. The Nab2 function depends on its methylation by Rmt1 (Green, et al., *J Biol Chem* 277:7752-7760, 2002). Arginine methylation of several transcriptional activators is important for gene activation (Mowen, et al., *Cell* 104:731-741, 2001; Zhu, et al., *J Biol Chem* 277:35787-35790, 2002). Rmt1 also methylates H4 at Arg3 in vitro (Lacoste, et al., *J Biol Chem* 277:30421-30424, 2002). In mammals, H4 Arg3 methylation is important for transcriptional induction by steroid hormones (Bauer, et al., *EMBO Rep* 3:39-44, 2002; Ma, et al., *Curr Biol* 11:1981-1985, 2001; McBride, *Cell* 106:5-8, 2001; Wang, et al., *Science* 293:853-857, 2001), although a similar phenomenon has not been seen in yeast. Further, deleting RMT1 does not appreciably diminish H4 Arg3 methylation (Lacoste, et al., *J Biol Chem* 277:30421-30424, 2002), indicating that Rmt1 may perform functions other than methylating the bulk histone H4.

Rpm2: Rpm2 (Ribonuclease P in mitochondria) was first identified as the protein subunit of the mitochondrial RNase P (Morales, et al., *Proc Natl Acad Sci USA* 89:9875-9879, 1992; Dang and Martin, *J Biol Chem* 268:19791-19796, 1993). Recent proteomic data suggest that Rpm2 may form a complex with a nuclear protein Hrr25 (Gavin, et al., *Nature* 415:141-147, 2002). Hrr25 is a protein kinase that perform a variety of nuclear functions, including DNA damage repair (DeMaggio, et al., *Proc Natl Acad Sci USA* 89:7008-7012, 1992; Ho, et al., *Proc Natl Acad Sci USA* 94:581-586, 1997; Hoekstra, et al., *Science* 253:1031-1034, 1991). Affinity purification of Hrr25 also identified histone H4 as another interacting (Gavin, et al., *Nature* 415:141-147, 2002). It is thus possible that Rpm2 interacts with acetylated histones and brings Hrr25 to the target loci for specific functions, such as repair the damages of the underlying loci.

In conclusion, results obtained from the high-throughput and the AD library screens indicate clearly that the Autocatalysis/Two-Hybrid system creates specifically and constitutively modified protein baits in vivo that are suitable for genetic test of protein-protein interactions involving specific post-translational modifications. The AC/2H design thus provides significant improvement over the existing genetic methods for protein-protein interactions.

EXAMPLE 4

This Example is to show activation domain library screening with H3-Gcn5 AC baits. Although the high-throughput Y2H method of the prior art has uncovered many insightful protein-protein interactions, there seems to be a high rate of false negatives in this approach (Auerbach, D., et al., "The post-genomic era of interactive proteomics: Facts and perspectives" *Proteomics* 2:611-623; Uetz, P., "Two-hybrid arrays" *Curr Opin Chem Biol* 6:57-62, 2002). For example, two independent, yet methodologically very similar Y2H genome-wide screens showed surprisingly small overlap (Ito, T., et al., "A comprehensive two-hybrid analysis to explore the yeast protein interactome" *Proc Natl Acad Sci USA* 98:4569-4574, 2001; Uetz, P., et al., "A comprehensive analysis of protein-protein interactions in *Saccharomyces cerevisiae*" *Nature* 403:623-627, 2000). Many previously documented interactions were not picked up by screen. Several explanations are considered. First, it is common that protein-protein interactions are more easily detectable when small domains are used, probably due to the removal of potential interference from the rest of the protein. The current (high-throughput) method uses the entire ORFs for AD fusion. Second, expressing the entire ORF of certain genes may cause adverse effects on growth, hence making the detection of interactions involving these ORFs less likely.

To compensate for the limitation of the high-throughput method, we initiated a traditional Y2H library screen. A library of yeast genomic DNA fragments fused to the Gal4 activation domain (AD) was acquired (James, P., J. Halladay, and E. A. Craig, "Genomic libraries and a host strain designed for highly efficient two-hybrid selection in yeast" *Genetics* 144:1425-1436, 1996) and transformed into the PJ69-4a yeast strain harboring either the GDBD-H3-Gcn5 (wt)-HA or GDBD-H3-Gcn5(F221A)-HA construct. The PJ69-4a strain is the same one used in the high-throughput screen. In this strain, three reporter genes are under the control of UASgal: HIS3 and ADE2 respectively confer histidine and adenine prototrophy, and lacZ allows colorimetric quantitation of the transcription and, accordingly, the relative strength of the interaction. It has been shown that ADE2 is a much more stringent reporter than HIS3 and generates significantly less false positives (James, P., J. Halladay, and E. A. Craig, "Genomic libraries and a host strain designed for highly efficient two-hybrid selection in yeast" *Genetics* 144:1425-1436, 1996). We thus use adenine prototrophy as the primary criterion to screen for AcBPs.

Thus far, ~30,000 AD fusion transformants (~3× coverage of the yeast genome) were obtained and replica plated to adenine omission plates. 162 (with wt Gcn5-H3 fusion) and 25 (with F221A Gcn5-H3 fusion) clones were confirmed to be $ADE^+$. Six of these AD plasmids were propagated and purified from *E. coli*, and shown by restriction mapping to contain distinct yeast DNA inserts. As depicted in FIG. 4A, these clones were then re-transformed into the parental strain bearing one of several Gcn5 fusion derivatives. These control plasmids can quickly weed out undesired interacting partners. FIG. 4B shows that two candidates (clones 5 and 1) interact exclusively with H3-Gcn5(wt), whereas clone 6 confers a $ADE^+$ phenotype whenever the bait contains the wildtype Gcn5; the remainder three did not repeat the $ADE^+$ phenotype in any combination (not shown) and will not be studied further. The identity of these two AD fusion, and further tests of the rest of the putative AcBPs are being pursued at the time of submitting this proposal.

EXAMPLE 5

This Example shows autoacetylation of a tumor suppressor protein, p53, by physically linked acetyltransferases. Additionally, this example shows that the acetyltransferase Gcn5 is able to mediate autocatalysis when a non-histone protein (p53) is included in the autocatalysis construct. It also indicates that other acetyltransferases, such as p300, may acetylate the fused p53 at different lysine residues. The tumor suppressor protein p53 plays a critical role in determining cell fate in response to DNA damage, nucleotide depletion, hypoxia, and several other genotoxic stresses. These stresses trigger a series of changes in p53 leading to the stabilization and activation of p53 in the nucleus. Activated p53 induces or inhibits the expression of more than 150 genes, many of which are essential for growth, cell cycle control, and apoptosis. The ultimate function of p53 is to commit cells to either DNA damage repair or apoptosis such that mutations are prevented from being passed on to progeny cells. It is estimated that 50% of all human cancers are linked to loss-of-function mutations in p53 that result in uncontrolled cellular proliferation. Moreover, suppression of p53 activity in tumor cells can cause tumor relapse after chemotherapy. Interestingly, "superactive" p53 mutants that are predicted to provide enhanced genomic surveillance can cause premature cellular senescence. Therefore, p53 maintains a delicate balance between normal cell proliferation and aging.

A landmark event associated with p53 activation is the post-translational modification (PTM) of p53, most notably acetylation (Gu, W., and R. G. Roeder, "Activation of p53 sequence-specific DNA binding by acetylation of the p53 C-terminal domain" *Cell* 90:595-606, 1997) and phosphorylation (Wang, Y., and C. Prives, "Increased and altered DNA binding of human p53 by S and G2/M but not G1 cyclin-dependent kinases" *Nature* 376:88-91, 1995). Like numerous other covalently modified proteins, the exact molecular functions played by various p53 modifications are largely unknown. One likely possibility is that these modifications effect downstream events such as transcriptional activation or repression of p53 target genes. We hypothesize that critical protein-protein interactions that mediate p53 function are controlled by site-specific modifications. For example, interactions between p53 and a downstream protein factor, such as a transcriptional co-activator, may be mediated by a modification at a specific p53 site. Alternatively, some p53 modifications may serve as "repellants" to displace factors that normally associate with p53 in its unmodified, inactive state. Thus, it is possible that site-specific modifications are responsible for determining cellular fate, specifically, to proliferate, apoptose, or senesce. p53-GCN5 fusion: PCAF acetylates K320 of p53 upon UV treatment. The catalytic domains of PCAF and yeast Gcn5 share 56% identity and 71% similarity. Furthermore, the proline 16 of histone H3 that is critical for Gcn5-H3 interaction is conserved in p53 (p53: QPK320KKPLD; H3: TGG14KAPRK) (Rojas, et al., "Structure of Tetrahymena GCN5 bound to coenzyme A and a histone H3 peptide" *Nature* 401:93-8, 1999). It is thus possible that K320 can be acetylated within the context of p53-yGcn5 chimera as well. To test this possibility, the H3 fragment used in Examples 1-9 have been replaced with amino acids 300 to 393 of p53, and the resultant fusion proteins (with the wildtype and the mutant Gcn5) were immunoprecipitated from yeast extracts, followed by western analyses to test the acetylation status at Lys320. The results are shown in FIG. 10. It is clear that Lys320 of p53, though a non-histone protein, is effectively acetylated by the fused Gcn5 protein, but not the mutant Gcn5. These results firmly establish the feasibility of autoacetylation of general proteins, providing the appropriate enzymes are included in the autocatalytic baits. p53-p300 fusion: p300/CBP acetylates p53 in response to UV and IR treatment. The acetylation sites have been mapped to K372, 373, 381 and 382, with K373 and 382 being the major targets (Gu, W., and R. G. Roeder, "Activation of p53 sequence-specific DNA binding by acetylation of the p53 C-terminal domain" *Cell* 90:595-606, 1999; Liu, et al., "p53 sites acetylated in vitro by PCAF and p300 are acetylated in vivo in response to DNA damage" *Mol Cell Biol* 19:1202-9, 1999). To see whether p300/CBP can be used in p53 autocatalysis, we will follow the strategy stated above to create p53-CBP fusion proteins. In the meantime, a point mutant, F1451A will be included in a parallel construction as the counter selection. F1451 is at the position equivalent to F221 of the yeast Gcn5 and the F1451A mutant loses its ability to acetylate histones and to activate transcription (Martinez-Balbas, et al., "The acetyltransferase activity of CBP stimulates transcription" *EMBO J* 17:2886-93, 1998).

EXAMPLE 6

Figure 11:
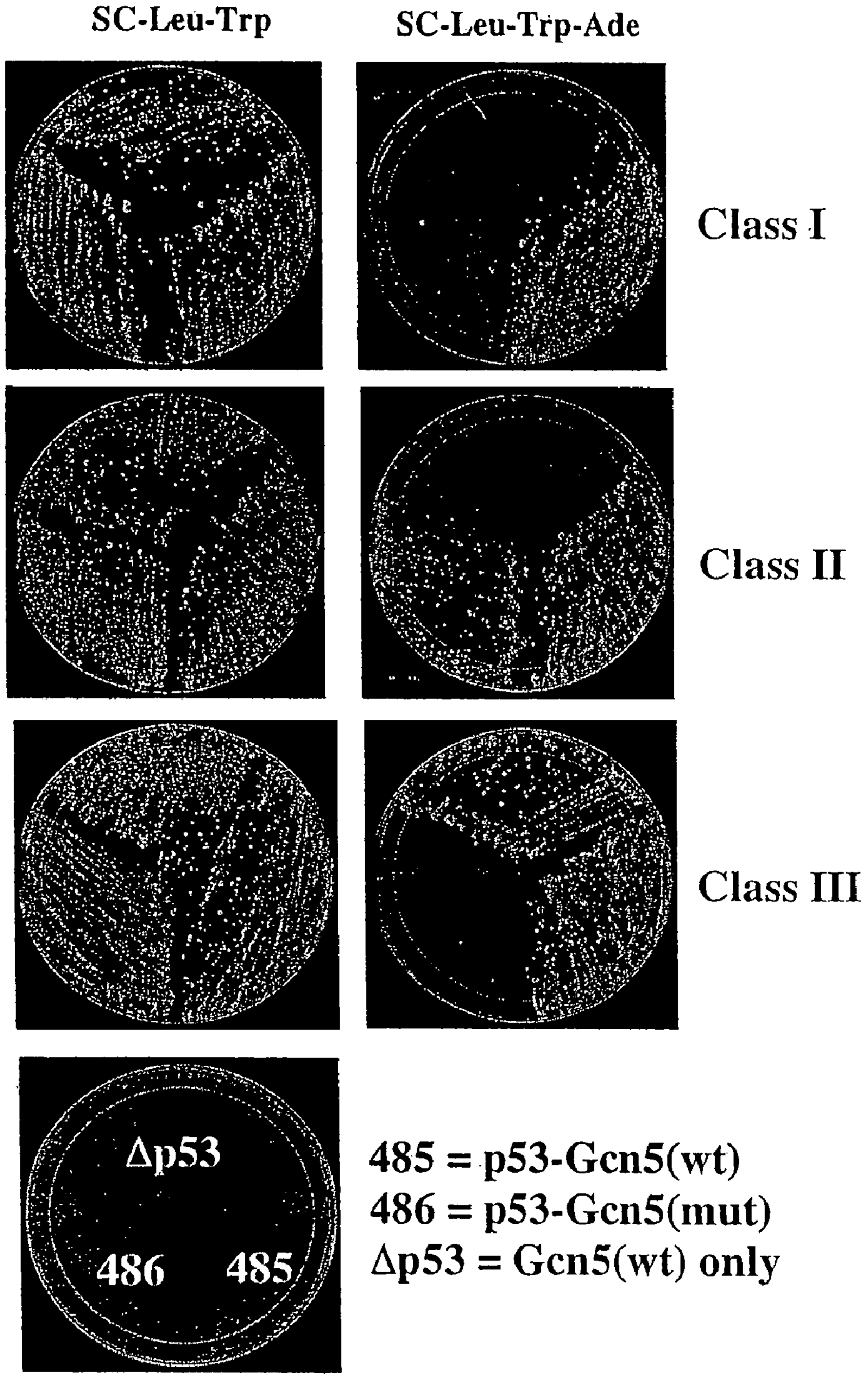
FIG. 11 shows the identification of proteins that interact with acetylated or unacetylated p53 protein. The GDBD-p53-Gcn5(wt)-HA (pMK485, FIG. 24, SEQ ID NOS: 13 and 27), GDBD-p53-Gcn5(mutant)-HA (pMK486, FIG. 25, SEQ ID NOS: 14 and 28), as well GDBD-Gcn5(wt)-HA were used as the baits in the yeast two-hybrid method to screen for human proteins that interact with specific p53 species. The yeast transformants bearing the activation domain-human cDNA fusion constructs and are able to active the ADE2 reporter gene became ADE+ and were tested for their ability to survive in the absence of adenine (SC -Leu -Trp -Ade plates) in one of the three baits mentioned above. Three classes of the candidates were identified: Class I represents those that only interact with the wildtype Gcn5 fusion of p53 (i.e. the acetylated p53 protein); Class II represents those that interact with both wildtype and mutant Gcn5 fusion of p53 (i.e., p53 interactors independent of the acetylation status); Class III represent those that interact with both wildtype Gcn5-p53 fusion as well as the wildtype Gcn5 alone.

This Example shows the identification of human proteins that are able to interact with p53 in acetylation-dependent and -independent manners. Additionally, this example shows that the p53 protein, when fused to the wildtype or mutant Gcn5 acetyltransferase, recruits certain human proteins. As seen in FIG. 11, a human cDNA-activation domain (AD) library was transformed into yeast two-hybrid strains containing the GDBD-p53-Gcn5(wt)-HA bait. The transformants were tested for their ability to survive in the absence of adenine. Activation of the ADE2 reporter gene resulted from positive two-hybrid interactions allows cells to form colonies. More then 350,000 yeast transformants were screened and several candidates were obtained. These candidates were further tested for two-hybrid interactions with GDBD-p53-Gcn5(wt)-HA, GDBD-p53-Gcn5(mutant)-HA, and GDBD-Gcn5(wt)-HA. Three classes of interactions were observed: Class I represents those that only interact with the wildtype Gcn5 fusion of p53 (i.e. the acetylated p53 protein); Class II represents those that interact with both wildtype and mutant Gcn5 fusion of p53 (i.e., p53 interactors independent of the acetylation status); Class III represent those that interact with both wildtype Gcn5-p53 fusion as well as the wildtype Gcn5 alone.

Based on these results, it is highly likely that certain proteins indeed function as acetylated-p53 binding proteins. These Class I proteins may play roles in relaying the p53 functions in transcriptional regulation, cell cycle arrest, and apoptosis. They may also conduct functions in turning over the activated p53 protein when the need of p53 no longer exists.

EXAMPLE 7

This Example shows the autophosphorylation of the CTD by Kin28 and Ctk1 kinases. Phosphorylation is the best known PTM. Protein-protein interactions triggered by phosphorylation of one of the two interacting partners have been reported in different systems, and it is very likely that many more such interactions exist in divergent cellular functions. It is well known that 14-3-3 proteins bind phosphoserine/phosphothreonine proteins, whereas SH2 and PTB proteins bind phosphotyrosine in a context-dependent manner (see, above). On the other hand, proteins lacking the 14-3-3, SH2, or PTB modules may be novel proteins that bind specifically phosphorylated protein targets. One example is the WW domain protein Ess1 that interacts with the phosphorylated Carboxyl Terminal Domain (CTD) of the largest subunit of the RNA polymerase II in eukaryotes (Myers, et al., "Phosphorylation of RNA polymerase II CTD fragments results in tight binding to the WW domain from the yeast prolyl isomerase Ess1" *Biochemistry* 40:8479-86, 2001). At least two other proteins also interact with the phosphorylated CTD (Ho, et al., "The guanylyltransferase domain of mammalian mRNA capping enzyme binds to the phosphorylated carboxyl-terminal domain of RNA polymerase II" *J Biol Chem* 273:9577-85, 1998; McCracken, et al., "5'-Capping enzymes are targeted to pre-mRNA by binding to the phosphorylated carboxy-terminal domain of RNA polymerase II" *Genes Dev* 11:3306-18, 1997). CTD phosphorylation is intimately associated with transcriptional elongation (Riedl, T., and J. M. Egly, "Phosphorylation in transcription: the CTD and more" *Gene Expr* 9:3-13, 2000). Several autoimmune diseases result from auto-antibodies against the CTD (Dahmus, M. E., "Phosphorylation of the C-terminal domain of RNA polymerase II" *Biochim Biophys Acta* 1261:171-82, 1995). Therefore, the phosphorylated CTD is an excellent model for search for proteins that bind phosphorylated proteins, with the known phosphoprotein-binding modules or not.

The CTD of the largest subunit of RNA polymerase II is composed of tandem repeats of a heptapeptide Tyr1-Ser2-Pro3-Thr4-Ser5-Pro6-Ser7. Different kinases phosphorylate different residues. For example, Ser2 is phosphorylated by Csk1, and Ser5 is the preferred target for Kin28 and several other protein kinases (Bensaude, et al., "Regulated phosphorylation of the RNA polymerase II C-terminal domain (CTD)" *Biochem Cell Biol* 77:249-55, 1999; Keogh, et al., "Kin28 is found within TFIIH and a Kin28-Ccl1-Tfb3 trimer complex with differential sensitivities to T-loop phosphorylation" *Mol Cell Biol* 22:1288-97, 2002; Murray, et al., "Phosphorylation of the RNA polymerase II carboxy-terminal domain by the Bur1 cyclin-dependent kinase" *Mol Cell Biol* 21:4089-96, 2001). To see if CTD, phosphorylated at Ser2 or Ser5, may act as the target for protein-protein interactions, it is contemplated that CTD-Csk1 and CTD-Kin28 can be created and ligated in-frame to GDBD-HA construct to create autophosphorylation baits. Methodologies described in Examples 1-5 can thus be employed to characterize the phosphorylation status of the fused CTD within the autocatalysis context. Genetic screens will follow to identify proteins that function as phosphorylated CTD-binding proteins. (Ho, et al., "The guanylyltransferase domain of mammalian mRNA capping enzyme binds to the phosphorylated carboxyl-terminal domain of RNA polymerase II" *J Biol Chem* 273:9577-85, 1998; McCracken, et al., "5'-Capping enzymes are targeted to pre-mRNA by binding to the phosphorylated carboxy-terminal domain of RNA polymerase II" *Genes Dev* 11:3306-18, 1997; Myers, et al., "Phosphorylation of RNA polymerase II CTD fragments results in tight binding to the WW domain from the yeast prolyl isomerase Ess1" *Biochemistry* 40:8479-86, 2001).

EXAMPLE 8

This Example shows the automethylation of histones H3 and H4. Additionally, this example indicates the potential use of the AC/2H method in identifying proteins that bind specifically methylated histones. The past two years have seen spectacular explosion of interest in histone methylation and its role in transcriptional regulation. Transcriptional activation is associated with histones H3 and H4 Arg3 methylation as well as H3 Lys4 methylation (Strahl, et al., "Methylation of histone H4 at arginine 3 occurs in vivo and is mediated by the nuclear receptor coactivator PRMT1" *Curr Biol* 11:996-1000, 2001; Wang, et al., "Methylation of histone H4 at arginine 3 facilitating transcriptional activation by nuclear hormone receptor" *Science* 293:853-7, 2001), whereas transcriptional repression and silencing are associated with histone H3 Lsy9 methylation (Lachner, et al., "Methylation of histone H3 lysine 9 creates a binding site for HP1 proteins" *Nature* 410:116-20, 2001; Nakayama, et al., "Role of histone H3 lysine 9 methylation in epigenetic control of heterochromatin assembly" *Science* 292:110-3, 2001). Lys9 methylation is known to recruit chromodomain-containing proteins (Lachner, et al., "Methylation of histone H3 lysine 9 creates a binding site for HP1 proteins" *Nature* 410:116-20, 2001). Although histones methylated at arginine residues have not been shown to bind other proteins, arginine methylation in SmD1 and SmD3 was shown to be recognized by the Survivor of Motor Neurons (SMN) protein (Friesen, et al., "SMN, the product of the spinal muscular atrophy gene, binds preferentially to dimethylarginine-containing protein targets" *Mol Cell* 7:1111-7, 2001). The search for extra proteins that interact specifically with methylated proteins is thus of high significance in both basic and clinical research. In the yeast *Saccharomyces cerevisiae*, at least three lysine methyltransferases modify histone H3: Set1 (Lys4) (Briggs, et al., "Histone H3 lysine 4 methylation is mediated by Set1 and required for cell growth and rDNA silencing in *Saccharomyces cerevisiae*" *Genes Dev* 15:3286-95, 2001; Bryk, et al., "Evidence that Set1, a factor required for methylation of histone H3, regulates rDNA silencing in *S. cerevisiae* by a Sir2-independent mechanism" *Curr Biol* 12:165-70, 2002), Set2 (Lys36) (Strahl, et al., "Set2 is a nucleosomal histone H3-selective methyltransferase that mediates transcriptional repression" *Mol Cell Biol* 22:1298-306, 2002), and Dot1 (Lys79) (Dlakic, M., "Chromatin silencing protein and pachytene checkpoint regulator Dot1p has a methyltransferase fold" *Trends Biochem Sci* 26:405-7, 2001; van Leeuwen, et al., "Dot1p modulates silencing in yeast by methylation of the nucleosome core" *Cell* 109:745-56, 2001). In addition, Arg3 of H4 is methylated by Rmt1 (Lacoste, et al., "Disruptor of Telomeric Silencing-1 Is a Chromatin-specific Histone H3 Methyltransferase" *J Biol Chem* 277:30421-4, 2002). The collection of different methylated histone species provides an excellent model to screen for methylated histone binding proteins (MHBPs). Toward this end, we have initiated the construction of H3-Set1, H3-Set2, H3-Dot1, and H4-Rmt1 fusion constructs. In short, these fusion fragments will be inserted in-frame with GDBD-HA and expressed in yeast for immunochemical characterization for the desired modifications. Enzymatically inactive versions of each enzyme will be included in the counter-screening constructs as the negative control for subsequent genetic screening. When the automethylation is confirmed, genetic screening for the MHBPs will be carried out.

TABLE 2

| Examples of autocatalytic substrate-enzyme fusion | | | |
|---|---|---|---|
| Substrate | Enzyme | PTM | Note |
| Histone H3 | Gcn5 | Acetylation | Examples 1-4 |
| Histone H4 | Gcn5 | Acetylation | Examples 1-4 |
| p53 | Gcn5 | Acetylation | Example 5 |
| p53 | p300/CBP | Acetylation | Example 5 |
| Histone H3 | Set1 | Methylation (lysine) | Example 7 |
| Histone H4 | Rmt1 | Methylation (arginine) | Example 7 |
| Histone H3 | Set2 | Methylation (lysine) | Example 7 |
| Histone H3 | Dot1 | Methylation (lysine) | Example 7 |
| CTD | Kin28 | Phosphorylation | Example 6 |
| CTD | Ctk1 | Phosphorylation | Example 6 |
| Histone H3 | Snf1 | Phosphorylation | |
| p53 | PIAS | Sumoylation | |
| Histone H2B | Rad6 | Ubiquitylation | |

EXAMPLE 9

Autoacetylation of A Tumor Suppressor Protein, p53, by A Physically Linked Acetyltransferase.

This example shows that the acetyltransferase Gcn5 is able to mediate autocatalysis when a non-histone protein (p53) is included in the autocatalysis construct. It also indicates that other acetyltransferases, such as p300, may acetylate the fused p53 at different lysine residues.

The tumor suppressor protein p53 is believed to play a critical role in determining cell fate in response to DNA damage, nucleotide depletion, hypoxia, and several other genotoxic stresses. These stresses trigger a series of changes in p53 leading to the stabilization and activation of p53 in the nucleus. Activated p53 induces or inhibits the expression of more than 150 genes, many of which are essential for growth, cell cycle control, and apoptosis. The ultimate function of p53 is to commit cells to either DNA damage repair or apoptosis such that mutations are prevented from being passed on to progeny cells. It is estimated that 50% of all human cancers are linked to loss-of-function mutations in p53 that result in uncontrolled cellular proliferation. Moreover, suppression of p53 activity in tumor cells can cause tumor relapse after chemotherapy. Interestingly, "superactive" p53 mutants that are predicted to provide enhanced genomic surveillance can cause premature cellular senescence. Therefore, p53 maintains a delicate balance between normal cell proliferation and aging.

A landmark event associated with p53 activation is the post-translational modification (PTM) of p53, most notably acetylation (Gu, W., and R. G. Roeder, "Activation of p53 sequence-specific DNA binding by acetylation of the p53 C-terminal domain" Cell 90:595-606, 1997) and phosphorylation (Wang, Y., and C. Prives, "Increased and altered DNA binding of human p53 by S and G2/M but not G1 cyclin-dependent kinases" Nature 376:88-91, 1995). Like numerous other covalently modified proteins, the exact molecular functions played by various p53 modifications are largely unknown. One likely possibility is that these modifications effect downstream events such as transcriptional activation or repression of p53 target genes. We have found that that critical protein-protein interactions that mediate p53 function are controlled by site-specific modifications. For example, interactions between p53 and a downstream protein factor, such as a transcriptional co-activator, may be mediated by a modification at a specific p53 site. Alternatively, some p53 modifications may serve as "repellants" to displace factors that normally associate with p53 in its unmodified, inactive state. Thus, it is possible that site-specific modifications are responsible for determining cellular fate, that is, to proliferate, apoptose, or senesce. p53-GCN5 fusion: PCAF acetylates K320 of p53 upon UV treatment. The catalytic domains of PCAF and yeast Gcn5 share 56% identity and 71% similarity. Furthermore, the proline 16 of histone H3 that is critical for Gcn5-H3 interaction is conserved in p53 (p53: QPK320KKPLD; H3: TGG14KAPRK) (Rojas, et al., "Structure of Tetrahymena GCN5 bound to coenzyme A and a histone H3 peptide" Nature 401:93-8, 1999). It is thus possible that K320 can be acetylated within the context of p53-yGcn5 chimera as well. To test this possibility, the H3 fragment used in Examples 1-3 have been replaced with amino acids 300 to 393 of p53, and the resultant fusion proteins (with the wildtype and the mutant Gcn5) were immunoprecipitated from yeast extracts, followed by western analyses to test the acetylation status at Lys320. The results are shown in FIG. 10. It is clear that Lys320 of p53, though a non-histone protein, is effectively acetylated by the fused Gcn5 protein (pMK485), but not the mutant Gcn5 (pMK486). These results firmly establish the feasibility of autoacetylation of general proteins, providing the appropriate enzymes are included in the autocatalytic baits.

p53-p300 fusion: p300/CBP acetylates p53 in response to UV and IR treatment. The acetylation sites have been mapped to K372, 373, 381 and 382, with K373 and 382 being the major targets (Gu, W., and R. G. Roeder, "Activation of p53 sequence-specific DNA binding by acetylation of the p53 C-terminal domain" Cell 90:595-606, 1999; Liu, et al, "p53 sites acetylated in vitro by PCAF and p300 are acetylated in vivo in response to DNA damage" Mol Cell Biol 19:1202-9, 1999). To see whether p300/CBP can be used in p53 autocatalysis, we will follow the strategy stated above to create p53-CBP fusion proteins. In the meantime, a point mutant, F1451A will be included in a parallel construction as the counter selection. F1451 is at the position equivalent to F221 of the yeast Gcn5 and the F1451A mutant loses its ability to acetylate histones and to activate transcription (Martinez-Balbas, et al, "The acetyltransferase activity of CBP stimulates transcription" EMBO J 17:2886-93, 1998).

EXAMPLE 10

Identification of Human Proteins Interacting with p53 in Acetylation-Dependent and -Independent Manners.

This example shows that the p53 protein, when fused to the wildtype or mutant Gcn5 acetyltransferase, recruits certain human proteins.

The p53 protein acetylated at Lys320 by the linked wildtype Gcn5 enzyme (FIG. 10, pMK485) was subjected to Y2H screening using a human HeLa cell cDNA library fused to the Gal4 activation domain. Two-hybrid interactions were revealed by the ability of yeast cells to grow in the absence of adenine (-Ade plates). More then 350,000 yeast transformants were screened and several candidates were obtained. FIG. 11 shows that three classes of interactions were observed: Class I represents those that only interact with the wildtype Gcn5 fusion of p53 (i.e., an acetylated p53); Class II represents those that interact with both wildtype and mutant Gcn5 fusion of p53 (i.e., p53 interactors independent of the acetylation status); Class III represent those that interact with both wildtype Gcn5-p53 fusion as well as the wildtype Gcn5 alone (pDG28).

These results show that the class I proteins function as acetylated-p53 binding proteins. These proteins may play roles in relaying the p53 functions in transcriptional regulation, cell cycle arrest, and apoptosis. They may also conduct functions in turning over the activated p53 protein when the need of p53 no longer exists. The class II proteins represent general p53 interacting proteins. The class III proteins may represent human acetylated histone binding proteins as the wildtype Gcn5 protein tethered to the promoter region may acetylate adjacent histones that recruit the human acetylated histone binding protein-AD fusion to activate the downstream ADE2 gene.

EXAMPLE 11

Phosphorylation of the Carboxyl Terminal Domain(CTD) by the Tethered Kin28 Kinase.

Figure 26:
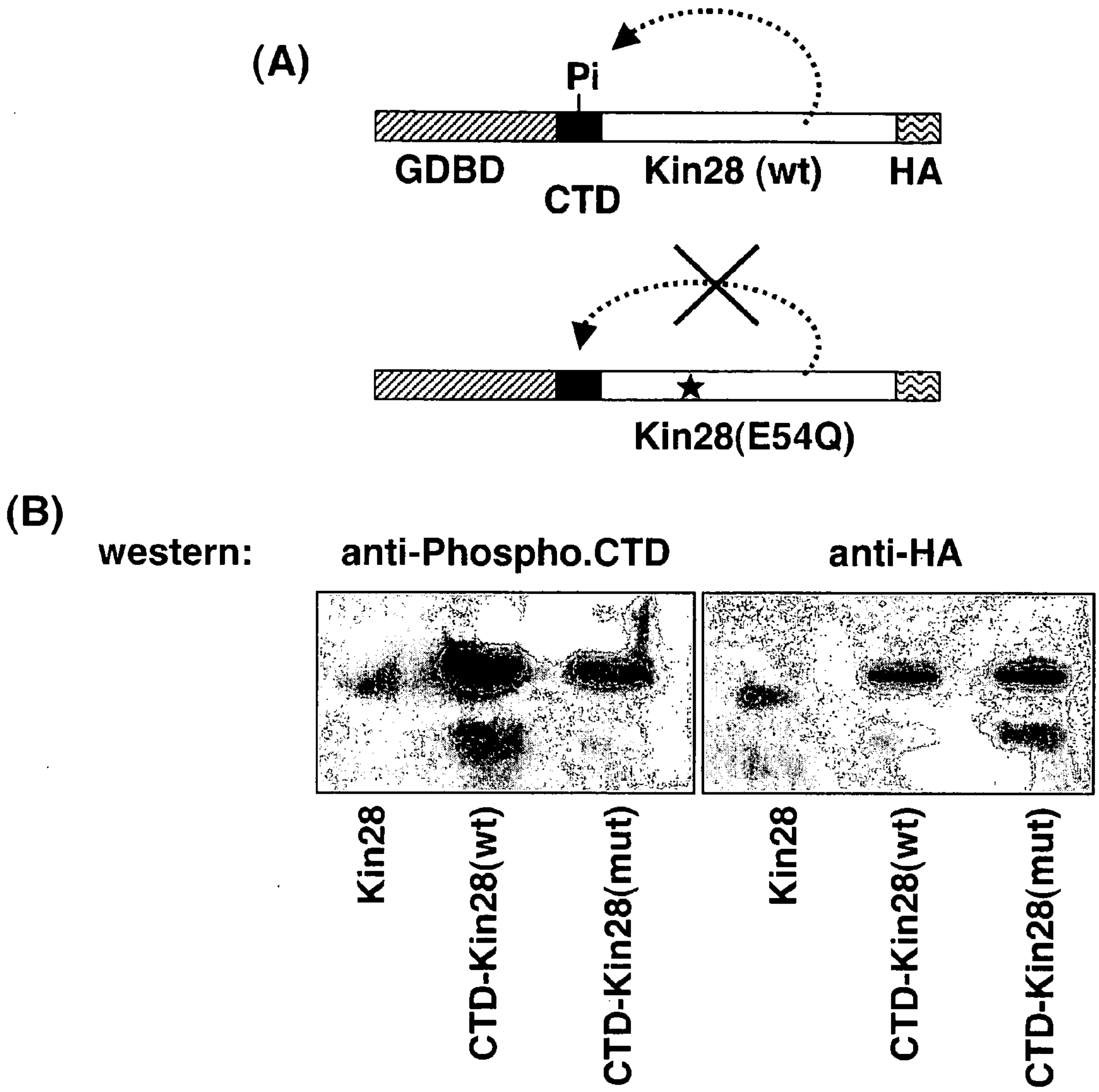
FIG. 26 shows the phosphorylation of the carboxyl terminal domain (CTD) by the tethered Kin28 kinase. (A) is a diagrammatic representation of the procedure. (B) is a Westernblot (see, Example 11).

As shown in FIG. 26A, the CTD (consisting of three tandem copies of YSTPSPS) was fused to the Gal4 DNA-binding domain and the wildtype Kin28 [SEQ ID NO: 35], or a E54Q catalytically inactive mutant Kin28, and the HA epitope [SEQ IN NO: 37]. As shown in FIG. 26B, the fusion proteins were isolated and subjected to western analyses using an antibody specific for CTD phosphorylated at the fifth residue (Ser5). The immunoblot shows that the CTD can be phosphorylated by the wildtype Kin28 protein, whereas the mutant Kin28 fusion is recognized significantly weaker by this antibody, indicating the lack of phosphorylation in this fusion protein.

EXAMPLE 12

Identification of Proteins that Interact Specifically with the Phosphorylated CTD.

Figure 27:
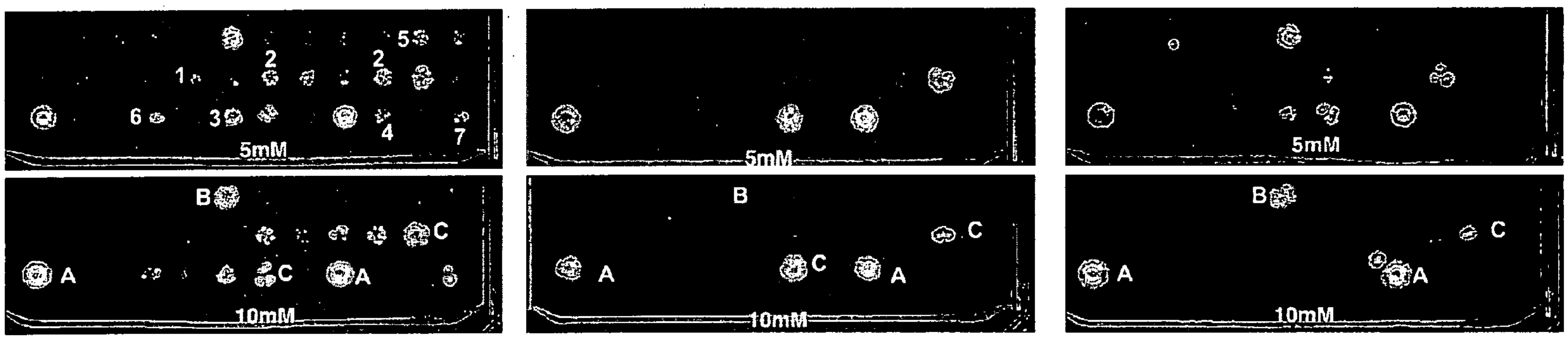
FIG. 27 shows identification of proteins that interact specifically with the phosphorylated CTD.

As shown in FIG. 27, the yeast two-hybrid screens were conducted using Kin28 alone [SEQ ID NO: 33], CTD fused to the wildtype Kin28 [SEQ ID NO: 35], and CTD fused to the mutant Kin28 [SEQ ID NO: 37], as the baits. Proteins that interact specifically with the CTD-Kin28 (wildtype) but neither of the other two baits are considered phosphorylated CTD-interacting proteins. Yeast strains containing one of the three baits and a variety of preys (activation domain fusion proteins) were tested for their ability to grow in the presence of different concentration of 3-AT. The ability to grow in such medium indicates stable interactions between the bait(s) and the prey(s). The following proteins (numbered 1-7) are considered phosphorylated CTD-interacting proteins: Fcp1 (a phosphatase known to act on phosphorylated CTD), Ssn8 (or Srb11, a component of the RNA polymerase II holoenzyme), Tfb3 (a component of the RNA polymerase II holoenzyme), Whi2 (a protein involved in cellular growth and a component of a protein phosphatase complex containing the Psr1 catalytic subunit), and three novel proteins (YMR181c, YPL229w, and YDR428c) whose functional links to CTD phosphorylation are novel. In addition, previously known (i.e. Ccl1 and Pcl10) and unknown (YDL100c) Kin28-interacting proteins were also identified in this screen (A-C). Several putative phosphorylated CTD interacting proteins are not labeled due to the current lack of the sequence information.

EXAMPLE 13

Autophosphorylation of the Histone H3 at the Ser10 Residue by the Tethered Ipl1 Protein Kinase.

Figure 28:
FIG. 28 shows the autophosphorylation of the histone H3 at the Ser10 residue by the tethered Ip11 protein kinase.

As shown in FIG. 28, the histone H3 amino acids 1-59 were fused to the Gal4 DNA binding domain, the wildtype and a catalytically inactive kinase Ipl1, and the HA epitope tag [SEQ ID NO: 29]. The mutations of Ipl1 (E152Q V153L) [SEQ ID NO: 31] completely inactivate the catalytic ability of this enzyme. The fusion proteins were expressed and purified from yeast and subjected to western analyses using an antibody specific for the H3 peptide phosphorylated by the Ser10 position. The western data showed that H3, when fused to the wildtype Ipl1, can be easily recognized by the anti-phosphorylated H3 antibody (anti-H3.Pi). On the other hand, the mutant Ipl1 fusion, though expressed at a significantly higher level than its wildtype counterpart (compare the first and second lanes with anti-HA antibody, left panel), its staining by the phosphorylation-specific antibody is weaker than the wildtype Ipl1 fusion. These results confirm that the H3-Ipl1 (wildtype) autophosphorylates at the H3 Ser10 position.

EXAMPLE 14

The PIASxα and PIASxβ Proteins Interact with p53 in an Acetylation-Dependent and -Independent Manner.

Figure 29:
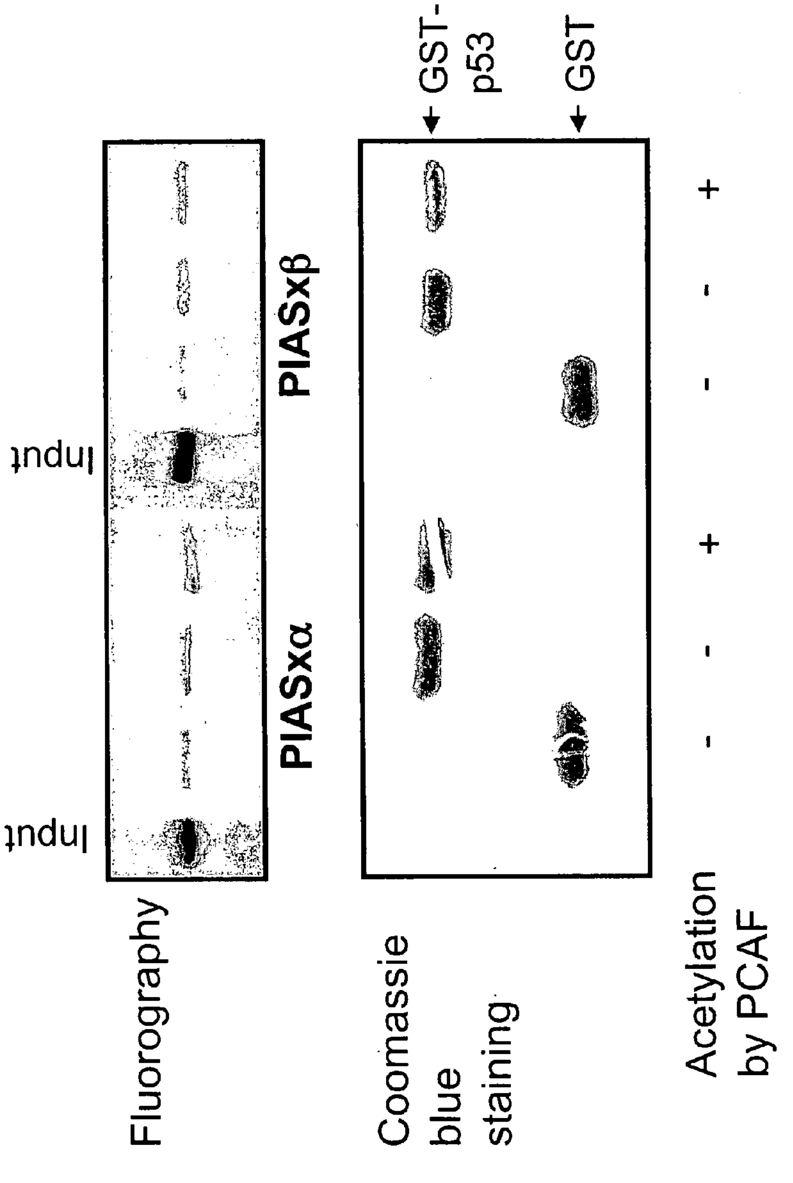
FIG. 29 shows the PIASxα and PIASxβ proteins interact with p53 in an acetylation-dependent and -independent manner.

The two proteins identified in the yeast two-hybrid screen shown in FIG. 11 were sequenced and found to be PIASxα and PIASxβ (class I and II, respectively). As shown in FIG. 29, to demonstrate the physical interaction in a biochemical means, the p53 was expressed as a GST fusion protein and purified from bacteria. A recombinant acetyltransferase, PCAF (the orthologue of the yeast Gcn5 protein), was purified and used to acetylate the p53 protein. The p53 protein, treated with the PCAF for Lys320 acetylation, along with the untreated, unacetylated counterpart, were immobilized to the glutathione beads and incubated with 35S-labelled, in vitro translated PIASxα and PIASxβ proteins. The unbound proteins were washed extensively and the final products bound to the glutathione beads via interaction with the p53 (acetylated or unacetylated) were analyzed by SDS-PAGE and visualized by fluorography. The results show that the PIASxα interacts preferentially with the acetylated p53, whereas the PIASxβ associates with p53 regardless of its acetylation status. These biochemical results are completely consistent with the yeast two-hybrid growth tests shown in FIG. 11, providing the definitive evidence that these two PIAS proteins display distinctive affinity for p53 depending on its acetylation status.

As can be seen from the forging, the present invention provides novel compounds and methods for the detection of interactive proteins wherein such interaction is dependent on one or more post translational modifications.

I claim:

1. A method for detecting protein-protein interactions, said interactions requiring a post translational modification of one of the said proteins, said method comprising:

(a) providing a host cell comprising a detectable gene wherein the detectable gene expresses a detectable protein when the detectable gene is activated by an amino acid sequence comprising a transcriptional activation domain when the transcriptional activation domain is in sufficient proximity to the detectable gene; (b) providing a first chimeric gene that is capable of being expressed in the host cell, the first chimeric gene comprising a DNA sequence that encodes a first hybrid protein, the first hybrid protein comprising: (i) a DNA-binding moiety that recognizes a binding site on the detectable gene in the host cell, said DNA-binding moiety comprising the Gal4 DNA binding domain, hereinafter GDBD; (ii) a first test protein or fragment thereof, comprising a reactive moiety capable of being modified through catalysis, that is to be tested for interaction with at least one second test protein or fragment thereof, said reactive moiety comprising a histone amino terminal tail capable of being acetylated by Gcn5; and (iii) a catalytic moiety that is capable of catalyzing said first test protein, said catalytic moiety comprising the catalytic domain of Gcn5; (c) providing a second chimeric gene that is capable of being expressed in the host cell, the second chimeric gene comprising a DNA sequence that encodes a second hybrid protein, the second hybrid protein comprising: (i) the transcriptional activation domain; and (ii) a second test protein or fragment thereof that is to be tested for interaction with the first test protein or fragment thereof when said first test protein has been modified by the catalysis of said reactive moiety to create a modified first test protein; wherein interaction between the first modified test protein and the second test protein in the host cell causes the transcriptional activation domain to activate transcription of the detectable gene; (d) introducing the first chimeric gene and the second chimeric gene into the host cell; (e) subjecting the host cell to conditions under which the first hybrid protein and the second hybrid protein are expressed in sufficient quantity for the detectable gene to be activated; and (f) determining whether the detectable gene has been expressed to a degree greater than expression in the absence of an interaction between the first test protein and the second test protein.

2. The method of claim 1, wherein said first test protein and said second test protein are encoded on a library of plasmids containing DNA inserts selected from the group consisting of genomic DNA, cDNA, and synthetically generated DNA.

3. The method of claim 1, wherein said first test protein is selected from the group consisting of bacterial protein, viral protein, oncogene-encoded protein, fungal protein and plant protein.

4. A method for detecting protein-protein interactions, comprising: (a) providing a host cell comprising a detectable gene, wherein the detectable gene expresses a detectable protein when the detectable gene is activated by an amino acid sequence comprising a transcriptional activation domain; (b) providing a first chimeric gene that is capable of being expressed in said host cell, the first chimeric gene comprising a DNA sequence that encodes a first hybrid protein, the first hybrid protein comprising: (i) a DNA-binding moiety that recognizes a binding site on the detectable gene in the host cell, said DNA-binding moiety comprising the Gal4 DNA binding domain, hereinafter GDBD; (ii) a reactive moiety capable of being modified through catalysis, said reactive moiety comprising a histone amino terminal tail capable of being acetylated by Gcn5; and (iii) a catalytic moiety that is capable of catalyzing said reactive moiety, said catalytic moiety comprising the catalytic domain of Gcn5; (c) providing a second chimeric gene that is capable of being expressed in the host cell, the second chimeric gene comprising a DNA sequence that encodes a second hybrid protein, the second hybrid protein comprising a transcriptional activation domain; and (d) introducing the first chimeric gene and the second chimeric gene into the host cell under conditions wherein the first hybrid protein and the second hybrid protein are expressed.

5. The method of claim 4, comprising determining whether the detectable gene has been expressed.

* * * * *

SEQUENCE LISTING

<160> NUMBER OF SEQ ID NOS: 38

<210> SEQ ID NO 1
<211> LENGTH: 8285
<212> TYPE: DNA
<213> ORGANISM: Artificial Sequence
<220> FEATURE:
<223> OTHER INFORMATION: Synthetic

<400> SEQUENCE: 1
gtggtacata acgaactaat actgtagccc tagacttgat agccatcatc atatcgaagt 60
ttcactaccc tttttccatt tgccatctat tgaagtaata ataggcgcat gcaacttctt 120
ttcttttttt ttcttttctc tctcccccgt tgttgtctca ccatatccgc aatgacaaaa 180
aaatgatgga agacactaaa ggaaaaaatt aacgacaaag acagcaccaa cagatgtcgt 240
tgttccagag ctgatgaggg gtatctcgaa gcacacgaaa ctttttcctt ccttcattga 300
cctgcaatta ttaatctttt gtttcctcgt cattgttctc gttccctttc ttccttgttt 360
ctttttctgc acaatatttc aagctatacc aagcatacaa tcaactccaa gcttgaagca 420
agcctcctga aagatgaagc tactgtcttc tatcgaacaa gcatgcgata tttgccgact 480
taaaaagctc aagtgctcca aagaaaaacc gaagtgcgcc aagtgtctga agaacaactg 540
ggagtgtcgc tactctccca aaaccaaaag gtctccgctg actagggcac atctgacaga 600
agtggaatca aggctagaaa gactggaaca gctatttcta ctgatttttc ctcgagaaga 660
ccttgacatg attttgaaaa tggattcttt acaggatata aaagcattgt taacaggatt 720
atttgtacaa gataatgtga ataaagatgc cgtcacagat agattggctt cagtggagac 780
tgatatgcct ctaacattga gacagcatag aataagtgcg acatcatcat cggaagagag 840
tagtaacaaa ggtcaaagac agttgactgt atcgaactat ctattcgatg atgaagatac 900
cccaccaaac ccaaaaaaag agatcgaatt ccagctgacc accatgttta tggccagaac 960
aaagcaaaca gcaagaaagt ccactggtgg taaggcccca agaaagcaat tagcttctaa 1020
ggctgccaga aaatccgccc catctaccgg tggtgttaag aagcctcaca gatataagcc 1080
aggtactgtt gctttgagag aaatcagaag attccaaaaa tctactgaac ccgggtcccc 1140
tatactaggt tattggaaag gtcgacgcga ccatcctcca aaatcggatc tgatcgaagg 1200
tcgtggagat cccgaagtta aacgggtaaa attagaaaac aacgttgaag aaatacaacc 1260
tgagcaggct gagaccaata aacaagaggg caccgataaa gagaataaag gaaagttcga 1320
gaaagaaact gagagaatag gaggatctga agtggttaca gatgtggaaa aaggaattgt 1380
caaatttgaa tttgatggtg ttgaatacac attcaaagag agacccagtg tcgtagagga 1440
aaatgaaggt aaaattgagt ttagggtggt gaataatgat aatactaaag aaaacatgat 1500
ggtcctaact ggattaaaaa acatttttca aaagcaatta ccaaaaaatgc ccaaagaata 1560 cattgccagg ttagtctatg atcgaagtca tctttccatg gctgtcatta ggaagccatt 1620
gactgtcgta ggtggcataa catatcgacc tttcgataag agagaattcg cagaaattgt 1680
tttctgtgcc atcagttcga cggaacaggt acgcggttat ggtgcgcatc taatgaatca 1740
cttaaaagac tatgttagaa atacctcgaa cataaaatat tttttgacat atgcagataa 1800
ttacgctatt ggatacttta aaaagcaagg ctttactaaa gaaatcacgt tggataaaag 1860
tatatggatg ggatatatta aagattatga aggtggtacg ctgatgcaat gtaacatggc 1920
aattcccggt ggcggccgca tcttttaccc atacgatgtt cctgactatg cgggctatcc 1980

-continued

```
ctatgacgtc ccggactatg caggatccta tccatatgac gttccagatt acgctgctca   2040
gtgcggccgc tctagctaga actagtggat cccccgatac cgtcgacctg cagagatcta   2100
tgaatcgtag atactgaaaa accccgcaag ttcacttcaa ctgtgcatcg tgcaccatct   2160
caatttcttt catttataca tcgttttgcc ttcttttatg taactatact cctctaagtt   2220
tcaatcttgg ccatgtaacc tctgatctat agaatttttt aaatgactag aattaatgcc   2280
catctttttt ttggacctaa attcttcatg aaaatatatt acgagggctt attcagaagc   2340
tttggacttc ttcgccagag gtttggtcaa gtctccaatc aaggttgtcg gcttgtctac   2400
cttgccagaa atttacgaaa agatggaaaa gggtcaaatc gttggtagat acgttgttga   2460
cacttctaaa taagcgaatt tcttatgatt tatgattttt attattaaat aagttataaa   2520
aaaaataagt gtatacaaat tttaaagtga ctcttaggtt ttaaaacgaa aattcttatt   2580
cttgagtaac tctttcctgt aggtcaggtt gctttctcag gtatagcatg aggtcgctct   2640
tattgaccac acctctaccg gcatgccgag caaatgcctg caaatcgctc cccatttcac   2700
ccaattgtag atatgctaac tccagcaatg agttgatgaa tctcggtgtg tattttatgt   2760
cctcagagga caacacctgt tgtaatcgtt cttccacacg gatcctggcg taatagcgaa   2820
gaggcccgca ccgatcgccc ttcccaacag ttgcgcagcc tgaatggcga atggcgcctg   2880
atgcggtatt ttctccttac gcatctgtgc ggtatttcac accgcatata tcgctgggcc   2940
attctcatga agaatatctt gaatttattg tcatattact agttggtgtg gaagtccata   3000
tatcggtgat caatatagtg gttgacatgc tggctagtca acattgagcc ttttgatcat   3060
gcaaatatat tacggtattt tacaatcaaa tatcaaactt aactattgac tttataactt   3120
atttaggtgg taacattctt ataaaaaaga aaaaaattac tgcaaaacag tactagcttt   3180
taacttgtat cctaggttat ctatgctgtc tcaccataga gaatattacc tatttcagaa   3240
tgtatgtcca tgattcgccg ggtaaataca tataatacac aaatctggct taataaagtc   3300
tataatatat ctcataaaga agtgctaaat tggctagtgc tatatatttt taagaaaatt   3360
tcttttgact aagtccatat cgactttgta aaagttcact ttagcataca tatattacac   3420
gagccagaaa ttgtaacttt tgcctaaaat cacaaattgc aaaatttaat tgcttgcaaa   3480
aggtcacatg cttataatca actttttaa aaatttaaaa tacttttta tttttattt   3540
ttaaacataa atgaaataat ttatttattg tttatgatta ccgaaacata aaacctgctc   3600
aagaaaaaga aactgttttg tccttggaaa aaaagcacta cctaggagcg gccaaaatgc   3660
cgaggctttc atagcttaaa ctctttacag aaaataggca ttatagatca gttcgagttt   3720
tcttattctt ccttccggtt ttatcgtcac agttttacag taaataagta tcacctctta   3780
gagttcgatg ataagctgtc aaacatgaga attaattcca catgttaaaa tagtgaagga   3840
gcatgttcgg cacacagtgg accgaacgtg gggtaagtgc actagggtcc ggttaaacgg   3900
atctcgcatt gatgaggcaa cgctaattat caacatatag attgttatct atctgcatga   3960
acacgaaatc tttacttgac gacttgaggc tgatggtgtt tatgcaaaga aaccactgtg   4020
tttaatatgt gtcactgttt gatattactg tcagcgtaga agataatagt aaaagcggtt   4080
aataagtgta tttgagataa gtgtgataaa gtttttacag cgaaaagacg ataaatacaa   4140
gaaaatgatt acgaggatac ggagagaggt atgtacatgt gtatttatat actaagctgc   4200
cggcggttgt ttgcaagacc gagaaaaggc tagcaagaat cgggtcattg tagcgtatgc   4260
gcctgtgaac attctcttca acaagtttga ttccattgcg gtgaaatggt aaaagtcaac   4320
```

-continued

```
cccctgcgat gtatattttc ctgtacaatc aatcaaaaag ccaaatgatt tagcattatc   4380

tttacatctt gttattttac agattttatg tttagatctt ttatgcttgc ttttcaaaag   4440

gcttgcaggc aagtgcacaa acaatactta aataaatact actcagtaat aacctatttc   4500

ttagcatttt tgacgaaatt tgctattttg ttagagtctt ttacaccatt tgtctccaca   4560

cctccgctta catcaacacc aataacgcca tttaatctaa gcgcatcacc aacattttct   4620

ggcgtcagtc caccagctaa cataaaatgt aagctctcgg ggctctcttg ccttccaacc   4680

cagtcagaaa tcgagttcca atccaaaagt tcacctgtcc cacctgcttc tgaatcaaac   4740

aagggaataa acgaatgagg tttctgtgaa gctgcactga gtagtatgtt gcagtctttt   4800

ggaaatacga gtcttttaat aactggcaaa ccgaggaact cttggtattc ttgccacgac   4860

tcatctccat gcagttggac gatatcaatg ccgtaatcat tgaccagagc caaaacatcc   4920

tccttaggtt gattacgaaa cacgccaacc aagtatttcg gagtgcctga actattttta   4980

tatgctttta caagacttga aattttcctt gcaataaccg ggtcaattgt tctctttcta   5040

ttgggcacac atataatacc cagcaagtca gcatcggaat ctagtgcaca ttctgcggcc   5100

tctgtgctct gcaagccgca aactttcacc aatggaccag aactacctgt gaaattaata   5160

acagacatac tccaagctgc ctttgtgtgc ttaatcacgt atactcacgt gctcaatagt   5220

caccaatgcc ctccctcttg gccctctcct tttctttttt cgaccgaatt aattcttgaa   5280

gacgaaaggg cctcgtgata cgcctatttt tataggttaa tgtcatgata ataatggttt   5340

cttagacgtc aggtggcact tttcggggaa atgtgcgcgg aacccctatt tgtttatttt   5400

tctaaataca ttcaaatatg tatccgctca tgagacaata accctgataa atgcttcaat   5460

aatattgaaa aaggaagagt atgagtattc aacatttccg tgtcgccctt attccctttt   5520

ttgcggcatt ttgccttcct gtttttgctc acccagaaac gctggtgaaa gtaaaagatg   5580

ctgaagatca gttgggtgca cgagtgggtt acatcgaact ggatctcaac agcggtaaga   5640

tccttgagag ttttcgcccc gaagaacgtt ttccaatgat gagcactttt aaagttctgc   5700

tatgtggcgc ggtattatcc cgtattgacg ccgggcaaga gcaactcggt cgccgcatac   5760

actattctca gaatgacttg gttgagtact caccagtcac agaaaagcat cttacggatg   5820

gcatgacagt aagagaatta tgcagtgctg ccataaccat gagtgataac actgcggcca   5880

acttacttct gacaacgatc ggaggaccga aggagctaac cgcttttttg cacaacatgg   5940

gggatcatgt aactcgcctt gatcgttggg aaccggagct gaatgaagcc ataccaaacg   6000

acgagcgtga caccacgatg cctgtagcaa tggcaacaac gttgcgcaaa ctattaactg   6060

gcgaactact tactctagct tcccggcaac aattaataga ctggatggag gcggataaag   6120

ttgcaggacc acttctgcgc tcggcccttc cggctggctg gtttattgct gataaatctg   6180

gagccggtga gcgtgggtct cgcggtatca ttgcagcact ggggccagat ggtaagccct   6240

cccgtatcgt agttatctac acgacgggga gtcaggcaac tatggatgaa cgaaatagac   6300

agatcgctga gataggtgcc tcactgatta agcattggta actgtcagac caagtttact   6360

catatatact ttagattgat ttaaaacttc atttttaatt taaaaggatc taggtgaaga   6420

tcctttttga taatctcatg accaaaatcc cttaacgtga gttttcgttc cactgagcgt   6480

cagaccccgt agaaaagatc aaaggatctt cttgagatcc tttttttctg cgcgtaatct   6540

gctgcttgca aacaaaaaaa ccaccgctac cagcggtggt ttgtttgccg gatcaagagc   6600

taccaactct ttttccgaag gtaactggct tcagcagagc gcagatacca aatactgtcc   6660

ttctagtgta gccgtagtta ggccaccact tcaagaactc tgtagcaccg cctacatacc   6720
```

-continued

```
tcgctctgct aatcctgtta ccagtggctg ctgccagtgg cgataagtcg tgtcttaccg   6780
ggttggactc aagacgatag ttaccggata aggcgcagcg gtcgggctga acggggggtt   6840
cgtgcacaca gcccagcttg gagcgaacga cctacaccga actgagatac ctacagcgtg   6900
agctatgaga aagcgccacg cttcccgaag ggagaaaggc ggacaggtat ccggtaagcg   6960
gcagggtcgg aacaggagag cgcacgaggg agcttccagg gggaaacgcc tggtatcttt   7020
atagtcctgt cgggtttcgc cacctctgac ttgagcgtcg atttttgtga tgctcgtcag   7080
gggggcggag cctatggaaa aacgccagca acgcggcctt tttacggttc ctggcctttt   7140
gctggccttt tgctcacatg ttctttcctg cgttatcccc tgattctgtg gataaccgta   7200
ttaccgcctt tgagtgagct gataccgctc gccgcagccg aacgaccgag cgcagcgagt   7260
cagtgagcga ggaagcggaa gagcgcccaa tacgcaaacc gcctctcccc gcgcgttggc   7320
cgattcatta atgcaggatc cgggatcgaa gaaatgatgg taaatgaaat aggaaatcaa   7380
ggagcatgaa ggcaaaagac aaatataagg gtcgaacgaa aaataaagtg aaaagtgttg   7440
atatgatgta tttggctttg cggcgccgaa aaaacgagtt tacgcaattg cacaatcatg   7500
ctgactctgt ggcggacccg cgctcttgcc ggcccggcga taacgctggg cgtgaggctg   7560
tgcccggcgg agtttttttgc gcctgcattt tccaaggttt accctgcgct aaggggcgag   7620
attggagaag caataagaat gccggttggg gttgcgatga tgacgaccac gacaactggt   7680
gtcattattt aagttgccga aagaacctga gtgcatttgc aacatgagta tactagaaga   7740
atgagccaag acttgcgaga cgcgagtttg ccggtggtgc gaacaataga gcgaccatga   7800
ccttgaaggt gagacgcgca taaccgctag agtactttga agaggaaaca gcaatagggt   7860
tgctaccagt ataaatagac aggtacatac aacactggaa atggttgtct gtttgagtac   7920
gctttcaatt catttgggtg tgcactttat tatgttacaa tatggaaggg aactttacac   7980
ttctcctatg cacatatatt aattaaagtc caatgctagt agagaagggg ggtaacaccc   8040
ctccgcgctc ttttccgatt tttttctaaa ccgtggaata tttcggatat ccttttgttg   8100
tttccgggtg tacaatatgg acttcctctt ttctggcaac caaacccata catcgggatt   8160
cctataatac cttcgttggt ctccctaaca tgtaggtggc ggaggggaga tatacaatag   8220
aacagatacc agacaagaca taatgggcta aacaagacta caccaattac actgcctcat   8280
tgatg                                                               8285
```

```
<210> SEQ ID NO 2
<211> LENGTH: 8285
<212> TYPE: DNA
<213> ORGANISM: Artificial Sequence
<220> FEATURE:
<223> OTHER INFORMATION: Synthetic

<400> SEQUENCE: 2

gtggtacata acgaactaat actgtagccc tagacttgat agccatcatc atatcgaagt     60
ttcactaccc tttttccatt tgccatctat tgaagtaata ataggcgcat gcaacttctt    120
ttcttttttt ttcttttctc tctcccccgt tgttgtctca ccatatccgc aatgacaaaa    180
aaatgatgga agacactaaa ggaaaaaatt aacgacaaag acagcaccaa cagatgtcgt    240
tgttccagag ctgatgaggg gtatctcgaa gcacacgaaa ctttttcctt ccttcattga    300
cctgcaatta ttaatctttt gtttcctcgt cattgttctc gttccctttc ttccttgttt    360
ctttttctgc acaatatttc aagctatacc aagcatacaa tcaactccaa gcttgaagca    420
```

-continued

```
agcctcctga aagatgaagc tactgtcttc tatcgaacaa gcatgcgata tttgccgact    480
taaaaagctc aagtgctcca aagaaaaacc gaagtgcgcc aagtgtctga agaacaactg    540
ggagtgtcgc tactctccca aaaccaaaag gtctccgctg actagggcac atctgacaga    600
agtggaatca aggctagaaa gactggaaca gctatttcta ctgatttttc ctcgagaaga    660
ccttgacatg attttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
tagtaacaaa ggtcaaagac agttgactgt atcgaactat ctattcgatg atgaagatac    900
cccaccaaac ccaaaaaaag agatcgaatt ccagctgacc accatgttta tggccagaac    960
aaagcaaaca gcaagaaagt ccactggtgg taaggcccca agaaagcaat tagcttctaa   1020
ggctgccaga aaatccgccc catctaccgg tggtgttaag aagcctcaca gatataagcc   1080
aggtactgtt gctttgagag aaatcagaag attccaaaaa tctactgaac ccgggtcccc   1140
tatactaggt tattggaaag gtcgacgcga ccatcctcca aaatcggatc tgatcgaagg   1200
tcgtggagat cccgaagtta aacgggtaaa attagaaaac aacgttgaag aaatacaacc   1260
tgagcaggct gagaccaata aacaagaggg caccgataaa gagaataaag gaaagttcga   1320
gaaagaaact gagagaatag gaggatctga agtggttaca gatgtggaaa aaggaattgt   1380
caaatttgaa tttgatggtg ttgaatacac attcaaagag agacccagtg tcgtagagga   1440
aaatgaaggt aaaattgagt ttagggtggt gaataatgat aatactaaag aaaacatgat   1500
ggtcctaact ggattaaaaa acatttttca aaagcaatta ccaaaaaatgc ccaaagaata   1560
cattgccagg ttagtctatg atcgaagtca tctttccatg gctgtcatta ggaagccatt   1620
gactgtcgta ggtggcataa catatcgacc tttcgataag agagaattcg cagaaattgt   1680
tttctgtgcc atcagttcga cggaacaggt acgcggttat ggtgcgcatc taatgaatca   1740
cttaaaagac tatgttagaa atacctcgaa cataaaatat tttttgacat atgcagataa   1800
ttacgctatt ggatacttta aaaagcaagg ctttactaaa gaaatcacgt tggataaaag   1860
tatatggatg ggatatatta aagattatga aggtggtacg ctgatgcaat gtaacatggc   1920
aattcccggt ggcggccgca tcttttaccc atacgatgtt cctgactatg cgggctatcc   1980
ctatgacgtc ccggactatg caggatccta tccatatgac gttccagatt acgctgctca   2040
gtgcggccgc tctagctaga actagtggat cccccgatac cgtcgacctg cagagatcta   2100
tgaatcgtag atactgaaaa accccgcaag ttcacttcaa ctgtgcatcg tgcaccatct   2160
caatttcttt catttataca tcgttttgcc ttcttttatg taactatact cctctaagtt   2220
tcaatcttgg ccatgtaacc tctgatctat agaatttttt aaatgactag aattaatgcc   2280
catctttttt ttggacctaa attcttcatg aaaatatatt acgagggctt attcagaagc   2340
tttggacttc ttcgccagag gtttggtcaa gtctccaatc aaggttgtcg gcttgtctac   2400
cttgccagaa atttacgaaa agatggaaaa gggtcaaatc gttggtagat acgttgttga   2460
cacttctaaa taagcgaatt tcttatgatt tatgattttt attattaaat aagttataaa   2520
aaaaataagt gtatacaaat tttaaagtga ctcttaggtt ttaaaacgaa aattcttatt   2580
cttgagtaac tctttcctgt aggtcaggtt gctttctcag gtatagcatg aggtcgctct   2640
tattgaccac acctctaccg gcatgccgag caaatgcctg caaatcgctc cccatttcac   2700
ccaattgtag atatgctaac tccagcaatg agttgatgaa tctcggtgtg tattttatgt   2760
cctcagagga caacacctgt tgtaatcgtt cttccacacg gatcctggcg taatagcgaa   2820
```

-continued gaggcccgca ccgatcgccc ttcccaacag ttgcgcagcc tgaatggcga atggcgcctg 2880
atgcggtatt ttctccttac gcatctgtgc ggtatttcac accgcatata tcgctgggcc 2940
attctcatga agaatatctt gaatttattg tcatattact agttggtgtg gaagtccata 3000
tatcggtgat caatatagtg gttgacatgc tggctagtca acattgagcc ttttgatcat 3060
gcaaatatat tacggtattt tacaatcaaa tatcaaactt aactattgac tttataactt 3120
atttaggtgg taacattctt ataaaaaaga aaaaaattac tgcaaaacag tactagcttt 3180
taacttgtat cctaggttat ctatgctgtc tcaccataga gaatattacc tatttcagaa 3240
tgtatgtcca tgattcgccg ggtaaataca tataatacac aaatctggct taataaagtc 3300
tataatatat ctcataaaga agtgctaaat tggctagtgc tatatatttt taagaaaatt 3360
tcttttgact aagtccatat cgactttgta aaagttcact ttagcataca tatattacac 3420
gagccagaaa ttgtaacttt tgcctaaaat cacaaattgc aaaatttaat tgcttgcaaa 3480
aggtcacatg cttataatca actttttaa aaatttaaaa tactttttta tttttattt 3540 ttaaacataa atgaaataat ttatttattg tttatgatta ccgaaacata aaacctgctc 3600
aagaaaaaga aactgttttg tccttggaaa aaaagcacta cctaggagcg gccaaaatgc 3660
cgaggctttc atagcttaaa ctctttacag aaaataggca ttatagatca gttcgagttt 3720
tcttattctt ccttccggtt ttatcgtcac agttttacag taaataagta tcacctctta 3780
gagttcgatg ataagctgtc aaacatgaga attaattcca catgttaaaa tagtgaagga 3840
gcatgttcgg cacacagtgg accgaacgtg gggtaagtgc actagggtcc ggttaaacgg 3900
atctcgcatt gatgaggcaa cgctaattat caacatatag attgttatct atctgcatga 3960
acacgaaatc tttacttgac gacttgaggc tgatggtgtt tatgcaaaga aaccactgtg 4020
tttaatatgt gtcactgttt gatattactg tcagcgtaga agataatagt aaaagcggtt 4080
aataagtgta tttgagataa gtgtgataaa gtttttacag cgaaaagacg ataaatacaa 4140
gaaaatgatt acgaggatac ggagagaggt atgtacatgt gtatttatat actaagctgc 4200
cggcggttgt ttgcaagacc gagaaaaggc tagcaagaat cgggtcattg tagcgtatgc 4260
gcctgtgaac attctcttca acaagtttga ttccattgcg gtgaaatggt aaaagtcaac 4320
cccctgcgat gtatattttc ctgtacaatc aatcaaaaag ccaaatgatt tagcattatc 4380
tttacatctt gttattttac agattttatg tttagatctt ttatgcttgc ttttcaaaag 4440
gcttgcaggc aagtgcacaa acaatactta aataaatact actcagtaat aacctatttc 4500
ttagcatttt tgacgaaatt tgctattttg ttagagtctt ttacaccatt tgtctccaca 4560
cctccgctta catcaacacc aataacgcca tttaatctaa gcgcatcacc aacattttct 4620
ggcgtcagtc caccagctaa cataaaatgt aagctctcgg ggctctcttg ccttccaacc 4680
cagtcagaaa tcgagttcca atccaaaagt tcacctgtcc cacctgcttc tgaatcaaac 4740
aagggaataa acgaatgagg tttctgtgaa gctgcactga gtagtatgtt gcagtctttt 4800
ggaaatacga gtcttttaat aactggcaaa ccgaggaact cttggtattc ttgccacgac 4860
tcatctccat gcagttggac gatatcaatg ccgtaatcat tgaccagagc caaaacatcc 4920
tccttaggtt gattacgaaa cacgccaacc aagtatttcg gagtgcctga actattttta 4980
tatgctttta caagacttga aattttcctt gcaataaccg ggtcaattgt tctctttcta 5040
ttgggcacac atataatacc cagcaagtca gcatcggaat ctagtgcaca ttctgcggcc 5100
tctgtgctct gcaagccgca aactttcacc aatggaccag aactacctgt gaaattaata 5160

-continued

```
acagacatac tccaagctgc ctttgtgtgc ttaatcacgt atactcacgt gctcaatagt   5220
caccaatgcc ctccctcttg gccctctcct tttctttttt cgaccgaatt aattcttgaa   5280
gacgaaaggg cctcgtgata cgcctatttt tataggttaa tgtcatgata ataatggttt   5340
cttagacgtc aggtggcact tttcggggaa atgtgcgcgg aacccctatt tgtttatttt   5400
tctaaataca ttcaaatatg tatccgctca tgagacaata accctgataa atgcttcaat   5460
aatattgaaa aaggaagagt atgagtattc aacatttccg tgtcgccctt attccctttt   5520
ttgcggcatt ttgccttcct gtttttgctc acccagaaac gctggtgaaa gtaaaagatg   5580
ctgaagatca gttgggtgca cgagtgggtt acatcgaact ggatctcaac agcggtaaga   5640
tccttgagag ttttcgcccc gaagaacgtt ttccaatgat gagcactttt aaagttctgc   5700
tatgtggcgc ggtattatcc cgtattgacg ccgggcaaga gcaactcggt cgccgcatac   5760
actattctca gaatgacttg gttgagtact caccagtcac agaaaagcat cttacggatg   5820
gcatgacagt aagagaatta tgcagtgctg ccataaccat gagtgataac actgcggcca   5880
acttacttct gacaacgatc ggaggaccga aggagctaac cgcttttttg cacaacatgg   5940
gggatcatgt aactcgcctt gatcgttggg aaccggagct gaatgaagcc ataccaaacg   6000
acgagcgtga caccacgatg cctgtagcaa tggcaacaac gttgcgcaaa ctattaactg   6060
gcgaactact tactctagct tcccggcaac aattaataga ctggatggag gcggataaag   6120
ttgcaggacc acttctgcgc tcggcccttc cggctggctg gtttattgct gataaatctg   6180
gagccggtga gcgtgggtct cgcggtatca ttgcagcact ggggccagat ggtaagccct   6240
cccgtatcgt agttatctac acgacgggga gtcaggcaac tatggatgaa cgaaatagac   6300
agatcgctga gataggtgcc tcactgatta agcattggta actgtcagac caagtttact   6360
catatatact ttagattgat ttaaaacttc atttttaatt taaaaggatc taggtgaaga   6420
tcctttttga taatctcatg accaaaatcc cttaacgtga gttttcgttc cactgagcgt   6480
cagaccccgt agaaaagatc aaaggatctt cttgagatcc tttttttctg cgcgtaatct   6540
gctgcttgca aacaaaaaaa ccaccgctac cagcggtggt ttgtttgccg gatcaagagc   6600
taccaactct ttttccgaag gtaactggct tcagcagagc gcagatacca aatactgtcc   6660
ttctagtgta gccgtagtta ggccaccact tcaagaactc tgtagcaccg cctacatacc   6720
tcgctctgct aatcctgtta ccagtggctg ctgccagtgg cgataagtcg tgtcttaccg   6780
ggttggactc aagacgatag ttaccggata aggcgcagcg gtcgggctga acggggggtt   6840
cgtgcacaca gcccagcttg gagcgaacga cctacaccga actgagatac ctacagcgtg   6900
agctatgaga aagcgccacg cttcccgaag ggagaaaggc ggacaggtat ccggtaagcg   6960
gcagggtcgg aacaggagag cgcacgaggg agcttccagg gggaaacgcc tggtatcttt   7020
atagtcctgt cgggtttcgc cacctctgac ttgagcgtcg atttttgtga tgctcgtcag   7080
gggggcggag cctatggaaa aacgccagca acgcggcctt tttacggttc ctggcctttt   7140
gctggccttt tgctcacatg ttctttcctg cgttatcccc tgattctgtg gataaccgta   7200
ttaccgcctt tgagtgagct gataccgctc gccgcagccg aacgaccgag cgcagcgagt   7260
cagtgagcga ggaagcggaa gagcgcccaa tacgcaaacc gcctctcccc gcgcgttggc   7320
cgattcatta atgcaggatc cgggatcgaa gaaatgatgg taaatgaaat aggaaatcaa   7380
ggagcatgaa ggcaaaagac aaatataagg gtcgaacgaa aaataaagtg aaaagtgttg   7440
atatgatgta tttggctttg cggcgccgaa aaaacgagtt tacgcaattg cacaatcatg   7500
ctgactctgt ggcggacccg cgctcttgcc ggcccggcga taacgctggg cgtgaggctg   7560
```

-continued

```
tgcccggcgg agttttttgc gcctgcattt tccaaggttt accctgcgct aaggggcgag   7620

attggagaag caataagaat gccggttggg gttgcgatga tgacgaccac gacaactggt   7680

gtcattattt aagttgccga aagaacctga gtgcatttgc aacatgagta tactagaaga   7740

atgagccaag acttgcgaga cgcgagtttg ccggtggtgc gaacaataga gcgaccatga   7800

ccttgaaggt gagacgcgca taaccgctag agtactttga agaggaaaca gcaatagggt   7860

tgctaccagt ataaatagac aggtacatac aacactggaa atggttgtct gtttgagtac   7920

gctttcaatt catttgggtg tgcactttat tatgttacaa tatggaaggg aactttacac   7980

ttctcctatg cacatatatt aattaaagtc caatgctagt agagaagggg ggtaacaccc   8040

ctccgcgctc ttttccgatt tttttctaaa ccgtggaata tttcggatat ccttttgttg   8100

tttccgggtg tacaatatgg acttcctctt ttctggcaac caaacccata catcgggatt   8160

cctataatac cttcgttggt ctccctaaca tgtaggtggc ggaggggaga tatacaatag   8220

aacagatacc agacaagaca taatgggcta aacaagacta caccaattac actgcctcat   8280

tgatg                                                               8285
```

<210> SEQ ID NO 3
<211> LENGTH: 8189
<212> TYPE: DNA
<213> ORGANISM: Artificial Sequence
<220> FEATURE:
<223> OTHER INFORMATION: Synthetic

<400> SEQUENCE: 3

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840

tagtaacaaa ggtcaaagac agttgactgt atcgaactat ctattcgatg atgaagatac    900

cccaccaaac ccaaaaaaag agatcgaatt ccagctgacc accatgtccg gtagaggtaa    960

aggtggtaaa ggtctaggaa aaggtggtgc caagcgtcac agaaagattc taagagataa   1020

catccaaggt atttccgggt cccctatact aggttattgg aaaggtcgac gcgaccatcc   1080

tccaaaatcg gatctgatcg aaggtcgtgg agatcccgaa gttaaacggg taaaattaga   1140

aaacaacgtt gaagaaatac aacctgagca ggctgagacc aataaacaag agggcaccga   1200

taaagagaat aaaggaaagt tcgagaaaga aactgagaga ataggaggat ctgaagtggt   1260
```

-continued

```
tacagatgtg gaaaaaggaa ttgtcaaatt tgaatttgat ggtgttgaat acacattcaa   1320
agagagaccc agtgtcgtag aggaaaatga aggtaaaatt gagtttaggg tggtgaataa   1380
tgataatact aaagaaaaca tgatggtcct aactggatta aaaaacattt ttcaaaagca   1440
attaccaaaa atgcccaaag aatacattgc caggttagtc tatgatcgaa gtcatctttc   1500
catggctgtc attaggaagc cattgactgt cgtaggtggc ataacatatc gacctttcga   1560
taagagagaa ttcgcagaaa ttgttttctg tgccatcagt tcgacggaac aggtacgcgg   1620
ttatggtgcg catctaatga atcacttaaa agactatgtt agaaatacct cgaacataaa   1680
atatttttg acatatgcag ataattacgc tattggatac tttaaaaagc aaggctttac   1740
taaagaaatc acgttggata aaagtatatg gatgggatat attaaagatt atgaaggtgg   1800
tacgctgatg caatgttcca tggcaattcc cggtggcggc cgcatctttt acccatacga   1860
tgttcctgac tatgcgggct atccctatga cgtcccggac tatgcaggat cctatccata   1920
tgacgttcca gattacgctg ctcagtgcgg ccgctctagc tagaactagt ggatcccccg   1980
ataccgtcga cctgcagaga tctatgaatc gtagatactg aaaaaccccg caagttcact   2040
tcaactgtgc atcgtgcacc atctcaattt ctttcattta tacatcgttt tgccttcttt   2100
tatgtaacta tactcctcta agtttcaatc ttggccatgt aacctctgat ctatagaatt   2160
ttttaaatga ctagaattaa tgcccatctt ttttttggac ctaaattctt catgaaaata   2220
tattacgagg gcttattcag aagctttgga cttcttcgcc agaggtttgg tcaagtctcc   2280
aatcaaggtt gtcggcttgt ctaccttgcc agaaatttac gaaaagatgg aaaagggtca   2340
aatcgttggt agatacgttg ttgacacttc taaataagcg aatttcttat gatttatgat   2400
ttttattatt aaataagtta taaaaaaaat aagtgtatac aaattttaaa gtgactctta   2460
ggttttaaaa cgaaaattct tattcttgag taactctttc ctgtaggtca ggttgctttc   2520
tcaggtatag catgaggtcg ctcttattga ccacacctct accggcatgc cgagcaaatg   2580
cctgcaaatc gctccccatt tcacccaatt gtagatatgc taactccagc aatgagttga   2640
tgaatctcgg tgtgtatttt atgtcctcag aggacaacac ctgttgtaat cgttcttcca   2700
cacggatcct ggcgtaatag cgaagaggcc cgcaccgatc gcccttccca acagttgcgc   2760
agcctgaatg gcgaatggcg cctgatgcgg tattttctcc ttacgcatct gtgcggtatt   2820
tcacaccgca tatatcgctg ggccattctc atgaagaata tcttgaattt attgtcatat   2880
tactagttgg tgtggaagtc catatatcgg tgatcaatat agtggttgac atgctggcta   2940
gtcaacattg agccttttga tcatgcaaat atattacggt attttacaat caaatatcaa   3000
acttaactat tgactttata acttatttag gtggtaacat tcttataaaa aagaaaaaaa   3060
ttactgcaaa acagtactag cttttaactt gtatcctagg ttatctatgc tgtctcacca   3120
tagagaatat tacctatttc agaatgtatg tccatgattc gccgggtaaa tacatataat   3180
acacaaatct ggcttaataa agtctataat atatctcata aagaagtgct aaattggcta   3240
gtgctatata tttttaagaa aatttctttt gactaagtcc atatcgactt tgtaaaagtt   3300
cactttagca tacatatatt acacgagcca gaaattgtaa cttttgccta aaatcacaaa   3360
ttgcaaaatt taattgcttg caaaaggtca catgcttata atcaactttt ttaaaaattt   3420
aaaatacttt tttatttttt atttttaaac ataaatgaaa taatttattt attgtttatg   3480
attaccgaaa cataaaacct gctcaagaaa aagaaactgt tttgtccttg gaaaaaaagc   3540
actacctagg agcggccaaa atgccgaggc tttcatagct taaactcttt acagaaaata   3600
ggcattatag atcagttcga gttttcttat tcttccttcc ggttttatcg tcacagtttt   3660
```

-continued

```
acagtaaata agtatcacct cttagagttc gatgataagc tgtcaaacat gagaattaat   3720
tccacatgtt aaaatagtga aggagcatgt tcggcacaca gtggaccgaa cgtggggtaa   3780
gtgcactagg gtccggttaa acggatctcg cattgatgag gcaacgctaa ttatcaacat   3840
atagattgtt atctatctgc atgaacacga aatctttact tgacgacttg aggctgatgg   3900
tgtttatgca aagaaaccac tgtgtttaat atgtgtcact gtttgatatt actgtcagcg   3960
tagaagataa tagtaaaagc ggttaataag tgtatttgag ataagtgtga taaagttttt   4020
acagcgaaaa gacgataaat acaagaaaat gattacgagg atacggagag aggtatgtac   4080
atgtgtattt atatactaag ctgccggcgg ttgtttgcaa gaccgagaaa aggctagcaa   4140
gaatcgggtc attgtagcgt atgcgcctgt gaacattctc ttcaacaagt ttgattccat   4200
tgcggtgaaa tggtaaaagt caacccccctg cgatgtatat tttcctgtac aatcaatcaa   4260
aaagccaaat gatttagcat tatctttaca tcttgttatt ttacagattt tatgtttaga   4320
tcttttatgc ttgcttttca aaaggcttgc aggcaagtgc acaaacaata cttaaataaa   4380
tactactcag taataaccta tttcttagca tttttgacga aatttgctat tttgttagag   4440
tcttttacac catttgtctc cacacctccg cttacatcaa caccaataac gccatttaat   4500
ctaagcgcat caccaacatt ttctggcgtc agtccaccag ctaacataaa atgtaagctc   4560
tcggggctct cttgccttcc aacccagtca gaaatcgagt tccaatccaa aagttcacct   4620
gtcccacctg cttctgaatc aaacaaggga ataaacgaat gaggtttctg tgaagctgca   4680
ctgagtagta tgttgcagtc ttttggaaat acgagtcttt taataactgg caaaccgagg   4740
aactcttggt attcttgcca cgactcatct ccatgcagtt ggacgatatc aatgccgtaa   4800
tcattgacca gagccaaaac atcctcctta ggttgattac gaaacacgcc aaccaagtat   4860
ttcggagtgc ctgaactatt tttatatgct tttacaagac ttgaaatttt ccttgcaata   4920
accgggtcaa ttgttctctt tctattgggc acacatataa tacccagcaa gtcagcatcg   4980
gaatctagtg cacattctgc ggcctctgtg ctctgcaagc cgcaaacttt caccaatgga   5040
ccagaactac ctgtgaaatt aataacagac atactccaag ctgcctttgt gtgcttaatc   5100
acgtatactc acgtgctcaa tagtcaccaa tgccctccct cttggccctc tccttttctt   5160
ttttcgaccg aattaattct tgaagacgaa agggcctcgt gatacgccta tttttatagg   5220
ttaatgtcat gataataatg gtttcttaga cgtcaggtgg cacttttcgg ggaaatgtgc   5280
gcggaacccc tatttgttta tttttctaaa tacattcaaa tatgtatccg ctcatgagac   5340
aataaccctg ataaatgctt caataatatt gaaaaaggaa gagtatgagt attcaacatt   5400
tccgtgtcgc ccttattccc ttttttgcgg cattttgcct tcctgttttt gctcacccag   5460
aaacgctggt gaaagtaaaa gatgctgaag atcagttggg tgcacgagtg ggttacatcg   5520
aactggatct caacagcggt aagatccttg agagttttcg ccccgaagaa cgttttccaa   5580
tgatgagcac ttttaaagtt ctgctatgtg gcgcggtatt atcccgtatt gacgccgggc   5640
aagagcaact cggtcgccgc atacactatt ctcagaatga cttggttgag tactcaccag   5700
tcacagaaaa gcatcttacg gatggcatga cagtaagaga attatgcagt gctgccataa   5760
ccatgagtga taacactgcg gccaacttac ttctgacaac gatcggagga ccgaaggagc   5820
taaccgcttt tttgcacaac atgggggatc atgtaactcg ccttgatcgt tgggaaccgg   5880
agctgaatga agccatacca aacgacgagc gtgacaccac gatgcctgta gcaatggcaa   5940
caacgttgcg caaactatta actggcgaac tacttactct agcttcccgg caacaattaa   6000
```

-continued

```
tagactggat ggaggcggat aaagttgcag gaccacttct gcgctcggcc cttccggctg   6060

gctggtttat tgctgataaa tctggagccg gtgagcgtgg gtctcgcggt atcattgcag   6120

cactggggcc agatggtaag ccctcccgta tcgtagttat ctacacgacg gggagtcagg   6180

caactatgga tgaacgaaat agacagatcg ctgagatagg tgcctcactg attaagcatt   6240

ggtaactgtc agaccaagtt tactcatata tactttagat tgatttaaaa cttcattttt   6300

aatttaaaag gatctaggtg aagatccttt ttgataatct catgaccaaa atcccttaac   6360

gtgagttttc gttccactga gcgtcagacc ccgtagaaaa gatcaaagga tcttcttgag   6420

atcctttttt tctgcgcgta atctgctgct tgcaaacaaa aaaaccaccg ctaccagcgg   6480

tggtttgttt gccggatcaa gagctaccaa ctctttttcc gaaggtaact ggcttcagca   6540

gagcgcagat accaaatact gtccttctag tgtagccgta gttaggccac cacttcaaga   6600

actctgtagc accgcctaca tacctcgctc tgctaatcct gttaccagtg gctgctgcca   6660

gtggcgataa gtcgtgtctt accgggttgg actcaagacg atagttaccg gataaggcgc   6720

agcggtcggg ctgaacgggg ggttcgtgca cacagcccag cttggagcga acgacctaca   6780

ccgaactgag atacctacag cgtgagctat gagaaagcgc cacgcttccc gaagggagaa   6840

aggcggacag gtatccggta agcggcaggg tcggaacagg agagcgcacg agggagcttc   6900

caggggggaaa cgcctggtat ctttatagtc ctgtcgggtt tcgccacctc tgacttgagc   6960

gtcgattttt gtgatgctcg tcaggggggc ggagcctatg gaaaaacgcc agcaacgcgg   7020

cctttttacg gttcctggcc ttttgctggc cttttgctca catgttcttt cctgcgttat   7080

cccctgattc tgtggataac cgtattaccg cctttgagtg agctgatacc gctcgccgca   7140

gccgaacgac cgagcgcagc gagtcagtga gcgaggaagc ggaagagcgc ccaatacgca   7200

aaccgcctct ccccgcgcgt tggccgattc attaatgcag gatccgggat cgaagaaatg   7260

atggtaaatg aaataggaaa tcaaggagca tgaaggcaaa agacaaatat aagggtcgaa   7320

cgaaaaataa agtgaaaagt gttgatatga tgtatttggc tttgcggcgc cgaaaaaacg   7380

agtttacgca attgcacaat catgctgact ctgtggcgga cccgcgctct tgccggcccg   7440

gcgataacgc tgggcgtgag gctgtgcccg gcggagtttt ttgcgcctgc attttccaag   7500

gtttaccctg cgctaagggg cgagattgga gaagcaataa gaatgccggt tggggttgcg   7560

atgatgacga ccacgacaac tggtgtcatt atttaagttg ccgaaagaac ctgagtgcat   7620

ttgcaacatg agtatactag aagaatgagc caagacttgc gagacgcgag tttgccggtg   7680

gtgcgaacaa tagagcgacc atgaccttga aggtgagacg cgcataaccg ctagagtact   7740

ttgaagagga aacagcaata gggttgctac cagtataaat agacaggtac atacaacact   7800

ggaaatggtt gtctgtttga gtacgctttc aattcatttg ggtgtgcact ttattatgtt   7860

acaatatgga agggaacttt acacttctcc tatgcacata tattaattaa agtccaatgc   7920

tagtagagaa ggggggtaac acccctccgc gctcttttcc gattttttc taaaccgtgg   7980

aatatttcgg atatcctttt gttgtttccg ggtgtacaat atggacttcc tcttttctgg   8040

caaccaaacc catacatcgg gattcctata ataccttcgt tggtctccct aacatgtagg   8100

tggcggaggg gagatataca atagaacaga taccagacaa gacataatgg gctaaacaag   8160

actacaccaa ttacactgcc tcattgatg                                     8189
```

<210> SEQ ID NO 4
<211> LENGTH: 8189
<212> TYPE: DNA
<213> ORGANISM: Artificial Sequence -continued
<220> FEATURE:
<223> OTHER INFORMATION: Synthetic

<400> SEQUENCE: 4
gtggtacata acgaactaat actgtagccc tagacttgat agccatcatc atatcgaagt 60
ttcactaccc tttttccatt tgccatctat tgaagtaata ataggcgcat gcaacttctt 120
ttcttttttt ttcttttctc tctcccccgt tgttgtctca ccatatccgc aatgacaaaa 180
aaatgatgga agacactaaa ggaaaaaatt aacgacaaag acagcaccaa cagatgtcgt 240
tgttccagag ctgatgaggg gtatctcgaa gcacacgaaa ctttttcctt ccttcattga 300
cctgcaatta ttaatctttt gtttcctcgt cattgttctc gttccctttc ttccttgttt 360
ctttttctgc acaatatttc aagctatacc aagcatacaa tcaactccaa gcttgaagca 420
agcctcctga aagatgaagc tactgtcttc tatcgaacaa gcatgcgata tttgccgact 480
taaaaagctc aagtgctcca aagaaaaacc gaagtgcgcc aagtgtctga agaacaactg 540
ggagtgtcgc tactctccca aaaccaaaag gtctccgctg actagggcac atctgacaga 600
agtggaatca aggctagaaa gactggaaca gctatttcta ctgatttttc ctcgagaaga 660
ccttgacatg attttgaaaa tggattcttt acaggatata aaagcattgt taacaggatt 720
atttgtacaa gataatgtga ataaagatgc cgtcacagat agattggctt cagtggagac 780
tgatatgcct ctaacattga gacagcatag aataagtgcg acatcatcat cggaagagag 840
tagtaacaaa ggtcaaagac agttgactgt atcgaactat ctattcgatg atgaagatac 900 ccccaccaaac ccaaaaaaag agatcgaatt ccagctgacc accatgtccg gtagaggtaa 960
aggtggtaaa ggtctaggaa aaggtggtgc caagcgtcac agaaagattc taagagataa 1020
catccaaggt atttccgggt cccctatact aggttattgg aaaggtcgac gcgaccatcc 1080
tccaaaatcg gatctgatcg aaggtcgtgg agatcccgaa gttaaacggg taaaattaga 1140
aaacaacgtt gaagaaatac aacctgagca ggctgagacc aataaacaag agggcaccga 1200
taaagagaat aaaggaaagt tcgagaaaga aactgagaga ataggaggat ctgaagtggt 1260
tacagatgtg gaaaaaggaa ttgtcaaatt tgaatttgat ggtgttgaat acacattcaa 1320
agagagaccc agtgtcgtag aggaaaatga aggtaaaatt gagtttaggg tggtgaataa 1380
tgataatact aaagaaaaca tgatggtcct aactggatta aaaaacattt ttcaaaagca 1440
attaccaaaa atgcccaaag aatacattgc caggttagtc tatgatcgaa gtcatctttc 1500
catggctgtc attaggaagc cattgactgt cgtaggtggc ataacatatc gacctttcga 1560
taagagagaa ttcgcagaaa ttgttttctg tgccatcagt tcgacggaac aggtacgcgg 1620
ttatggtgcg catctaatga atcacttaaa agactatgtt agaaatacct cgaacataaa 1680 atatttttttg acatatgcag ataattacgc tattggatac tttaaaaagc aaggctttac 1740
taaagaaatc acgttggata aaagtatatg gatgggatat attaaagatt atgaaggtgg 1800
tacgctgatg caatgttcca tggcaattcc cggtggcggc cgcatctttt acccatacga 1860
tgttcctgac tatgcgggct atccctatga cgtcccggac tatgcaggat cctatccata 1920
tgacgttcca gattacgctg ctcagtgcgg ccgctctagc tagaactagt ggatcccccg 1980
ataccgtcga cctgcagaga tctatgaatc gtagatactg aaaaaccccg caagttcact 2040
tcaactgtgc atcgtgcacc atctcaattt ctttcattta tacatcgttt tgccttcttt 2100
tatgtaacta tactcctcta agtttcaatc ttggccatgt aacctctgat ctatagaatt 2160
ttttaaatga ctagaattaa tgcccatctt ttttttggac ctaaattctt catgaaaata 2220

-continued

```
tattacgagg gcttattcag aagctttgga cttcttcgcc agaggtttgg tcaagtctcc   2280
aatcaaggtt gtcggcttgt ctaccttgcc agaaatttac gaaaagatgg aaaagggtca   2340
aatcgttggt agatacgttg ttgacacttc taaataagcg aatttcttat gatttatgat   2400
ttttattatt aaataagtta taaaaaaaat aagtgtatac aaattttaaa gtgactctta   2460
ggttttaaaa cgaaaattct tattcttgag taactctttc ctgtaggtca ggttgctttc   2520
tcaggtatag catgaggtcg ctcttattga ccacacctct accggcatgc cgagcaaatg   2580
cctgcaaatc gctccccatt tcacccaatt gtagatatgc taactccagc aatgagttga   2640
tgaatctcgg tgtgtatttt atgtcctcag aggacaacac ctgttgtaat cgttcttcca   2700
cacggatcct ggcgtaatag cgaagaggcc cgcaccgatc gcccttccca acagttgcgc   2760
agcctgaatg gcgaatggcg cctgatgcgg tattttctcc ttacgcatct gtgcggtatt   2820
tcacaccgca tatatcgctg ggccattctc atgaagaata tcttgaattt attgtcatat   2880
tactagttgg tgtggaagtc catatatcgg tgatcaatat agtggttgac atgctggcta   2940
gtcaacattg agccttttga tcatgcaaat atattacggt attttacaat caaatatcaa   3000
acttaactat tgactttata acttatttag gtggtaacat tcttataaaa aagaaaaaaa   3060
ttactgcaaa acagtactag cttttaactt gtatcctagg ttatctatgc tgtctcacca   3120
tagagaatat tacctatttc agaatgtatg tccatgattc gccgggtaaa tacatataat   3180
acacaaatct ggcttaataa agtctataat atatctcata aagaagtgct aaattggcta   3240
gtgctatata tttttaagaa aatttctttt gactaagtcc atatcgactt tgtaaaagtt   3300
cactttagca tacatatatt acacgagcca gaaattgtaa cttttgccta aaatcacaaa   3360
ttgcaaaatt taattgcttg caaaaggtca catgcttata atcaactttt ttaaaaattt   3420
aaaatacttt tttattttt atttttaaac ataaatgaaa taatttattt attgtttatg   3480
attaccgaaa cataaaacct gctcaagaaa aagaaactgt tttgtccttg gaaaaaaagc   3540
actacctagg agcggccaaa atgccgaggc tttcatagct taaactcttt acagaaaata   3600
ggcattatag atcagttcga gtttcttat tcttccttcc ggttttatcg tcacagtttt   3660
acagtaaata agtatcacct cttagagttc gatgataagc tgtcaaacat gagaattaat   3720
tccacatgtt aaaatagtga aggagcatgt tcggcacaca gtggaccgaa cgtggggtaa   3780
gtgcactagg gtccggttaa acggatctcg cattgatgag gcaacgctaa ttatcaacat   3840
atagattgtt atctatctgc atgaacacga aatctttact tgacgacttg aggctgatgg   3900
tgtttatgca aagaaaccac tgtgtttaat atgtgtcact gtttgatatt actgtcagcg   3960
tagaagataa tagtaaaagc ggttaataag tgtatttgag ataagtgtga taaagttttt   4020
acagcgaaaa gacgataaat acaagaaaat gattacgagg atacggagag aggtatgtac   4080
atgtgtattt atatactaag ctgccggcgg ttgtttgcaa gaccgagaaa aggctagcaa   4140
gaatcgggtc attgtagcgt atgcgcctgt gaacattctc ttcaacaagt ttgattccat   4200
tgcggtgaaa tggtaaaagt caaccccctg cgatgtatat tttcctgtac aatcaatcaa   4260
aaagccaaat gatttagcat tatctttaca tcttgttatt ttacagattt tatgtttaga   4320
tcttttatgc ttgcttttca aaaggcttgc aggcaagtgc acaaacaata cttaaataaa   4380
tactactcag taataaccta tttcttagca tttttgacga aatttgctat tttgttagag   4440
tcttttacac catttgtctc cacacctccg cttacatcaa caccaataac gccatttaat   4500
ctaagcgcat caccaacatt ttctggcgtc agtccaccag ctaacataaa atgtaagctc   4560
tcggggctct cttgccttcc aacccagtca gaaatcgagt tccaatccaa aagttcacct   4620
```

-continued

```
gtcccacctg cttctgaatc aaacaaggga ataaacgaat gaggtttctg tgaagctgca   4680
ctgagtagta tgttgcagtc ttttggaaat acgagtcttt taataactgg caaaccgagg   4740
aactcttggt attcttgcca cgactcatct ccatgcagtt ggacgatatc aatgccgtaa   4800
tcattgacca gagccaaaac atcctcctta ggttgattac gaaacacgcc aaccaagtat   4860
ttcggagtgc ctgaactatt tttatatgct tttacaagac ttgaaatttt ccttgcaata   4920
accgggtcaa ttgttctctt tctattgggc acacatataa tacccagcaa gtcagcatcg   4980
gaatctagtg cacattctgc ggcctctgtg ctctgcaagc cgcaaacttt caccaatgga   5040
ccagaactac ctgtgaaatt aataacagac atactccaag ctgcctttgt gtgcttaatc   5100
acgtatactc acgtgctcaa tagtcaccaa tgccctccct cttggccctc tccttttctt   5160
ttttcgaccg aattaattct tgaagacgaa agggcctcgt gatacgccta tttttatagg   5220
ttaatgtcat gataataatg gtttcttaga cgtcaggtgg cacttttcgg ggaaatgtgc   5280
gcggaacccc tatttgttta tttttctaaa tacattcaaa tatgtatccg ctcatgagac   5340
aataaccctg ataaatgctt caataatatt gaaaaaggaa gagtatgagt attcaacatt   5400
tccgtgtcgc ccttattccc ttttttgcgg cattttgcct tcctgttttt gctcacccag   5460
aaacgctggt gaaagtaaaa gatgctgaag atcagttggg tgcacgagtg ggttacatcg   5520
aactggatct caacagcggt aagatccttg agagttttcg ccccgaagaa cgttttccaa   5580
tgatgagcac ttttaaagtt ctgctatgtg gcgcggtatt atcccgtatt gacgccgggc   5640
aagagcaact cggtcgccgc atacactatt ctcagaatga cttggttgag tactcaccag   5700
tcacagaaaa gcatcttacg gatggcatga cagtaagaga attatgcagt gctgccataa   5760
ccatgagtga taacactgcg gccaacttac ttctgacaac gatcggagga ccgaaggagc   5820
taaccgcttt tttgcacaac atgggggatc atgtaactcg ccttgatcgt tgggaaccgg   5880
agctgaatga agccatacca aacgacgagc gtgacaccac gatgcctgta gcaatggcaa   5940
caacgttgcg caaactatta actggcgaac tacttactct agcttcccgg caacaattaa   6000
tagactggat ggaggcggat aaagttgcag gaccacttct gcgctcggcc cttccggctg   6060
gctggtttat tgctgataaa tctggagccg gtgagcgtgg gtctcgcggt atcattgcag   6120
cactggggcc agatggtaag ccctcccgta tcgtagttat ctacacgacg gggagtcagg   6180
caactatgga tgaacgaaat agacagatcg ctgagatagg tgcctcactg attaagcatt   6240
ggtaactgtc agaccaagtt tactcatata tactttagat tgatttaaaa cttcattttt   6300
aatttaaaag gatctaggtg aagatccttt ttgataatct catgaccaaa atcccttaac   6360
gtgagttttc gttccactga gcgtcagacc ccgtagaaaa gatcaaagga tcttcttgag   6420
atcctttttt tctgcgcgta atctgctgct tgcaaacaaa aaaaccaccg ctaccagcgg   6480
tggtttgttt gccggatcaa gagctaccaa ctctttttcc gaaggtaact ggcttcagca   6540
gagcgcagat accaaatact gtccttctag tgtagccgta gttaggccac cacttcaaga   6600
actctgtagc accgcctaca tacctcgctc tgctaatcct gttaccagtg gctgctgcca   6660
gtggcgataa gtcgtgtctt accgggttgg actcaagacg atagttaccg gataaggcgc   6720
agcggtcggg ctgaacgggg ggttcgtgca cacagcccag cttggagcga acgacctaca   6780
ccgaactgag atacctacag cgtgagctat gagaaagcgc cacgcttccc gaagggagaa   6840
aggcggacag gtatccggta agcggcaggg tcggaacagg agagcgcacg agggagcttc   6900
caggggggaaa cgcctggtat ctttatagtc ctgtcgggtt tcgccacctc tgacttgagc   6960
```

-continued

```
gtcgattttt gtgatgctcg tcaggggggc ggagcctatg gaaaaacgcc agcaacgcgg   7020

cctttttacg gttcctggcc ttttgctggc cttttgctca catgttcttt cctgcgttat   7080

cccctgattc tgtggataac cgtattaccg cctttgagtg agctgatacc gctcgccgca   7140

gccgaacgac cgagcgcagc gagtcagtga gcgaggaagc ggaagagcgc ccaatacgca   7200

aaccgcctct ccccgcgcgt tggccgattc attaatgcag gatccgggat cgaagaaatg   7260

atggtaaatg aaataggaaa tcaaggagca tgaaggcaaa agacaaatat aagggtcgaa   7320

cgaaaaataa agtgaaaagt gttgatatga tgtatttggc tttgcggcgc cgaaaaaacg   7380

agtttacgca attgcacaat catgctgact ctgtggcgga cccgcgctct tgccggcccg   7440

gcgataacgc tgggcgtgag gctgtgcccg gcggagtttt ttgcgcctgc attttccaag   7500

gtttaccctg cgctaagggg cgagattgga gaagcaataa gaatgccggt tggggttgcg   7560

atgatgacga ccacgacaac tggtgtcatt atttaagttg ccgaaagaac ctgagtgcat   7620

ttgcaacatg agtatactag aagaatgagc caagacttgc gagacgcgag tttgccggtg   7680

gtgcgaacaa tagagcgacc atgaccttga aggtgagacg cgcataaccg ctagagtact   7740

ttgaagagga aacagcaata gggttgctac cagtataaat agacaggtac atacaacact   7800

ggaaatggtt gtctgtttga gtacgctttc aattcatttg ggtgtgcact ttattatgtt   7860

acaatatgga agggaacttt acacttctcc tatgcacata tattaattaa agtccaatgc   7920

tagtagagaa ggggggtaac acccctccgc gctcttttcc gatttttttc taaaccgtgg   7980

aatatttcgg atatcctttt gttgtttccg ggtgtacaat atggacttcc tcttttctgg   8040

caaccaaacc catacatcgg gattcctata ataccttcgt tggtctccct aacatgtagg   8100

tggcggaggg gagatataca atagaacaga taccagacaa gacataatgg gctaaacaag   8160

actacaccaa ttacactgcc tcattgatg                                    8189
```

<210> SEQ ID NO 5
<211> LENGTH: 7891
<212> TYPE: DNA
<213> ORGANISM: Artificial Sequence
<220> FEATURE:
<223> OTHER INFORMATION: Synthetic

<400> SEQUENCE: 5

```
tcttccgctt cctcgctcac tgactcgctg cgctcggtcg ttcggctgcg gcgagcggta     60

tcagctcact caaaggcggt aatacggtta tccacagaat caggggataa cgcaggaaag    120

aacatgtgag caaaaggcca gcaaaaggcc aggaaccgta aaaaggccgc gttgctggcg    180

tttttccata ggctccgccc ccctgacgag catcacaaaa atcgacgctc aagtcagagg    240

tggcgaaacc cgacaggact ataaagatac caggcgtttc cccctggaag ctccctcgtg    300

cgctctcctg ttccgaccct gccgcttacc ggatacctgt ccgcctttct cccttcggga    360

agcgtggcgc tttctcatag ctcacgctgt aggtatctca gttcggtgta ggtcgttcgc    420

tccaagctgg gctgtgtgca cgaacccccc gttcagcccg accgctgcgc cttatccggt    480

aactatcgtc ttgagtccaa cccggtaaga cacgacttat cgccactggc agcagccact    540

ggtaacagga ttagcagagc gaggtatgta ggcggtgcta cagagttctt gaagtggtgg    600

cctaactacg gctacactag aaggacagta tttggtatct gcgctctgct gaagccagtt    660

accttcggaa aaagagttgg tagctcttga tccggcaaac aaaccaccgc tggtagcggt    720

ggtttttttg tttgcaagca gcagattacg cgcagaaaaa aaggatctca agaagatcct    780

ttgatctttt ctacggggtc tgacgctcag tggaacgaaa actcacgtta agggattttg    840
```

-continued

```
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tcttcaagaa ttaactgtgg gaatactcag gtatcgtaag   2040
atgcaagagt tcgaatctct tagcaaccat tatttttttc ctcaacataa cgagaacaca   2100
caggggcgct atcgcacaga caaattcgat gactggaaat ttttgttaa tttcagaggt    2160
cgccgcgcat ataccttttt caactgaaaa attgggagaa aaaggaaagg tgagaggccg   2220
gaaccggctt ttcatataga atagagaagc gttcatgact aaatgcttgc atcacaatac   2280
ttgaagttga caatattatt taaggaccta ttgttttttc caataggtgg ttagcaatcg   2340
tcttattcta acttttctta ccttttacat ttcagcaata tatatatata tttcaaggat   2400
atacattcta atgtctgccc ctatgtctgc ccctaagaag atcgtcgttt tgccaggtga   2460
ccacgttggt caagatcaca gccgaagcca ttaaggttct taaagctatt tctgatgttc   2520
gttccaatgt caagttcgat ttcgaaaatc atttaattgg tggtgctgct atcgatgcta   2580
caggtgtccc acttccagat gaggcgctgg aagcctccaa gaaggttgat gccgttttgt   2640
taggtgctgt gggtggtcct aaatggggta caggtagtgt tagacctgaa caaggtttac   2700
taaaaatccg taaagaactt caattgtacg ccaacttaag accatgtaac tttgcatccg   2760
actctctttt agacttatct ccaatcaagc cacaatttgc taaaggtact gacttcgttg   2820
ttgtcagaga attagtggga ggtatttact ttggtaagag aaaggaagac gatggtgatg   2880
gtgtcgcttg ggatagtgaa caatacaccg ttccagaagt gcaaagaatc acaagaatgg   2940
ccgctttcat ggccctacaa catgagccac cattgcctat ttggtccttg gataaagcta   3000
atgttttggc ctcttcaaga ttatggagaa aaactgtgga ggaaaccatc aagaacgaat   3060
ttcctacatt gaaggttcaa catcaattga ttgattctgc cgccatgatc ctagttaaga   3120
acccaaccca cctaaatggt attataatca ccagcaacat gtttggtgat atcatctccg   3180
```

-continued

```
atgaagcctc cgttatccca ggttccttgg gtttgttgcc atctgcgtcc ttggcctctt   3240
tgccagacaa gaacaccgca tttggtttgt acgaaccatg ccacggttct gctccagatt   3300
tgccaaagaa taaggttgac cctatcgcca ctatcttgtc tgctgcaatg atgttgaaat   3360
tgtcattgaa cttgcctgaa gaaggtaagg ccattgaaga tgcagttaaa aaggttttgg   3420
atgcaggtat cagaactggt gatttaggtg gttccaacag taccaccgaa gtcggtgatg   3480
ctgtcgccga agaagttaag aaaatccttg cttaaaaaga ttctcttttt ttatgatatt   3540
tgtacataaa ctttataaat gaaattcata atagaaacga cacgaaatta caaaatggaa   3600
tatgttcata gggtagaatt aattctcatg tttgacagct tatcatcgga tcgatccaat   3660
atcaaaggaa atgatagcat tgaaggatga gactaatcca attgaggagt ggcagcatat   3720
agaacagcta aagggtagtg ctgaaggaag catacgatac cccgcatgga atgggataat   3780
atcacaggag gtactagact acctttcatc ctacataaat agacgcatat aagtacgcat   3840
ttaagcataa acacgcacta tgccgttctt ctcatgtata tatatataca ggcaacacgc   3900
agatataggt gcgacgtgaa cagtgagctg tatgtgcgca gctcgcgttg cattttcgga   3960
agcgctcgtt ttcggaaacg ctttgaagtt cctattccga agttcctatt ctctagctag   4020
aaagtatagg aacttcagag cgcttttgaa aaccaaaagc gctctgaaga cgcactttca   4080
aaaaaccaaa aacgcaccgg actgtaacga gctactaaaa tattgcgaat accgcttcca   4140
caaacattgc tcaaaagtat ctctttgcta tatatctctg tgctatatcc ctatataacc   4200
tacccatcca cctttcgctc cttgaacttg catctaaact cgacctctac atttttatg    4260
tttatctcta gtattactct ttagacaaaa aaattgtagt aagaactatt catagagtga   4320
atcgaaaaca atacgaaaat gtaaacattt cctatacgta gtatatagag acaaaataga   4380
agaaaccgtt cataattttc tgaccaatga agaatcatca acgctatcac tttctgttca   4440
caaagtatgc gcaatccaca tcggtataga atataatcgg ggatgccttt atcttgaaaa   4500
aatgcacccg cagcttcgct agtaatcagt aaacgcggga agtggagtca ggcttttttt   4560
atggaagaga aaatagacac caaagtagcc ttcttctaac cttaacggac ctacagtgca   4620
aaaagttatc aagagactgc attatagagc gcacaaagga gaaaaaaagt aatctaagat   4680
gctttgttag aaaaatagcg ctctcgggat gcatttttgt agaacaaaaa agaagtatag   4740
attctttgtt ggtaaaatag cgctctcgcg ttgcatttct gttctgtaaa aatgcagctc   4800
agattctttg tttgaaaaat tagcgctctc gcgttgcatt tttgttttac aaaaatgaag   4860
cacagattct tcgttggtaa aatagcgctt tcgcgttgca tttctgttct gtaaaaatgc   4920
agctcagatt ctttgtttga aaaattagcg ctctcgcgtt gcatttttgt tctacaaaat   4980
gaagcacaga tgcttcgtta acaaagatat gctattgaag tgcaagatgg aaacgcagaa   5040
aatgaaccgg ggatgcgacg tgcaagatta cctatgcaat agatgcaata gtttctccag   5100
gaaccgaaat acatacattg tcttccgtaa agcgctagac tatatattat tatacaggtt   5160
caaatatact atctgtttca gggaaaactc ccaggttcgg atgttcaaaa ttcaatgatg   5220
ggtaacaagt acgatccgat atatgcggtg tgaaataccg cacagatgcg taaggagaaa   5280
ataccgcatc aggcgccatt cgccattcag gctgcgcaac tgttgggaag ggcgatcggt   5340
gcgggcctct tcgctattac gccagctggc gaaaggggga tgtgctgcaa ggcgattaag   5400
ttgggtaacg ccagggtttt cccagtcacg acgttgtaaa acgacggcca gtgaattcat   5460
gtaggtggcg gaggggagat atacaataga acagatacca gacaagacat aatgggctaa   5520
acaagactac accaattaca ctgcctcatt gatggtggta cataacgaac taatactgta   5580
```

-continued gccctagact tgatagccat catcatatcg aagtttcact accctttttc catttgccat 5640
ctattgaagt aataataggc gcatgcaact tcttttcttt ttttttcttt tctctctccc 5700
ccgttgttgt ctcaccatat ccgcaatgac aaaaaaatga tggaagacac taaaggaaaa 5760
aattaacgac aaagacagca ccaacagatg tcgttgttcc agagctgatg aggggtatct 5820
cgaagcacac gaaacttttt ccttccttca ttgacctgca attattaatc ttttgtttcc 5880
tcgtcattgt tctcgttccc tttcttcctt gtttcttttt ctgcacaata tttcaagcta 5940
taccaagcat acaatcaact ccaagcttga agcaagcctc ctgaaagatg aagctactgt 6000
cttctatcga acaagcatgc gatatttgcc gacttaaaaa gctcaagtgc tccaaagaaa 6060
aaccgaagtg cgccaagtgt ctgaagaaca actgggagtg tcgctactct cccaaaacca 6120
aaaggtctcc gctgactagg gcacatctga cagaagtgga atcaaggcta gaaagactgg 6180
aacagctatt tctactgatt tttcctcgag aagaccttga catgattttg aaaatggatt 6240
ctttacagga tataaaagca ttgttaacag gattatttgt acaagataat gtgaataaag 6300
atgccgtcac agatagattg gcttcagtgg agactgatat gcctctaaca ttgagacagc 6360
atagaataag tgcgacatca tcatcggaag agagtagtaa caaaggtcaa agacagttga 6420
ctgtatcgaa ctatctattc gatgatgaag ataccccacc aaacccaaaa aaagagatcg 6480
aattccagct gaccaccatg tttatggcca gaacaaagca aacagcaaga aagtccactg 6540
gtggtaaggc ccccaagaaag caattagctt ctaaggctgc cagaaaatcc gccccatcta 6600
ccggtggtgt taagaagcct cacagatata agccaggtac tgttgctttg agagaaatca 6660
gaagattcca aaaatctact gaacccgggt cccctatact aggttattgg aaaggtcgac 6720
gcgaccatcc tccaaaatcg gatctgatcg aaggtcgtgg agatcccgaa gttaaacggg 6780
taaaattaga aaacaacgtt gaagaaatac aacctgagca ggctgagacc aataaacaag 6840
agggcaccga taaagagaat aaaggaaagt tcgagaaaga aactgagaga ataggaggat 6900
ctgaagtggt tacagatgtg gaaaaaggaa ttgtcaaatt tgaatttgat ggtgttgaat 6960
acacattcaa agagagaccc agtgtcgtag aggaaaatga aggtaaaatt gagtttaggg 7020
tggtgaataa tgataatact aaagaaaaca tgatggtcct aactggatta aaaaacattt 7080
ttcaaaagca attaccaaaa atgcccaaag aatacattgc caggttagtc tatgatcgaa 7140
gtcatctttc catggctgtc attaggaagc cattgactgt cgtaggtggc ataacatatc 7200
gacctttcga taagagagaa ttcgcagaaa ttgttttctg tgccatcagt tcgacggaac 7260
aggtacgcgg ttatggtgcg catctaatga atcacttaaa agactatgtt agaaatacct 7320
cgaacataaa atatttttg acatatgcag ataattacgc tattggatac tttaaaaagc 7380
aaggctttac taaagaaatc acgttggata aaagtatatg gatgggatat attaaagatt 7440
atgaaggtgg tacgctgatg caatgtaaca tggcaattcc cggtggcggc cgcatctttt 7500
acccatacga tgttcctgac tatgcgggct atccctatga cgtcccggac tatgcaggat 7560
cctatccata tgacgttcca gattacgctg ctcagtgcgg ccgctctagc tagaactagt 7620
ggatcccccg ataccgtcga cctgcaggca tgcaagcttg gcgtaatcat ggtcatagct 7680
gtttcctgtg tgaaattgtt atccgctcac aattccacac aacatacgag ccggaagcat 7740
aaagtgtaaa gcctggggtg cctaatgagt gagctaactc acattaattg cgttgcgctc 7800
actgcccgct ttccagtcgg gaaacctgtc gtgccagctg cattaatgaa tcggccaacg 7860
cgcggggaga ggcggtttgc gtattgggcg c 7891

-continued

<210> SEQ ID NO 6
<211> LENGTH: 7891
<212> TYPE: DNA
<213> ORGANISM: Artificial Sequence
<220> FEATURE:
<223> OTHER INFORMATION: Synthetic

<400> SEQUENCE: 6
tcttccgctt cctcgctcac tgactcgctg cgctcggtcg ttcggctgcg gcgagcggta 60
tcagctcact caaaggcggt aatacggtta tccacagaat caggggataa cgcaggaaag 120
aacatgtgag caaaaggcca gcaaaaggcc aggaaccgta aaaaggccgc gttgctggcg 180
tttttccata ggctccgccc ccctgacgag catcacaaaa atcgacgctc aagtcagagg 240
tggcgaaacc cgacaggact ataaagatac caggcgtttc cccctggaag ctccctcgtg 300
cgctctcctg ttccgaccct gccgcttacc ggatacctgt ccgcctttct cccttcggga 360
agcgtggcgc tttctcatag ctcacgctgt aggtatctca gttcggtgta ggtcgttcgc 420
tccaagctgg gctgtgtgca cgaacccccc gttcagcccg accgctgcgc cttatccggt 480
aactatcgtc ttgagtccaa cccggtaaga cacgacttat cgccactggc agcagccact 540
ggtaacagga ttagcagagc gaggtatgta ggcggtgcta cagagttctt gaagtggtgg 600
cctaactacg gctacactag aaggacagta tttggtatct gcgctctgct gaagccagtt 660
accttcggaa aaagagttgg tagctcttga tccggcaaac aaaccaccgc tggtagcggt 720
ggtttttttg tttgcaagca gcagattacg cgcagaaaaa aaggatctca agaagatcct 780
ttgatctttt ctacggggtc tgacgctcag tggaacgaaa actcacgtta agggattttg 840
gtcatgagat tatcaaaaag gatcttcacc tagatccttt taaattaaaa atgaagtttt 900
aaatcaatct aaagtatata tgagtaaact tggtctgaca gttaccaatg cttaatcagt 960
gaggcaccta tctcagcgat ctgtctattt cgttcatcca tagttgcctg actccccgtc 1020
gtgtagataa ctacgatacg ggagggctta ccatctggcc ccagtgctgc aatgataccg 1080
cgagacccac gctcaccggc tccagattta tcagcaataa accagccagc cggaagggcc 1140
gagcgcagaa gtggtcctgc aactttatcc gcctccatcc agtctattaa ttgttgccgg 1200
gaagctagag taagtagttc gccagttaat agtttgcgca acgttgttgc cattgctaca 1260
ggcatcgtgg tgtcacgctc gtcgtttggt atggcttcat tcagctccgg ttcccaacga 1320
tcaaggcgag ttacatgatc ccccatgttg tgcaaaaaag cggttagctc cttcggtcct 1380
ccgatcgttg tcagaagtaa gttggccgca gtgttatcac tcatggttat ggcagcactg 1440
cataattctc ttactgtcat gccatccgta agatgctttt ctgtgactgg tgagtactca 1500
accaagtcat tctgagaata gtgtatgcgg cgaccgagtt gctcttgccc ggcgtcaata 1560
cgggataata ccgcgccaca tagcagaact ttaaaagtgc tcatcattgg aaaacgttct 1620
tcggggcgaa aactctcaag gatcttaccg ctgttgagat ccagttcgat gtaacccact 1680
cgtgcaccca actgatcttc agcatctttt actttcacca gcgtttctgg gtgagcaaaa 1740
acaggaaggc aaaatgccgc aaaaaaggga ataagggcga cacggaaatg ttgaatactc 1800
atactcttcc tttttcaata ttattgaagc atttatcagg gttattgtct catgagcgga 1860
tacatatttg aatgtattta gaaaaataaa caaatagggg ttccgcgcac atttccccga 1920
aaagtgccac ctgacgtcta agaaaccatt attatcatga cattaaccta taaaaatagg 1980
cgtatcacga ggccctttcg tcttcaagaa ttaactgtgg gaatactcag gtatcgtaag 2040
atgcaagagt tcgaatctct tagcaaccat tatttttttc ctcaacataa cgagaacaca 2100

-continued

```
caggggcgct atcgcacaga caaattcgat gactggaaat tttttgttaa tttcagaggt   2160
cgccgcgcat ataccttttt caactgaaaa attgggagaa aaaggaaagg tgagaggccg   2220
gaaccggctt ttcatataga atagagaagc gttcatgact aaatgcttgc atcacaatac   2280
ttgaagttga caatattatt taaggaccta ttgtttttttc caataggtgg ttagcaatcg   2340
tcttattcta acttttctta ccttttacat ttcagcaata tatatatata tttcaaggat   2400
atacattcta atgtctgccc ctatgtctgc ccctaagaag atcgtcgttt tgccaggtga   2460
ccacgttggt caagatcaca gccgaagcca ttaaggttct taaagctatt tctgatgttc   2520
gttccaatgt caagttcgat ttcgaaaatc atttaattgg tggtgctgct atcgatgcta   2580
caggtgtccc acttccagat gaggcgctgg aagcctccaa gaaggttgat gccgttttgt   2640
taggtgctgt gggtggtcct aaatggggta caggtagtgt tagacctgaa caaggtttac   2700
taaaaatccg taaagaactt caattgtacg ccaacttaag accatgtaac tttgcatccg   2760
actctctttt agacttatct ccaatcaagc cacaatttgc taaaggtact gacttcgttg   2820
ttgtcagaga attagtggga ggtatttact ttggtaagag aaaggaagac gatggtgatg   2880
gtgtcgcttg ggatagtgaa caatacaccg ttccagaagt gcaaagaatc acaagaatgg   2940
ccgctttcat ggccctacaa catgagccac cattgcctat ttggtccttg gataaagcta   3000
atgttttggc ctcttcaaga ttatggagaa aaactgtgga ggaaaccatc aagaacgaat   3060
ttcctacatt gaaggttcaa catcaattga ttgattctgc cgccatgatc ctagttaaga   3120
acccaaccca cctaaatggt attataatca ccagcaacat gtttggtgat atcatctccg   3180
atgaagcctc cgttatccca ggttccttgg gtttgttgcc atctgcgtcc ttggcctctt   3240
tgccagacaa gaacaccgca tttggtttgt acgaaccatg ccacggttct gctccagatt   3300
tgccaaagaa taaggttgac cctatcgcca ctatcttgtc tgctgcaatg atgttgaaat   3360
tgtcattgaa cttgcctgaa gaaggtaagg ccattgaaga tgcagttaaa aaggttttgg   3420
atgcaggtat cagaactggt gatttaggtg gttccaacag taccaccgaa gtcggtgatg   3480
ctgtcgccga agaagttaag aaaatccttg cttaaaaaga ttctcttttt ttatgatatt   3540
tgtacataaa ctttataaat gaaattcata atagaaacga cacgaaatta caaaatggaa   3600
tatgttcata gggtagaatt aattctcatg tttgacagct tatcatcgga tcgatccaat   3660
atcaaaggaa atgatagcat tgaaggatga gactaatcca attgaggagt ggcagcatat   3720
agaacagcta aagggtagtg ctgaaggaag catacgatac cccgcatgga atgggataat   3780
atcacaggag gtactagact acctttcatc ctacataaat agacgcatat aagtacgcat   3840
ttaagcataa acacgcacta tgccgttctt ctcatgtata tatatataca ggcaacacgc   3900
agatataggt gcgacgtgaa cagtgagctg tatgtgcgca gctcgcgttg cattttcgga   3960
agcgctcgtt ttcggaaacg ctttgaagtt cctattccga agttcctatt ctctagctag   4020
aaagtatagg aacttcagag cgcttttgaa aaccaaaagc gctctgaaga cgcactttca   4080
aaaaaccaaa aacgcaccgg actgtaacga gctactaaaa tattgcgaat accgcttcca   4140
caaacattgc tcaaaagtat ctctttgcta tatatctctg tgctatatcc ctatataacc   4200
tacccatcca cctttcgctc cttgaacttg catctaaact cgacctctac attttttatg   4260
tttatctcta gtattactct ttagacaaaa aaattgtagt aagaactatt catagagtga   4320
atcgaaaaca atacgaaaat gtaaacattt cctatacgta gtatatagag acaaaataga   4380
agaaaccgtt cataattttc tgaccaatga agaatcatca acgctatcac tttctgttca   4440
```

-continued

```
caaagtatgc gcaatccaca tcggtataga atataatcgg ggatgccttt atcttgaaaa   4500
aatgcacccg cagcttcgct agtaatcagt aaacgcggga agtggagtca ggcttttttt   4560
atggaagaga aaatagacac caaagtagcc ttcttctaac cttaacggac ctacagtgca   4620
aaaagttatc aagagactgc attatagagc gcacaaagga gaaaaaaagt aatctaagat   4680
gctttgttag aaaaatagcg ctctcgggat gcatttttgt agaacaaaaa agaagtatag   4740
attctttgtt ggtaaaatag cgctctcgcg ttgcatttct gttctgtaaa aatgcagctc   4800
agattctttg tttgaaaaat tagcgctctc gcgttgcatt tttgttttac aaaaatgaag   4860
cacagattct tcgttggtaa aatagcgctt tcgcgttgca tttctgttct gtaaaaatgc   4920
agctcagatt ctttgtttga aaaattagcg ctctcgcgtt gcatttttgt tctacaaaat   4980
gaagcacaga tgcttcgtta acaaagatat gctattgaag tgcaagatgg aaacgcagaa   5040
aatgaaccgg ggatgcgacg tgcaagatta cctatgcaat agatgcaata gtttctccag   5100
gaaccgaaat acatacattg tcttccgtaa agcgctagac tatatattat tatacaggtt   5160
caaatatact atctgtttca gggaaaactc ccaggttcgg atgttcaaaa ttcaatgatg   5220
ggtaacaagt acgatccgat atatgcggtg tgaaataccg cacagatgcg taaggagaaa   5280
ataccgcatc aggcgccatt cgccattcag gctgcgcaac tgttgggaag ggcgatcggt   5340
gcgggcctct tcgctattac gccagctggc gaaaggggga tgtgctgcaa ggcgattaag   5400
ttgggtaacg ccagggtttt cccagtcacg acgttgtaaa acgacggcca gtgaattcat   5460
gtaggtggcg gaggggagat atacaataga acagatacca gacaagacat aatgggctaa   5520
acaagactac accaattaca ctgcctcatt gatggtggta cataacgaac taatactgta   5580
gccctagact tgatagccat catcatatcg aagtttcact accctttttc catttgccat   5640
ctattgaagt aataataggc gcatgcaact tcttttcttt tttttctttt tctctctccc   5700
ccgttgttgt ctcaccatat ccgcaatgac aaaaaaatga tggaagacac taaaggaaaa   5760
aattaacgac aaagacagca ccaacagatg tcgttgttcc agagctgatg aggggtatct   5820
cgaagcacac gaaacttttt ccttccttca ttgacctgca attattaatc ttttgtttcc   5880
tcgtcattgt tctcgttccc tttcttcctt gtttcttttt ctgcacaata tttcaagcta   5940
taccaagcat acaatcaact ccaagcttga agcaagcctc ctgaaagatg aagctactgt   6000
cttctatcga acaagcatgc gatatttgcc gacttaaaaa gctcaagtgc tccaaagaaa   6060
aaccgaagtg cgccaagtgt ctgaagaaca actgggagtg tcgctactct cccaaaacca   6120
aaaggtctcc gctgactagg gcacatctga cagaagtgga atcaaggcta gaaagactgg   6180
aacagctatt tctactgatt tttcctcgag aagaccttga catgattttg aaaatggatt   6240
ctttacagga tataaaagca ttgttaacag gattatttgt acaagataat gtgaataaag   6300
atgccgtcac agatagattg gcttcagtgg agactgatat gcctctaaca ttgagacagc   6360
atagaataag tgcgacatca tcatcggaag agagtagtaa caaaggtcaa agacagttga   6420
ctgtatcgaa ctatctattc gatgatgaag ataccccacc aaacccaaaa aaagagatcg   6480
aattccagct gaccaccatg tttatggcca gaacaaagca aacagcaaga aagtccactg   6540
gtggtaaggc cccaagaaag caattagctt ctaaggctgc cagaaaatcc gccccatcta   6600
ccggtggtgt taagaagcct cacagatata agccaggtac tgttgctttg agagaaatca   6660
gaagattcca aaaatctact gaacccgggt cccctatact aggttattgg aaaggtcgac   6720
gcgaccatcc tccaaaatcg gatctgatcg aaggtcgtgg agatcccgaa gttaaacggg   6780
taaaattaga aaacaacgtt gaagaaatac aacctgagca ggctgagacc aataaacaag   6840
```

-continued agggcaccga taaagagaat aaaggaaagt tcgagaaaga aactgagaga ataggaggat 6900
ctgaagtggt tacagatgtg gaaaaaggaa ttgtcaaatt tgaatttgat ggtgttgaat 6960
acacattcaa agagagaccc agtgtcgtag aggaaaatga aggtaaaatt gagtttaggg 7020
tggtgaataa tgataatact aaagaaaaca tgatggtcct aactggatta aaaaacattt 7080
ttcaaaagca attaccaaaa atgcccaaag aatacattgc caggttagtc tatgatcgaa 7140
gtcatctttc catggctgtc attaggaagc cattgactgt cgtaggtggc ataacatatc 7200
gacctttcga taagagagaa ttcgcagaaa ttgttttctg tgccatcagt tcgacggaac 7260
aggtacgcgg ttatggtgcg catctaatga atcacttaaa agactatgtt agaaatacct 7320
cgaacataaa atattttttg acatatgcag ataattacgc tattggatac gctaaaaagc 7380
aaggcttcac taaagaaatc acgttggata aaagtatatg gatgggatat attaaagatt 7440
atgaaggtgg tacgctgatg caatgtaaca tggcaattcc cggtggcggc cgcatctttt 7500
acccatacga tgttcctgac tatgcgggct atccctatga cgtcccggac tatgcaggat 7560
cctatccata tgacgttcca gattacgctg ctcagtgcgg ccgctctagc tagaactagt 7620
ggatcccccg ataccgtcga cctgcaggca tgcaagcttg gcgtaatcat ggtcatagct 7680
gtttcctgtg tgaaattgtt atccgctcac aattccacac aacatacgag ccggaagcat 7740
aaagtgtaaa gcctggggtg cctaatgagt gagctaactc acattaattg cgttgcgctc 7800
actgcccgct ttccagtcgg gaaacctgtc gtgccagctg cattaatgaa tcggccaacg 7860
cgcggggaga ggcggtttgc gtattgggcg c 7891

<210> SEQ ID NO 7
<211> LENGTH: 7795
<212> TYPE: DNA
<213> ORGANISM: Artificial Sequence
<220> FEATURE:
<223> OTHER INFORMATION: Synthetic

<400> SEQUENCE: 7
tcttccgctt cctcgctcac tgactcgctg cgctcggtcg ttcggctgcg gcgagcggta 60
tcagctcact caaaggcggt aatacggtta tccacagaat caggggataa cgcaggaaag 120
aacatgtgag caaaaggcca gcaaaaggcc aggaaccgta aaaaggccgc gttgctggcg 180
tttttccata ggctccgccc ccctgacgag catcacaaaa atcgacgctc aagtcagagg 240
tggcgaaacc cgacaggact ataaagatac caggcgtttc cccctggaag ctccctcgtg 300
cgctctcctg ttccgaccct gccgcttacc ggatacctgt ccgcctttct cccttcggga 360
agcgtggcgc tttctcatag ctcacgctgt aggtatctca gttcggtgta ggtcgttcgc 420
tccaagctgg gctgtgtgca cgaacccccc gttcagcccg accgctgcgc cttatccggt 480
aactatcgtc ttgagtccaa cccggtaaga cacgacttat cgccactggc agcagccact 540
ggtaacagga ttagcagagc gaggtatgta ggcggtgcta cagagttctt gaagtggtgg 600
cctaactacg gctacactag aaggacagta tttggtatct gcgctctgct gaagccagtt 660
accttcggaa aaagagttgg tagctcttga tccggcaaac aaaccaccgc tggtagcggt 720
ggtttttttg tttgcaagca gcagattacg cgcagaaaaa aaggatctca agaagatcct 780
ttgatctttt ctacggggtc tgacgctcag tggaacgaaa actcacgtta agggattttg 840
gtcatgagat tatcaaaaag gatcttcacc tagatccttt taaattaaaa atgaagtttt 900
aaatcaatct aaagtatata tgagtaaact tggtctgaca gttaccaatg cttaatcagt 960

-continued gaggcaccta tctcagcgat ctgtctattt cgttcatcca tagttgcctg actccccgtc 1020
gtgtagataa ctacgatacg ggagggctta ccatctggcc ccagtgctgc aatgataccg 1080
cgagacccac gctcaccggc tccagattta tcagcaataa accagccagc cggaagggcc 1140
gagcgcagaa gtggtcctgc aactttatcc gcctccatcc agtctattaa ttgttgccgg 1200
gaagctagag taagtagttc gccagttaat agtttgcgca acgttgttgc cattgctaca 1260
ggcatcgtgg tgtcacgctc gtcgtttggt atggcttcat tcagctccgg ttcccaacga 1320
tcaaggcgag ttacatgatc ccccatgttg tgcaaaaaag cggttagctc cttcggtcct 1380
ccgatcgttg tcagaagtaa gttggccgca gtgttatcac tcatggttat ggcagcactg 1440
cataattctc ttactgtcat gccatccgta agatgctttt ctgtgactgg tgagtactca 1500
accaagtcat tctgagaata gtgtatgcgg cgaccgagtt gctcttgccc ggcgtcaata 1560
cgggataata ccgcgccaca tagcagaact ttaaaagtgc tcatcattgg aaaacgttct 1620
tcggggcgaa aactctcaag gatcttaccg ctgttgagat ccagttcgat gtaacccact 1680
cgtgcaccca actgatcttc agcatctttt actttcacca gcgtttctgg gtgagcaaaa 1740
acaggaaggc aaaatgccgc aaaaaaggga ataagggcga cacggaaatg ttgaatactc 1800
atactcttcc tttttcaata ttattgaagc atttatcagg gttattgtct catgagcgga 1860
tacatatttg aatgtattta gaaaaataaa caaatagggg ttccgcgcac atttccccga 1920
aaagtgccac ctgacgtcta agaaaccatt attatcatga cattaaccta taaaaatagg 1980
cgtatcacga ggccctttcg tcttcaagaa ttaactgtgg gaatactcag gtatcgtaag 2040
atgcaagagt tcgaatctct tagcaaccat tatttttttc ctcaacataa cgagaacaca 2100
caggggcgct atcgcacaga caaattcgat gactggaaat ttttgttaa tttcagaggt 2160 cgccgcgcat ataccttttt caactgaaaa attgggagaa aaaggaaagg tgagaggccg 2220
gaaccggctt ttcatataga atagagaagc gttcatgact aaatgcttgc atcacaatac 2280
ttgaagttga caatattatt taaggaccta ttgtttttc caataggtgg ttagcaatcg 2340
tcttattcta acttttctta ccttttacat ttcagcaata tatatatata tttcaaggat 2400
atacattcta atgtctgccc ctatgtctgc ccctaagaag atcgtcgttt tgccaggtga 2460
ccacgttggt caagatcaca gccgaagcca ttaaggttct taaagctatt tctgatgttc 2520
gttccaatgt caagttcgat ttcgaaaatc atttaattgg tggtgctgct atcgatgcta 2580
caggtgtccc acttccagat gaggcgctgg aagcctccaa gaaggttgat gccgttttgt 2640
taggtgctgt gggtggtcct aaatggggta caggtagtgt tagacctgaa caaggtttac 2700
taaaaatccg taaagaactt caattgtacg ccaacttaag accatgtaac tttgcatccg 2760
actctctttt agacttatct ccaatcaagc cacaatttgc taaaggtact gacttcgttg 2820
ttgtcagaga attagtggga ggtatttact ttggtaagag aaaggaagac gatggtgatg 2880
gtgtcgcttg ggatagtgaa caatacaccg ttccagaagt gcaaagaatc acaagaatgg 2940
ccgctttcat ggccctacaa catgagccac cattgcctat ttggtccttg gataaagcta 3000
atgttttggc ctcttcaaga ttatggagaa aaactgtgga ggaaaccatc aagaacgaat 3060
ttcctacatt gaaggttcaa catcaattga ttgattctgc cgccatgatc ctagttaaga 3120
acccaaccca cctaaatggt attataatca ccagcaacat gtttggtgat atcatctccg 3180
atgaagcctc cgttatccca ggttccttgg gtttgttgcc atctgcgtcc ttggcctctt 3240
tgccagacaa gaacaccgca tttggtttgt acgaaccatg ccacggttct gctccagatt 3300
tgccaaagaa taaggttgac cctatcgcca ctatcttgtc tgctgcaatg atgttgaaat 3360

-continued

```
tgtcattgaa cttgcctgaa gaaggtaagg ccattgaaga tgcagttaaa aaggttttgg   3420
atgcaggtat cagaactggt gatttaggtg gttccaacag taccaccgaa gtcggtgatg   3480
ctgtcgccga agaagttaag aaaatccttg cttaaaaaga ttctcttttt ttatgatatt   3540
tgtacataaa ctttataaat gaaattcata atagaaacga cacgaaatta caaaatggaa   3600
tatgttcata gggtagaatt aattctcatg tttgacagct tatcatcgga tcgatccaat   3660
atcaaaggaa atgatagcat tgaaggatga gactaatcca attgaggagt ggcagcatat   3720
agaacagcta aagggtagtg ctgaaggaag catacgatac cccgcatgga atgggataat   3780
atcacaggag gtactagact acctttcatc ctacataaat agacgcatat aagtacgcat   3840
ttaagcataa acacgcacta tgccgttctt ctcatgtata tatatataca ggcaacacgc   3900
agatataggt gcgacgtgaa cagtgagctg tatgtgcgca gctcgcgttg cattttcgga   3960
agcgctcgtt ttcggaaacg ctttgaagtt cctattccga agttcctatt ctctagctag   4020
aaagtatagg aacttcagag cgcttttgaa aaccaaaagc gctctgaaga cgcactttca   4080
aaaaaccaaa aacgcaccgg actgtaacga gctactaaaa tattgcgaat accgcttcca   4140
caaacattgc tcaaaagtat ctctttgcta tatatctctg tgctatatcc ctatataacc   4200
tacccatcca cctttcgctc cttgaacttg catctaaact cgacctctac atttttatg    4260
tttatctcta gtattactct ttagacaaaa aaattgtagt aagaactatt catagagtga   4320
atcgaaaaca atacgaaaat gtaaacattt cctatacgta gtatatagag acaaaataga   4380
agaaaccgtt cataattttc tgaccaatga agaatcatca acgctatcac tttctgttca   4440
caaagtatgc gcaatccaca tcggtataga atataatcgg ggatgccttt atcttgaaaa   4500
aatgcacccg cagcttcgct agtaatcagt aaacgcggga agtggagtca ggcttttttt   4560
atggaagaga aaatagacac caaagtagcc ttcttctaac cttaacggac ctacagtgca   4620
aaaagttatc aagagactgc attatagagc gcacaaagga gaaaaaaagt aatctaagat   4680
gctttgttag aaaaatagcg ctctcgggat gcatttttgt agaacaaaaa agaagtatag   4740
attctttgtt ggtaaaatag cgctctcgcg ttgcatttct gttctgtaaa aatgcagctc   4800
agattctttg tttgaaaaat tagcgctctc gcgttgcatt tttgttttac aaaaatgaag   4860
cacagattct tcgttggtaa aatagcgctt tcgcgttgca tttctgttct gtaaaaatgc   4920
agctcagatt ctttgtttga aaaattagcg ctctcgcgtt gcatttttgt tctacaaaat   4980
gaagcacaga tgcttcgtta acaaagatat gctattgaag tgcaagatgg aaacgcagaa   5040
aatgaaccgg ggatgcgacg tgcaagatta cctatgcaat agatgcaata gtttctccag   5100
gaaccgaaat acatacattg tcttccgtaa agcgctagac tatatattat tatacaggtt   5160
caaatatact atctgtttca gggaaaactc ccaggttcgg atgttcaaaa ttcaatgatg   5220
ggtaacaagt acgatccgat atatgcggtg tgaaataccg cacagatgcg taaggagaaa   5280
ataccgcatc aggcgccatt cgccattcag gctgcgcaac tgttgggaag ggcgatcggt   5340
gcgggcctct tcgctattac gccagctggc gaaaggggga tgtgctgcaa ggcgattaag   5400
ttgggtaacg ccagggtttt cccagtcacg acgttgtaaa acgacggcca gtgaattcat   5460
gtaggtggcg gaggggagat atacaataga acagatacca gacaagacat aatgggctaa   5520
acaagactac accaattaca ctgcctcatt gatggtggta cataacgaac taatactgta   5580
gccctagact tgatagccat catcatatcg aagtttcact accctttttc catttgccat   5640
ctattgaagt aataataggc gcatgcaact tcttttcttt ttttttcttt tctctctccc   5700
```

-continued

```
ccgttgttgt ctcaccatat ccgcaatgac aaaaaaatga tggaagacac taaaggaaaa   5760

aattaacgac aaagacagca ccaacagatg tcgttgttcc agagctgatg aggggtatct   5820

cgaagcacac gaaacttttt ccttccttca ttgacctgca attattaatc ttttgtttcc   5880

tcgtcattgt tctcgttccc tttcttcctt gtttcttttt ctgcacaata tttcaagcta   5940

taccaagcat acaatcaact ccaagcttga agcaagcctc ctgaaagatg aagctactgt   6000

cttctatcga acaagcatgc gatatttgcc gacttaaaaa gctcaagtgc tccaaagaaa   6060

aaccgaagtg cgccaagtgt ctgaagaaca actgggagtg tcgctactct cccaaaacca   6120

aaaggtctcc gctgactagg gcacatctga cagaagtgga atcaaggcta gaaagactgg   6180

aacagctatt tctactgatt tttcctcgag aagaccttga catgattttg aaaatggatt   6240

ctttacagga tataaaagca ttgttaacag gattatttgt acaagataat gtgaataaag   6300

atgccgtcac agatagattg gcttcagtgg agactgatat gcctctaaca ttgagacagc   6360

atagaataag tgcgacatca tcatcggaag agagtagtaa caaaggtcaa agacagttga   6420

ctgtatcgaa ctatctattc gatgatgaag ataccccacc aaacccaaaa aaagagatcg   6480

aattccagct gaccaccatg tccggtagag gtaaaggtgg taaaggtcta ggaaaaggtg   6540

gtgccaagcg tcacagaaag attctaagag ataacatcca aggtatttcc gggtccccta   6600

tactaggtta ttggaaaggt cgacgcgacc atcctccaaa atcggatctg atcgaaggtc   6660

gtggagatcc cgaagttaaa cgggtaaaat tagaaaacaa cgttgaagaa atacaacctg   6720

agcaggctga gaccaataaa caagagggca ccgataaaga gaataaagga aagttcgaga   6780

aagaaactga gagaatagga ggatctgaag tggttacaga tgtggaaaaa ggaattgtca   6840

aatttgaatt tgatggtgtt gaatacacat tcaaagagag acccagtgtc gtagaggaaa   6900

atgaaggtaa aattgagttt agggtggtga ataatgataa tactaaagaa aacatgatgg   6960

tcctaactgg attaaaaaac atttttcaaa agcaattacc aaaaatgccc aaagaataca   7020

ttgccaggtt agtctatgat cgaagtcatc tttccatggc tgtcattagg aagccattga   7080

ctgtcgtagg tggcataaca tatcgacctt tcgataagag agaattcgca gaaattgttt   7140

tctgtgccat cagttcgacg gaacaggtac gcggttatgg tgcgcatcta atgaatcact   7200

taaaagacta tgttagaaat acctcgaaca taaaatattt tttgacatat gcagataatt   7260

acgctattgg atactttaaa aagcaaggct tcactaaaga aatcacgttg gataaaagta   7320

tatggatggg atatattaaa gattatgaag gtggtacgct gatgcaatgt tccatggcaa   7380

ttcccggtgg cggccgcatc ttttacccat acgatgttcc tgactatgcg ggctatccct   7440

atgacgtccc ggactatgca ggatcctatc catatgacgt tccagattac gctgctcagt   7500

gcggccgctc tagctagaac tagtggatcc cccgataccg tcgacctgca ggcatgcaag   7560

cttggcgtaa tcatggtcat agctgtttcc tgtgtgaaat tgttatccgc tcacaattcc   7620

acacaacata cgagccggaa gcataaagtg taaagcctgg ggtgcctaat gagtgagcta   7680

actcacatta attgcgttgc gctcactgcc cgctttccag tcgggaaacc tgtcgtgcca   7740

gctgcattaa tgaatcggcc aacgcgcggg gagaggcggt ttgcgtattg ggcgc        7795
```

<210> SEQ ID NO 8
<211> LENGTH: 7795
<212> TYPE: DNA
<213> ORGANISM: Artificial Sequence
<220> FEATURE:
<223> OTHER INFORMATION: Synthetic

<400> SEQUENCE: 8

-continued

```
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tcttcaagaa ttaactgtgg gaatactcag gtatcgtaag   2040
atgcaagagt tcgaatctct tagcaaccat tatttttttc ctcaacataa cgagaacaca   2100
caggggcgct atcgcacaga caaattcgat gactggaaat tttttgttaa tttcagaggt   2160
cgccgcgcat ataccttttt caactgaaaa attgggagaa aaaggaaagg tgagaggccg   2220
gaaccggctt ttcatataga atagagaagc gttcatgact aaatgcttgc atcacaatac   2280
ttgaagttga caatattatt taaggaccta ttgttttttc caataggtgg ttagcaatcg   2340
```

-continued

```
tcttattcta acttttctta ccttttacat ttcagcaata tatatatata tttcaaggat   2400
atacattcta atgtctgccc ctatgtctgc ccctaagaag atcgtcgttt tgccaggtga   2460
ccacgttggt caagatcaca gccgaagcca ttaaggttct taaagctatt tctgatgttc   2520
gttccaatgt caagttcgat ttcgaaaatc atttaattgg tggtgctgct atcgatgcta   2580
caggtgtccc acttccagat gaggcgctgg aagcctccaa gaaggttgat gccgttttgt   2640
taggtgctgt gggtggtcct aaatggggta caggtagtgt tagacctgaa caaggtttac   2700
taaaaatccg taaagaactt caattgtacg ccaacttaag accatgtaac tttgcatccg   2760
actctctttt agacttatct ccaatcaagc cacaatttgc taaaggtact gacttcgttg   2820
ttgtcagaga attagtggga ggtatttact ttggtaagag aaaggaagac gatggtgatg   2880
gtgtcgcttg ggatagtgaa caatacaccg ttccagaagt gcaaagaatc acaagaatgg   2940
ccgctttcat ggccctacaa catgagccac cattgcctat ttggtccttg gataaagcta   3000
atgttttggc ctcttcaaga ttatggagaa aaactgtgga ggaaaccatc aagaacgaat   3060
ttcctacatt gaaggttcaa catcaattga ttgattctgc cgccatgatc ctagttaaga   3120
acccaaccca cctaaatggt attataatca ccagcaacat gtttggtgat atcatctccg   3180
atgaagcctc cgttatccca ggttccttgg gtttgttgcc atctgcgtcc ttggcctctt   3240
tgccagacaa gaacaccgca tttggtttgt acgaaccatg ccacggttct gctccagatt   3300
tgccaaagaa taaggttgac cctatcgcca ctatcttgtc tgctgcaatg atgttgaaat   3360
tgtcattgaa cttgcctgaa gaaggtaagg ccattgaaga tgcagttaaa aaggttttgg   3420
atgcaggtat cagaactggt gatttaggtg gttccaacag taccaccgaa gtcggtgatg   3480
ctgtcgccga agaagttaag aaaatccttg cttaaaaaga ttctcttttt ttatgatatt   3540
tgtacataaa ctttataaat gaaattcata atagaaacga cacgaaatta caaaatggaa   3600
tatgttcata gggtagaatt aattctcatg tttgacagct tatcatcgga tcgatccaat   3660
atcaaaggaa atgatagcat tgaaggatga gactaatcca attgaggagt ggcagcatat   3720
agaacagcta aagggtagtg ctgaaggaag catacgatac cccgcatgga atgggataat   3780
atcacaggag gtactagact acctttcatc ctacataaat agacgcatat aagtacgcat   3840
ttaagcataa acacgcacta tgccgttctt ctcatgtata tatatataca ggcaacacgc   3900
agatataggt gcgacgtgaa cagtgagctg tatgtgcgca gctcgcgttg cattttcgga   3960
agcgctcgtt ttcggaaacg ctttgaagtt cctattccga agttcctatt ctctagctag   4020
aaagtatagg aacttcagag cgcttttgaa aaccaaaagc gctctgaaga cgcactttca   4080
aaaaaccaaa aacgcaccgg actgtaacga gctactaaaa tattgcgaat accgcttcca   4140
caaacattgc tcaaaagtat ctctttgcta tatatctctg tgctatatcc ctatataacc   4200
tacccatcca cctttcgctc cttgaacttg catctaaact cgacctctac atttttttatg   4260
tttatctcta gtattactct ttagacaaaa aaattgtagt aagaactatt catagagtga   4320
atcgaaaaca atacgaaaat gtaaacattt cctatacgta gtatatagag acaaaataga   4380
agaaaccgtt cataattttc tgaccaatga agaatcatca acgctatcac tttctgttca   4440
caaagtatgc gcaatccaca tcggtataga atataatcgg ggatgccttt atcttgaaaa   4500
aatgcacccg cagcttcgct agtaatcagt aaacgcggga agtggagtca ggcttttttt   4560
atggaagaga aaatagacac caaagtagcc ttcttctaac cttaacggac ctacagtgca   4620
aaaagttatc aagagactgc attatagagc gcacaaagga gaaaaaaagt aatctaagat   4680
gctttgttag aaaaatagcg ctctcgggat gcatttttgt agaacaaaaa agaagtatag   4740
```

-continued

```
attctttgtt ggtaaaatag cgctctcgcg ttgcatttct gttctgtaaa aatgcagctc   4800
agattctttg tttgaaaaat tagcgctctc gcgttgcatt tttgttttac aaaaatgaag   4860
cacagattct tcgttggtaa aatagcgctt tcgcgttgca tttctgttct gtaaaaatgc   4920
agctcagatt ctttgtttga aaaattagcg ctctcgcgtt gcatttttgt tctacaaaat   4980
gaagcacaga tgcttcgtta acaaagatat gctattgaag tgcaagatgg aaacgcagaa   5040
aatgaaccgg ggatgcgacg tgcaagatta cctatgcaat agatgcaata gtttctccag   5100
gaaccgaaat acatacattg tcttccgtaa agcgctagac tatatattat tatacaggtt   5160
caaatatact atctgtttca gggaaaactc ccaggttcgg atgttcaaaa ttcaatgatg   5220
ggtaacaagt acgatccgat atatgcggtg tgaaataccg cacagatgcg taaggagaaa   5280
ataccgcatc aggcgccatt cgccattcag gctgcgcaac tgttgggaag ggcgatcggt   5340
gcgggcctct tcgctattac gccagctggc gaaaggggga tgtgctgcaa ggcgattaag   5400
ttgggtaacg ccagggtttt cccagtcacg acgttgtaaa acgacggcca gtgaattcat   5460
gtaggtggcg gaggggagat atacaataga acagatacca gacaagacat aatgggctaa   5520
acaagactac accaattaca ctgcctcatt gatggtggta cataacgaac taatactgta   5580
gccctagact tgatagccat catcatatcg aagtttcact accctttttc catttgccat   5640
ctattgaagt aataataggc gcatgcaact tcttttcttt tttttcttt tctctctccc   5700
ccgttgttgt ctcaccatat ccgcaatgac aaaaaaatga tggaagacac taaaggaaaa   5760
aattaacgac aaagacagca ccaacagatg tcgttgttcc agagctgatg aggggtatct   5820
cgaagcacac gaaacttttt ccttccttca ttgacctgca attattaatc ttttgtttcc   5880
tcgtcattgt tctcgttccc tttcttcctt gtttcttttt ctgcacaata tttcaagcta   5940
taccaagcat acaatcaact ccaagcttga agcaagcctc ctgaaagatg aagctactgt   6000
cttctatcga acaagcatgc gatatttgcc gacttaaaaa gctcaagtgc tccaaagaaa   6060
aaccgaagtg cgccaagtgt ctgaagaaca actgggagtg tcgctactct cccaaaacca   6120
aaaggtctcc gctgactagg gcacatctga cagaagtgga atcaaggcta gaaagactgg   6180
aacagctatt tctactgatt tttcctcgag aagaccttga catgattttg aaaatggatt   6240
ctttacagga tataaaagca ttgttaacag gattatttgt acaagataat gtgaataaag   6300
atgccgtcac agatagattg gcttcagtgg agactgatat gcctctaaca ttgagacagc   6360
atagaataag tgcgacatca tcatcggaag agagtagtaa caaaggtcaa agacagttga   6420
ctgtatcgaa ctatctattc gatgatgaag ataccccacc aaacccaaaa aaagagatcg   6480
aattccagct gaccaccatg tccggtagag gtaaaggtgg taaaggtcta ggaaaaggtg   6540
gtgccaagcg tcacagaaag attctaagag ataacatcca aggtatttcc gggtccccta   6600
tactaggtta ttggaaaggt cgacgcgacc atcctccaaa atcggatctg atcgaaggtc   6660
gtggagatcc cgaagttaaa cgggtaaaat tagaaaacaa cgttgaagaa atacaacctg   6720
agcaggctga gaccaataaa caagagggca ccgataaaga gaataaagga aagttcgaga   6780
aagaaactga gagaatagga ggatctgaag tggttacaga tgtggaaaaa ggaattgtca   6840
aatttgaatt tgatggtgtt gaatacacat tcaaagagag acccagtgtc gtagaggaaa   6900
atgaaggtaa aattgagttt agggtggtga ataatgataa tactaaagaa aacatgatgg   6960
tcctaactgg attaaaaaac atttttcaaa agcaattacc aaaaatgccc aaagaataca   7020
ttgccaggtt agtctatgat cgaagtcatc tttccatggc tgtcattagg aagccattga   7080
```

-continued

```
ctgtcgtagg tggcataaca tatcgacctt tcgataagag agaattcgca gaaattgttt   7140

tctgtgccat cagttcgacg gaacaggtac gcggttatgg tgcgcatcta atgaatcact   7200

taaaagacta tgttagaaat acctcgaaca taaaatattt tttgacatat gcagataatt   7260

acgctattgg atacgctaaa aagcaaggct tcactaaaga aatcacgttg gataaaagta   7320

tatggatggg atatattaaa gattatgaag gtggtacgct gatgcaatgt tccatggcaa   7380

ttcccggtgg cggccgcatc ttttacccat acgatgttcc tgactatgcg ggctatccct   7440

atgacgtccc ggactatgca ggatcctatc catatgacgt tccagattac gctgctcagt   7500

gcggccgctc tagctagaac tagtggatcc cccgataccg tcgacctgca ggcatgcaag   7560

cttggcgtaa tcatggtcat agctgtttcc tgtgtgaaat tgttatccgc tcacaattcc   7620

acacaacata cgagccggaa gcataaagtg taaagcctgg ggtgcctaat gagtgagcta   7680

actcacatta attgcgttgc gctcactgcc cgctttccag tcgggaaacc tgtcgtgcca   7740

gctgcattaa tgaatcggcc aacgcgcggg gagaggcggt ttgcgtattg ggcgc        7795
```

<210> SEQ ID NO 9
<211> LENGTH: 8087
<212> TYPE: DNA
<213> ORGANISM: Artificial Sequence
<220> FEATURE:
<223> OTHER INFORMATION: Synthetic

<400> SEQUENCE: 9

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840

tagtaacaaa ggtcaaagac agttgactgt atcgaactat ctattcgatg atgaagatac    900

cccaccaaac ccaaaaaaag agatcgaatt ccaggggtcc cctatactag gttattggaa    960

aggtcgacgc gaccatcctc caaaatcgga tctgatcgaa ggtcgtggag atcccgaagt   1020

taaacgggta aaattagaaa acaacgttga agaaatacaa cctgagcagg ctgagaccaa   1080

taaacaagag ggcaccgata aagagaataa aggaaagttc gagaaagaaa ctgagagaat   1140

aggaggatct gaagtggtta cagatgtgga aaaaggaatt gtcaaatttg aatttgatgg   1200

tgttgaatac acattcaaag agagacccag tgtcgtagag gaaaatgaag gtaaaattga   1260

gtttagggtg gtgaataatg ataatactaa agaaaacatg atggtcctaa ctggattaaa   1320

aaacattttt caaaagcaat taccaaaaat gcccaaagaa tacattgcca ggttagtcta   1380
```

-continued

```
tgatcgaagt catctttcca tggctgtcat taggaagcca ttgactgtcg taggtggcat   1440
aacatatcga cctttcgata agagagaatt cgcagaaatt gttttctgtg ccatcagttc   1500
gacggaacag gtacgcggtt atggtgcgca tctaatgaat cacttaaaag actatgttag   1560
aaatacctcg aacataaaat attttttgac atatgcagat aattacgcta ttggatactt   1620
taaaaagcaa ggctttacta aagaaatcac gttggataaa agtatatgga tgggatatat   1680
taaagattat gaaggtggta cgctgatgca atgtaacatg gcaattcccg gtggcggccg   1740
catcttttac ccatacgatg ttcctgacta tgcgggctat ccctatgacg tcccggacta   1800
tgcaggatcc tatccatatg acgttccaga ttacgctgct cagtgcggcc gctctagcta   1860
gaactagtgg atcccccgat accgtcgacc tgcagagatc tatgaatcgt agatactgaa   1920
aaaccccgca agttcacttc aactgtgcat cgtgcaccat ctcaatttct ttcatttata   1980
catcgttttg ccttctttta tgtaactata ctcctctaag tttcaatctt ggccatgtaa   2040
cctctgatct atagaatttt ttaaatgact agaattaatg cccatctttt ttttggacct   2100
aaattcttca tgaaaatata ttacgagggc ttattcagaa gctttggact tcttcgccag   2160
aggtttggtc aagtctccaa tcaaggttgt cggcttgtct accttgccag aaatttacga   2220
aaagatggaa aagggtcaaa tcgttggtag atacgttgtt gacacttcta aataagcgaa   2280
tttcttatga tttatgattt ttattattaa ataagttata aaaaaaataa gtgtatacaa   2340
attttaaagt gactcttagg ttttaaaacg aaaattctta ttcttgagta actctttcct   2400
gtaggtcagg ttgctttctc aggtatagca tgaggtcgct cttattgacc acacctctac   2460
cggcatgccg agcaaatgcc tgcaaatcgc tccccatttc acccaattgt agatatgcta   2520
actccagcaa tgagttgatg aatctcggtg tgtattttat gtcctcagag gacaacacct   2580
gttgtaatcg ttcttccaca cggatcctgg cgtaatagcg aagaggcccg caccgatcgc   2640
ccttcccaac agttgcgcag cctgaatggc gaatggcgcc tgatgcggta ttttctcctt   2700
acgcatctgt gcggtatttc acaccgcata tatcgctggg ccattctcat gaagaatatc   2760
ttgaatttat tgtcatatta ctagttggtg tggaagtcca tatatcggtg atcaatatag   2820
tggttgacat gctggctagt caacattgag ccttttgatc atgcaaatat attacggtat   2880
tttacaatca aatatcaaac ttaactattg actttataac ttatttaggt ggtaacattc   2940
ttataaaaaa gaaaaaaatt actgcaaaac agtactagct tttaacttgt atcctaggtt   3000
atctatgctg tctcaccata gagaatatta cctatttcag aatgtatgtc catgattcgc   3060
cgggtaaata catataatac acaaatctgg cttaataaag tctataatat atctcataaa   3120
gaagtgctaa attggctagt gctatatatt tttaagaaaa tttcttttga ctaagtccat   3180
atcgactttg taaaagttca ctttagcata catatattac acgagccaga aattgtaact   3240
tttgcctaaa atcacaaatt gcaaaattta attgcttgca aaaggtcaca tgcttataat   3300
caactttttt aaaaatttaa aatacttttt tattttttat ttttaaacat aaatgaaata   3360
atttatttat tgtttatgat taccgaaaca taaaacctgc tcaagaaaaa gaaactgttt   3420
tgtccttgga aaaaaagcac tacctaggag cggccaaaat gccgaggctt tcatagctta   3480
aactctttac agaaaatagg cattatagat cagttcgagt tttcttattc ttccttccgg   3540
ttttatcgtc acagttttac agtaaataag tatcacctct tagagttcga tgataagctg   3600
tcaaacatga gaattaattc cacatgttaa aatagtgaag gagcatgttc ggcacacagt   3660
ggaccgaacg tggggtaagt gcactagggt ccggttaaac ggatctcgca ttgatgaggc   3720
```

-continued

```
aacgctaatt atcaacatat agattgttat ctatctgcat gaacacgaaa tctttacttg   3780
acgacttgag gctgatggtg tttatgcaaa gaaaccactg tgtttaatat gtgtcactgt   3840
ttgatattac tgtcagcgta gaagataata gtaaaagcgg ttaataagtg tatttgagat   3900
aagtgtgata aagtttttac agcgaaaaga cgataaatac aagaaaatga ttacgaggat   3960
acggagagag gtatgtacat gtgtatttat atactaagct gccggcggtt gtttgcaaga   4020
ccgagaaaag gctagcaaga atcgggtcat tgtagcgtat gcgcctgtga acattctctt   4080
caacaagttt gattccattg cggtgaaatg gtaaaagtca accccctgcg atgtatattt   4140
tcctgtacaa tcaatcaaaa agccaaatga tttagcatta tctttacatc ttgttatttt   4200
acagatttta tgtttagatc ttttatgctt gcttttcaaa aggcttgcag gcaagtgcac   4260
aaacaatact taaataaata ctactcagta ataacctatt tcttagcatt tttgacgaaa   4320
tttgctattt tgttagagtc ttttacacca tttgtctcca cacctccgct tacatcaaca   4380
ccaataacgc catttaatct aagcgcatca ccaacatttt ctggcgtcag tccaccagct   4440
aacataaaat gtaagctctc ggggctctct tgccttccaa cccagtcaga aatcgagttc   4500
caatccaaaa gttcacctgt cccacctgct tctgaatcaa acaagggaat aaacgaatga   4560
ggtttctgtg aagctgcact gagtagtatg ttgcagtctt ttggaaatac gagtctttta   4620
ataactggca aaccgaggaa ctcttggtat tcttgccacg actcatctcc atgcagttgg   4680
acgatatcaa tgccgtaatc attgaccaga gccaaaacat cctccttagg ttgattacga   4740
aacacgccaa ccaagtattt cggagtgcct gaactatttt tatatgcttt tacaagactt   4800
gaaattttcc ttgcaataac cgggtcaatt gttctctttc tattgggcac acatataata   4860
cccagcaagt cagcatcgga atctagtgca cattctgcgg cctctgtgct ctgcaagccg   4920
caaactttca ccaatggacc agaactacct gtgaaattaa taacagacat actccaagct   4980
gcctttgtgt gcttaatcac gtatactcac gtgctcaata gtcaccaatg ccctccctct   5040
tggccctctc cttttctttt ttcgaccgaa ttaattcttg aagacgaaag ggcctcgtga   5100
tacgcctatt tttataggtt aatgtcatga taataatggt ttcttagacg tcaggtggca   5160
cttttcgggg aaatgtgcgc ggaaccccta tttgtttatt tttctaaata cattcaaata   5220
tgtatccgct catgagacaa taaccctgat aaatgcttca ataatattga aaaaggaaga   5280
gtatgagtat tcaacatttc cgtgtcgccc ttattccctt ttttgcggca ttttgccttc   5340
ctgtttttgc tcacccagaa acgctggtga aagtaaaaga tgctgaagat cagttgggtg   5400
cacgagtggg ttacatcgaa ctggatctca acagcggtaa gatccttgag agttttcgcc   5460
ccgaagaacg ttttccaatg atgagcactt ttaaagttct gctatgtggc gcggtattat   5520
cccgtattga cgccgggcaa gagcaactcg gtcgccgcat acactattct cagaatgact   5580
tggttgagta ctcaccagtc acagaaaagc atcttacgga tggcatgaca gtaagagaat   5640
tatgcagtgc tgccataacc atgagtgata acactgcggc caacttactt ctgacaacga   5700
tcggaggacc gaaggagcta accgcttttt tgcacaacat gggggatcat gtaactcgcc   5760
ttgatcgttg ggaaccggag ctgaatgaag ccataccaaa cgacgagcgt gacaccacga   5820
tgcctgtagc aatggcaaca acgttgcgca aactattaac tggcgaacta cttactctag   5880
cttcccggca acaattaata gactggatgg aggcggataa agttgcagga ccacttctgc   5940
gctcggccct tccggctggc tggtttattg ctgataaatc tggagccggt gagcgtgggt   6000
ctcgcggtat cattgcagca ctggggccag atggtaagcc ctcccgtatc gtagttatct   6060
acacgacggg gagtcaggca actatggatg aacgaaatag acagatcgct gagataggtg   6120
```

-continued cctcactgat taagcattgg taactgtcag accaagttta ctcatatata ctttagattg 6180
atttaaaact tcatttttaa tttaaaagga tctaggtgaa gatccttttt gataatctca 6240
tgaccaaaat cccttaacgt gagttttcgt tccactgagc gtcagacccc gtagaaaaga 6300
tcaaaggatc ttcttgagat cctttttttc tgcgcgtaat ctgctgcttg caaacaaaaa 6360
aaccaccgct accagcggtg gtttgtttgc cggatcaaga gctaccaact ctttttccga 6420
aggtaactgg cttcagcaga gcgcagatac caaatactgt ccttctagtg tagccgtagt 6480
taggccacca cttcaagaac tctgtagcac cgcctacata cctcgctctg ctaatcctgt 6540
taccagtggc tgctgccagt ggcgataagt cgtgtcttac cgggttggac tcaagacgat 6600
agttaccgga taaggcgcag cggtcgggct gaacgggggg ttcgtgcaca cagcccagct 6660
tggagcgaac gacctacacc gaactgagat acctacagcg tgagctatga gaaagcgcca 6720
cgcttcccga agggagaaag gcggacaggt atccggtaag cggcagggtc ggaacaggag 6780
agcgcacgag ggagcttcca gggggaaacg cctggtatct ttatagtcct gtcgggtttc 6840
gccacctctg acttgagcgt cgatttttgt gatgctcgtc aggggggcgg agcctatgga 6900
aaaacgccag caacgcggcc tttttacggt tcctggcctt ttgctggcct tttgctcaca 6960
tgttctttcc tgcgttatcc cctgattctg tggataaccg tattaccgcc tttgagtgag 7020
ctgataccgc tcgccgcagc cgaacgaccg agcgcagcga gtcagtgagc gaggaagcgg 7080
aagagcgccc aatacgcaaa ccgcctctcc ccgcgcgttg gccgattcat taatgcagga 7140
tccgggatcg aagaaatgat ggtaaatgaa ataggaaatc aaggagcatg aaggcaaaag 7200
acaaatataa gggtcgaacg aaaaataaag tgaaaagtgt tgatatgatg tatttggctt 7260
tgcggcgccg aaaaaacgag tttacgcaat tgcacaatca tgctgactct gtggcggacc 7320
cgcgctcttg ccggcccggc gataacgctg ggcgtgaggc tgtgcccggc ggagtttttt 7380
gcgcctgcat tttccaaggt ttaccctgcg ctaaggggcg agattggaga agcaataaga 7440
atgccggttg gggttgcgat gatgacgacc acgacaactg gtgtcattat ttaagttgcc 7500
gaaagaacct gagtgcattt gcaacatgag tatactagaa gaatgagcca agacttgcga 7560
gacgcgagtt tgccggtggt gcgaacaata gagcgaccat gaccttgaag gtgagacgcg 7620
cataaccgct agagtacttt gaagaggaaa cagcaatagg gttgctacca gtataaatag 7680
acaggtacat acaacactgg aaatggttgt ctgtttgagt acgctttcaa ttcatttggg 7740
tgtgcacttt attatgttac aatatggaag ggaactttac acttctccta tgcacatata 7800
ttaattaaag tccaatgcta gtagagaagg ggggtaacac ccctccgcgc tcttttccga 7860
tttttttcta aaccgtggaa tatttcggat atccttttgt tgtttccggg tgtacaatat 7920
ggacttcctc ttttctggca accaaaccca tacatcggga ttcctataat accttcgttg 7980
gtctccctaa catgtaggtg gcggagggga gatatacaat agaacagata ccagacaaga 8040
cataatgggc taaacaagac tacaccaatt acactgcctc attgatg 8087

<210> SEQ ID NO 10
<211> LENGTH: 8087
<212> TYPE: DNA
<213> ORGANISM: Artificial Sequence
<220> FEATURE:
<223> OTHER INFORMATION: Synthetic

<400> SEQUENCE: 10
gtggtacata acgaactaat actgtagccc tagacttgat agccatcatc atatcgaagt 60

-continued

```
ttcactaccc tttttccatt tgccatctat tgaagtaata ataggcgcat gcaacttctt    120
ttcttttttt ttcttttctc tctcccccgt tgttgtctca ccatatccgc aatgacaaaa    180
aaatgatgga agacactaaa ggaaaaaatt aacgacaaag acagcaccaa cagatgtcgt    240
tgttccagag ctgatgaggg gtatctcgaa gcacacgaaa ctttttcctt ccttcattga    300
cctgcaatta ttaatctttt gtttcctcgt cattgttctc gttccctttc ttccttgttt    360
ctttttctgc acaatatttc aagctatacc aagcatacaa tcaactccaa gcttgaagca    420
agcctcctga aagatgaagc tactgtcttc tatcgaacaa gcatgcgata tttgccgact    480
taaaaagctc aagtgctcca aagaaaaacc gaagtgcgcc aagtgtctga agaacaactg    540
ggagtgtcgc tactctccca aaaccaaaag gtctccgctg actagggcac atctgacaga    600
agtggaatca aggctagaaa gactggaaca gctatttcta ctgatttttc ctcgagaaga    660
ccttgacatg attttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
tagtaacaaa ggtcaaagac agttgactgt atcgaactat ctattcgatg atgaagatac    900
cccaccaaac ccaaaaaaag agatcgaatt ccaggggtcc cctatactag gttattggaa    960
aggtcgacgc gaccatcctc caaaatcgga tctgatcgaa ggtcgtggag atcccgaagt   1020
taaacgggta aaattagaaa acaacgttga agaaatacaa cctgagcagg ctgagaccaa   1080
taaacaagag ggcaccgata aagagaataa aggaaagttc gagaaagaaa ctgagagaat   1140
aggaggatct gaagtggtta cagatgtgga aaaaggaatt gtcaaatttg aatttgatgg   1200
tgttgaatac acattcaaag agagacccag tgtcgtagag gaaaatgaag gtaaaattga   1260
gtttagggtg gtgaataatg ataatactaa agaaaacatg atggtcctaa ctggattaaa   1320
aaacattttt caaaagcaat taccaaaaat gcccaaagaa tacattgcca ggttagtcta   1380
tgatcgaagt catctttcca tggctgtcat taggaagcca ttgactgtcg taggtggcat   1440
aacatatcga cctttcgata agagagaatt cgcagaaatt gttttctgtg ccatcagttc   1500
gacggaacag gtacgcggtt atggtgcgca tctaatgaat cacttaaaag actatgttag   1560
aaatacctcg aacataaaat attttttgac atatgcagat aattacgcta ttggatacgc   1620
taaaaagcaa ggctttacta aagaaatcac gttggataaa agtatatgga tgggatatat   1680
taaagattat gaaggtggta cgctgatgca atgtaacatg gcaattcccg gtggcggccg   1740
catcttttac ccatacgatg ttcctgacta tgcgggctat ccctatgacg tcccggacta   1800
tgcaggatcc tatccatatg acgttccaga ttacgctgct cagtgcggcc gctctagcta   1860
gaactagtgg atcccccgat accgtcgacc tgcagagatc tatgaatcgt agatactgaa   1920
aaaccccgca agttcacttc aactgtgcat cgtgcaccat ctcaatttct ttcatttata   1980
catcgttttg ccttctttta tgtaactata ctcctctaag tttcaatctt ggccatgtaa   2040
cctctgatct atagaatttt ttaaatgact agaattaatg cccatctttt ttttggacct   2100
aaattcttca tgaaaatata ttacgagggc ttattcagaa gctttggact tcttcgccag   2160
aggtttggtc aagtctccaa tcaaggttgt cggcttgtct accttgccag aaatttacga   2220
aaagatggaa aagggtcaaa tcgttggtag atacgttgtt gacacttcta aataagcgaa   2280
tttcttatga tttatgattt ttattattaa ataagttata aaaaaaataa gtgtatacaa   2340
attttaaagt gactcttagg ttttaaaacg aaaattctta ttcttgagta actctttcct   2400
gtaggtcagg ttgctttctc aggtatagca tgaggtcgct cttattgacc acacctctac   2460
```

-continued

```
cggcatgccg agcaaatgcc tgcaaatcgc tccccatttc acccaattgt agatatgcta   2520
actccagcaa tgagttgatg aatctcggtg tgtattttat gtcctcagag gacaacacct   2580
gttgtaatcg ttcttccaca cggatcctgg cgtaatagcg aagaggcccg caccgatcgc   2640
ccttcccaac agttgcgcag cctgaatggc gaatggcgcc tgatgcggta ttttctcctt   2700
acgcatctgt gcggtatttc acaccgcata tatcgctggg ccattctcat gaagaatatc   2760
ttgaatttat tgtcatatta ctagttggtg tggaagtcca tatatcggtg atcaatatag   2820
tggttgacat gctggctagt caacattgag ccttttgatc atgcaaatat attacggtat   2880
tttacaatca aatatcaaac ttaactattg actttataac ttatttaggt ggtaacattc   2940
ttataaaaaa gaaaaaaatt actgcaaaac agtactagct tttaacttgt atcctaggtt   3000
atctatgctg tctcaccata gagaatatta cctatttcag aatgtatgtc catgattcgc   3060
cgggtaaata catataatac acaaatctgg cttaataaag tctataatat atctcataaa   3120
gaagtgctaa attggctagt gctatatatt tttaagaaaa tttcttttga ctaagtccat   3180
atcgactttg taaaagttca ctttagcata catatattac acgagccaga aattgtaact   3240
tttgcctaaa atcacaaatt gcaaaattta attgcttgca aaaggtcaca tgcttataat   3300
caactttttt aaaaatttaa aatacttttt tattttttat ttttaaacat aaatgaaata   3360
atttatttat tgtttatgat taccgaaaca taaaacctgc tcaagaaaaa gaaactgttt   3420
tgtccttgga aaaaaagcac tacctaggag cggccaaaat gccgaggctt tcatagctta   3480
aactctttac agaaaatagg cattatagat cagttcgagt tttcttattc ttccttccgg   3540
ttttatcgtc acagttttac agtaaataag tatcacctct tagagttcga tgataagctg   3600
tcaaacatga gaattaattc cacatgttaa aatagtgaag gagcatgttc ggcacacagt   3660
ggaccgaacg tggggtaagt gcactagggt ccggttaaac ggatctcgca ttgatgaggc   3720
aacgctaatt atcaacatat agattgttat ctatctgcat gaacacgaaa tctttacttg   3780
acgacttgag gctgatggtg tttatgcaaa gaaaccactg tgtttaatat gtgtcactgt   3840
ttgatattac tgtcagcgta gaagataata gtaaaagcgg ttaataagtg tatttgagat   3900
aagtgtgata aagtttttac agcgaaaaga cgataaatac aagaaaatga ttacgaggat   3960
acggagagag gtatgtacat gtgtatttat atactaagct gccggcggtt gtttgcaaga   4020
ccgagaaaag gctagcaaga atcgggtcat tgtagcgtat gcgcctgtga acattctctt   4080
caacaagttt gattccattg cggtgaaatg gtaaaagtca accccctgcg atgtatattt   4140
tcctgtacaa tcaatcaaaa agccaaatga tttagcatta tctttacatc ttgttatttt   4200
acagatttta tgtttagatc ttttatgctt gcttttcaaa aggcttgcag gcaagtgcac   4260
aaacaatact taaataaata ctactcagta ataacctatt tcttagcatt tttgacgaaa   4320
tttgctattt tgttagagtc ttttacacca tttgtctcca cacctccgct tacatcaaca   4380
ccaataacgc catttaatct aagcgcatca ccaacatttt ctggcgtcag tccaccagct   4440
aacataaaat gtaagctctc ggggctctct tgccttccaa cccagtcaga aatcgagttc   4500
caatccaaaa gttcacctgt cccacctgct tctgaatcaa acaagggaat aaacgaatga   4560
ggtttctgtg aagctgcact gagtagtatg ttgcagtctt ttggaaatac gagtctttta   4620
ataactggca aaccgaggaa ctcttggtat tcttgccacg actcatctcc atgcagttgg   4680
acgatatcaa tgccgtaatc attgaccaga gccaaaacat cctccttagg ttgattacga   4740
aacacgccaa ccaagtattt cggagtgcct gaactatttt tatatgcttt tacaagactt   4800
```

-continued

```
gaaattttcc ttgcaataac cgggtcaatt gttctctttc tattgggcac acatataata   4860
cccagcaagt cagcatcgga atctagtgca cattctgcgg cctctgtgct ctgcaagccg   4920
caaactttca ccaatggacc agaactacct gtgaaattaa taacagacat actccaagct   4980
gcctttgtgt gcttaatcac gtatactcac gtgctcaata gtcaccaatg ccctccctct   5040
tggccctctc cttttctttt ttcgaccgaa ttaattcttg aagacgaaag ggcctcgtga   5100
tacgcctatt tttataggtt aatgtcatga taataatggt ttcttagacg tcaggtggca   5160
cttttcgggg aaatgtgcgc ggaaccccta tttgtttatt tttctaaata cattcaaata   5220
tgtatccgct catgagacaa taaccctgat aaatgcttca ataatattga aaaaggaaga   5280
gtatgagtat tcaacatttc cgtgtcgccc ttattccctt ttttgcggca ttttgccttc   5340
ctgtttttgc tcacccagaa acgctggtga aagtaaaaga tgctgaagat cagttgggtg   5400
cacgagtggg ttacatcgaa ctggatctca acagcggtaa gatccttgag agttttcgcc   5460
ccgaagaacg ttttccaatg atgagcactt ttaaagttct gctatgtggc gcggtattat   5520
cccgtattga cgccgggcaa gagcaactcg gtcgccgcat acactattct cagaatgact   5580
tggttgagta ctcaccagtc acagaaaagc atcttacgga tggcatgaca gtaagagaat   5640
tatgcagtgc tgccataacc atgagtgata acactgcggc caacttactt ctgacaacga   5700
tcggaggacc gaaggagcta accgcttttt tgcacaacat gggggatcat gtaactcgcc   5760
ttgatcgttg ggaaccggag ctgaatgaag ccataccaaa cgacgagcgt gacaccacga   5820
tgcctgtagc aatggcaaca acgttgcgca aactattaac tggcgaacta cttactctag   5880
cttcccggca acaattaata gactggatgg aggcggataa agttgcagga ccacttctgc   5940
gctcggccct tccggctggc tggtttattg ctgataaatc tggagccggt gagcgtgggt   6000
ctcgcggtat cattgcagca ctggggccag atggtaagcc ctcccgtatc gtagttatct   6060
acacgacggg gagtcaggca actatggatg aacgaaatag acagatcgct gagataggtg   6120
cctcactgat taagcattgg taactgtcag accaagttta ctcatatata ctttagattg   6180
atttaaaact tcatttttaa tttaaaagga tctaggtgaa gatccttttt gataatctca   6240
tgaccaaaat cccttaacgt gagttttcgt tccactgagc gtcagacccc gtagaaaaga   6300
tcaaaggatc ttcttgagat cctttttttc tgcgcgtaat ctgctgcttg caaacaaaaa   6360
aaccaccgct accagcggtg gtttgtttgc cggatcaaga gctaccaact ctttttccga   6420
aggtaactgg cttcagcaga gcgcagatac caaatactgt ccttctagtg tagccgtagt   6480
taggccacca cttcaagaac tctgtagcac cgcctacata cctcgctctg ctaatcctgt   6540
taccagtggc tgctgccagt ggcgataagt cgtgtcttac cgggttggac tcaagacgat   6600
agttaccgga taaggcgcag cggtcgggct gaacgggggg ttcgtgcaca cagcccagct   6660
tggagcgaac gacctacacc gaactgagat acctacagcg tgagctatga gaaagcgcca   6720
cgcttcccga agggagaaag gcggacaggt atccggtaag cggcagggtc ggaacaggag   6780
agcgcacgag ggagcttcca gggggaaacg cctggtatct ttatagtcct gtcgggtttc   6840
gccacctctg acttgagcgt cgatttttgt gatgctcgtc aggggggcgg agcctatgga   6900
aaaacgccag caacgcggcc tttttacggt tcctggcctt ttgctggcct tttgctcaca   6960
tgttctttcc tgcgttatcc cctgattctg tggataaccg tattaccgcc tttgagtgag   7020
ctgataccgc tcgccgcagc cgaacgaccg agcgcagcga gtcagtgagc gaggaagcgg   7080
aagagcgccc aatacgcaaa ccgcctctcc ccgcgcgttg gccgattcat taatgcagga   7140
tccgggatcg aagaaatgat ggtaaatgaa ataggaaatc aaggagcatg aaggcaaaag   7200
```

-continued

```
acaaatataa gggtcgaacg aaaaataaag tgaaaagtgt tgatatgatg tatttggctt   7260
tgcggcgccg aaaaaacgag tttacgcaat tgcacaatca tgctgactct gtggcggacc   7320
cgcgctcttg ccggcccggc gataacgctg ggcgtgaggc tgtgcccggc ggagtttttt   7380
gcgcctgcat tttccaaggt ttaccctgcg ctaaggggcg agattggaga agcaataaga   7440
atgccggttg gggttgcgat gatgacgacc acgacaactg gtgtcattat ttaagttgcc   7500
gaaagaacct gagtgcattt gcaacatgag tatactagaa gaatgagcca agacttgcga   7560
gacgcgagtt tgccggtggt gcgaacaata gagcgaccat gaccttgaag gtgagacgcg   7620
cataaccgct agagtacttt gaagaggaaa cagcaatagg gttgctacca gtataaatag   7680
acaggtacat acaacactgg aaatggttgt ctgtttgagt acgctttcaa ttcatttggg   7740
tgtgcacttt attatgttac aatatggaag ggaactttac acttctccta tgcacatata   7800
ttaattaaag tccaatgcta gtagagaagg ggggtaacac ccctccgcgc tcttttccga   7860
tttttttcta aaccgtggaa tatttcggat atccttttgt tgtttccggg tgtacaatat   7920
ggacttcctc ttttctggca accaaaccca tacatcggga ttcctataat accttcgttg   7980
gtctccctaa catgtaggtg gcggagggga gatatacaat agaacagata ccagacaaga   8040
cataatgggc taaacaagac tacaccaatt acactgcctc attgatg                 8087
```

```
<210> SEQ ID NO 11
<211> LENGTH: 8120
<212> TYPE: DNA
<213> ORGANISM: Artificial Sequence
<220> FEATURE:
<223> OTHER INFORMATION: Synthetic

<400> SEQUENCE: 11
```

```
gtggtacata acgaactaat actgtagccc tagacttgat agccatcatc atatcgaagt     60
ttcactaccc tttttccatt tgccatctat tgaagtaata ataggcgcat gcaacttctt    120
ttcttttttt ttcttttctc tctcccccgt tgttgtctca ccatatccgc aatgacaaaa    180
aaatgatgga agacactaaa ggaaaaaatt aacgacaaag acagcaccaa cagatgtcgt    240
tgttccagag ctgatgaggg gtatctcgaa gcacacgaaa ctttttcctt ccttcattga    300
cctgcaatta ttaatctttt gtttcctcgt cattgttctc gttccctttc ttccttgttt    360
ctttttctgc acaatatttc aagctatacc aagcatacaa tcaactccaa gcttgaagca    420
agcctcctga aagatgaagc tactgtcttc tatcgaacaa gcatgcgata tttgccgact    480
taaaaagctc aagtgctcca aagaaaaacc gaagtgcgcc aagtgtctga agaacaactg    540
ggagtgtcgc tactctccca aaaccaaaag gtctccgctg actagggcac atctgacaga    600
agtggaatca aggctagaaa gactggaaca gctatttcta ctgatttttc ctcgagaaga    660
ccttgacatg attttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
tagtaacaaa ggtcaaagac agttgactgt atcgaactat ctattcgatg atgaagatac    900
cccaccaaac ccaaaaaaag agatcgaatt ccagggtacc atgcatgagc tcccgcggct    960
cgagcccggg tcccctatac taggttattg gaaaggtcga cgcgaccatc ctccaaaatc   1020
ggatctgatc gaaggtcgtg gagatcccga agttaaacgg gtaaaattag aaaacaacgt   1080
tgaagaaata caacctgagc aggctgagac caataaacaa gagggcaccg ataaagagaa   1140
```

-continued taaaggaaag ttcgagaaag aaactgagag aataggagga tctgaagtgg ttacagatgt 1200
ggaaaaagga attgtcaaat ttgaatttga tggtgttgaa tacacattca aagagagacc 1260
cagtgtcgta gaggaaaatg aaggtaaaat tgagtttagg gtggtgaata atgataatac 1320
taaagaaaac atgatggtcc taactggatt aaaaaacatt tttcaaaagc aattaccaaa 1380
aatgcccaaa gaatacattg ccaggttagt ctatgatcga agtcatcttt ccatggctgt 1440
cattaggaag ccattgactg tcgtaggtgg cataacatat cgacctttcg ataagagaga 1500
attcgcagaa attgttttct gtgccatcag ttcgacggaa caggtacgcg gttatggtgc 1560
gcatctaatg aatcacttaa aagactatgt tagaaatacc tcgaacataa aatatttttt 1620
gacatatgca gataattacg ctattggata ctttaaaaag caaggcttta ctaaagaaat 1680
cacgttggat aaaagtatat ggatgggata tattaaagat tatgaaggtg gtacgctgat 1740
gcaatgtaac atggcaattc ccggtggcgg ccgcatcttt tacccatacg atgttcctga 1800
ctatgcgggc tatccctatg acgtcccgga ctatgcagga tcctatccat atgacgttcc 1860
agattacgct gctcagtgcg gccgctctag ctagaactag tggatccccc gataccgtcg 1920
acctgcagag atctatgaat cgtagatact gaaaaacccc gcaagttcac ttcaactgtg 1980
catcgtgcac catctcaatt tctttcattt atacatcgtt ttgccttctt ttatgtaact 2040
atactcctct aagtttcaat cttggccatg taacctctga tctatagaat tttttaaatg 2100
actagaatta atgcccatct ttttttttgga cctaaattct tcatgaaaat atattacgag 2160
ggcttattca gaagctttgg acttcttcgc cagaggtttg gtcaagtctc caatcaaggt 2220
tgtcggcttg tctaccttgc cagaaattta cgaaaagatg gaaaagggtc aaatcgttgg 2280
tagatacgtt gttgacactt ctaaataagc gaatttctta tgatttatga tttttattat 2340
taaataagtt ataaaaaaaa taagtgtata caaattttaa agtgactctt aggttttaaa 2400
acgaaaattc ttattcttga gtaactcttt cctgtaggtc aggttgcttt ctcaggtata 2460
gcatgaggtc gctcttattg accacacctc taccggcatg ccgagcaaat gcctgcaaat 2520
cgctccccat ttcacccaat tgtagatatg ctaactccag caatgagttg atgaatctcg 2580
gtgtgtattt tatgtcctca gaggacaaca cctgttgtaa tcgttcttcc acacggatcc 2640
tggcgtaata gcgaagaggc ccgcaccgat cgcccttccc aacagttgcg cagcctgaat 2700
ggcgaatggc gcctgatgcg gtattttctc cttacgcatc tgtgcggtat ttcacaccgc 2760
atatatcgct gggccattct catgaagaat atcttgaatt tattgtcata ttactagttg 2820
gtgtggaagt ccatatatcg gtgatcaata tagtggttga catgctggct agtcaacatt 2880
gagccttttg atcatgcaaa tatattacgg tattttacaa tcaaatatca aacttaacta 2940
ttgactttat aacttattta ggtggtaaca ttcttataaa aaagaaaaaa attactgcaa 3000
aacagtacta gcttttaact tgtatcctag gttatctatg ctgtctcacc atagagaata 3060
ttacctattt cagaatgtat gtccatgatt cgccgggtaa atacatataa tacacaaatc 3120
tggcttaata aagtctataa tatatctcat aaagaagtgc taaattggct agtgctatat 3180
atttttaaga aaatttcttt tgactaagtc catatcgact ttgtaaaagt tcactttagc 3240
atacatatat tacacgagcc agaaattgta acttttgcct aaaatcacaa attgcaaaat 3300
ttaattgctt gcaaaaggtc acatgcttat aatcaacttt tttaaaaatt taaaatactt 3360
ttttattttt tatttttaaa cataaatgaa ataatttatt tattgtttat gattaccgaa 3420
acataaaacc tgctcaagaa aaagaaactg ttttgtcctt ggaaaaaaag cactacctag 3480
gagcggccaa aatgccgagg ctttcatagc ttaaactctt tacagaaaat aggcattata 3540

-continued

```
gatcagttcg agttttctta ttcttccttc cggttttatc gtcacagttt tacagtaaat   3600
aagtatcacc tcttagagtt cgatgataag ctgtcaaaca tgagaattaa ttccacatgt   3660
taaaatagtg aaggagcatg ttcggcacac agtggaccga acgtggggta agtgcactag   3720
ggtccggtta aacggatctc gcattgatga ggcaacgcta attatcaaca tatagattgt   3780
tatctatctg catgaacacg aaatctttac ttgacgactt gaggctgatg gtgtttatgc   3840
aaagaaacca ctgtgtttaa tatgtgtcac tgtttgatat tactgtcagc gtagaagata   3900
atagtaaaag cggttaataa gtgtatttga gataagtgtg ataaagtttt tacagcgaaa   3960
agacgataaa tacaagaaaa tgattacgag gatacggaga gaggtatgta catgtgtatt   4020
tatatactaa gctgccggcg gttgtttgca agaccgagaa aaggctagca agaatcgggt   4080
cattgtagcg tatgcgcctg tgaacattct cttcaacaag tttgattcca ttgcggtgaa   4140
atggtaaaag tcaacccccct gcgatgtata ttttcctgta caatcaatca aaaagccaaa   4200
tgatttagca ttatctttac atcttgttat tttacagatt ttatgtttag atcttttatg   4260
cttgcttttc aaaaggcttg caggcaagtg cacaaacaat acttaaataa atactactca   4320
gtaataacct atttcttagc atttttgacg aaatttgcta ttttgttaga gtcttttaca   4380
ccatttgtct ccacacctcc gcttacatca acaccaataa cgccatttaa tctaagcgca   4440
tcaccaacat tttctggcgt cagtccacca gctaacataa aatgtaagct ctcggggctc   4500
tcttgccttc caacccagtc agaaatcgag ttccaatcca aaagttcacc tgtcccacct   4560
gcttctgaat caaacaaggg aataaacgaa tgaggtttct gtgaagctgc actgagtagt   4620
atgttgcagt cttttggaaa tacgagtctt ttaataactg gcaaaccgag gaactcttgg   4680
tattcttgcc acgactcatc tccatgcagt tggacgatat caatgccgta atcattgacc   4740
agagccaaaa catcctcctt aggttgatta cgaaacacgc caaccaagta tttcggagtg   4800
cctgaactat ttttatatgc ttttacaaga cttgaaattt tccttgcaat aaccgggtca   4860
attgttctct ttctattggg cacacatata atacccagca agtcagcatc ggaatctagt   4920
gcacattctg cggcctctgt gctctgcaag ccgcaaactt tcaccaatgg accagaacta   4980
cctgtgaaat taataacaga catactccaa gctgcctttg tgtgcttaat cacgtatact   5040
cacgtgctca atagtcacca atgccctccc tcttggccct ctccttttct tttttcgacc   5100
gaattaattc ttgaagacga aagggcctcg tgatacgcct atttttatag gttaatgtca   5160
tgataataat ggtttcttag acgtcaggtg gcacttttcg gggaaatgtg cgcggaaccc   5220
ctatttgttt atttttctaa atacattcaa atatgtatcc gctcatgaga caataaccct   5280
gataaatgct tcaataatat tgaaaaagga agagtatgag tattcaacat ttccgtgtcg   5340
cccttattcc cttttttgcg gcattttgcc ttcctgtttt tgctcaccca gaaacgctgg   5400
tgaaagtaaa agatgctgaa gatcagttgg gtgcacgagt gggttacatc gaactggatc   5460
tcaacagcgg taagatcctt gagagttttc gccccgaaga acgttttcca atgatgagca   5520
cttttaaagt tctgctatgt ggcgcggtat tatcccgtat tgacgccggg caagagcaac   5580
tcggtcgccg catacactat tctcagaatg acttggttga gtactcacca gtcacagaaa   5640
agcatcttac ggatggcatg acagtaagag aattatgcag tgctgccata accatgagtg   5700
ataacactgc ggccaactta cttctgacaa cgatcggagg accgaaggag ctaaccgctt   5760
ttttgcacaa catgggggat catgtaactc gccttgatcg ttgggaaccg gagctgaatg   5820
aagccatacc aaacgacgag cgtgacacca cgatgcctgt agcaatggca acaacgttgc   5880
```

-continued

```
gcaaactatt aactggcgaa ctacttactc tagcttcccg gcaacaatta atagactgga   5940
tggaggcgga taaagttgca ggaccacttc tgcgctcggc ccttccggct ggctggttta   6000
ttgctgataa atctggagcc ggtgagcgtg ggtctcgcgg tatcattgca gcactggggc   6060
cagatggtaa gccctcccgt atcgtagtta tctacacgac ggggagtcag gcaactatgg   6120
atgaacgaaa tagacagatc gctgagatag gtgcctcact gattaagcat tggtaactgt   6180
cagaccaagt ttactcatat atactttaga ttgatttaaa acttcatttt taatttaaaa   6240
ggatctaggt gaagatcctt tttgataatc tcatgaccaa aatcccttaa cgtgagtttt   6300
cgttccactg agcgtcagac cccgtagaaa agatcaaagg atcttcttga gatccttttt   6360
ttctgcgcgt aatctgctgc ttgcaaacaa aaaaaccacc gctaccagcg gtggtttgtt   6420
tgccggatca agagctacca actctttttc cgaaggtaac tggcttcagc agagcgcaga   6480
taccaaatac tgtccttcta gtgtagccgt agttaggcca ccacttcaag aactctgtag   6540
caccgcctac atacctcgct ctgctaatcc tgttaccagt ggctgctgcc agtggcgata   6600
agtcgtgtct taccgggttg gactcaagac gatagttacc ggataaggcg cagcggtcgg   6660
gctgaacggg gggttcgtgc acacagccca gcttggagcg aacgacctac accgaactga   6720
gatacctaca gcgtgagcta tgagaaagcg ccacgcttcc cgaagggaga aaggcggaca   6780
ggtatccggt aagcggcagg gtcggaacag gagagcgcac gagggagctt ccagggggaa   6840
acgcctggta tctttatagt cctgtcgggt ttcgccacct ctgacttgag cgtcgatttt   6900
tgtgatgctc gtcagggggg cggagcctat ggaaaaacgc cagcaacgcg gcctttttac   6960
ggttcctggc cttttgctgg ccttttgctc acatgttctt tcctgcgtta tcccctgatt   7020
ctgtggataa ccgtattacc gcctttgagt gagctgatac cgctcgccgc agccgaacga   7080
ccgagcgcag cgagtcagtg agcgaggaag cggaagagcg cccaatacgc aaaccgcctc   7140
tccccgcgcg ttggccgatt cattaatgca ggatccggga tcgaagaaat gatggtaaat   7200
gaaataggaa atcaaggagc atgaaggcaa aagacaaata taagggtcga acgaaaaata   7260
aagtgaaaag tgttgatatg atgtatttgg ctttgcggcg ccgaaaaaac gagtttacgc   7320
aattgcacaa tcatgctgac tctgtggcgg acccgcgctc ttgccggccc ggcgataacg   7380
ctgggcgtga ggctgtgccc ggcggagttt tttgcgcctg cattttccaa ggtttaccct   7440
gcgctaaggg gcgagattgg agaagcaata agaatgccgg ttggggttgc gatgatgacg   7500
accacgacaa ctggtgtcat tatttaagtt gccgaaagaa cctgagtgca tttgcaacat   7560
gagtatacta gaagaatgag ccaagacttg cgagacgcga gtttgccggt ggtgcgaaca   7620
atagagcgac catgaccttg aaggtgagac gcgcataacc gctagagtac tttgaagagg   7680
aaacagcaat agggttgcta ccagtataaa tagacaggta catacaacac tggaaatggt   7740
tgtctgtttg agtacgcttt caattcattt gggtgtgcac tttattatgt tacaatatgg   7800
aagggaactt tacacttctc ctatgcacat atattaatta aagtccaatg ctagtagaga   7860
aggggggtaa cacccctccg cgctcttttc cgattttttt ctaaaccgtg gaatatttcg   7920
gatatccttt tgttgtttcc gggtgtacaa tatggacttc ctcttttctg gcaaccaaac   7980
ccatacatcg ggattcctat aataccttcg ttggtctccc taacatgtag gtggcggagg   8040
ggagatatac aatagaacag ataccagaca agacataatg ggctaaacaa gactacacca   8100
attacactgc ctcattgatg                                               8120
```

<210> SEQ ID NO 12
<211> LENGTH: 8120

-continued

<212> TYPE: DNA
<213> ORGANISM: Artificial Sequence
<220> FEATURE:
<223> OTHER INFORMATION: Synthetic

<400> SEQUENCE: 12
gtggtacata acgaactaat actgtagccc tagacttgat agccatcatc atatcgaagt 60
ttcactaccc tttttccatt tgccatctat tgaagtaata ataggcgcat gcaacttctt 120
ttcttttttt ttcttttctc tctcccccgt tgttgtctca ccatatccgc aatgacaaaa 180
aaatgatgga agacactaaa ggaaaaaatt aacgacaaag acagcaccaa cagatgtcgt 240
tgttccagag ctgatgaggg gtatctcgaa gcacacgaaa ctttttcctt ccttcattga 300
cctgcaatta ttaatctttt gtttcctcgt cattgttctc gttccctttc ttccttgttt 360
ctttttctgc acaatatttc aagctatacc aagcatacaa tcaactccaa gcttgaagca 420
agcctcctga aagatgaagc tactgtcttc tatcgaacaa gcatgcgata tttgccgact 480
taaaaagctc aagtgctcca aagaaaaacc gaagtgcgcc aagtgtctga agaacaactg 540
ggagtgtcgc tactctccca aaaccaaaag gtctccgctg actagggcac atctgacaga 600
agtggaatca aggctagaaa gactggaaca gctatttcta ctgatttttc ctcgagaaga 660
ccttgacatg attttgaaaa tggattcttt acaggatata aaagcattgt taacaggatt 720
atttgtacaa gataatgtga ataaagatgc cgtcacagat agattggctt cagtggagac 780
tgatatgcct ctaacattga gacagcatag aataagtgcg acatcatcat cggaagagag 840
tagtaacaaa ggtcaaagac agttgactgt atcgaactat ctattcgatg atgaagatac 900
cccaccaaac ccaaaaaaag agatcgaatt ccagggtacc atgcatgagc tcccgcggct 960
cgagcccggg tcccctatac taggttattg gaaaggtcga cgcgaccatc ctccaaaatc 1020
ggatctgatc gaaggtcgtg gagatcccga agttaaacgg gtaaaattag aaaacaacgt 1080
tgaagaaata caacctgagc aggctgagac caataaacaa gagggcaccg ataaagagaa 1140
taaaggaaag ttcgagaaag aaactgagag aataggagga tctgaagtgg ttacagatgt 1200
ggaaaaagga attgtcaaat ttgaatttga tggtgttgaa tacacattca aagagagacc 1260
cagtgtcgta gaggaaaatg aaggtaaaat tgagtttagg gtggtgaata atgataatac 1320
taaagaaaac atgatggtcc taactggatt aaaaaacatt tttcaaaagc aattaccaaa 1380
aatgcccaaa gaatacattg ccaggttagt ctatgatcga agtcatcttt ccatggctgt 1440
cattaggaag ccattgactg tcgtaggtgg cataacatat cgacctttcg ataagagaga 1500
attcgcagaa attgttttct gtgccatcag ttcgacggaa caggtacgcg gttatggtgc 1560
gcatctaatg aatcacttaa aagactatgt tagaaatacc tcgaacataa aatatttttt 1620
gacatatgca gataattacg ctattggata cgctaaaaag caaggcttta ctaaagaaat 1680
cacgttggat aaaagtatat ggatgggata tattaaagat tatgaaggtg gtacgctgat 1740
gcaatgtaac atggcaattc ccggtggcgg ccgcatcttt tacccatacg atgttcctga 1800
ctatgcgggc tatccctatg acgtcccgga ctatgcagga tcctatccat atgacgttcc 1860
agattacgct gctcagtgcg gccgctctag ctagaactag tggatccccc gataccgtcg 1920
acctgcagag atctatgaat cgtagatact gaaaaacccc gcaagttcac ttcaactgtg 1980
catcgtgcac catctcaatt tctttcattt atacatcgtt ttgccttctt ttatgtaact 2040
atactcctct aagtttcaat cttggccatg taacctctga tctatagaat tttttaaatg 2100
actagaatta atgcccatct ttttttgga cctaaattct tcatgaaaat atattacgag 2160

-continued

```
ggcttattca gaagctttgg acttcttcgc cagaggtttg gtcaagtctc caatcaaggt   2220
tgtcggcttg tctaccttgc cagaaattta cgaaaagatg gaaaagggtc aaatcgttgg   2280
tagatacgtt gttgacactt ctaaataagc gaatttctta tgatttatga tttttattat   2340
taaataagtt ataaaaaaaa taagtgtata caaattttaa agtgactctt aggttttaaa   2400
acgaaaattc ttattcttga gtaactcttt cctgtaggtc aggttgcttt ctcaggtata   2460
gcatgaggtc gctcttattg accacacctc taccggcatg ccgagcaaat gcctgcaaat   2520
cgctccccat ttcacccaat tgtagatatg ctaactccag caatgagttg atgaatctcg   2580
gtgtgtattt tatgtcctca gaggacaaca cctgttgtaa tcgttcttcc acacggatcc   2640
tggcgtaata gcgaagaggc ccgcaccgat cgcccttccc aacagttgcg cagcctgaat   2700
ggcgaatggc gcctgatgcg gtattttctc cttacgcatc tgtgcggtat ttcacaccgc   2760
atatatcgct gggccattct catgaagaat atcttgaatt tattgtcata ttactagttg   2820
gtgtggaagt ccatatatcg gtgatcaata tagtggttga catgctggct agtcaacatt   2880
gagccttttg atcatgcaaa tatattacgg tattttacaa tcaaatatca aacttaacta   2940
ttgactttat aacttattta ggtggtaaca ttcttataaa aaagaaaaaa attactgcaa   3000
aacagtacta gcttttaact tgtatcctag gttatctatg ctgtctcacc atagagaata   3060
ttacctattt cagaatgtat gtccatgatt cgccgggtaa atacatataa tacacaaatc   3120
tggcttaata aagtctataa tatatctcat aaagaagtgc taaattggct agtgctatat   3180
atttttaaga aaatttcttt tgactaagtc catatcgact ttgtaaaagt tcactttagc   3240
atacatatat tacacgagcc agaaattgta acttttgcct aaaatcacaa attgcaaaat   3300
ttaattgctt gcaaaaggtc acatgcttat aatcaacttt tttaaaaatt taaaatactt   3360
ttttattttt tatttttaaa cataaatgaa ataatttatt tattgtttat gattaccgaa   3420
acataaaacc tgctcaagaa aaagaaactg ttttgtcctt ggaaaaaaag cactacctag   3480
gagcggccaa aatgccgagg ctttcatagc ttaaactctt tacagaaaat aggcattata   3540
gatcagttcg agttttctta ttcttccttc cggttttatc gtcacagttt tacagtaaat   3600
aagtatcacc tcttagagtt cgatgataag ctgtcaaaca tgagaattaa ttccacatgt   3660
taaaatagtg aaggagcatg ttcggcacac agtggaccga acgtggggta agtgcactag   3720
ggtccggtta aacggatctc gcattgatga ggcaacgcta attatcaaca tatagattgt   3780
tatctatctg catgaacacg aaatctttac ttgacgactt gaggctgatg gtgtttatgc   3840
aaagaaacca ctgtgtttaa tatgtgtcac tgtttgatat tactgtcagc gtagaagata   3900
atagtaaaag cggttaataa gtgtatttga gataagtgtg ataaagtttt tacagcgaaa   3960
agacgataaa tacaagaaaa tgattacgag gatacggaga gaggtatgta catgtgtatt   4020
tatatactaa gctgccggcg gttgtttgca agaccgagaa aaggctagca agaatcgggt   4080
cattgtagcg tatgcgcctg tgaacattct cttcaacaag tttgattcca ttgcggtgaa   4140
atggtaaaag tcaacccccct gcgatgtata ttttcctgta caatcaatca aaaagccaaa   4200
tgatttagca ttatctttac atcttgttat tttacagatt ttatgtttag atcttttatg   4260
cttgcttttc aaaaggcttg caggcaagtg cacaaacaat acttaaataa atactactca   4320
gtaataacct atttcttagc atttttgacg aaatttgcta ttttgttaga gtcttttaca   4380
ccatttgtct ccacacctcc gcttacatca acaccaataa cgccatttaa tctaagcgca   4440
tcaccaacat tttctggcgt cagtccacca gctaacataa aatgtaagct ctcggggctc   4500
tcttgccttc caacccagtc agaaatcgag ttccaatcca aaagttcacc tgtcccacct   4560
```

-continued gcttctgaat caaacaaggg aataaacgaa tgaggtttct gtgaagctgc actgagtagt 4620
atgttgcagt cttttggaaa tacgagtctt ttaataactg gcaaaccgag gaactcttgg 4680
tattcttgcc acgactcatc tccatgcagt tggacgatat caatgccgta atcattgacc 4740
agagccaaaa catcctcctt aggttgatta cgaaacacgc caaccaagta tttcggagtg 4800
cctgaactat ttttatatgc ttttacaaga cttgaaattt tccttgcaat aaccgggtca 4860
attgttctct ttctattggg cacacatata atacccagca agtcagcatc ggaatctagt 4920
gcacattctg cggcctctgt gctctgcaag ccgcaaactt tcaccaatgg accagaacta 4980
cctgtgaaat taataacaga catactccaa gctgcctttg tgtgcttaat cacgtatact 5040
cacgtgctca atagtcacca atgccctccc tcttggccct ctccttttct tttttcgacc 5100
gaattaattc ttgaagacga aagggcctcg tgatacgcct atttttatag gttaatgtca 5160
tgataataat ggtttcttag acgtcaggtg gcacttttcg gggaaatgtg cgcggaaccc 5220
ctatttgttt atttttctaa atacattcaa atatgtatcc gctcatgaga caataaccct 5280
gataaatgct tcaataatat tgaaaaagga agagtatgag tattcaacat ttccgtgtcg 5340
cccttattcc cttttttgcg gcattttgcc ttcctgtttt tgctcaccca gaaacgctgg 5400
tgaaagtaaa agatgctgaa gatcagttgg gtgcacgagt gggttacatc gaactggatc 5460
tcaacagcgg taagatcctt gagagttttc gccccgaaga acgttttcca atgatgagca 5520
cttttaaagt tctgctatgt ggcgcggtat tatcccgtat tgacgccggg caagagcaac 5580
tcggtcgccg catacactat tctcagaatg acttggttga gtactcacca gtcacagaaa 5640
agcatcttac ggatggcatg acagtaagag aattatgcag tgctgccata accatgagtg 5700
ataacactgc ggccaactta cttctgacaa cgatcggagg accgaaggag ctaaccgctt 5760
ttttgcacaa catgggggat catgtaactc gccttgatcg ttgggaaccg gagctgaatg 5820
aagccatacc aaacgacgag cgtgacacca cgatgcctgt agcaatggca acaacgttgc 5880
gcaaactatt aactggcgaa ctacttactc tagcttcccg gcaacaatta atagactgga 5940
tggaggcgga taaagttgca ggaccacttc tgcgctcggc ccttccggct ggctggttta 6000
ttgctgataa atctggagcc ggtgagcgtg ggtctcgcgg tatcattgca gcactggggc 6060
cagatggtaa gccctcccgt atcgtagtta tctacacgac ggggagtcag gcaactatgg 6120
atgaacgaaa tagacagatc gctgagatag gtgcctcact gattaagcat tggtaactgt 6180
cagaccaagt ttactcatat atactttaga ttgatttaaa acttcatttt taatttaaaa 6240
ggatctaggt gaagatcctt tttgataatc tcatgaccaa aatcccttaa cgtgagtttt 6300
cgttccactg agcgtcagac cccgtagaaa agatcaaagg atcttcttga gatccttttt 6360
ttctgcgcgt aatctgctgc ttgcaaacaa aaaaaccacc gctaccagcg gtggtttgtt 6420
tgccggatca agagctacca actctttttc cgaaggtaac tggcttcagc agagcgcaga 6480
taccaaatac tgtccttcta gtgtagccgt agttaggcca ccacttcaag aactctgtag 6540
caccgcctac atacctcgct ctgctaatcc tgttaccagt ggctgctgcc agtggcgata 6600
agtcgtgtct taccgggttg gactcaagac gatagttacc ggataaggcg cagcggtcgg 6660
gctgaacggg gggttcgtgc acacagccca gcttggagcg aacgacctac accgaactga 6720
gatacctaca gcgtgagcta tgagaaagcg ccacgcttcc cgaagggaga aaggcggaca 6780
ggtatccggt aagcggcagg gtcggaacag gagagcgcac gagggagctt ccagggggaa 6840
acgcctggta tctttatagt cctgtcgggt ttcgccacct ctgacttgag cgtcgatttt 6900

-continued

```
tgtgatgctc gtcagggggg cggagcctat ggaaaaacgc cagcaacgcg gcctttttac   6960
ggttcctggc cttttgctgg ccttttgctc acatgttctt tcctgcgtta tcccctgatt   7020
ctgtggataa ccgtattacc gcctttgagt gagctgatac cgctcgccgc agccgaacga   7080
ccgagcgcag cgagtcagtg agcgaggaag cggaagagcg cccaatacgc aaaccgcctc   7140
tccccgcgcg ttggccgatt cattaatgca ggatccggga tcgaagaaat gatggtaaat   7200
gaaataggaa atcaaggagc atgaaggcaa aagacaaata taagggtcga acgaaaaata   7260
aagtgaaaag tgttgatatg atgtatttgg ctttgcggcg ccgaaaaaac gagtttacgc   7320
aattgcacaa tcatgctgac tctgtggcgg acccgcgctc ttgccggccc ggcgataacg   7380
ctgggcgtga ggctgtgccc ggcggagttt tttgcgcctg cattttccaa ggtttaccct   7440
gcgctaaggg gcgagattgg agaagcaata agaatgccgg ttggggttgc gatgatgacg   7500
accacgacaa ctggtgtcat tatttaagtt gccgaaagaa cctgagtgca tttgcaacat   7560
gagtatacta gaagaatgag ccaagacttg cgagacgcga gtttgccggt ggtgcgaaca   7620
atagagcgac catgaccttg aaggtgagac gcgcataacc gctagagtac tttgaagagg   7680
aaacagcaat agggttgcta ccagtataaa tagacaggta catacaacac tggaaatggt   7740
tgtctgtttg agtacgcttt caattcattt gggtgtgcac tttattatgt tacaatatgg   7800
aagggaactt tacacttctc ctatgcacat atattaatta aagtccaatg ctagtagaga   7860
agggggtaa cacccctccg cgctcttttc cgattttttt ctaaaccgtg gaatatttcg   7920
gatatccttt tgttgtttcc gggtgtacaa tatggacttc ctcttttctg gcaaccaaac   7980
ccatacatcg ggattcctat aataccttcg ttggtctccc taacatgtag gtggcggagg   8040
ggagatatac aatagaacag ataccagaca agacataatg ggctaaacaa gactacacca   8100
attacactgc ctcattgatg                                                8120
```

<210> SEQ ID NO 13
<211> LENGTH: 8372
<212> TYPE: DNA
<213> ORGANISM: Artificial Sequence
<220> FEATURE:
<223> OTHER INFORMATION: Synthetic

<400> SEQUENCE: 13

```
gtggtacata acgaactaat actgtagccc tagacttgat agccatcatc atatcgaagt     60
ttcactaccc tttttccatt tgccatctat tgaagtaata ataggcgcat gcaacttctt    120
ttcttttttt ttcttttctc tctcccccgt tgttgtctca ccatatccgc aatgacaaaa    180
aaatgatgga agacactaaa ggaaaaaatt aacgacaaag acagcaccaa cagatgtcgt    240
tgttccagag ctgatgaggg gtatctcgaa gcacacgaaa ctttttcctt ccttcattga    300
cctgcaatta ttaatctttt gtttcctcgt cattgttctc gttccctttc ttccttgttt    360
ctttttctgc acaatatttc aagctatacc aagcatacaa tcaactccaa gcttgaagca    420
agcctcctga aagatgaagc tactgtcttc tatcgaacaa gcatgcgata tttgccgact    480
taaaaagctc aagtgctcca aagaaaaacc gaagtgcgcc aagtgtctga agaacaactg    540
ggagtgtcgc tactctccca aaaccaaaag gtctccgctg actagggcac atctgacaga    600
agtggaatca aggctagaaa gactggaaca gctatttcta ctgatttttc ctcgagaaga    660
ccttgacatg attttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
```

-continued

```
tagtaacaaa ggtcaaagac agttgactgt atcgaactat ctattcgatg atgaagatac    900
cccaccaaac ccaaaaaaag agatcgaatt ccagctgcca gggagcacta agcgagcact    960
gcccaacaac accagctcct ctccccagcc aaagaagaaa ccactggatg gagaatattt   1020
caccccttcag atccgtgggc gtgagcgctt cgagatgttc cgagagctga atgaggcctt   1080
ggaactcaag gatgcccagg ctgggaagga gccagggggg agcagggctc actccagcca   1140
cctgaagtcc aaaaagggtc agtctacctc ccgccataaa aaactcatgt tcaagacaga   1200
agggcctgac tcagaccccg ggtcccctat actaggttat tggaaaggtc gacgcgacca   1260
tcctccaaaa tcggatctga tcgaaggtcg tggagatccc gaagttaaac gggtaaaatt   1320
agaaaacaac gttgaagaaa tacaacctga gcaggctgag accaataaac aagagggcac   1380
cgataaagag aataaaggaa agttcgagaa agaaactgag agaataggag gatctgaagt   1440
ggttacagat gtggaaaaag gaattgtcaa atttgaattt gatggtgttg aatacacatt   1500
caaagagaga cccagtgtcg tagaggaaaa tgaaggtaaa attgagttta gggtggtgaa   1560
taatgataat actaaagaaa acatgatggt cctaactgga ttaaaaaaca tttttcaaaa   1620
gcaattacca aaaatgccca aagaatacat tgccaggtta gtctatgatc gaagtcatct   1680
ttccatggct gtcattagga agccattgac tgtcgtaggt ggcataacat atcgaccttt   1740
cgataagaga gaattcgcag aaattgtttt ctgtgccatc agttcgacgg aacaggtacg   1800
cggttatggt gcgcatctaa tgaatcactt aaaagactat gttagaaata cctcgaacat   1860
aaaatatttt ttgacatatg cagataatta cgctattgga tactttaaaa agcaaggctt   1920
tactaaagaa atcacgttgg ataaaagtat atggatggga tatattaaag attatgaagg   1980
tggtacgctg atgcaatgta acatggcaat tcccggtggc ggccgcatct tttacccata   2040
cgatgttcct gactatgcgg gctatcccta tgacgtcccg gactatgcag gatcctatcc   2100
atatgacgtt ccagattacg ctgctcagtg cggccgctct agctagaact agtggatccc   2160
ccgataccgt cgacctgcag agatctatga atcgtagata ctgaaaaacc ccgcaagttc   2220
acttcaactg tgcatcgtgc accatctcaa tttctttcat ttatacatcg ttttgccttc   2280
ttttatgtaa ctatactcct ctaagtttca atcttggcca tgtaacctct gatctataga   2340
atttttttaaa tgactagaat taatgcccat cttttttttg gacctaaatt cttcatgaaa   2400
atatattacg agggcttatt cagaagcttt ggacttcttc gccagaggtt tggtcaagtc   2460
tccaatcaag gttgtcggct tgtctacctt gccagaaatt tacgaaaaga tggaaaaggg   2520
tcaaatcgtt ggtagatacg ttgttgacac ttctaaataa gcgaatttct tatgatttat   2580
gatttttatt attaaataag ttataaaaaa aataagtgta tacaaatttt aaagtgactc   2640
ttaggtttta aaacgaaaat tcttattctt gagtaactct ttcctgtagg tcaggttgct   2700
ttctcaggta tagcatgagg tcgctcttat tgaccacacc tctaccggca tgccgagcaa   2760
atgcctgcaa atcgctcccc atttcaccca attgtagata tgctaactcc agcaatgagt   2820
tgatgaatct cggtgtgtat tttatgtcct cagaggacaa cacctgttgt aatcgttctt   2880
ccacacggat cctggcgtaa tagcgaagag gcccgcaccg atcgcccttc ccaacagttg   2940
cgcagcctga atggcgaatg gcgcctgatg cggtattttc tccttacgca tctgtgcggt   3000
atttcacacc gcatatatcg ctgggccatt ctcatgaaga atatcttgaa tttattgtca   3060
tattactagt tggtgtggaa gtccatatat cggtgatcaa tatagtggtt gacatgctgg   3120
ctagtcaaca ttgagccttt tgatcatgca aatatattac ggtattttac aatcaaatat   3180
```

-continued caaacttaac tattgacttt ataacttatt taggtggtaa cattcttata aaaaagaaaa 3240
aaattactgc aaaacagtac tagcttttaa cttgtatcct aggttatcta tgctgtctca 3300
ccatagagaa tattacctat ttcagaatgt atgtccatga ttcgccgggt aaatacatat 3360
aatacacaaa tctggcttaa taaagtctat aatatatctc ataaagaagt gctaaattgg 3420
ctagtgctat atatttttaa gaaaatttct tttgactaag tccatatcga ctttgtaaaa 3480
gttcacttta gcatacatat attacacgag ccagaaattg taacttttgc ctaaaatcac 3540
aaattgcaaa atttaattgc ttgcaaaagg tcacatgctt ataatcaact tttttaaaaa 3600
tttaaaatac tttttttattt tttattttta aacataaatg aaataattta tttattgttt 3660
atgattaccg aaacataaaa cctgctcaag aaaaagaaac tgttttgtcc ttggaaaaaa 3720
agcactacct aggagcggcc aaaatgccga ggctttcata gcttaaactc tttacagaaa 3780
ataggcatta tagatcagtt cgagttttct tattcttcct tccggtttta tcgtcacagt 3840
tttacagtaa ataagtatca cctcttagag ttcgatgata agctgtcaaa catgagaatt 3900
aattccacat gttaaaatag tgaaggagca tgttcggcac acagtggacc gaacgtgggg 3960
taagtgcact agggtccggt taaacggatc tcgcattgat gaggcaacgc taattatcaa 4020
catatagatt gttatctatc tgcatgaaca cgaaatcttt acttgacgac ttgaggctga 4080
tggtgtttat gcaaagaaac cactgtgttt aatatgtgtc actgtttgat attactgtca 4140
gcgtagaaga taatagtaaa agcggttaat aagtgtattt gagataagtg tgataaagtt 4200
tttacagcga aaagacgata aatacaagaa aatgattacg aggatacgga gagaggtatg 4260
tacatgtgta tttatatact aagctgccgg cggttgtttg caagaccgag aaaaggctag 4320
caagaatcgg gtcattgtag cgtatgcgcc tgtgaacatt ctcttcaaca agtttgattc 4380
cattgcggtg aaatggtaaa agtcaacccc ctgcgatgta tattttcctg tacaatcaat 4440
caaaaagcca aatgatttag cattatcttt acatcttgtt attttacaga ttttatgttt 4500
agatctttta tgcttgcttt tcaaaaggct tgcaggcaag tgcacaaaca atacttaaat 4560
aaatactact cagtaataac ctatttctta gcatttttga cgaaatttgc tattttgtta 4620
gagtctttta caccatttgt ctccacacct ccgcttacat caacaccaat aacgccattt 4680
aatctaagcg catcaccaac attttctggc gtcagtccac cagctaacat aaaatgtaag 4740
ctctcggggc tctcttgcct tccaacccag tcagaaatcg agttccaatc caaaagttca 4800
cctgtcccac ctgcttctga atcaaacaag ggaataaacg aatgaggttt ctgtgaagct 4860
gcactgagta gtatgttgca gtcttttgga aatacgagtc ttttaataac tggcaaaccg 4920
aggaactctt ggtattcttg ccacgactca tctccatgca gttggacgat atcaatgccg 4980
taatcattga ccagagccaa aacatcctcc ttaggttgat tacgaaacac gccaaccaag 5040
tatttcggag tgcctgaact atttttatat gcttttacaa gacttgaaat tttccttgca 5100
ataaccgggt caattgttct ctttctattg ggcacacata taatacccag caagtcagca 5160
tcggaatcta gtgcacattc tgcggcctct gtgctctgca agccgcaaac tttcaccaat 5220
ggaccagaac tacctgtgaa attaataaca gacatactcc aagctgcctt tgtgtgctta 5280
atcacgtata ctcacgtgct caatagtcac caatgccctc cctcttggcc ctctcctttt 5340
ctttttttcga ccgaattaat tcttgaagac gaaagggcct cgtgatacgc ctatttttat 5400
aggttaatgt catgataata atggtttctt agacgtcagg tggcactttt cggggaaatg 5460
tgcgcggaac ccctatttgt ttatttttct aaatacattc aaatatgtat ccgctcatga 5520
gacaataacc ctgataaatg cttcaataat attgaaaaag gaagagtatg agtattcaac 5580

-continued

```
atttccgtgt cgcccttatt cccttttttg cggcattttg ccttcctgtt tttgctcacc   5640
cagaaacgct ggtgaaagta aaagatgctg aagatcagtt gggtgcacga gtgggttaca   5700
tcgaactgga tctcaacagc ggtaagatcc ttgagagttt tcgccccgaa gaacgttttc   5760
caatgatgag cacttttaaa gttctgctat gtggcgcggt attatcccgt attgacgccg   5820
ggcaagagca actcggtcgc cgcatacact attctcagaa tgacttggtt gagtactcac   5880
cagtcacaga aaagcatctt acggatggca tgacagtaag agaattatgc agtgctgcca   5940
taaccatgag tgataacact gcggccaact tacttctgac aacgatcgga ggaccgaagg   6000
agctaaccgc ttttttgcac aacatggggg atcatgtaac tcgccttgat cgttgggaac   6060
cggagctgaa tgaagccata ccaaacgacg agcgtgacac cacgatgcct gtagcaatgg   6120
caacaacgtt gcgcaaacta ttaactggcg aactacttac tctagcttcc cggcaacaat   6180
taatagactg gatggaggcg gataaagttg caggaccact tctgcgctcg gcccttccgg   6240
ctggctggtt tattgctgat aaatctggag ccggtgagcg tgggtctcgc ggtatcattg   6300
cagcactggg gccagatggt aagccctccc gtatcgtagt tatctacacg acggggagtc   6360
aggcaactat ggatgaacga aatagacaga tcgctgagat aggtgcctca ctgattaagc   6420
attggtaact gtcagaccaa gtttactcat atatacttta gattgattta aaacttcatt   6480
tttaatttaa aaggatctag gtgaagatcc tttttgataa tctcatgacc aaaatccctt   6540
aacgtgagtt ttcgttccac tgagcgtcag accccgtaga aaagatcaaa ggatcttctt   6600
gagatccttt ttttctgcgc gtaatctgct gcttgcaaac aaaaaaacca ccgctaccag   6660
cggtggtttg tttgccggat caagagctac caactctttt tccgaaggta actggcttca   6720
gcagagcgca gataccaaat actgtccttc tagtgtagcc gtagttaggc caccacttca   6780
agaactctgt agcaccgcct acatacctcg ctctgctaat cctgttacca gtggctgctg   6840
ccagtggcga taagtcgtgt cttaccgggt tggactcaag acgatagtta ccggataagg   6900
cgcagcggtc gggctgaacg gggggttcgt gcacacagcc cagcttggag cgaacgacct   6960
acaccgaact gagataccta cagcgtgagc tatgagaaag cgccacgctt cccgaaggga   7020
gaaaggcgga caggtatccg gtaagcggca gggtcggaac aggagagcgc acgagggagc   7080
ttccaggggg aaacgcctgg tatctttata gtcctgtcgg gtttcgccac ctctgacttg   7140
agcgtcgatt tttgtgatgc tcgtcagggg ggcggagcct atggaaaaac gccagcaacg   7200
cggccttttt acggttcctg gccttttgct ggccttttgc tcacatgttc tttcctgcgt   7260
tatcccctga ttctgtggat aaccgtatta ccgcctttga gtgagctgat accgctcgcc   7320
gcagccgaac gaccgagcgc agcgagtcag tgagcgagga agcggaagag cgcccaatac   7380
gcaaaccgcc tctccccgcg cgttggccga ttcattaatg caggatccgg gatcgaagaa   7440
atgatggtaa atgaaatagg aaatcaagga gcatgaaggc aaaagacaaa tataagggtc   7500
gaacgaaaaa taaagtgaaa agtgttgata tgatgtattt ggctttgcgg cgccgaaaaa   7560
acgagtttac gcaattgcac aatcatgctg actctgtggc ggacccgcgc tcttgccggc   7620
ccggcgataa cgctgggcgt gaggctgtgc ccggcggagt tttttgcgcc tgcattttcc   7680
aaggtttacc ctgcgctaag ggcgagattg ggagaagcaa taagaatgcc ggttggggtt   7740
gcgatgatga cgaccacgac aactggtgtc attatttaag ttgccgaaag aacctgagtg   7800
catttgcaac atgagtatac tagaagaatg agccaagact tgcgagacgc gagtttgccg   7860
gtggtgcgaa caatagagcg accatgacct tgaaggtgag acgcgcataa ccgctagagt   7920
```

-continued

```
actttgaaga ggaaacagca atagggttgc taccagtata aatagacagg tacatacaac   7980

actggaaatg gttgtctgtt tgagtacgct ttcaattcat ttgggtgtgc actttattat   8040

gttacaatat ggaagggaac tttacacttc tcctatgcac atatattaat taaagtccaa   8100

tgctagtaga gaagggggt aacacccctc cgcgctcttt tccgattttt ttctaaaccg   8160

tggaatattt cggatatcct tttgttgttt ccgggtgtac aatatggact tcctcttttc   8220

tggcaaccaa acccatacat cgggattcct ataatacctt cgttggtctc cctaacatgt   8280

aggtggcgga ggggagatat acaatagaac agataccaga caagacataa tgggctaaac   8340

aagactacac caattacact gcctcattga tg                                 8372
```

<210> SEQ ID NO 14
<211> LENGTH: 8372
<212> TYPE: DNA
<213> ORGANISM: Artificial Sequence
<220> FEATURE:
<223> OTHER INFORMATION: Synthetic

<400> SEQUENCE: 14

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840

tagtaacaaa ggtcaaagac agttgactgt atcgaactat ctattcgatg atgaagatac    900

cccaccaaac ccaaaaaaag agatcgaatt ccagctgcca gggagcacta agcgagcact    960

gcccaacaac accagctcct ctccccagcc aaagaagaaa ccactggatg gagaatattt   1020

cacccttcag atccgtgggc gtgagcgctt cgagatgttc cgagagctga atgaggcctt   1080

ggaactcaag gatgcccagg ctgggaagga gccagggggg agcagggctc actccagcca   1140

cctgaagtcc aaaaagggtc agtctacctc ccgccataaa aaactcatgt tcaagacaga   1200

agggcctgac tcagaccccg ggtcccctat actaggttat tggaaaggtc gacgcgacca   1260

tcctccaaaa tcggatctga tcgaaggtcg tggagatccc gaagttaaac gggtaaaatt   1320

agaaaacaac gttgaagaaa tacaacctga gcaggctgag accaataaac aagagggcac   1380

cgataaagag aataaaggaa agttcgagaa agaaactgag agaataggag gatctgaagt   1440

ggttacagat gtggaaaaag gaattgtcaa atttgaattt gatggtgttg aatacacatt   1500

caaagagaga cccagtgtcg tagaggaaaa tgaaggtaaa attgagttta gggtggtgaa   1560

taatgataat actaaagaaa acatgatggt cctaactgga ttaaaaaaca tttttcaaaa   1620
```

-continued

```
gcaattacca aaaatgccca aagaatacat tgccaggtta gtctatgatc gaagtcatct   1680
ttccatggct gtcattagga agccattgac tgtcgtaggt ggcataacat atcgaccttt   1740
cgataagaga gaattcgcag aaattgtttt ctgtgccatc agttcgacgg aacaggtacg   1800
cggttatggt gcgcatctaa tgaatcactt aaaagactat gttagaaata cctcgaacat   1860
aaaatatttt ttgacatatg cagataatta cgctattgga tacgctaaaa agcaaggctt   1920
tactaaagaa atcacgttgg ataaaagtat atggatggga tatattaaag attatgaagg   1980
tggtacgctg atgcaatgta acatggcaat tcccggtggc ggccgcatct tttacccata   2040
cgatgttcct gactatgcgg gctatcccta tgacgtcccg gactatgcag gatcctatcc   2100
atatgacgtt ccagattacg ctgctcagtg cggccgctct agctagaact agtggatccc   2160
ccgataccgt cgacctgcag agatctatga atcgtagata ctgaaaaacc ccgcaagttc   2220
acttcaactg tgcatcgtgc accatctcaa tttctttcat ttatacatcg ttttgccttc   2280
ttttatgtaa ctatactcct ctaagtttca atcttggcca tgtaacctct gatctataga   2340
atttttaaa tgactagaat taatgcccat ctttttttg gacctaaatt cttcatgaaa   2400
atatattacg agggcttatt cagaagcttt ggacttcttc gccagaggtt tggtcaagtc   2460
tccaatcaag gttgtcggct tgtctacctt gccagaaatt tacgaaaaga tggaaaaggg   2520
tcaaatcgtt ggtagatacg ttgttgacac ttctaaataa gcgaatttct tatgatttat   2580
gatttttatt attaaataag ttataaaaaa aataagtgta tacaaatttt aaagtgactc   2640
ttaggtttta aaacgaaaat tcttattctt gagtaactct ttcctgtagg tcaggttgct   2700
ttctcaggta tagcatgagg tcgctcttat tgaccacacc tctaccggca tgccgagcaa   2760
atgcctgcaa atcgctcccc atttcaccca attgtagata tgctaactcc agcaatgagt   2820
tgatgaatct cggtgtgtat tttatgtcct cagaggacaa cacctgttgt aatcgttctt   2880
ccacacggat cctggcgtaa tagcgaagag gcccgcaccg atcgcccttc ccaacagttg   2940
cgcagcctga atggcgaatg gcgcctgatg cggtattttc tccttacgca tctgtgcggt   3000
atttcacacc gcatatatcg ctgggccatt ctcatgaaga atatcttgaa tttattgtca   3060
tattactagt tggtgtggaa gtccatatat cggtgatcaa tatagtggtt gacatgctgg   3120
ctagtcaaca ttgagccttt tgatcatgca aatatattac ggtattttac aatcaaatat   3180
caaacttaac tattgacttt ataacttatt taggtggtaa cattcttata aaaaagaaaa   3240
aaattactgc aaaacagtac tagcttttaa cttgtatcct aggttatcta tgctgtctca   3300
ccatagagaa tattacctat ttcagaatgt atgtccatga ttcgccgggt aaatacatat   3360
aatacacaaa tctggcttaa taaagtctat aatatatctc ataaagaagt gctaaattgg   3420
ctagtgctat atatttttaa gaaaatttct tttgactaag tccatatcga ctttgtaaaa   3480
gttcacttta gcatacatat attacacgag ccagaaattg taacttttgc ctaaaatcac   3540
aaattgcaaa atttaattgc ttgcaaaagg tcacatgctt ataatcaact tttttaaaaa   3600
tttaaaatac ttttttattt tttattttta aacataaatg aaataattta tttattgttt   3660
atgattaccg aaacataaaa cctgctcaag aaaaagaaac tgttttgtcc ttggaaaaaa   3720
agcactacct aggagcggcc aaaatgccga ggctttcata gcttaaactc tttacagaaa   3780
ataggcatta tagatcagtt cgagttttct tattcttcct tccggtttta tcgtcacagt   3840
tttacagtaa ataagtatca cctcttagag ttcgatgata agctgtcaaa catgagaatt   3900
aattccacat gttaaaatag tgaaggagca tgttcggcac acagtggacc gaacgtgggg   3960
```

-continued

```
taagtgcact agggtccggt taaacggatc tcgcattgat gaggcaacgc taattatcaa   4020
catatagatt gttatctatc tgcatgaaca cgaaatcttt acttgacgac ttgaggctga   4080
tggtgtttat gcaaagaaac cactgtgttt aatatgtgtc actgtttgat attactgtca   4140
gcgtagaaga taatagtaaa agcggttaat aagtgtattt gagataagtg tgataaagtt   4200
tttacagcga aaagacgata aatacaagaa aatgattacg aggatacgga gagaggtatg   4260
tacatgtgta tttatatact aagctgccgg cggttgtttg caagaccgag aaaaggctag   4320
caagaatcgg gtcattgtag cgtatgcgcc tgtgaacatt ctcttcaaca agtttgattc   4380
cattgcggtg aaatggtaaa agtcaacccc ctgcgatgta tattttcctg tacaatcaat   4440
caaaaagcca aatgatttag cattatcttt acatcttgtt attttacaga ttttatgttt   4500
agatctttta tgcttgcttt tcaaaaggct tgcaggcaag tgcacaaaca atacttaaat   4560
aaatactact cagtaataac ctatttctta gcatttttga cgaaatttgc tattttgtta   4620
gagtctttta caccatttgt ctccacacct ccgcttacat caacaccaat aacgccattt   4680
aatctaagcg catcaccaac attttctggc gtcagtccac cagctaacat aaaatgtaag   4740
ctctcggggc tctcttgcct tccaacccag tcagaaatcg agttccaatc caaaagttca   4800
cctgtcccac ctgcttctga atcaaacaag ggaataaacg aatgaggttt ctgtgaagct   4860
gcactgagta gtatgttgca gtcttttgga aatacgagtc ttttaataac tggcaaaccg   4920
aggaactctt ggtattcttg ccacgactca tctccatgca gttggacgat atcaatgccg   4980
taatcattga ccagagccaa aacatcctcc ttaggttgat tacgaaacac gccaaccaag   5040
tatttcggag tgcctgaact atttttatat gcttttacaa gacttgaaat tttccttgca   5100
ataaccgggt caattgttct ctttctattg ggcacacata taatacccag caagtcagca   5160
tcggaatcta gtgcacattc tgcggcctct gtgctctgca agccgcaaac tttcaccaat   5220
ggaccagaac tacctgtgaa attaataaca gacatactcc aagctgcctt tgtgtgctta   5280
atcacgtata ctcacgtgct caatagtcac caatgccctc cctcttggcc ctctcctttt   5340
ctttttcga ccgaattaat tcttgaagac gaaagggcct cgtgatacgc ctatttttat   5400
aggttaatgt catgataata atggtttctt agacgtcagg tggcactttt cggggaaatg   5460
tgcgcggaac ccctatttgt ttatttttct aaatacattc aaatatgtat ccgctcatga   5520
gacaataacc ctgataaatg cttcaataat attgaaaaag gaagagtatg agtattcaac   5580
atttccgtgt cgcccttatt cccttttttg cggcattttg ccttcctgtt tttgctcacc   5640
cagaaacgct ggtgaaagta aaagatgctg aagatcagtt gggtgcacga gtgggttaca   5700
tcgaactgga tctcaacagc ggtaagatcc ttgagagttt tcgccccgaa gaacgttttc   5760
caatgatgag cacttttaaa gttctgctat gtggcgcggt attatcccgt attgacgccg   5820
ggcaagagca actcggtcgc cgcatacact attctcagaa tgacttggtt gagtactcac   5880
cagtcacaga aaagcatctt acggatggca tgacagtaag agaattatgc agtgctgcca   5940
taaccatgag tgataacact gcggccaact tacttctgac aacgatcgga ggaccgaagg   6000
agctaaccgc ttttttgcac aacatggggg atcatgtaac tcgccttgat cgttgggaac   6060
cggagctgaa tgaagccata ccaaacgacg agcgtgacac cacgatgcct gtagcaatgg   6120
caacaacgtt gcgcaaacta ttaactggcg aactacttac tctagcttcc cggcaacaat   6180
taatagactg gatggaggcg gataaagttg caggaccact tctgcgctcg gcccttccgg   6240
ctggctggtt tattgctgat aaatctggag ccggtgagcg tgggtctcgc ggtatcattg   6300
cagcactggg gccagatggt aagccctccc gtatcgtagt tatctacacg acggggagtc   6360
```

-continued

```
aggcaactat ggatgaacga aatagacaga tcgctgagat aggtgcctca ctgattaagc   6420
attggtaact gtcagaccaa gtttactcat atatacttta gattgattta aaacttcatt   6480
tttaatttaa aaggatctag gtgaagatcc tttttgataa tctcatgacc aaaatccctt   6540
aacgtgagtt ttcgttccac tgagcgtcag accccgtaga aaagatcaaa ggatcttctt   6600
gagatccttt ttttctgcgc gtaatctgct gcttgcaaac aaaaaaacca ccgctaccag   6660
cggtggtttg tttgccggat caagagctac caactctttt tccgaaggta actggcttca   6720
gcagagcgca gataccaaat actgtccttc tagtgtagcc gtagttaggc caccacttca   6780
agaactctgt agcaccgcct acatacctcg ctctgctaat cctgttacca gtggctgctg   6840
ccagtggcga taagtcgtgt cttaccgggt tggactcaag acgatagtta ccggataagg   6900
cgcagcggtc gggctgaacg gggggttcgt gcacacagcc cagcttggag cgaacgacct   6960
acaccgaact gagataccta cagcgtgagc tatgagaaag cgccacgctt cccgaaggga   7020
gaaaggcgga caggtatccg gtaagcggca gggtcggaac aggagagcgc acgagggagc   7080
ttccaggggg aaacgcctgg tatctttata gtcctgtcgg gtttcgccac ctctgacttg   7140
agcgtcgatt tttgtgatgc tcgtcagggg ggcggagcct atggaaaaac gccagcaacg   7200
cggccttttt acggttcctg gccttttgct ggccttttgc tcacatgttc tttcctgcgt   7260
tatcccctga ttctgtggat aaccgtatta ccgcctttga gtgagctgat accgctcgcc   7320
gcagccgaac gaccgagcgc agcgagtcag tgagcgagga agcggaagag cgcccaatac   7380
gcaaaccgcc tctccccgcg cgttggccga ttcattaatg caggatccgg gatcgaagaa   7440
atgatggtaa atgaaatagg aaatcaagga gcatgaaggc aaaagacaaa tataagggtc   7500
gaacgaaaaa taaagtgaaa agtgttgata tgatgtattt ggctttgcgg cgccgaaaaa   7560
acgagtttac gcaattgcac aatcatgctg actctgtggc ggacccgcgc tcttgccggc   7620
ccggcgataa cgctgggcgt gaggctgtgc ccggcggagt tttttgcgcc tgcattttcc   7680
aaggtttacc ctgcgctaag ggcgagattg gagaagcaa taagaatgcc ggttggggtt   7740
gcgatgatga cgaccacgac aactggtgtc attatttaag ttgccgaaag aacctgagtg   7800
catttgcaac atgagtatac tagaagaatg agccaagact tgcgagacgc gagtttgccg   7860
gtggtgcgaa caatagagcg accatgacct tgaaggtgag acgcgcataa ccgctagagt   7920
actttgaaga ggaaacagca atagggttgc taccagtata aatagacagg tacatacaac   7980
actggaaatg gttgtctgtt tgagtacgct ttcaattcat ttgggtgtgc actttattat   8040
gttacaatat ggaagggaac tttacacttc tcctatgcac atatattaat taaagtccaa   8100
tgctagtaga gaagggggt aacaccccctc cgcgctcttt tccgattttt ttctaaaccg   8160
tggaatattt cggatatcct tttgttgttt ccgggtgtac aatatggact tcctcttttc   8220
tggcaaccaa acccatacat cgggattcct ataataccttt cgttggtctc cctaacatgt   8280
aggtggcgga ggggagatat acaatagaac agataccaga caagacataa tgggctaaac   8340
aagactacac caattacact gcctcattga tg                                 8372
```

<210> SEQ ID NO 15
<211> LENGTH: 541
<212> TYPE: PRT
<213> ORGANISM: Artificial Sequence
<220> FEATURE:
<223> OTHER INFORMATION: Synthetic

<400> SEQUENCE: 15

-continued

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Phe Met Ala Arg Thr
                165                 170                 175

Lys Gln Thr Ala Arg Lys Ser Thr Gly Gly Lys Ala Pro Arg Lys Gln
            180                 185                 190

Leu Ala Ser Lys Ala Ala Arg Lys Ser Ala Pro Ser Thr Gly Gly Val
        195                 200                 205

Lys Lys Pro His Arg Tyr Lys Pro Gly Thr Val Ala Leu Arg Glu Ile
    210                 215                 220

Arg Arg Phe Gln Lys Ser Thr Glu Pro Gly Ser Pro Ile Leu Gly Tyr
225                 230                 235                 240

Trp Lys Gly Arg Arg Asp His Pro Pro Lys Ser Asp Leu Ile Glu Gly
                245                 250                 255

Arg Gly Asp Pro Glu Val Lys Arg Val Lys Leu Glu Asn Asn Val Glu
            260                 265                 270

Glu Ile Gln Pro Glu Gln Ala Glu Thr Asn Lys Gln Glu Gly Thr Asp
        275                 280                 285

Lys Glu Asn Lys Gly Lys Phe Glu Lys Glu Thr Glu Arg Ile Gly Gly
    290                 295                 300

Ser Glu Val Val Thr Asp Val Glu Lys Gly Ile Val Lys Phe Glu Phe
305                 310                 315                 320

Asp Gly Val Glu Tyr Thr Phe Lys Glu Arg Pro Ser Val Val Glu Glu
                325                 330                 335

Asn Glu Gly Lys Ile Glu Phe Arg Val Val Asn Asn Asp Asn Thr Lys
            340                 345                 350

Glu Asn Met Met Val Leu Thr Gly Leu Lys Asn Ile Phe Gln Lys Gln
        355                 360                 365

Leu Pro Lys Met Pro Lys Glu Tyr Ile Ala Arg Leu Val Tyr Asp Arg
    370                 375                 380

Ser His Leu Ser Met Ala Val Ile Arg Lys Pro Leu Thr Val Val Gly
385                 390                 395                 400

Gly Ile Thr Tyr Arg Pro Phe Asp Lys Arg Glu Phe Ala Glu Ile Val
                405                 410                 415

Phe Cys Ala Ile Ser Ser Thr Glu Gln Val Arg Gly Tyr Gly Ala His
```

-continued

```
        420                 425                 430

Leu Met Asn His Leu Lys Asp Tyr Val Arg Asn Thr Ser Asn Ile Lys
        435                 440                 445

Tyr Phe Leu Thr Tyr Ala Asp Asn Tyr Ala Ile Gly Tyr Phe Lys Lys
    450                 455                 460

Gln Gly Phe Thr Lys Glu Ile Thr Leu Asp Lys Ser Ile Trp Met Gly
465                 470                 475                 480

Tyr Ile Lys Asp Tyr Glu Gly Gly Thr Leu Met Gln Cys Asn Met Ala
                485                 490                 495

Ile Pro Gly Gly Gly Arg Ile Phe Tyr Pro Tyr Asp Val Pro Asp Tyr
            500                 505                 510

Ala Gly Tyr Pro Tyr Asp Val Pro Asp Tyr Ala Gly Ser Tyr Pro Tyr
        515                 520                 525

Asp Val Pro Asp Tyr Ala Ala Gln Cys Gly Arg Ser Ser
    530                 535                 540


<210> SEQ ID NO 16
<211> LENGTH: 541
<212> TYPE: PRT
<213> ORGANISM: Artificial Sequence
<220> FEATURE:
<223> OTHER INFORMATION: Synthetic

<400> SEQUENCE: 16

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Phe Met Ala Arg Thr
                165                 170                 175

Lys Gln Thr Ala Arg Lys Ser Thr Gly Gly Lys Ala Pro Arg Lys Gln
            180                 185                 190

Leu Ala Ser Lys Ala Ala Arg Lys Ser Ala Pro Ser Thr Gly Gly Val
        195                 200                 205

Lys Lys Pro His Arg Tyr Lys Pro Gly Thr Val Ala Leu Arg Glu Ile
    210                 215                 220

Arg Arg Phe Gln Lys Ser Thr Glu Pro Gly Ser Pro Ile Leu Gly Tyr
225                 230                 235                 240

Trp Lys Gly Arg Arg Asp His Pro Pro Lys Ser Asp Leu Ile Glu Gly
```

-continued

```
                245                 250                 255

Arg Gly Asp Pro Glu Val Lys Arg Val Lys Leu Glu Asn Asn Val Glu
            260                 265                 270

Glu Ile Gln Pro Glu Gln Ala Glu Thr Asn Lys Gln Glu Gly Thr Asp
        275                 280                 285

Lys Glu Asn Lys Gly Lys Phe Glu Lys Glu Thr Glu Arg Ile Gly Gly
    290                 295                 300

Ser Glu Val Val Thr Asp Val Glu Lys Gly Ile Val Lys Phe Glu Phe
305                 310                 315                 320

Asp Gly Val Glu Tyr Thr Phe Lys Glu Arg Pro Ser Val Val Glu Glu
                325                 330                 335

Asn Glu Gly Lys Ile Glu Phe Arg Val Val Asn Asn Asp Asn Thr Lys
            340                 345                 350

Glu Asn Met Met Val Leu Thr Gly Leu Lys Asn Ile Phe Gln Lys Gln
        355                 360                 365

Leu Pro Lys Met Pro Lys Glu Tyr Ile Ala Arg Leu Val Tyr Asp Arg
    370                 375                 380

Ser His Leu Ser Met Ala Val Ile Arg Lys Pro Leu Thr Val Val Gly
385                 390                 395                 400

Gly Ile Thr Tyr Arg Pro Phe Asp Lys Arg Glu Phe Ala Glu Ile Val
                405                 410                 415

Phe Cys Ala Ile Ser Ser Thr Glu Gln Val Arg Gly Tyr Gly Ala His
            420                 425                 430

Leu Met Asn His Leu Lys Asp Tyr Val Arg Asn Thr Ser Asn Ile Lys
        435                 440                 445

Tyr Phe Leu Thr Tyr Ala Asp Asn Tyr Ala Ile Gly Tyr Ala Lys Lys
    450                 455                 460

Gln Gly Phe Thr Lys Glu Ile Thr Leu Asp Lys Ser Ile Trp Met Gly
465                 470                 475                 480

Tyr Ile Lys Asp Tyr Glu Gly Gly Thr Leu Met Gln Cys Asn Met Ala
                485                 490                 495

Ile Pro Gly Gly Gly Arg Ile Phe Tyr Pro Tyr Asp Val Pro Asp Tyr
            500                 505                 510

Ala Gly Tyr Pro Tyr Asp Val Pro Asp Tyr Ala Gly Ser Tyr Pro Tyr
        515                 520                 525

Asp Val Pro Asp Tyr Ala Ala Gln Cys Gly Arg Ser Ser
    530                 535                 540


<210> SEQ ID NO 17
<211> LENGTH: 509
<212> TYPE: PRT
<213> ORGANISM: Artificial Sequence
<220> FEATURE:
<223> OTHER INFORMATION: Synthetic

<400> SEQUENCE: 17

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
```

-continued

```
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Ser Gly Arg Gly Lys
                165                 170                 175

Gly Gly Lys Gly Leu Gly Lys Gly Gly Ala Lys Arg His Arg Lys Ile
            180                 185                 190

Leu Arg Asp Asn Ile Gln Gly Ile Ser Gly Ser Pro Ile Leu Gly Tyr
        195                 200                 205

Trp Lys Gly Arg Arg Asp His Pro Pro Lys Ser Asp Leu Ile Glu Gly
    210                 215                 220

Arg Gly Asp Pro Glu Val Lys Arg Val Lys Leu Glu Asn Asn Val Glu
225                 230                 235                 240

Glu Ile Gln Pro Glu Gln Ala Glu Thr Asn Lys Gln Glu Gly Thr Asp
                245                 250                 255

Lys Glu Asn Lys Gly Lys Phe Glu Lys Glu Thr Glu Arg Ile Gly Gly
            260                 265                 270

Ser Glu Val Val Thr Asp Val Glu Lys Gly Ile Val Lys Phe Glu Phe
        275                 280                 285

Asp Gly Val Glu Tyr Thr Phe Lys Glu Arg Pro Ser Val Val Glu Glu
    290                 295                 300

Asn Glu Gly Lys Ile Glu Phe Arg Val Val Asn Asn Asp Asn Thr Lys
305                 310                 315                 320

Glu Asn Met Met Val Leu Thr Gly Leu Lys Asn Ile Phe Gln Lys Gln
                325                 330                 335

Leu Pro Lys Met Pro Lys Glu Tyr Ile Ala Arg Leu Val Tyr Asp Arg
            340                 345                 350

Ser His Leu Ser Met Ala Val Ile Arg Lys Pro Leu Thr Val Val Gly
        355                 360                 365

Gly Ile Thr Tyr Arg Pro Phe Asp Lys Arg Glu Phe Ala Glu Ile Val
    370                 375                 380

Phe Cys Ala Ile Ser Ser Thr Glu Gln Val Arg Gly Tyr Gly Ala His
385                 390                 395                 400

Leu Met Asn His Leu Lys Asp Tyr Val Arg Asn Thr Ser Asn Ile Lys
                405                 410                 415

Tyr Phe Leu Thr Tyr Ala Asp Asn Tyr Ala Ile Gly Tyr Phe Lys Lys
            420                 425                 430

Gln Gly Phe Thr Lys Glu Ile Thr Leu Asp Lys Ser Ile Trp Met Gly
        435                 440                 445

Tyr Ile Lys Asp Tyr Glu Gly Gly Thr Leu Met Gln Cys Ser Met Ala
    450                 455                 460

Ile Pro Gly Gly Gly Arg Ile Phe Tyr Pro Tyr Asp Val Pro Asp Tyr
465                 470                 475                 480

Ala Gly Tyr Pro Tyr Asp Val Pro Asp Tyr Ala Gly Ser Tyr Pro Tyr
                485                 490                 495
```

-continued

Asp Val Pro Asp Tyr Ala Ala Gln Cys Gly Arg Ser Ser
500 505

<210> SEQ ID NO 18
<211> LENGTH: 509
<212> TYPE: PRT
<213> ORGANISM: Artificial Sequence
<220> FEATURE:
<223> OTHER INFORMATION: Synthetic

<400> SEQUENCE: 18

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Asn Tyr Leu Phe Asp Asp Glu Asp Thr Pro Pro Asn Pro
145 150 155 160

Lys Lys Glu Ile Glu Phe Gln Leu Thr Thr Met Ser Gly Arg Gly Lys
165 170 175

Gly Gly Lys Gly Leu Gly Lys Gly Gly Ala Lys Arg His Arg Lys Ile
180 185 190

Leu Arg Asp Asn Ile Gln Gly Ile Ser Gly Ser Pro Ile Leu Gly Tyr
195 200 205

Trp Lys Gly Arg Arg Asp His Pro Pro Lys Ser Asp Leu Ile Glu Gly
210 215 220

Arg Gly Asp Pro Glu Val Lys Arg Val Lys Leu Glu Asn Asn Val Glu
225 230 235 240

Glu Ile Gln Pro Glu Gln Ala Glu Thr Asn Lys Gln Glu Gly Thr Asp
245 250 255

Lys Glu Asn Lys Gly Lys Phe Glu Lys Glu Thr Glu Arg Ile Gly Gly
260 265 270

Ser Glu Val Val Thr Asp Val Glu Lys Gly Ile Val Lys Phe Glu Phe
275 280 285

Asp Gly Val Glu Tyr Thr Phe Lys Glu Arg Pro Ser Val Val Glu Glu
290 295 300

Asn Glu Gly Lys Ile Glu Phe Arg Val Val Asn Asn Asp Asn Thr Lys
305 310 315 320

Glu Asn Met Met Val Leu Thr Gly Leu Lys Asn Ile Phe Gln Lys Gln
325 330 335

Leu Pro Lys Met Pro Lys Glu Tyr Ile Ala Arg Leu Val Tyr Asp Arg
340 345 350

-continued

```
Ser His Leu Ser Met Ala Val Ile Arg Lys Pro Leu Thr Val Val Gly
        355                 360                 365

Gly Ile Thr Tyr Arg Pro Phe Asp Lys Arg Glu Phe Ala Glu Ile Val
    370                 375                 380

Phe Cys Ala Ile Ser Ser Thr Glu Gln Val Arg Gly Tyr Gly Ala His
385                 390                 395                 400

Leu Met Asn His Leu Lys Asp Tyr Val Arg Asn Thr Ser Asn Ile Lys
                405                 410                 415

Tyr Phe Leu Thr Tyr Ala Asp Asn Tyr Ala Ile Gly Tyr Ala Lys Lys
            420                 425                 430

Gln Gly Phe Thr Lys Glu Ile Thr Leu Asp Lys Ser Ile Trp Met Gly
        435                 440                 445

Tyr Ile Lys Asp Tyr Glu Gly Gly Thr Leu Met Gln Cys Ser Met Ala
    450                 455                 460

Ile Pro Gly Gly Gly Arg Ile Phe Tyr Pro Tyr Asp Val Pro Asp Tyr
465                 470                 475                 480

Ala Gly Tyr Pro Tyr Asp Val Pro Asp Tyr Ala Gly Ser Tyr Pro Tyr
                485                 490                 495

Asp Val Pro Asp Tyr Ala Ala Gln Cys Gly Arg Ser Ser
            500                 505


<210> SEQ ID NO 19
<211> LENGTH: 541
<212> TYPE: PRT
<213> ORGANISM: Artificial Sequence
<220> FEATURE:
<223> OTHER INFORMATION: Synthetic

<400> SEQUENCE: 19

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Phe Met Ala Arg Thr
                165                 170                 175

Lys Gln Thr Ala Arg Lys Ser Thr Gly Gly Lys Ala Pro Arg Lys Gln
            180                 185                 190

Leu Ala Ser Lys Ala Ala Arg Lys Ser Ala Pro Ser Thr Gly Gly Val
        195                 200                 205
```

-continued

```
Lys Lys Pro His Arg Tyr Lys Pro Gly Thr Val Ala Leu Arg Glu Ile
    210                 215                 220

Arg Arg Phe Gln Lys Ser Thr Glu Pro Gly Ser Pro Ile Leu Gly Tyr
225                 230                 235                 240

Trp Lys Gly Arg Arg Asp His Pro Pro Lys Ser Asp Leu Ile Glu Gly
                245                 250                 255

Arg Gly Asp Pro Glu Val Lys Arg Val Lys Leu Glu Asn Asn Val Glu
            260                 265                 270

Glu Ile Gln Pro Glu Gln Ala Glu Thr Asn Lys Gln Glu Gly Thr Asp
        275                 280                 285

Lys Glu Asn Lys Gly Lys Phe Glu Lys Glu Thr Glu Arg Ile Gly Gly
    290                 295                 300

Ser Glu Val Val Thr Asp Val Glu Lys Gly Ile Val Lys Phe Glu Phe
305                 310                 315                 320

Asp Gly Val Glu Tyr Thr Phe Lys Glu Arg Pro Ser Val Val Glu Glu
                325                 330                 335

Asn Glu Gly Lys Ile Glu Phe Arg Val Val Asn Asn Asp Asn Thr Lys
            340                 345                 350

Glu Asn Met Met Val Leu Thr Gly Leu Lys Asn Ile Phe Gln Lys Gln
        355                 360                 365

Leu Pro Lys Met Pro Lys Glu Tyr Ile Ala Arg Leu Val Tyr Asp Arg
    370                 375                 380

Ser His Leu Ser Met Ala Val Ile Arg Lys Pro Leu Thr Val Val Gly
385                 390                 395                 400

Gly Ile Thr Tyr Arg Pro Phe Asp Lys Arg Glu Phe Ala Glu Ile Val
                405                 410                 415

Phe Cys Ala Ile Ser Ser Thr Glu Gln Val Arg Gly Tyr Gly Ala His
            420                 425                 430

Leu Met Asn His Leu Lys Asp Tyr Val Arg Asn Thr Ser Asn Ile Lys
        435                 440                 445

Tyr Phe Leu Thr Tyr Ala Asp Asn Tyr Ala Ile Gly Tyr Phe Lys Lys
    450                 455                 460

Gln Gly Phe Thr Lys Glu Ile Thr Leu Asp Lys Ser Ile Trp Met Gly
465                 470                 475                 480

Tyr Ile Lys Asp Tyr Glu Gly Gly Thr Leu Met Gln Cys Asn Met Ala
                485                 490                 495

Ile Pro Gly Gly Gly Arg Ile Phe Tyr Pro Tyr Asp Val Pro Asp Tyr
            500                 505                 510

Ala Gly Tyr Pro Tyr Asp Val Pro Asp Tyr Ala Gly Ser Tyr Pro Tyr
        515                 520                 525

Asp Val Pro Asp Tyr Ala Ala Gln Cys Gly Arg Ser Ser
    530                 535                 540


<210> SEQ ID NO 20
<211> LENGTH: 541
<212> TYPE: PRT
<213> ORGANISM: Artificial Sequence
<220> FEATURE:
<223> OTHER INFORMATION: Synthetic

<400> SEQUENCE: 20

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30
```

-continued

```
Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Phe Met Ala Arg Thr
                165                 170                 175

Lys Gln Thr Ala Arg Lys Ser Thr Gly Gly Lys Ala Pro Arg Lys Gln
            180                 185                 190

Leu Ala Ser Lys Ala Ala Arg Lys Ser Ala Pro Ser Thr Gly Gly Val
        195                 200                 205

Lys Lys Pro His Arg Tyr Lys Pro Gly Thr Val Ala Leu Arg Glu Ile
    210                 215                 220

Arg Arg Phe Gln Lys Ser Thr Glu Pro Gly Ser Pro Ile Leu Gly Tyr
225                 230                 235                 240

Trp Lys Gly Arg Arg Asp His Pro Pro Lys Ser Asp Leu Ile Glu Gly
                245                 250                 255

Arg Gly Asp Pro Glu Val Lys Arg Val Lys Leu Glu Asn Asn Val Glu
            260                 265                 270

Glu Ile Gln Pro Glu Gln Ala Glu Thr Asn Lys Gln Glu Gly Thr Asp
        275                 280                 285

Lys Glu Asn Lys Gly Lys Phe Glu Lys Glu Thr Glu Arg Ile Gly Gly
    290                 295                 300

Ser Glu Val Val Thr Asp Val Glu Lys Gly Ile Val Lys Phe Glu Phe
305                 310                 315                 320

Asp Gly Val Glu Tyr Thr Phe Lys Glu Arg Pro Ser Val Val Glu Glu
                325                 330                 335

Asn Glu Gly Lys Ile Glu Phe Arg Val Val Asn Asn Asp Asn Thr Lys
            340                 345                 350

Glu Asn Met Met Val Leu Thr Gly Leu Lys Asn Ile Phe Gln Lys Gln
        355                 360                 365

Leu Pro Lys Met Pro Lys Glu Tyr Ile Ala Arg Leu Val Tyr Asp Arg
    370                 375                 380

Ser His Leu Ser Met Ala Val Ile Arg Lys Pro Leu Thr Val Val Gly
385                 390                 395                 400

Gly Ile Thr Tyr Arg Pro Phe Asp Lys Arg Glu Phe Ala Glu Ile Val
                405                 410                 415

Phe Cys Ala Ile Ser Ser Thr Glu Gln Val Arg Gly Tyr Gly Ala His
            420                 425                 430

Leu Met Asn His Leu Lys Asp Tyr Val Arg Asn Thr Ser Asn Ile Lys
        435                 440                 445
```

-continued

```
Tyr Phe Leu Thr Tyr Ala Asp Asn Tyr Ala Ile Gly Tyr Ala Lys Lys
    450                 455                 460

Gln Gly Phe Thr Lys Glu Ile Thr Leu Asp Lys Ser Ile Trp Met Gly
465                 470                 475                 480

Tyr Ile Lys Asp Tyr Glu Gly Gly Thr Leu Met Gln Cys Asn Met Ala
                485                 490                 495

Ile Pro Gly Gly Gly Arg Ile Phe Tyr Pro Tyr Asp Val Pro Asp Tyr
            500                 505                 510

Ala Gly Tyr Pro Tyr Asp Val Pro Asp Tyr Ala Gly Ser Tyr Pro Tyr
        515                 520                 525

Asp Val Pro Asp Tyr Ala Ala Gln Cys Gly Arg Ser Ser
    530                 535                 540


<210> SEQ ID NO 21
<211> LENGTH: 509
<212> TYPE: PRT
<213> ORGANISM: Artificial Sequence
<220> FEATURE:
<223> OTHER INFORMATION: Synthetic

<400> SEQUENCE: 21

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Ser Gly Arg Gly Lys
                165                 170                 175

Gly Gly Lys Gly Leu Gly Lys Gly Gly Ala Lys Arg His Arg Lys Ile
            180                 185                 190

Leu Arg Asp Asn Ile Gln Gly Ile Ser Gly Ser Pro Ile Leu Gly Tyr
        195                 200                 205

Trp Lys Gly Arg Arg Asp His Pro Pro Lys Ser Asp Leu Ile Glu Gly
    210                 215                 220

Arg Gly Asp Pro Glu Val Lys Arg Val Lys Leu Glu Asn Asn Val Glu
225                 230                 235                 240

Glu Ile Gln Pro Glu Gln Ala Glu Thr Asn Lys Gln Glu Gly Thr Asp
                245                 250                 255

Lys Glu Asn Lys Gly Lys Phe Glu Lys Glu Thr Glu Arg Ile Gly Gly
            260                 265                 270
```

-continued

```
Ser Glu Val Val Thr Asp Val Glu Lys Gly Ile Val Lys Phe Glu Phe
        275                 280                 285

Asp Gly Val Glu Tyr Thr Phe Lys Glu Arg Pro Ser Val Val Glu Glu
    290                 295                 300

Asn Glu Gly Lys Ile Glu Phe Arg Val Val Asn Asn Asp Asn Thr Lys
305                 310                 315                 320

Glu Asn Met Met Val Leu Thr Gly Leu Lys Asn Ile Phe Gln Lys Gln
                325                 330                 335

Leu Pro Lys Met Pro Lys Glu Tyr Ile Ala Arg Leu Val Tyr Asp Arg
            340                 345                 350

Ser His Leu Ser Met Ala Val Ile Arg Lys Pro Leu Thr Val Val Gly
        355                 360                 365

Gly Ile Thr Tyr Arg Pro Phe Asp Lys Arg Glu Phe Ala Glu Ile Val
    370                 375                 380

Phe Cys Ala Ile Ser Ser Thr Glu Gln Val Arg Gly Tyr Gly Ala His
385                 390                 395                 400

Leu Met Asn His Leu Lys Asp Tyr Val Arg Asn Thr Ser Asn Ile Lys
                405                 410                 415

Tyr Phe Leu Thr Tyr Ala Asp Asn Tyr Ala Ile Gly Tyr Phe Lys Lys
            420                 425                 430

Gln Gly Phe Thr Lys Glu Ile Thr Leu Asp Lys Ser Ile Trp Met Gly
        435                 440                 445

Tyr Ile Lys Asp Tyr Glu Gly Gly Thr Leu Met Gln Cys Ser Met Ala
    450                 455                 460

Ile Pro Gly Gly Gly Arg Ile Phe Tyr Pro Tyr Asp Val Pro Asp Tyr
465                 470                 475                 480

Ala Gly Tyr Pro Tyr Asp Val Pro Asp Tyr Ala Gly Ser Tyr Pro Tyr
                485                 490                 495

Asp Val Pro Asp Tyr Ala Ala Gln Cys Gly Arg Ser Ser
            500                 505


<210> SEQ ID NO 22
<211> LENGTH: 509
<212> TYPE: PRT
<213> ORGANISM: Artificial Sequence
<220> FEATURE:
<223> OTHER INFORMATION: Synthetic

<400> SEQUENCE: 22

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125
```

-continued

```
Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Thr Thr Met Ser Gly Arg Gly Lys
                165                 170                 175

Gly Gly Lys Gly Leu Gly Lys Gly Gly Ala Lys Arg His Arg Lys Ile
            180                 185                 190

Leu Arg Asp Asn Ile Gln Gly Ile Ser Gly Ser Pro Ile Leu Gly Tyr
        195                 200                 205

Trp Lys Gly Arg Arg Asp His Pro Pro Lys Ser Asp Leu Ile Glu Gly
    210                 215                 220

Arg Gly Asp Pro Glu Val Lys Arg Val Lys Leu Glu Asn Asn Val Glu
225                 230                 235                 240

Glu Ile Gln Pro Glu Gln Ala Glu Thr Asn Lys Gln Glu Gly Thr Asp
                245                 250                 255

Lys Glu Asn Lys Gly Lys Phe Glu Lys Glu Thr Glu Arg Ile Gly Gly
            260                 265                 270

Ser Glu Val Val Thr Asp Val Glu Lys Gly Ile Val Lys Phe Glu Phe
        275                 280                 285

Asp Gly Val Glu Tyr Thr Phe Lys Glu Arg Pro Ser Val Val Glu Glu
    290                 295                 300

Asn Glu Gly Lys Ile Glu Phe Arg Val Val Asn Asn Asp Asn Thr Lys
305                 310                 315                 320

Glu Asn Met Met Val Leu Thr Gly Leu Lys Asn Ile Phe Gln Lys Gln
                325                 330                 335

Leu Pro Lys Met Pro Lys Glu Tyr Ile Ala Arg Leu Val Tyr Asp Arg
            340                 345                 350

Ser His Leu Ser Met Ala Val Ile Arg Lys Pro Leu Thr Val Val Gly
        355                 360                 365

Gly Ile Thr Tyr Arg Pro Phe Asp Lys Arg Glu Phe Ala Glu Ile Val
    370                 375                 380

Phe Cys Ala Ile Ser Ser Thr Glu Gln Val Arg Gly Tyr Gly Ala His
385                 390                 395                 400

Leu Met Asn His Leu Lys Asp Tyr Val Arg Asn Thr Ser Asn Ile Lys
                405                 410                 415

Tyr Phe Leu Thr Tyr Ala Asp Asn Tyr Ala Ile Gly Tyr Ala Lys Lys
            420                 425                 430

Gln Gly Phe Thr Lys Glu Ile Thr Leu Asp Lys Ser Ile Trp Met Gly
        435                 440                 445

Tyr Ile Lys Asp Tyr Glu Gly Gly Thr Leu Met Gln Cys Ser Met Ala
    450                 455                 460

Ile Pro Gly Gly Gly Arg Ile Phe Tyr Pro Tyr Asp Val Pro Asp Tyr
465                 470                 475                 480

Ala Gly Tyr Pro Tyr Asp Val Pro Asp Tyr Ala Gly Ser Tyr Pro Tyr
                485                 490                 495

Asp Val Pro Asp Tyr Ala Ala Gln Cys Gly Arg Ser Ser
            500                 505
```

<210> SEQ ID NO 23
<211> LENGTH: 475
<212> TYPE: PRT
<213> ORGANISM: Artificial Sequence
<220> FEATURE:
<223> OTHER INFORMATION: Synthetic -continued

<400> SEQUENCE: 23

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Gly Ser Pro Ile Leu Gly Tyr Trp Lys
                165                 170                 175

Gly Arg Arg Asp His Pro Pro Lys Ser Asp Leu Ile Glu Gly Arg Gly
            180                 185                 190

Asp Pro Glu Val Lys Arg Val Lys Leu Glu Asn Asn Val Glu Glu Ile
        195                 200                 205

Gln Pro Glu Gln Ala Glu Thr Asn Lys Gln Glu Gly Thr Asp Lys Glu
    210                 215                 220

Asn Lys Gly Lys Phe Glu Lys Glu Thr Glu Arg Ile Gly Gly Ser Glu
225                 230                 235                 240

Val Val Thr Asp Val Glu Lys Gly Ile Val Lys Phe Glu Phe Asp Gly
                245                 250                 255

Val Glu Tyr Thr Phe Lys Glu Arg Pro Ser Val Val Glu Glu Asn Glu
            260                 265                 270

Gly Lys Ile Glu Phe Arg Val Val Asn Asn Asp Asn Thr Lys Glu Asn
        275                 280                 285

Met Met Val Leu Thr Gly Leu Lys Asn Ile Phe Gln Lys Gln Leu Pro
    290                 295                 300

Lys Met Pro Lys Glu Tyr Ile Ala Arg Leu Val Tyr Asp Arg Ser His
305                 310                 315                 320

Leu Ser Met Ala Val Ile Arg Lys Pro Leu Thr Val Val Gly Gly Ile
                325                 330                 335

Thr Tyr Arg Pro Phe Asp Lys Arg Glu Phe Ala Glu Ile Val Phe Cys
            340                 345                 350

Ala Ile Ser Ser Thr Glu Gln Val Arg Gly Tyr Gly Ala His Leu Met
        355                 360                 365

Asn His Leu Lys Asp Tyr Val Arg Asn Thr Ser Asn Ile Lys Tyr Phe
    370                 375                 380

Leu Thr Tyr Ala Asp Asn Tyr Ala Ile Gly Tyr Phe Lys Lys Gln Gly
385                 390                 395                 400

Phe Thr Lys Glu Ile Thr Leu Asp Lys Ser Ile Trp Met Gly Tyr Ile
```

-continued

```
            405                 410                 415

Lys Asp Tyr Glu Gly Gly Thr Leu Met Gln Cys Asn Met Ala Ile Pro
            420                 425                 430

Gly Gly Gly Arg Ile Phe Tyr Pro Tyr Asp Val Pro Asp Tyr Ala Gly
        435                 440                 445

Tyr Pro Tyr Asp Val Pro Asp Tyr Ala Gly Ser Tyr Pro Tyr Asp Val
    450                 455                 460

Pro Asp Tyr Ala Ala Gln Cys Gly Arg Ser Ser
465                 470                 475


<210> SEQ ID NO 24
<211> LENGTH: 475
<212> TYPE: PRT
<213> ORGANISM: Artificial Sequence
<220> FEATURE:
<223> OTHER INFORMATION: Synthetic

<400> SEQUENCE: 24

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Gly Ser Pro Ile Leu Gly Tyr Trp Lys
                165                 170                 175

Gly Arg Arg Asp His Pro Pro Lys Ser Asp Leu Ile Glu Gly Arg Gly
            180                 185                 190

Asp Pro Glu Val Lys Arg Val Lys Leu Glu Asn Asn Val Glu Glu Ile
        195                 200                 205

Gln Pro Glu Gln Ala Glu Thr Asn Lys Gln Glu Gly Thr Asp Lys Glu
    210                 215                 220

Asn Lys Gly Lys Phe Glu Lys Glu Thr Glu Arg Ile Gly Gly Ser Glu
225                 230                 235                 240

Val Val Thr Asp Val Glu Lys Gly Ile Val Lys Phe Glu Phe Asp Gly
                245                 250                 255

Val Glu Tyr Thr Phe Lys Glu Arg Pro Ser Val Val Glu Glu Asn Glu
            260                 265                 270

Gly Lys Ile Glu Phe Arg Val Val Asn Asn Asp Asn Thr Lys Glu Asn
        275                 280                 285

Met Met Val Leu Thr Gly Leu Lys Asn Ile Phe Gln Lys Gln Leu Pro
```

-continued

```
    290                 295                 300

Lys Met Pro Lys Glu Tyr Ile Ala Arg Leu Val Tyr Asp Arg Ser His
305                 310                 315                 320

Leu Ser Met Ala Val Ile Arg Lys Pro Leu Thr Val Val Gly Gly Ile
                325                 330                 335

Thr Tyr Arg Pro Phe Asp Lys Arg Glu Phe Ala Glu Ile Val Phe Cys
            340                 345                 350

Ala Ile Ser Ser Thr Glu Gln Val Arg Gly Tyr Gly Ala His Leu Met
        355                 360                 365

Asn His Leu Lys Asp Tyr Val Arg Asn Thr Ser Asn Ile Lys Tyr Phe
    370                 375                 380

Leu Thr Tyr Ala Asp Asn Tyr Ala Ile Gly Tyr Ala Lys Lys Gln Gly
385                 390                 395                 400

Phe Thr Lys Glu Ile Thr Leu Asp Lys Ser Ile Trp Met Gly Tyr Ile
                405                 410                 415

Lys Asp Tyr Glu Gly Gly Thr Leu Met Gln Cys Asn Met Ala Ile Pro
            420                 425                 430

Gly Gly Gly Arg Ile Phe Tyr Pro Tyr Asp Val Pro Asp Tyr Ala Gly
        435                 440                 445

Tyr Pro Tyr Asp Val Pro Asp Tyr Ala Gly Ser Tyr Pro Tyr Asp Val
    450                 455                 460

Pro Asp Tyr Ala Ala Gln Cys Gly Arg Ser Ser
465                 470                 475


<210> SEQ ID NO 25
<211> LENGTH: 486
<212> TYPE: PRT
<213> ORGANISM: Artificial Sequence
<220> FEATURE:
<223> OTHER INFORMATION: Synthetic

<400> SEQUENCE: 25

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Gly Thr Met His Glu Leu Pro Arg Leu
                165                 170                 175

Glu Pro Gly Ser Pro Ile Leu Gly Tyr Trp Lys Gly Arg Arg Asp His
```

-continued

```
            180                 185                 190

Pro Pro Lys Ser Asp Leu Ile Glu Gly Arg Gly Asp Pro Glu Val Lys
        195                 200                 205

Arg Val Lys Leu Glu Asn Asn Val Glu Glu Ile Gln Pro Glu Gln Ala
    210                 215                 220

Glu Thr Asn Lys Gln Glu Gly Thr Asp Lys Glu Asn Lys Gly Lys Phe
225                 230                 235                 240

Glu Lys Glu Thr Glu Arg Ile Gly Gly Ser Glu Val Val Thr Asp Val
                245                 250                 255

Glu Lys Gly Ile Val Lys Phe Glu Phe Asp Gly Val Glu Tyr Thr Phe
            260                 265                 270

Lys Glu Arg Pro Ser Val Val Glu Glu Asn Glu Gly Lys Ile Glu Phe
        275                 280                 285

Arg Val Val Asn Asn Asp Asn Thr Lys Glu Asn Met Met Val Leu Thr
    290                 295                 300

Gly Leu Lys Asn Ile Phe Gln Lys Gln Leu Pro Lys Met Pro Lys Glu
305                 310                 315                 320

Tyr Ile Ala Arg Leu Val Tyr Asp Arg Ser His Leu Ser Met Ala Val
                325                 330                 335

Ile Arg Lys Pro Leu Thr Val Val Gly Gly Ile Thr Tyr Arg Pro Phe
            340                 345                 350

Asp Lys Arg Glu Phe Ala Glu Ile Val Phe Cys Ala Ile Ser Ser Thr
        355                 360                 365

Glu Gln Val Arg Gly Tyr Gly Ala His Leu Met Asn His Leu Lys Asp
    370                 375                 380

Tyr Val Arg Asn Thr Ser Asn Ile Lys Tyr Phe Leu Thr Tyr Ala Asp
385                 390                 395                 400

Asn Tyr Ala Ile Gly Tyr Phe Lys Lys Gln Gly Phe Thr Lys Glu Ile
                405                 410                 415

Thr Leu Asp Lys Ser Ile Trp Met Gly Tyr Ile Lys Asp Tyr Glu Gly
            420                 425                 430

Gly Thr Leu Met Gln Cys Asn Met Ala Ile Pro Gly Gly Gly Arg Ile
        435                 440                 445

Phe Tyr Pro Tyr Asp Val Pro Asp Tyr Ala Gly Tyr Pro Tyr Asp Val
    450                 455                 460

Pro Asp Tyr Ala Gly Ser Tyr Pro Tyr Asp Val Pro Asp Tyr Ala Ala
465                 470                 475                 480

Gln Cys Gly Arg Ser Ser
                485


<210> SEQ ID NO 26
<211> LENGTH: 486
<212> TYPE: PRT
<213> ORGANISM: Artificial Sequence
<220> FEATURE:
<223> OTHER INFORMATION: Synthetic

<400> SEQUENCE: 26

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
```

-continued

```
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Gly Thr Met His Glu Leu Pro Arg Leu
                165                 170                 175

Glu Pro Gly Ser Pro Ile Leu Gly Tyr Trp Lys Gly Arg Arg Asp His
            180                 185                 190

Pro Pro Lys Ser Asp Leu Ile Glu Gly Arg Gly Asp Pro Glu Val Lys
        195                 200                 205

Arg Val Lys Leu Glu Asn Asn Val Glu Glu Ile Gln Pro Glu Gln Ala
    210                 215                 220

Glu Thr Asn Lys Gln Glu Gly Thr Asp Lys Glu Asn Lys Gly Lys Phe
225                 230                 235                 240

Glu Lys Glu Thr Glu Arg Ile Gly Gly Ser Glu Val Val Thr Asp Val
                245                 250                 255

Glu Lys Gly Ile Val Lys Phe Glu Phe Asp Gly Val Glu Tyr Thr Phe
            260                 265                 270

Lys Glu Arg Pro Ser Val Val Glu Glu Asn Glu Gly Lys Ile Glu Phe
        275                 280                 285

Arg Val Val Asn Asn Asp Asn Thr Lys Glu Asn Met Met Val Leu Thr
    290                 295                 300

Gly Leu Lys Asn Ile Phe Gln Lys Gln Leu Pro Lys Met Pro Lys Glu
305                 310                 315                 320

Tyr Ile Ala Arg Leu Val Tyr Asp Arg Ser His Leu Ser Met Ala Val
                325                 330                 335

Ile Arg Lys Pro Leu Thr Val Val Gly Gly Ile Thr Tyr Arg Pro Phe
            340                 345                 350

Asp Lys Arg Glu Phe Ala Glu Ile Val Phe Cys Ala Ile Ser Ser Thr
        355                 360                 365

Glu Gln Val Arg Gly Tyr Gly Ala His Leu Met Asn His Leu Lys Asp
    370                 375                 380

Tyr Val Arg Asn Thr Ser Asn Ile Lys Tyr Phe Leu Thr Tyr Ala Asp
385                 390                 395                 400

Asn Tyr Ala Ile Gly Tyr Ala Lys Lys Gln Gly Phe Thr Lys Glu Ile
                405                 410                 415

Thr Leu Asp Lys Ser Ile Trp Met Gly Tyr Ile Lys Asp Tyr Glu Gly
            420                 425                 430

Gly Thr Leu Met Gln Cys Asn Met Ala Ile Pro Gly Gly Gly Arg Ile
        435                 440                 445

Phe Tyr Pro Tyr Asp Val Pro Asp Tyr Ala Gly Tyr Pro Tyr Asp Val
    450                 455                 460

Pro Asp Tyr Ala Gly Ser Tyr Pro Tyr Asp Val Pro Asp Tyr Ala Ala
465                 470                 475                 480
```

-continued

```
Gln Cys Gly Arg Ser Ser
                485


<210> SEQ ID NO 27
<211> LENGTH: 570
<212> TYPE: PRT
<213> ORGANISM: Artificial Sequence
<220> FEATURE:
<223> OTHER INFORMATION: Synthetic

<400> SEQUENCE: 27

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Leu Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
                245                 250                 255

Gly Pro Asp Ser Asp Pro Gly Ser Pro Ile Leu Gly Tyr Trp Lys Gly
            260                 265                 270

Arg Arg Asp His Pro Pro Lys Ser Asp Leu Ile Glu Gly Arg Gly Asp
        275                 280                 285

Pro Glu Val Lys Arg Val Lys Leu Glu Asn Asn Val Glu Glu Ile Gln
    290                 295                 300

Pro Glu Gln Ala Glu Thr Asn Lys Gln Glu Gly Thr Asp Lys Glu Asn
305                 310                 315                 320

Lys Gly Lys Phe Glu Lys Glu Thr Glu Arg Ile Gly Gly Ser Glu Val
                325                 330                 335

Val Thr Asp Val Glu Lys Gly Ile Val Lys Phe Glu Phe Asp Gly Val
            340                 345                 350
```

-continued

```
Glu Tyr Thr Phe Lys Glu Arg Pro Ser Val Val Glu Glu Asn Glu Gly
        355                 360                 365

Lys Ile Glu Phe Arg Val Val Asn Asn Asp Asn Thr Lys Glu Asn Met
    370                 375                 380

Met Val Leu Thr Gly Leu Lys Asn Ile Phe Gln Lys Gln Leu Pro Lys
385                 390                 395                 400

Met Pro Lys Glu Tyr Ile Ala Arg Leu Val Tyr Asp Arg Ser His Leu
                405                 410                 415

Ser Met Ala Val Ile Arg Lys Pro Leu Thr Val Val Gly Gly Ile Thr
            420                 425                 430

Tyr Arg Pro Phe Asp Lys Arg Glu Phe Ala Glu Ile Val Phe Cys Ala
        435                 440                 445

Ile Ser Ser Thr Glu Gln Val Arg Gly Tyr Gly Ala His Leu Met Asn
    450                 455                 460

His Leu Lys Asp Tyr Val Arg Asn Thr Ser Asn Ile Lys Tyr Phe Leu
465                 470                 475                 480

Thr Tyr Ala Asp Asn Tyr Ala Ile Gly Tyr Phe Lys Lys Gln Gly Phe
                485                 490                 495

Thr Lys Glu Ile Thr Leu Asp Lys Ser Ile Trp Met Gly Tyr Ile Lys
            500                 505                 510

Asp Tyr Glu Gly Gly Thr Leu Met Gln Cys Asn Met Ala Ile Pro Gly
        515                 520                 525

Gly Gly Arg Ile Phe Tyr Pro Tyr Asp Val Pro Asp Tyr Ala Gly Tyr
    530                 535                 540

Pro Tyr Asp Val Pro Asp Tyr Ala Gly Ser Tyr Pro Tyr Asp Val Pro
545                 550                 555                 560

Asp Tyr Ala Ala Gln Cys Gly Arg Ser Ser
                565                 570


<210> SEQ ID NO 28
<211> LENGTH: 570
<212> TYPE: PRT
<213> ORGANISM: Artificial Sequence
<220> FEATURE:
<223> OTHER INFORMATION: Synthetic

<400> SEQUENCE: 28

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140
```

-continued

```
Thr Val Ser Asn Tyr Leu Phe Asp Asp Glu Asp Thr Pro Pro Asn Pro
145                 150                 155                 160

Lys Lys Glu Ile Glu Phe Gln Leu Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
                245                 250                 255

Gly Pro Asp Ser Asp Pro Gly Ser Pro Ile Leu Gly Tyr Trp Lys Gly
            260                 265                 270

Arg Arg Asp His Pro Pro Lys Ser Asp Leu Ile Glu Gly Arg Gly Asp
        275                 280                 285

Pro Glu Val Lys Arg Val Lys Leu Glu Asn Asn Val Glu Glu Ile Gln
    290                 295                 300

Pro Glu Gln Ala Glu Thr Asn Lys Gln Glu Gly Thr Asp Lys Glu Asn
305                 310                 315                 320

Lys Gly Lys Phe Glu Lys Glu Thr Glu Arg Ile Gly Gly Ser Glu Val
                325                 330                 335

Val Thr Asp Val Glu Lys Gly Ile Val Lys Phe Glu Phe Asp Gly Val
            340                 345                 350

Glu Tyr Thr Phe Lys Glu Arg Pro Ser Val Val Glu Glu Asn Glu Gly
        355                 360                 365

Lys Ile Glu Phe Arg Val Val Asn Asn Asp Asn Thr Lys Glu Asn Met
    370                 375                 380

Met Val Leu Thr Gly Leu Lys Asn Ile Phe Gln Lys Gln Leu Pro Lys
385                 390                 395                 400

Met Pro Lys Glu Tyr Ile Ala Arg Leu Val Tyr Asp Arg Ser His Leu
                405                 410                 415

Ser Met Ala Val Ile Arg Lys Pro Leu Thr Val Val Gly Gly Ile Thr
            420                 425                 430

Tyr Arg Pro Phe Asp Lys Arg Glu Phe Ala Glu Ile Val Phe Cys Ala
        435                 440                 445

Ile Ser Ser Thr Glu Gln Val Arg Gly Tyr Gly Ala His Leu Met Asn
    450                 455                 460

His Leu Lys Asp Tyr Val Arg Asn Thr Ser Asn Ile Lys Tyr Phe Leu
465                 470                 475                 480

Thr Tyr Ala Asp Asn Tyr Ala Ile Gly Tyr Ala Lys Lys Gln Gly Phe
                485                 490                 495

Thr Lys Glu Ile Thr Leu Asp Lys Ser Ile Trp Met Gly Tyr Ile Lys
            500                 505                 510

Asp Tyr Glu Gly Gly Thr Leu Met Gln Cys Asn Met Ala Ile Pro Gly
        515                 520                 525

Gly Gly Arg Ile Phe Tyr Pro Tyr Asp Val Pro Asp Tyr Ala Gly Tyr
    530                 535                 540

Pro Tyr Asp Val Pro Asp Tyr Ala Gly Ser Tyr Pro Tyr Asp Val Pro
545                 550                 555                 560
```

-continued

```
Asp Tyr Ala Ala Gln Cys Gly Arg Ser Ser
                565                 570


<210> SEQ ID NO 29
<211> LENGTH: 8708
<212> TYPE: DNA
<213> ORGANISM: Artificial Sequence
<220> FEATURE:
<223> OTHER INFORMATION: Synthetic

<400> SEQUENCE: 29

gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840

tagtaacaaa ggtcaaagac agttgactgt atcgaactat ctattcgatg atgaagatac    900

cccaccaaac ccaaaaaaag agatcgaatt ccaggagaat ttgtattttc aaggtctgac    960

caccatgttt atggccagaa caaagcaaac agcaagaaag tccactggtg gtaaggcccc   1020

aagaaagcaa ttagcttcta aggctgccag aaaatccgcc ccatctaccg gtggtgttaa   1080

gaagcctcac agatataagc caggtactgt tgctttgaga gaaatcagaa gattccaaaa   1140

atctactgaa cccgggtccc ctatactagg ttattggaaa ggtcgacgcg accatcctcc   1200

aaaatcggat ctgatcgaag gtcgtggagg gccccaacgc aatagtttag taaatatcaa   1260

actaaacgct aattcgccat cgaaaaagac cacaacaaga ccaaatacgt ccaggatcaa   1320

taaaccatgg agaatatccc attcgccgca gcaaagaaac ccgaattcaa aaataccttc   1380

acctgtaaga gaaaaattga acagattacc tgtaaacaat aagaagtttt tggatatgga   1440

aagctccaaa attccatcac ctataaggaa agcgacttct tccaaaatga tacacgaaaa   1500

taagaagcta cctaaattta aatccctatc actcgatgac tttgaactgg ggaagaaatt   1560

aggaaagggt aaattcggta aagtttattg cgttcggcac aggagtacag gatatatttg   1620

cgcactgaaa gtaatggaga aggaagaaat aataaagtat aatttacaga aacaattcag   1680

aagggaggta gaaatacaaa catcgctaaa tcatccgaat ctaactaaat catacggcta   1740

ttttcatgat gaaaaaagag tgtacctgct aatggaatac ttagtcaatg gggaaatgta   1800

taaactattg aggttacacg gacccttcaa cgatatttta gcatcagatt atatttatca   1860

aattgccaat gccctagatt atatgcataa aaagaatatt attcatagag atattaaacc   1920

tgaaaatata ctaatagggt tcaataatgt cattaagtta acggacttcg gatggagtat   1980
```

-continued

```
aataaatccg ccagaaaata gaaggaaaac tgtctgtggg acaattgact acctttctcc   2040
agaaatggtg gagtcaaggg aatatgatca cactatagat gcatgggctc ttggcgtcct   2100
ggcgtttgaa ctactgaccg gtgcccctcc gttcgaagaa gaaatgaaag atactacata   2160
taaaaggata gcagcactgg atatcaaaat gcccagtaac atttctcagg atgcgcaaga   2220
tttaatactt aaactactaa aatacgaccc caaagataga atgcgccttg gagacgtaaa   2280
aatgcatcct tggatactaa gaaacaagcc cttttgggaa aataagcggt tagagctcat   2340
ggcaattccc ggtggcggcc gcatctttta cccatacgat gttcctgact atgcgggcta   2400
tccctatgac gtcccggact atgcaggatc ctatccatat gacgttccag attacgctgc   2460
tcagtgcggc cgctctagct agaactagtg gatcccccga taccgtcgac ctgcagagat   2520
ctatgaatcg tagatactga aaaaccccgc aagttcactt caactgtgca tcgtgcacca   2580
tctcaatttc tttcatttat acatcgtttt gccttctttt atgtaactat actcctctaa   2640
gtttcaatct tggccatgta acctctgatc tatagaattt tttaaatgac tagaattaat   2700
gcccatcttt tttttggacc taaattcttc atgaaaatat attacgaggg cttattcaga   2760
agctttggac ttcttcgcca gaggtttggt caagtctcca atcaaggttg tcggcttgtc   2820
taccttgcca gaaatttacg aaaagatgga aaagggtcaa atcgttggta gatacgttgt   2880
tgacacttct aaataagcga atttcttatg atttatgatt tttattatta aataagttat   2940
aaaaaaaata agtgtataca aattttaaag tgactcttag gttttaaaac gaaaattctt   3000
attcttgagt aactctttcc tgtaggtcag gttgctttct caggtatagc atgaggtcgc   3060
tcttattgac cacacctcta ccggcatgcc gagcaaatgc ctgcaaatcg ctccccattt   3120
cacccaattg tagatatgct aactccagca atgagttgat gaatctcggt gtgtatttta   3180
tgtcctcaga ggacaacacc tgttgtaatc gttcttccac acggatcctg gcgtaatagc   3240
gaagaggccc gcaccgatcg cccttcccaa cagttgcgca gcctgaatgg cgaatggcgc   3300
ctgatgcggt attttctcct tacgcatctg tgcggtattt cacaccgcat atatcgctgg   3360
gccattctca tgaagaatat cttgaattta ttgtcatatt actagttggt gtggaagtcc   3420
atatatcggt gatcaatata gtggttgaca tgctggctag tcaacattga gccttttgat   3480
catgcaaata tattacggta ttttacaatc aaatatcaaa cttaactatt gactttataa   3540
cttatttagg tggtaacatt cttataaaaa agaaaaaaat tactgcaaaa cagtactagc   3600
ttttaacttg tatcctaggt tatctatgct gtctcaccat agagaatatt acctatttca   3660
gaatgtatgt ccatgattcg ccgggtaaat acatataata cacaaatctg gcttaataaa   3720
gtctataata tatctcataa agaagtgcta aattggctag tgctatatat ttttaagaaa   3780
atttcttttg actaagtcca tatcgacttt gtaaaagttc actttagcat acatatatta   3840
cacgagccag aaattgtaac ttttgcctaa aatcacaaat tgcaaaattt aattgcttgc   3900
aaaaggtcac atgcttataa tcaacttttt taaaaattta aaatactttt ttattttta    3960
tttttaaaca taaatgaaat aatttattta ttgtttatga ttaccgaaac ataaaacctg   4020
ctcaagaaaa agaaactgtt ttgtccttgg aaaaaaagca ctacctagga gcggccaaaa   4080
tgccgaggct ttcatagctt aaactcttta cagaaaatag gcattataga tcagttcgag   4140
ttttcttatt cttccttccg gttttatcgt cacagtttta cagtaaataa gtatcacctc   4200
ttagagttcg atgataagct gtcaaacatg agaattaatt ccacatgtta aaatagtgaa   4260
ggagcatgtt cggcacacag tggaccgaac gtggggtaag tgcactaggg tccggttaaa   4320
cggatctcgc attgatgagg caacgctaat tatcaacata tagattgtta tctatctgca   4380
```

-continued

```
tgaacacgaa atctttactt gacgacttga ggctgatggt gtttatgcaa agaaaccact   4440
gtgtttaata tgtgtcactg tttgatatta ctgtcagcgt agaagataat agtaaaagcg   4500
gttaataagt gtatttgaga taagtgtgat aaagttttta cagcgaaaag acgataaata   4560
caagaaaatg attacgagga tacggagaga ggtatgtaca tgtgtattta tatactaagc   4620
tgccggcggt tgtttgcaag accgagaaaa ggctagcaag aatcgggtca ttgtagcgta   4680
tgcgcctgtg aacattctct tcaacaagtt tgattccatt gcggtgaaat ggtaaaagtc   4740
aaccccctgc gatgtatatt ttcctgtaca atcaatcaaa aagccaaatg atttagcatt   4800
atctttacat cttgttattt tacagatttt atgtttagat cttttatgct tgcttttcaa   4860
aaggcttgca ggcaagtgca caaacaatac ttaaataaat actactcagt aataacctat   4920
ttcttagcat tttgacgaa atttgctatt ttgttagagt cttttacacc atttgtctcc   4980
acacctccgc ttacatcaac accaataacg ccatttaatc taagcgcatc accaacattt   5040
tctggcgtca gtccaccagc taacataaaa tgtaagctct cggggctctc ttgccttcca   5100
acccagtcag aaatcgagtt ccaatccaaa agttcacctg tcccacctgc ttctgaatca   5160
aacaagggaa taaacgaatg aggtttctgt gaagctgcac tgagtagtat gttgcagtct   5220
tttggaaata cgagtctttt aataactggc aaaccgagga actcttggta ttcttgccac   5280
gactcatctc catgcagttg gacgatatca atgccgtaat cattgaccag agccaaaaca   5340
tcctccttag gttgattacg aaacacgcca accaagtatt tcggagtgcc tgaactattt   5400
ttatatgctt ttacaagact tgaaattttc cttgcaataa ccgggtcaat tgttctcttt   5460
ctattgggca cacatataat acccagcaag tcagcatcgg aatctagtgc acattctgcg   5520
gcctctgtgc tctgcaagcc gcaaactttc accaatggac cagaactacc tgtgaaatta   5580
ataacagaca tactccaagc tgcctttgtg tgcttaatca cgtatactca cgtgctcaat   5640
agtcaccaat gccctccctc ttggccctct ccttttcttt tttcgaccga attaattctt   5700
gaagacgaaa gggcctcgtg atacgcctat ttttataggt taatgtcatg ataataatgg   5760
tttcttagac gtcaggtggc acttttcggg gaaatgtgcg cggaacccct atttgtttat   5820
ttttctaaat acattcaaat atgtatccgc tcatgagaca ataaccctga taaatgcttc   5880
aataatattg aaaaaggaag agtatgagta ttcaacattt ccgtgtcgcc cttattccct   5940
tttttgcggc attttgcctt cctgtttttg ctcacccaga aacgctggtg aaagtaaaag   6000
atgctgaaga tcagttgggt gcacgagtgg gttacatcga actggatctc aacagcggta   6060
agatccttga gagttttcgc cccgaagaac gttttccaat gatgagcact tttaaagttc   6120
tgctatgtgg cgcggtatta tcccgtattg acgccgggca agagcaactc ggtcgccgca   6180
tacactattc tcagaatgac ttggttgagt actcaccagt cacagaaaag catcttacgg   6240
atggcatgac agtaagagaa ttatgcagtg ctgccataac catgagtgat aacactgcgg   6300
ccaacttact tctgacaacg atcggaggac cgaaggagct aaccgctttt ttgcacaaca   6360
tgggggatca tgtaactcgc cttgatcgtt gggaaccgga gctgaatgaa gccataccaa   6420
acgacgagcg tgacaccacg atgcctgtag caatggcaac aacgttgcgc aaactattaa   6480
ctggcgaact acttactcta gcttcccggc aacaattaat agactggatg gaggcggata   6540
aagttgcagg accacttctg cgctcggccc ttccggctgg ctggtttatt gctgataaat   6600
ctggagccgg tgagcgtggg tctcgcggta tcattgcagc actggggcca gatggtaagc   6660
cctcccgtat cgtagttatc tacacgacgg ggagtcaggc aactatggat gaacgaaata   6720
```

-continued

```
gacagatcgc tgagataggt gcctcactga ttaagcattg gtaactgtca gaccaagttt   6780
actcatatat actttagatt gatttaaaac ttcattttta atttaaaagg atctaggtga   6840
agatcctttt tgataatctc atgaccaaaa tcccttaacg tgagttttcg ttccactgag   6900
cgtcagaccc cgtagaaaag atcaaaggat cttcttgaga tccttttttt ctgcgcgtaa   6960
tctgctgctt gcaaacaaaa aaaccaccgc taccagcggt ggtttgtttg ccggatcaag   7020
agctaccaac tctttttccg aaggtaactg gcttcagcag agcgcagata ccaaatactg   7080
tccttctagt gtagccgtag ttaggccacc acttcaagaa ctctgtagca ccgcctacat   7140
acctcgctct gctaatcctg ttaccagtgg ctgctgccag tggcgataag tcgtgtctta   7200
ccgggttgga ctcaagacga tagttaccgg ataaggcgca gcggtcgggc tgaacggggg   7260
gttcgtgcac acagcccagc ttggagcgaa cgacctacac cgaactgaga tacctacagc   7320
gtgagctatg agaaagcgcc acgcttcccg aagggagaaa ggcggacagg tatccggtaa   7380
gcggcagggt cggaacagga gagcgcacga gggagcttcc agggggaaac gcctggtatc   7440
tttatagtcc tgtcgggttt cgccacctct gacttgagcg tcgatttttg tgatgctcgt   7500
caggggggcg gagcctatgg aaaaacgcca gcaacgcggc ctttttacgg ttcctggcct   7560
tttgctggcc ttttgctcac atgttctttc ctgcgttatc ccctgattct gtggataacc   7620
gtattaccgc ctttgagtga gctgataccg ctcgccgcag ccgaacgacc gagcgcagcg   7680
agtcagtgag cgaggaagcg gaagagcgcc caatacgcaa accgcctctc cccgcgcgtt   7740
ggccgattca ttaatgcagg atccgggatc gaagaaatga tggtaaatga aataggaaat   7800
caaggagcat gaaggcaaaa gacaaatata agggtcgaac gaaaaataaa gtgaaaagtg   7860
ttgatatgat gtatttggct ttgcggcgcc gaaaaaacga gtttacgcaa ttgcacaatc   7920
atgctgactc tgtggcggac ccgcgctctt gccggcccgg cgataacgct gggcgtgagg   7980
ctgtgcccgg cggagttttt tgcgcctgca ttttccaagg tttaccctgc gctaaggggc   8040
gagattggag aagcaataag aatgccggtt ggggttgcga tgatgacgac cacgacaact   8100
ggtgtcatta tttaagttgc cgaaagaacc tgagtgcatt tgcaacatga gtatactaga   8160
agaatgagcc aagacttgcg agacgcgagt ttgccggtgg tgcgaacaat agagcgacca   8220
tgaccttgaa ggtgagacgc gcataaccgc tagagtactt tgaagaggaa acagcaatag   8280
ggttgctacc agtataaata gacaggtaca tacaacactg gaaatggttg tctgtttgag   8340
tacgctttca attcatttgg gtgtgcactt tattatgtta caatatggaa gggaacttta   8400
cacttctcct atgcacatat attaattaaa gtccaatgct agtagagaag gggggtaaca   8460
cccctccgcg ctcttttccg attttttttct aaaccgtgga atatttcgga tatcctttttg   8520
ttgtttccgg gtgtacaata tggacttcct cttttctggc aaccaaaccc atacatcggg   8580
attcctataa taccttcgtt ggtctcccta acatgtaggt ggcggagggg agatatacaa   8640
tagaacagat accagacaag acataatggg ctaaacaaga ctacaccaat tacactgcct   8700
cattgatg                                                            8708
```

<210> SEQ ID NO 30
<211> LENGTH: 682
<212> TYPE: PRT
<213> ORGANISM: Artificial Sequence
<220> FEATURE:
<223> OTHER INFORMATION: Synthetic

<400> SEQUENCE: 30

Met Lys Leu Leu Ser Ser Ile Glu Gln Ala Cys Asp Ile Cys Arg Leu

-continued

```
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Glu Asn Leu Tyr Phe Gln Gly Leu Thr
                165                 170                 175

Thr Met Phe Met Ala Arg Thr Lys Gln Thr Ala Arg Lys Ser Thr Gly
            180                 185                 190

Gly Lys Ala Pro Arg Lys Gln Leu Ala Ser Lys Ala Ala Arg Lys Ser
        195                 200                 205

Ala Pro Ser Thr Gly Gly Val Lys Lys Pro His Arg Tyr Lys Pro Gly
    210                 215                 220

Thr Val Ala Leu Arg Glu Ile Arg Arg Phe Gln Lys Ser Thr Glu Pro
225                 230                 235                 240

Gly Ser Pro Ile Leu Gly Tyr Trp Lys Gly Arg Arg Asp His Pro Pro
                245                 250                 255

Lys Ser Asp Leu Ile Glu Gly Arg Gly Gly Pro Gln Arg Asn Ser Leu
            260                 265                 270

Val Asn Ile Lys Leu Asn Ala Asn Ser Pro Ser Lys Lys Thr Thr Thr
        275                 280                 285

Arg Pro Asn Thr Ser Arg Ile Asn Lys Pro Trp Arg Ile Ser His Ser
    290                 295                 300

Pro Gln Gln Arg Asn Pro Asn Ser Lys Ile Pro Ser Pro Val Arg Glu
305                 310                 315                 320

Lys Leu Asn Arg Leu Pro Val Asn Asn Lys Lys Phe Leu Asp Met Glu
                325                 330                 335

Ser Ser Lys Ile Pro Ser Pro Ile Arg Lys Ala Thr Ser Ser Lys Met
            340                 345                 350

Ile His Glu Asn Lys Lys Leu Pro Lys Phe Lys Ser Leu Ser Leu Asp
        355                 360                 365

Asp Phe Glu Leu Gly Lys Lys Leu Gly Lys Gly Lys Phe Gly Lys Val
    370                 375                 380

Tyr Cys Val Arg His Arg Ser Thr Gly Tyr Ile Cys Ala Leu Lys Val
385                 390                 395                 400

Met Glu Lys Glu Glu Ile Ile Lys Tyr Asn Leu Gln Lys Gln Phe Arg
                405                 410                 415

Arg Glu Val Glu Ile Gln Thr Ser Leu Asn His Pro Asn Leu Thr Lys
            420                 425                 430
```

-continued

```
Ser Tyr Gly Tyr Phe His Asp Glu Lys Arg Val Tyr Leu Leu Met Glu
        435                 440                 445

Tyr Leu Val Asn Gly Glu Met Tyr Lys Leu Leu Arg Leu His Gly Pro
    450                 455                 460

Phe Asn Asp Ile Leu Ala Ser Asp Tyr Ile Tyr Gln Ile Ala Asn Ala
465                 470                 475                 480

Leu Asp Tyr Met His Lys Lys Asn Ile Ile His Arg Asp Ile Lys Pro
                485                 490                 495

Glu Asn Ile Leu Ile Gly Phe Asn Asn Val Ile Lys Leu Thr Asp Phe
            500                 505                 510

Gly Trp Ser Ile Ile Asn Pro Pro Glu Asn Arg Arg Lys Thr Val Cys
        515                 520                 525

Gly Thr Ile Asp Tyr Leu Ser Pro Glu Met Val Glu Ser Arg Glu Tyr
    530                 535                 540

Asp His Thr Ile Asp Ala Trp Ala Leu Gly Val Leu Ala Phe Glu Leu
545                 550                 555                 560

Leu Thr Gly Ala Pro Pro Phe Glu Glu Glu Met Lys Asp Thr Thr Tyr
                565                 570                 575

Lys Arg Ile Ala Ala Leu Asp Ile Lys Met Pro Ser Asn Ile Ser Gln
            580                 585                 590

Asp Ala Gln Asp Leu Ile Leu Lys Leu Leu Lys Tyr Asp Pro Lys Asp
        595                 600                 605

Arg Met Arg Leu Gly Asp Val Lys Met His Pro Trp Ile Leu Arg Asn
    610                 615                 620

Lys Pro Phe Trp Glu Asn Lys Arg Leu Glu Leu Met Ala Ile Pro Gly
625                 630                 635                 640

Gly Gly Arg Ile Phe Tyr Pro Tyr Asp Val Pro Asp Tyr Ala Gly Tyr
                645                 650                 655

Pro Tyr Asp Val Pro Asp Tyr Ala Gly Ser Tyr Pro Tyr Asp Val Pro
            660                 665                 670

Asp Tyr Ala Ala Gln Cys Gly Arg Ser Ser
        675                 680
```

<210> SEQ ID NO 31
<211> LENGTH: 8708
<212> TYPE: DNA
<213> ORGANISM: Artificial Sequence
<220> FEATURE:
<223> OTHER INFORMATION: Synthetic

<400> SEQUENCE: 31

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600
```

-continued

```
agtggaatca aggctagaaa gactggaaca gctatttcta ctgatttttc ctcgagaaga    660
ccttgacatg attttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
tagtaacaaa ggtcaaagac agttgactgt atcgaactat ctattcgatg atgaagatac    900
cccaccaaac ccaaaaaaag agatcgaatt ccaggagaat ttgtattttc aaggtctgac    960
caccatgttt atggccagaa caaagcaaac agcaagaaag tccactggtg gtaaggcccc   1020
aagaaagcaa ttagcttcta aggctgccag aaaatccgcc ccatctaccg gtggtgttaa   1080
gaagcctcac agatataagc caggtactgt tgctttgaga gaaatcagaa gattccaaaa   1140
atctactgaa cccgggtccc ctatactagg ttattggaaa ggtcgacgcg accatcctcc   1200
aaaatcggat ctgatcgaag gtcgtggagg gccccaacgc aatagtttag taaatatcaa   1260
actaaacgct aattcgccat cgaaaaagac cacaacaaga ccaaatacgt ccaggatcaa   1320
taaaccatgg agaatatccc attcgccgca gcaaagaaac ccgaattcaa aaataccttc   1380
acctgtaaga gaaaaattga acagattacc tgtaaacaat aagaagtttt tggatatgga   1440
aagctccaaa attccatcac ctataaggaa agcgacttct tccaaaatga tacacgaaaa   1500
taagaagcta cctaaattta aatccctatc actcgatgac tttgaactgg ggaagaaatt   1560
aggaaagggt aaattcggta aagtttattg cgttcggcac aggagtacag gatatatttg   1620
cgcactgaaa gtaatggaga aggaagaaat aataaagtat aatttacaga aacaattcag   1680
aaggcagctg gaaatacaaa catcgctaaa tcatccgaat ctaactaaat catacggcta   1740
ttttcatgat gaaaaaagag tgtacctgct aatggaatac ttagtcaatg gggaaatgta   1800
taaactattg aggttacacg gacccttcaa cgatatttta gcatcagatt atatttatca   1860
aattgccaat gccctagatt atatgcataa aaagaatatt attcatagag atattaaacc   1920
tgaaaatata ctaatagggt tcaataatgt cattaagtta acggacttcg gatggagtat   1980
aataaatccg ccagaaaata gaaggaaaac tgtctgtggg acaattgact acctttctcc   2040
agaaatggtg gagtcaaggg aatatgatca cactatagat gcatgggctc ttggcgtcct   2100
ggcgtttgaa ctactgaccg gtgcccctcc gttcgaagaa gaaatgaaag atactacata   2160
taaaaggata gcagcactgg atatcaaaat gcccagtaac atttctcagg atgcgcaaga   2220
tttaatactt aaactactaa aatacgaccc caaagataga atgcgccttg gagacgtaaa   2280
aatgcatcct tggatactaa gaaacaagcc cttttgggaa aataagcggt tagagctcat   2340
ggcaattccc ggtggcggcc gcatctttta cccatacgat gttcctgact atgcgggcta   2400
tccctatgac gtcccggact atgcaggatc ctatccatat gacgttccag attacgctgc   2460
tcagtgcggc cgctctagct agaactagtg gatcccccga taccgtcgac ctgcagagat   2520
ctatgaatcg tagatactga aaaaccccgc aagttcactt caactgtgca tcgtgcacca   2580
tctcaatttc tttcatttat acatcgtttt gccttctttt atgtaactat actcctctaa   2640
gtttcaatct tggccatgta acctctgatc tatagaattt tttaaatgac tagaattaat   2700
gcccatcttt tttttggacc taaattcttc atgaaaatat attacgaggg cttattcaga   2760
agctttggac ttcttcgcca gaggtttggt caagtctcca atcaaggttg tcggcttgtc   2820
taccttgcca gaaatttacg aaaagatgga aaagggtcaa atcgttggta gatacgttgt   2880
tgacacttct aaataagcga atttcttatg atttatgatt tttattatta aataagttat   2940
aaaaaaaata agtgtataca aattttaaag tgactcttag gttttaaaac gaaaattctt   3000
```

-continued attcttgagt aactctttcc tgtaggtcag gttgctttct caggtatagc atgaggtcgc 3060
tcttattgac cacacctcta ccggcatgcc gagcaaatgc ctgcaaatcg ctccccattt 3120
cacccaattg tagatatgct aactccagca atgagttgat gaatctcggt gtgtatttta 3180
tgtcctcaga ggacaacacc tgttgtaatc gttcttccac acggatcctg gcgtaatagc 3240
gaagaggccc gcaccgatcg cccttcccaa cagttgcgca gcctgaatgg cgaatggcgc 3300
ctgatgcggt attttctcct tacgcatctg tgcggtattt cacaccgcat atatcgctgg 3360
gccattctca tgaagaatat cttgaattta ttgtcatatt actagttggt gtggaagtcc 3420
atatatcggt gatcaatata gtggttgaca tgctggctag tcaacattga gccttttgat 3480
catgcaaata tattacggta ttttacaatc aaatatcaaa cttaactatt gactttataa 3540
cttatttagg tggtaacatt cttataaaaa agaaaaaaat tactgcaaaa cagtactagc 3600
ttttaacttg tatcctaggt tatctatgct gtctcaccat agagaatatt acctatttca 3660
gaatgtatgt ccatgattcg ccgggtaaat acatataata cacaaatctg gcttaataaa 3720
gtctataata tatctcataa agaagtgcta aattggctag tgctatatat ttttaagaaa 3780
atttcttttg actaagtcca tatcgacttt gtaaaagttc actttagcat acatatatta 3840
cacgagccag aaattgtaac ttttgcctaa aatcacaaat tgcaaaattt aattgcttgc 3900
aaaaggtcac atgcttataa tcaacttttt taaaaattta aaatactttt ttattttttta 3960 tttttaaaca taaatgaaat aatttattta ttgtttatga ttaccgaaac ataaaacctg 4020
ctcaagaaaa agaaactgtt ttgtccttgg aaaaaaagca ctacctagga gcggccaaaa 4080
tgccgaggct ttcatagctt aaactcttta cagaaaatag gcattataga tcagttcgag 4140
ttttcttatt cttccttccg gttttatcgt cacagtttta cagtaaataa gtatcacctc 4200
ttagagttcg atgataagct gtcaaacatg agaattaatt ccacatgtta aaatagtgaa 4260
ggagcatgtt cggcacacag tggaccgaac gtggggtaag tgcactaggg tccggttaaa 4320
cggatctcgc attgatgagg caacgctaat tatcaacata tagattgtta tctatctgca 4380
tgaacacgaa atctttactt gacgacttga ggctgatggt gtttatgcaa agaaaccact 4440
gtgtttaata tgtgtcactg tttgatatta ctgtcagcgt agaagataat agtaaaagcg 4500
gttaataagt gtatttgaga taagtgtgat aaagttttta cagcgaaaag acgataaata 4560
caagaaaatg attacgagga tacggagaga ggtatgtaca tgtgtattta tatactaagc 4620
tgccggcggt tgtttgcaag accgagaaaa ggctagcaag aatcgggtca ttgtagcgta 4680
tgcgcctgtg aacattctct tcaacaagtt tgattccatt gcggtgaaat ggtaaaagtc 4740
aaccccctgc gatgtatatt ttcctgtaca atcaatcaaa aagccaaatg atttagcatt 4800
atctttacat cttgttattt tacagatttt atgtttagat cttttatgct tgcttttcaa 4860
aaggcttgca ggcaagtgca caaacaatac ttaaataaat actactcagt aataacctat 4920
ttcttagcat ttttgacgaa atttgctatt ttgttagagt cttttacacc atttgtctcc 4980
acacctccgc ttacatcaac accaataacg ccatttaatc taagcgcatc accaacattt 5040
tctggcgtca gtccaccagc taacataaaa tgtaagctct cggggctctc ttgccttcca 5100
acccagtcag aaatcgagtt ccaatccaaa agttcacctg tcccacctgc ttctgaatca 5160
aacaagggaa taaacgaatg aggtttctgt gaagctgcac tgagtagtat gttgcagtct 5220
tttggaaata cgagtctttt aataactggc aaaccgagga actcttggta ttcttgccac 5280
gactcatctc catgcagttg gacgatatca atgccgtaat cattgaccag agccaaaaca 5340

-continued

```
tcctccttag gttgattacg aaacacgcca accaagtatt tcggagtgcc tgaactattt   5400
ttatatgctt ttacaagact tgaaattttc cttgcaataa ccgggtcaat tgttctcttt   5460
ctattgggca cacatataat acccagcaag tcagcatcgg aatctagtgc acattctgcg   5520
gcctctgtgc tctgcaagcc gcaaactttc accaatggac cagaactacc tgtgaaatta   5580
ataacagaca tactccaagc tgcctttgtg tgcttaatca cgtatactca cgtgctcaat   5640
agtcaccaat gccctccctc ttggccctct ccttttcttt tttcgaccga attaattctt   5700
gaagacgaaa gggcctcgtg atacgcctat ttttataggt taatgtcatg ataataatgg   5760
tttcttagac gtcaggtggc acttttcggg gaaatgtgcg cggaacccct atttgtttat   5820
ttttctaaat acattcaaat atgtatccgc tcatgagaca ataaccctga taaatgcttc   5880
aataatattg aaaaaggaag agtatgagta ttcaacattt ccgtgtcgcc cttattccct   5940
tttttgcggc attttgcctt cctgtttttg ctcacccaga aacgctggtg aaagtaaaag   6000
atgctgaaga tcagttgggt gcacgagtgg gttacatcga actggatctc aacagcggta   6060
agatccttga gagttttcgc cccgaagaac gttttccaat gatgagcact tttaaagttc   6120
tgctatgtgg cgcggtatta tcccgtattg acgccgggca agagcaactc ggtcgccgca   6180
tacactattc tcagaatgac ttggttgagt actcaccagt cacagaaaag catcttacgg   6240
atggcatgac agtaagagaa ttatgcagtg ctgccataac catgagtgat aacactgcgg   6300
ccaacttact tctgacaacg atcggaggac cgaaggagct aaccgctttt ttgcacaaca   6360
tgggggatca tgtaactcgc cttgatcgtt gggaaccgga gctgaatgaa gccataccaa   6420
acgacgagcg tgacaccacg atgcctgtag caatggcaac aacgttgcgc aaactattaa   6480
ctggcgaact acttactcta gcttcccggc aacaattaat agactggatg gaggcggata   6540
aagttgcagg accacttctg cgctcggccc ttccggctgg ctggtttatt gctgataaat   6600
ctggagccgg tgagcgtggg tctcgcggta tcattgcagc actggggcca gatggtaagc   6660
cctcccgtat cgtagttatc tacacgacgg ggagtcaggc aactatggat gaacgaaata   6720
gacagatcgc tgagataggt gcctcactga ttaagcattg gtaactgtca gaccaagttt   6780
actcatatat actttagatt gatttaaaac ttcattttta atttaaaagg atctaggtga   6840
agatcctttt tgataatctc atgaccaaaa tcccttaacg tgagttttcg ttccactgag   6900
cgtcagaccc cgtagaaaag atcaaaggat cttcttgaga tccttttttt ctgcgcgtaa   6960
tctgctgctt gcaaacaaaa aaaccaccgc taccagcggt ggtttgtttg ccggatcaag   7020
agctaccaac tctttttccg aaggtaactg gcttcagcag agcgcagata ccaaatactg   7080
tccttctagt gtagccgtag ttaggccacc acttcaagaa ctctgtagca ccgcctacat   7140
acctcgctct gctaatcctg ttaccagtgg ctgctgccag tggcgataag tcgtgtctta   7200
ccgggttgga ctcaagacga tagttaccgg ataaggcgca gcggtcgggc tgaacggggg   7260
gttcgtgcac acagcccagc ttggagcgaa cgacctacac cgaactgaga tacctacagc   7320
gtgagctatg agaaagcgcc acgcttcccg aagggagaaa ggcggacagg tatccggtaa   7380
gcggcagggt cggaacagga gagcgcacga gggagcttcc agggggaaac gcctggtatc   7440
tttatagtcc tgtcgggttt cgccacctct gacttgagcg tcgatttttg tgatgctcgt   7500
caggggggcg gagcctatgg aaaaacgcca gcaacgcggc ctttttacgg ttcctggcct   7560
tttgctggcc ttttgctcac atgttctttc ctgcgttatc ccctgattct gtggataacc   7620
gtattaccgc ctttgagtga gctgataccg ctcgccgcag ccgaacgacc gagcgcagcg   7680
agtcagtgag cgaggaagcg gaagagcgcc caatacgcaa accgcctctc cccgcgcgtt   7740
```

-continued

```
ggccgattca ttaatgcagg atccgggatc gaagaaatga tggtaaatga aataggaaat   7800

caaggagcat gaaggcaaaa gacaaatata agggtcgaac gaaaaataaa gtgaaaagtg   7860

ttgatatgat gtatttggct ttgcggcgcc gaaaaaacga gtttacgcaa ttgcacaatc   7920

atgctgactc tgtggcggac ccgcgctctt gccggcccgg cgataacgct gggcgtgagg   7980

ctgtgcccgg cggagttttt tgcgcctgca ttttccaagg tttaccctgc gctaaggggc   8040

gagattggag aagcaataag aatgccggtt ggggttgcga tgatgacgac cacgacaact   8100

ggtgtcatta tttaagttgc cgaaagaacc tgagtgcatt tgcaacatga gtatactaga   8160

agaatgagcc aagacttgcg agacgcgagt ttgccggtgg tgcgaacaat agagcgacca   8220

tgaccttgaa ggtgagacgc gcataaccgc tagagtactt tgaagaggaa acagcaatag   8280

ggttgctacc agtataaata gacaggtaca tacaacactg gaaatggttg tctgtttgag   8340

tacgctttca attcatttgg gtgtgcactt tattatgtta caatatggaa gggaacttta   8400

cacttctcct atgcacatat attaattaaa gtccaatgct agtagagaag gggggtaaca   8460

cccctccgcg ctcttttccg atttttttct aaaccgtgga atatttcgga tatccttttg   8520

ttgtttccgg gtgtacaata tggacttcct cttttctggc aaccaaaccc atacatcggg   8580

attcctataa taccttcgtt ggtctcccta acatgtaggt ggcggagggg agatatacaa   8640

tagaacagat accagacaag acataatggg ctaaacaaga ctacaccaat tacactgcct   8700

cattgatg                                                            8708
```

```
<210> SEQ ID NO 32
<211> LENGTH: 682
<212> TYPE: PRT
<213> ORGANISM: Artificial Sequence
<220> FEATURE:
<223> OTHER INFORMATION: Synthetic

<400> SEQUENCE: 32

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Phe Gln Glu Asn Leu Tyr Phe Gln Gly Leu Thr
                165                 170                 175

Thr Met Phe Met Ala Arg Thr Lys Gln Thr Ala Arg Lys Ser Thr Gly
```

-continued

```
            180                 185                 190

Gly Lys Ala Pro Arg Lys Gln Leu Ala Ser Lys Ala Ala Arg Lys Ser
        195                 200                 205

Ala Pro Ser Thr Gly Gly Val Lys Lys Pro His Arg Tyr Lys Pro Gly
    210                 215                 220

Thr Val Ala Leu Arg Glu Ile Arg Arg Phe Gln Lys Ser Thr Glu Pro
225                 230                 235                 240

Gly Ser Pro Ile Leu Gly Tyr Trp Lys Gly Arg Arg Asp His Pro Pro
                245                 250                 255

Lys Ser Asp Leu Ile Glu Gly Arg Gly Gly Pro Gln Arg Asn Ser Leu
            260                 265                 270

Val Asn Ile Lys Leu Asn Ala Asn Ser Pro Ser Lys Lys Thr Thr Thr
        275                 280                 285

Arg Pro Asn Thr Ser Arg Ile Asn Lys Pro Trp Arg Ile Ser His Ser
    290                 295                 300

Pro Gln Gln Arg Asn Pro Asn Ser Lys Ile Pro Ser Pro Val Arg Glu
305                 310                 315                 320

Lys Leu Asn Arg Leu Pro Val Asn Asn Lys Lys Phe Leu Asp Met Glu
                325                 330                 335

Ser Ser Lys Ile Pro Ser Pro Ile Arg Lys Ala Thr Ser Ser Lys Met
            340                 345                 350

Ile His Glu Asn Lys Lys Leu Pro Lys Phe Lys Ser Leu Ser Leu Asp
        355                 360                 365

Asp Phe Glu Leu Gly Lys Lys Leu Gly Lys Gly Lys Phe Gly Lys Val
    370                 375                 380

Tyr Cys Val Arg His Arg Ser Thr Gly Tyr Ile Cys Ala Leu Lys Val
385                 390                 395                 400

Met Glu Lys Glu Glu Ile Ile Lys Tyr Asn Leu Gln Lys Gln Phe Arg
                405                 410                 415

Arg Gln Leu Glu Ile Gln Thr Ser Leu Asn His Pro Asn Leu Thr Lys
            420                 425                 430

Ser Tyr Gly Tyr Phe His Asp Glu Lys Arg Val Tyr Leu Leu Met Glu
        435                 440                 445

Tyr Leu Val Asn Gly Glu Met Tyr Lys Leu Leu Arg Leu His Gly Pro
    450                 455                 460

Phe Asn Asp Ile Leu Ala Ser Asp Tyr Ile Tyr Gln Ile Ala Asn Ala
465                 470                 475                 480

Leu Asp Tyr Met His Lys Lys Asn Ile Ile His Arg Asp Ile Lys Pro
                485                 490                 495

Glu Asn Ile Leu Ile Gly Phe Asn Asn Val Ile Lys Leu Thr Asp Phe
            500                 505                 510

Gly Trp Ser Ile Ile Asn Pro Pro Glu Asn Arg Arg Lys Thr Val Cys
        515                 520                 525

Gly Thr Ile Asp Tyr Leu Ser Pro Glu Met Val Glu Ser Arg Glu Tyr
    530                 535                 540

Asp His Thr Ile Asp Ala Trp Ala Leu Gly Val Leu Ala Phe Glu Leu
545                 550                 555                 560

Leu Thr Gly Ala Pro Pro Phe Glu Glu Glu Met Lys Asp Thr Thr Tyr
                565                 570                 575

Lys Arg Ile Ala Ala Leu Asp Ile Lys Met Pro Ser Asn Ile Ser Gln
            580                 585                 590

Asp Ala Gln Asp Leu Ile Leu Lys Leu Leu Lys Tyr Asp Pro Lys Asp
        595                 600                 605
```

-continued

```
Arg Met Arg Leu Gly Asp Val Lys Met His Pro Trp Ile Leu Arg Asn
    610                 615                 620

Lys Pro Phe Trp Glu Asn Lys Arg Leu Glu Leu Met Ala Ile Pro Gly
625                 630                 635                 640

Gly Gly Arg Ile Phe Tyr Pro Tyr Asp Val Pro Asp Tyr Ala Gly Tyr
                645                 650                 655

Pro Tyr Asp Val Pro Asp Tyr Ala Gly Ser Tyr Pro Tyr Asp Val Pro
            660                 665                 670

Asp Tyr Ala Ala Gln Cys Gly Arg Ser Ser
        675                 680
```

<210> SEQ ID NO 33
<211> LENGTH: 8267
<212> TYPE: DNA
<213> ORGANISM: Artificial Sequence
<220> FEATURE:
<223> OTHER INFORMATION: Synthetic

<400> SEQUENCE: 33

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840

tagtaacaaa ggtcaaagac agttgactgt atcgaactat ctattcgatg atgaagatac    900

cccaccaaac ccaaaaaaag agatcgaatt ggagaatttg tattttcagg gcgaattcca    960

gctgaccacc atggcaatga aagtgaatat ggagtacaca aaggaaaaga aagttggtga   1020

gggtacttat gcggttgttt acttgggttg tcaacactct actggaagaa agattgctat   1080

taaggagatc aaaacatccg aatttaaaga tggtttagat atgtcagcta tccgtgaagt   1140

taagtacctc caagaaatgc agcatccgaa cgtcatagaa ctaatagaca tatttatggc   1200

ttatgataat ttaaatctcg ttctggagtt cctaccaact gatctagagg tggtaataaa   1260

agacaaatca atactgttta caccagcaga tattaaggca tggatgctta tgactttgag   1320

gggcgtgtat cattgccaca gaaatttcat tttgcacagg gatctgaaac caaacaattt   1380

attattttca cctgatggcc agataaaagt agcagatttc ggtctagcaa gggcgatacc   1440

ggccccacat gagatactga caagtaacgt cgtaacaaga tggtatagag cgccagaatt   1500

gttgtttgga gctaaacatt acacatcggc tattgatatc tggtcagtag gcgttatatt   1560

cgcggaatta atgctaagga taccttattt accaggacag aatgatgtcg atcaaatgga   1620
```

-continued

```
agtaacgttc agggccttag ggacacctac agatagagat tggcccgaag tttcttcctt   1680
tatgacgtat aacaagttac aaatatatcc gccccccttca agagatgaat tgaggaaaag   1740
gttcattgct gctagcgaat acgccttaga ttttatgtgt ggaatgctaa cgatgaaccc   1800
acaaaagagg tggaccgctg ttcagtgttt agaaagtgat tatttcaaag aattaccacc   1860
accaagtgac ccgtcttcaa taaaaatacg taacgtcatg gcaattcccg gtggcggccg   1920
catcttttac ccatacgatg ttcctgacta tgcgggctat ccctatgacg tcccggacta   1980
tgcaggatcc tatccatatg acgttccaga ttacgctgct cagtgcggcc gctctagcta   2040
gaactagtgg atcccccgat accgtcgacc tgcagagatc tatgaatcgt agatactgaa   2100
aaaccccgca agttcacttc aactgtgcat cgtgcaccat ctcaatttct ttcatttata   2160
catcgttttg ccttctttta tgtaactata ctcctctaag tttcaatctt ggccatgtaa   2220
cctctgatct atagaatttt ttaaatgact agaattaatg cccatctttt ttttggacct   2280
aaattcttca tgaaaatata ttacgagggc ttattcagaa gctttggact tcttcgccag   2340
aggtttggtc aagtctccaa tcaaggttgt cggcttgtct accttgccag aaatttacga   2400
aaagatggaa aagggtcaaa tcgttggtag atacgttgtt gacacttcta aataagcgaa   2460
tttcttatga tttatgattt ttattattaa ataagttata aaaaaaaataa gtgtatacaa   2520
attttaaagt gactcttagg ttttaaaacg aaaattctta ttcttgagta actctttcct   2580
gtaggtcagg ttgctttctc aggtatagca tgaggtcgct cttattgacc acacctctac   2640
cggcatgccg agcaaatgcc tgcaaatcgc tccccatttc acccaattgt agatatgcta   2700
actccagcaa tgagttgatg aatctcggtg tgtattttat gtcctcagag gacaacacct   2760
gttgtaatcg ttcttccaca cggatcctgg cgtaatagcg aagaggcccg caccgatcgc   2820
ccttcccaac agttgcgcag cctgaatggc gaatggcgcc tgatgcggta ttttctcctt   2880
acgcatctgt gcggtatttc acaccgcata tatcgctggg ccattctcat gaagaatatc   2940
ttgaatttat tgtcatatta ctagttggtg tggaagtcca tatatcggtg atcaatatag   3000
tggttgacat gctggctagt caacattgag ccttttgatc atgcaaatat attacggtat   3060
tttacaatca aatatcaaac ttaactattg actttataac ttatttaggt ggtaacattc   3120
ttataaaaaa gaaaaaaatt actgcaaaac agtactagct tttaacttgt atcctaggtt   3180
atctatgctg tctcaccata gagaatatta cctatttcag aatgtatgtc catgattcgc   3240
cgggtaaata catataatac acaaatctgg cttaataaag tctataatat atctcataaa   3300
gaagtgctaa attggctagt gctatatatt tttaagaaaa tttcttttga ctaagtccat   3360
atcgactttg taaaagttca ctttagcata catatattac acgagccaga aattgtaact   3420
tttgcctaaa atcacaaatt gcaaaattta attgcttgca aaaggtcaca tgcttataat   3480
caactttttt aaaaatttaa aatacttttt tattttttat ttttaaacat aaatgaaata   3540
atttatttat tgtttatgat taccgaaaca taaaacctgc tcaagaaaaa gaaactgttt   3600
tgtccttgga aaaaaagcac tacctaggag cggccaaaat gccgaggctt tcatagctta   3660
aactctttac agaaaatagg cattatagat cagttcgagt tttcttattc ttccttccgg   3720
ttttatcgtc acagttttac agtaaataag tatcacctct tagagttcga tgataagctg   3780
tcaaacatga gaattaattc cacatgttaa aatagtgaag gagcatgttc ggcacacagt   3840
ggaccgaacg tggggtaagt gcactagggt ccggttaaac ggatctcgca ttgatgaggc   3900
aacgctaatt atcaacatat agattgttat ctatctgcat gaacacgaaa tctttacttg   3960
```

-continued

```
acgacttgag gctgatggtg tttatgcaaa gaaaccactg tgtttaatat gtgtcactgt   4020
ttgatattac tgtcagcgta gaagataata gtaaaagcgg ttaataagtg tatttgagat   4080
aagtgtgata aagtttttac agcgaaaaga cgataaatac aagaaaatga ttacgaggat   4140
acggagagag gtatgtacat gtgtatttat atactaagct gccggcggtt gtttgcaaga   4200
ccgagaaaag gctagcaaga atcgggtcat tgtagcgtat gcgcctgtga acattctctt   4260
caacaagttt gattccattg cggtgaaatg gtaaaagtca accccctgcg atgtatattt   4320
tcctgtacaa tcaatcaaaa agccaaatga tttagcatta tctttacatc ttgttatttt   4380
acagatttta tgtttagatc ttttatgctt gcttttcaaa aggcttgcag gcaagtgcac   4440
aaacaatact taaataaata ctactcagta ataacctatt tcttagcatt tttgacgaaa   4500
tttgctattt tgttagagtc ttttacacca tttgtctcca cacctccgct tacatcaaca   4560
ccaataacgc catttaatct aagcgcatca ccaacatttt ctggcgtcag tccaccagct   4620
aacataaaat gtaagctctc ggggctctct tgccttccaa cccagtcaga aatcgagttc   4680
caatccaaaa gttcacctgt cccacctgct tctgaatcaa acaagggaat aaacgaatga   4740
ggtttctgtg aagctgcact gagtagtatg ttgcagtctt ttggaaatac gagtctttta   4800
ataactggca aaccgaggaa ctcttggtat tcttgccacg actcatctcc atgcagttgg   4860
acgatatcaa tgccgtaatc attgaccaga gccaaaacat cctccttagg ttgattacga   4920
aacacgccaa ccaagtattt cggagtgcct gaactatttt tatatgcttt tacaagactt   4980
gaaattttcc ttgcaataac cgggtcaatt gttctctttc tattgggcac acatataata   5040
cccagcaagt cagcatcgga atctagtgca cattctgcgg cctctgtgct ctgcaagccg   5100
caaactttca ccaatggacc agaactacct gtgaaattaa taacagacat actccaagct   5160
gcctttgtgt gcttaatcac gtatactcac gtgctcaata gtcaccaatg ccctccctct   5220
tggccctctc cttttctttt ttcgaccgaa ttaattcttg aagacgaaag ggcctcgtga   5280
tacgcctatt tttataggtt aatgtcatga taataatggt ttcttagacg tcaggtggca   5340
cttttcgggg aaatgtgcgc ggaaccccta tttgtttatt tttctaaata cattcaaata   5400
tgtatccgct catgagacaa taaccctgat aaatgcttca ataatattga aaaaggaaga   5460
gtatgagtat tcaacatttc cgtgtcgccc ttattccctt ttttgcggca ttttgccttc   5520
ctgtttttgc tcacccagaa acgctggtga aagtaaaaga tgctgaagat cagttgggtg   5580
cacgagtggg ttacatcgaa ctggatctca acagcggtaa gatccttgag agttttcgcc   5640
ccgaagaacg ttttccaatg atgagcactt ttaaagttct gctatgtggc gcggtattat   5700
cccgtattga cgccgggcaa gagcaactcg gtcgccgcat acactattct cagaatgact   5760
tggttgagta ctcaccagtc acagaaaagc atcttacgga tggcatgaca gtaagagaat   5820
tatgcagtgc tgccataacc atgagtgata acactgcggc caacttactt ctgacaacga   5880
tcggaggacc gaaggagcta accgcttttt tgcacaacat gggggatcat gtaactcgcc   5940
ttgatcgttg ggaaccggag ctgaatgaag ccataccaaa cgacgagcgt gacaccacga   6000
tgcctgtagc aatggcaaca acgttgcgca aactattaac tggcgaacta cttactctag   6060
cttcccggca acaattaata gactggatgg aggcggataa agttgcagga ccacttctgc   6120
gctcggccct tccggctggc tggtttattg ctgataaatc tggagccggt gagcgtgggt   6180
ctcgcggtat cattgcagca ctggggccag atggtaagcc ctcccgtatc gtagttatct   6240
acacgacggg gagtcaggca actatggatg aacgaaatag acagatcgct gagataggtg   6300
cctcactgat taagcattgg taactgtcag accaagttta ctcatatata ctttagattg   6360
```

-continued

```
atttaaaact tcatttttaa tttaaaagga tctaggtgaa gatccttttt gataatctca   6420
tgaccaaaat cccttaacgt gagttttcgt tccactgagc gtcagacccc gtagaaaaga   6480
tcaaaggatc ttcttgagat cctttttttc tgcgcgtaat ctgctgcttg caaacaaaaa   6540
aaccaccgct accagcggtg gtttgtttgc cggatcaaga gctaccaact ctttttccga   6600
aggtaactgg cttcagcaga gcgcagatac caaatactgt ccttctagtg tagccgtagt   6660
taggccacca cttcaagaac tctgtagcac cgcctacata cctcgctctg ctaatcctgt   6720
taccagtggc tgctgccagt ggcgataagt cgtgtcttac cgggttggac tcaagacgat   6780
agttaccgga taaggcgcag cggtcgggct gaacgggggg ttcgtgcaca cagcccagct   6840
tggagcgaac gacctacacc gaactgagat acctacagcg tgagctatga gaaagcgcca   6900
cgcttcccga agggagaaag gcggacaggt atccggtaag cggcagggtc ggaacaggag   6960
agcgcacgag ggagcttcca gggggaaacg cctggtatct ttatagtcct gtcgggtttc   7020
gccacctctg acttgagcgt cgatttttgt gatgctcgtc aggggggcgg agcctatgga   7080
aaaacgccag caacgcggcc tttttacggt tcctggcctt ttgctggcct tttgctcaca   7140
tgttctttcc tgcgttatcc cctgattctg tggataaccg tattaccgcc tttgagtgag   7200
ctgataccgc tcgccgcagc cgaacgaccg agcgcagcga gtcagtgagc gaggaagcgg   7260
aagagcgccc aatacgcaaa ccgcctctcc ccgcgcgttg gccgattcat taatgcagga   7320
tccgggatcg aagaaatgat ggtaaatgaa ataggaaatc aaggagcatg aaggcaaaag   7380
acaaatataa gggtcgaacg aaaaataaag tgaaaagtgt tgatatgatg tatttggctt   7440
tgcggcgccg aaaaaacgag tttacgcaat tgcacaatca tgctgactct gtggcggacc   7500
cgcgctcttg ccggcccggc gataacgctg ggcgtgaggc tgtgcccggc ggagtttttt   7560
gcgcctgcat ttccaaggt ttaccctgcg ctaaggggcg agattggaga agcaataaga   7620
atgccggttg gggttgcgat gatgacgacc acgacaactg gtgtcattat ttaagttgcc   7680
gaaagaacct gagtgcattt gcaacatgag tatactagaa gaatgagcca agacttgcga   7740
gacgcgagtt tgccggtggt gcgaacaata gagcgaccat gaccttgaag gtgagacgcg   7800
cataaccgct agagtacttt gaagaggaaa cagcaatagg gttgctacca gtataaatag   7860
acaggtacat acaacactgg aaatggttgt ctgtttgagt acgctttcaa ttcatttggg   7920
tgtgcacttt attatgttac aatatggaag ggaactttac acttctccta tgcacatata   7980
ttaattaaag tccaatgcta gtagagaagg ggggtaacac ccctccgcgc tcttttccga   8040
tttttttcta aaccgtggaa tatttcggat atccttttgt tgtttccggg tgtacaatat   8100
ggacttcctc ttttctggca accaaaccca tacatcggga ttcctataat accttcgttg   8160
gtctccctaa catgtaggtg gcggagggga gatatacaat agaacagata ccagacaaga   8220
cataatgggc taaacaagac tacaccaatt acactgcctc attgatg                 8267
```

<210> SEQ ID NO 34
<211> LENGTH: 612
<212> TYPE: PRT
<213> ORGANISM: Artificial Sequence
<220> FEATURE:
<223> OTHER INFORMATION: Synthetic

<400> SEQUENCE: 34

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
```

-continued

```
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Leu Glu Asn Leu Tyr Phe Gln Gly Glu Phe Gln
                165                 170                 175

Leu Thr Thr Met Ala Met Lys Val Asn Met Glu Tyr Thr Lys Glu Lys
            180                 185                 190

Lys Val Gly Glu Gly Thr Tyr Ala Val Val Tyr Leu Gly Cys Gln His
        195                 200                 205

Ser Thr Gly Arg Lys Ile Ala Ile Lys Glu Ile Lys Thr Ser Glu Phe
    210                 215                 220

Lys Asp Gly Leu Asp Met Ser Ala Ile Arg Glu Val Lys Tyr Leu Gln
225                 230                 235                 240

Glu Met Gln His Pro Asn Val Ile Glu Leu Ile Asp Ile Phe Met Ala
                245                 250                 255

Tyr Asp Asn Leu Asn Leu Val Leu Glu Phe Leu Pro Thr Asp Leu Glu
            260                 265                 270

Val Val Ile Lys Asp Lys Ser Ile Leu Phe Thr Pro Ala Asp Ile Lys
        275                 280                 285

Ala Trp Met Leu Met Thr Leu Arg Gly Val Tyr His Cys His Arg Asn
    290                 295                 300

Phe Ile Leu His Arg Asp Leu Lys Pro Asn Asn Leu Leu Phe Ser Pro
305                 310                 315                 320

Asp Gly Gln Ile Lys Val Ala Asp Phe Gly Leu Ala Arg Ala Ile Pro
                325                 330                 335

Ala Pro His Glu Ile Leu Thr Ser Asn Val Val Thr Arg Trp Tyr Arg
            340                 345                 350

Ala Pro Glu Leu Leu Phe Gly Ala Lys His Tyr Thr Ser Ala Ile Asp
        355                 360                 365

Ile Trp Ser Val Gly Val Ile Phe Ala Glu Leu Met Leu Arg Ile Pro
    370                 375                 380

Tyr Leu Pro Gly Gln Asn Asp Val Asp Gln Met Glu Val Thr Phe Arg
385                 390                 395                 400

Ala Leu Gly Thr Pro Thr Asp Arg Asp Trp Pro Glu Val Ser Ser Phe
                405                 410                 415

Met Thr Tyr Asn Lys Leu Gln Ile Tyr Pro Pro Pro Ser Arg Asp Glu
            420                 425                 430

Leu Arg Lys Arg Phe Ile Ala Ala Ser Glu Tyr Ala Leu Asp Phe Met
        435                 440                 445
```

-continued

```
Cys Gly Met Leu Thr Met Asn Pro Gln Lys Arg Trp Thr Ala Val Gln
    450                 455                 460

Cys Leu Glu Ser Asp Tyr Phe Lys Glu Leu Pro Pro Pro Ser Asp Pro
465                 470                 475                 480

Ser Ser Ile Lys Ile Arg Asn Val Met Ala Ile Pro Gly Gly Gly Arg
                485                 490                 495

Ile Phe Tyr Pro Tyr Asp Val Pro Asp Tyr Ala Gly Tyr Pro Tyr Asp
            500                 505                 510

Val Pro Asp Tyr Ala Gly Ser Tyr Pro Tyr Asp Val Pro Asp Tyr Ala
        515                 520                 525

Ala Gln Cys Gly Arg Ser Ser Asn Trp Ile Pro Arg Tyr Arg Arg Pro
    530                 535                 540

Ala Glu Ile Tyr Glu Ser Ile Leu Lys Asn Pro Ala Ser Ser Leu Gln
545                 550                 555                 560

Leu Cys Ile Val His His Leu Asn Phe Phe His Leu Tyr Ile Val Leu
                565                 570                 575

Pro Ser Phe Met Leu Tyr Ser Ser Lys Phe Gln Ser Trp Pro Cys Asn
            580                 585                 590

Leu Ser Ile Glu Phe Phe Lys Leu Glu Leu Met Pro Ile Phe Phe Leu
        595                 600                 605

Asp Leu Asn Ser
    610
```

<210> SEQ ID NO 35
<211> LENGTH: 8330
<212> TYPE: DNA
<213> ORGANISM: Artificial Sequence
<220> FEATURE:
<223> OTHER INFORMATION: Synthetic

<400> SEQUENCE: 35

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840

tagtaacaaa ggtcaaagac agttgactgt atcgaactat ctattcgatg atgaagatac    900

cccaccaaac ccaaaaaaag agatcgaatt ggagaatttg tattttcagg gtgaattcca    960

gtattcgcca actagtcctt cgtattcgcc aactagtcct tcgtattcgc caactagtcc   1020

ttcgctgacc accatggcaa tgaaagtgaa tatggagtac acaaaggaaa agaaagttgg   1080
```

-continued

```
tgagggtact tatgcggttg tttacttggg ttgtcaacac tctactggaa gaaagattgc   1140
tattaaggag atcaaaacat ccgaatttaa agatggttta gatatgtcag ctatccgtga   1200
agttaagtac ctccaagaaa tgcagcatcc gaacgtcata gaactaatag acatatttat   1260
ggcttatgat aatttaaatc tcgttctgga gttcctacca actgatctag aggtggtaat   1320
aaaagacaaa tcaatactgt ttacaccagc agatattaag gcatggatgc ttatgacttt   1380
gaggggcgtg tatcattgcc acagaaattt cattttgcac agggatctga aaccaaacaa   1440
tttattattt tcacctgatg gccagataaa agtagcagat ttcggtctag caagggcgat   1500
accggcccca catgagatac tgacaagtaa cgtcgtaaca agatggtata gagcgccaga   1560
attgttgttt ggagctaaac attacacatc ggctattgat atctggtcag taggcgttat   1620
attcgcggaa ttaatgctaa ggatacctta tttaccagga cagaatgatg tcgatcaaat   1680
ggaagtaacg ttcagggcct tagggacacc tacagataga gattggcccg aagtttcttc   1740
ctttatgacg tataacaagt tacaaatata tccgcccccct tcaagagatg aattgaggaa   1800
aaggttcatt gctgctagcg aatacgcctt agattttatg tgtggaatgc taacgatgaa   1860
cccacaaaag aggtggaccg ctgttcagtg tttagaaagt gattatttca aagaattacc   1920
accaccaagt gacccgtctt caataaaaat acgtaacgtc atggcaattc ccggtggcgg   1980
ccgcatcttt tacccatacg atgttcctga ctatgcgggc tatccctatg acgtcccgga   2040
ctatgcagga tcctatccat atgacgttcc agattacgct gctcagtgcg gccgctctag   2100
ctagaactag tggatccccc gataccgtcg acctgcagag atctatgaat cgtagatact   2160
gaaaaacccc gcaagttcac ttcaactgtg catcgtgcac catctcaatt tctttcattt   2220
atacatcgtt ttgccttctt ttatgtaact atactcctct aagtttcaat cttggccatg   2280
taacctctga tctatagaat tttttaaatg actagaatta atgcccatct tttttttgga   2340
cctaaattct tcatgaaaat atattacgag ggcttattca gaagctttgg acttcttcgc   2400
cagaggtttg gtcaagtctc caatcaaggt tgtcggcttg tctaccttgc cagaaattta   2460
cgaaaagatg gaaaagggtc aaatcgttgg tagatacgtt gttgacactt ctaaataagc   2520
gaatttctta tgatttatga tttttattat taaataagtt ataaaaaaaa taagtgtata   2580
caaattttaa agtgactctt aggttttaaa acgaaaattc ttattcttga gtaactcttt   2640
cctgtaggtc aggttgcttt ctcaggtata gcatgaggtc gctcttattg accacacctc   2700
taccggcatg ccgagcaaat gcctgcaaat cgctccccat ttcacccaat tgtagatatg   2760
ctaactccag caatgagttg atgaatctcg gtgtgtattt tatgtcctca gaggacaaca   2820
cctgttgtaa tcgttcttcc acacggatcc tggcgtaata gcgaagaggc ccgcaccgat   2880
cgcccttccc aacagttgcg cagcctgaat ggcgaatggc gcctgatgcg gtattttctc   2940
cttacgcatc tgtgcggtat ttcacaccgc atatatcgct gggccattct catgaagaat   3000
atcttgaatt tattgtcata ttactagttg gtgtggaagt ccatatatcg gtgatcaata   3060
tagtggttga catgctggct agtcaacatt gagccttttg atcatgcaaa tatattacgg   3120
tattttacaa tcaaatatca aacttaacta ttgactttat aacttattta ggtggtaaca   3180
ttcttataaa aaagaaaaaa attactgcaa aacagtacta gcttttaact tgtatcctag   3240
gttatctatg ctgtctcacc atagagaata ttacctattt cagaatgtat gtccatgatt   3300
cgccgggtaa atacatataa tacacaaatc tggcttaata aagtctataa tatatctcat   3360
aaagaagtgc taaattggct agtgctatat atttttaaga aatttcttt tgactaagtc    3420
```

-continued

```
catatcgact ttgtaaaagt tcactttagc atacatatat tacacgagcc agaaattgta   3480
acttttgcct aaaatcacaa attgcaaaat ttaattgctt gcaaaaggtc acatgcttat   3540
aatcaacttt tttaaaaatt taaaatactt ttttattttt tatttttaaa cataaatgaa   3600
ataatttatt tattgtttat gattaccgaa acataaaacc tgctcaagaa aaagaaactg   3660
ttttgtcctt ggaaaaaaag cactacctag gagcggccaa aatgccgagg ctttcatagc   3720
ttaaactctt tacagaaaat aggcattata gatcagttcg agttttctta ttcttccttc   3780
cggttttatc gtcacagttt tacagtaaat aagtatcacc tcttagagtt cgatgataag   3840
ctgtcaaaca tgagaattaa ttccacatgt taaaatagtg aaggagcatg ttcggcacac   3900
agtggaccga acgtggggta agtgcactag ggtccggtta aacggatctc gcattgatga   3960
ggcaacgcta attatcaaca tatagattgt tatctatctg catgaacacg aaatctttac   4020
ttgacgactt gaggctgatg gtgtttatgc aaagaaacca ctgtgtttaa tatgtgtcac   4080
tgtttgatat tactgtcagc gtagaagata atagtaaaag cggttaataa gtgtatttga   4140
gataagtgtg ataaagtttt tacagcgaaa agacgataaa tacaagaaaa tgattacgag   4200
gatacggaga gaggtatgta catgtgtatt tatatactaa gctgccggcg gttgtttgca   4260
agaccgagaa aaggctagca agaatcgggt cattgtagcg tatgcgcctg tgaacattct   4320
cttcaacaag tttgattcca ttgcggtgaa atggtaaaag tcaaccccct gcgatgtata   4380
ttttcctgta caatcaatca aaaagccaaa tgatttagca ttatctttac atcttgttat   4440
tttacagatt ttatgtttag atcttttatg cttgcttttc aaaaggcttg caggcaagtg   4500
cacaaacaat acttaaataa atactactca gtaataacct atttcttagc atttttgacg   4560
aaatttgcta ttttgttaga gtcttttaca ccatttgtct ccacacctcc gcttacatca   4620
acaccaataa cgccatttaa tctaagcgca tcaccaacat tttctggcgt cagtccacca   4680
gctaacataa aatgtaagct ctcggggctc tcttgccttc caacccagtc agaaatcgag   4740
ttccaatcca aaagttcacc tgtcccacct gcttctgaat caaacaaggg aataaacgaa   4800
tgaggtttct gtgaagctgc actgagtagt atgttgcagt cttttggaaa tacgagtctt   4860
ttaataactg gcaaaccgag gaactcttgg tattcttgcc acgactcatc tccatgcagt   4920
tggacgatat caatgccgta atcattgacc agagccaaaa catcctcctt aggttgatta   4980
cgaaacacgc caaccaagta tttcggagtg cctgaactat ttttatatgc ttttacaaga   5040
cttgaaattt tccttgcaat aaccgggtca attgttctct ttctattggg cacacatata   5100
atacccagca agtcagcatc ggaatctagt gcacattctg cggcctctgt gctctgcaag   5160
ccgcaaactt tcaccaatgg accagaacta cctgtgaaat taataacaga catactccaa   5220
gctgcctttg tgtgcttaat cacgtatact cacgtgctca atagtcacca atgccctccc   5280
tcttggccct ctccttttct tttttcgacc gaattaattc ttgaagacga aagggcctcg   5340
tgatacgcct atttttatag gttaatgtca tgataataat ggtttcttag acgtcaggtg   5400
gcacttttcg gggaaatgtg cgcggaaccc ctatttgttt atttttctaa atacattcaa   5460
atatgtatcc gctcatgaga caataaccct gataaatgct tcaataatat tgaaaaagga   5520
agagtatgag tattcaacat ttccgtgtcg cccttattcc cttttttgcg gcattttgcc   5580
ttcctgtttt tgctcaccca gaaacgctgg tgaaagtaaa agatgctgaa gatcagttgg   5640
gtgcacgagt gggttacatc gaactggatc tcaacagcgg taagatcctt gagagttttc   5700
gccccgaaga acgttttcca atgatgagca cttttaaagt tctgctatgt ggcgcggtat   5760
tatcccgtat tgacgccggg caagagcaac tcggtcgccg catacactat tctcagaatg   5820
```

-continued

```
acttggttga gtactcacca gtcacagaaa agcatcttac ggatggcatg acagtaagag   5880
aattatgcag tgctgccata accatgagtg ataacactgc ggccaactta cttctgacaa   5940
cgatcggagg accgaaggag ctaaccgctt ttttgcacaa catgggggat catgtaactc   6000
gccttgatcg ttgggaaccg gagctgaatg aagccatacc aaacgacgag cgtgacacca   6060
cgatgcctgt agcaatggca acaacgttgc gcaaactatt aactggcgaa ctacttactc   6120
tagcttcccg gcaacaatta atagactgga tggaggcgga taaagttgca ggaccacttc   6180
tgcgctcggc ccttccggct ggctggttta ttgctgataa atctggagcc ggtgagcgtg   6240
ggtctcgcgg tatcattgca gcactggggc cagatggtaa gccctcccgt atcgtagtta   6300
tctacacgac ggggagtcag gcaactatgg atgaacgaaa tagacagatc gctgagatag   6360
gtgcctcact gattaagcat tggtaactgt cagaccaagt ttactcatat atactttaga   6420
ttgatttaaa acttcatttt taatttaaaa ggatctaggt gaagatcctt tttgataatc   6480
tcatgaccaa aatcccttaa cgtgagtttt cgttccactg agcgtcagac cccgtagaaa   6540
agatcaaagg atcttcttga gatccttttt ttctgcgcgt aatctgctgc ttgcaaacaa   6600
aaaaaccacc gctaccagcg gtggtttgtt tgccggatca agagctacca actctttttc   6660
cgaaggtaac tggcttcagc agagcgcaga taccaaatac tgtccttcta gtgtagccgt   6720
agttaggcca ccacttcaag aactctgtag caccgcctac atacctcgct ctgctaatcc   6780
tgttaccagt ggctgctgcc agtggcgata agtcgtgtct taccgggttg gactcaagac   6840
gatagttacc ggataaggcg cagcggtcgg gctgaacggg gggttcgtgc acacagccca   6900
gcttggagcg aacgacctac accgaactga gatacctaca gcgtgagcta tgagaaagcg   6960
ccacgcttcc cgaagggaga aaggcggaca ggtatccggt aagcggcagg gtcggaacag   7020
gagagcgcac gagggagctt ccagggggaa acgcctggta tctttatagt cctgtcgggt   7080
ttcgccacct ctgacttgag cgtcgatttt tgtgatgctc gtcagggggg cggagcctat   7140
ggaaaaacgc cagcaacgcg gcctttttac ggttcctggc cttttgctgg ccttttgctc   7200
acatgttctt tcctgcgtta tcccctgatt ctgtggataa ccgtattacc gcctttgagt   7260
gagctgatac cgctcgccgc agccgaacga ccgagcgcag cgagtcagtg agcgaggaag   7320
cggaagagcg cccaatacgc aaaccgcctc tccccgcgcg ttggccgatt cattaatgca   7380
ggatccggga tcgaagaaat gatggtaaat gaaataggaa atcaaggagc atgaaggcaa   7440
aagacaaata taagggtcga acgaaaaata aagtgaaaag tgttgatatg atgtatttgg   7500
ctttgcggcg ccgaaaaaac gagtttacgc aattgcacaa tcatgctgac tctgtggcgg   7560
acccgcgctc ttgccggccc ggcgataacg ctgggcgtga ggctgtgccc ggcggagttt   7620
tttgcgcctg cattttccaa ggtttaccct gcgctaaggg gcgagattgg agaagcaata   7680
agaatgccgg ttggggttgc gatgatgacg accacgacaa ctggtgtcat tatttaagtt   7740
gccgaaagaa cctgagtgca tttgcaacat gagtatacta gaagaatgag ccaagacttg   7800
cgagacgcga gtttgccggt ggtgcgaaca atagagcgac catgaccttg aaggtgagac   7860
gcgcataacc gctagagtac tttgaagagg aaacagcaat agggttgcta ccagtataaa   7920
tagacaggta catacaacac tggaaatggt tgtctgtttg agtacgcttt caattcattt   7980
gggtgtgcac tttattatgt tacaatatgg aagggaactt tacacttctc ctatgcacat   8040
atattaatta aagtccaatg ctagtagaga agggggggtaa cacccctccg cgctcttttc   8100
cgattttttt ctaaaccgtg gaatatttcg gatatccttt tgttgtttcc gggtgtacaa   8160
```

-continued

```
tatggacttc ctcttttctg gcaaccaaac ccatacatcg ggattcctat aataccttcg   8220

ttggtctccc taacatgtag gtggcggagg ggagatatac aatagaacag ataccagaca   8280

agacataatg ggctaaacaa gactacacca attacactgc ctcattgatg              8330


<210> SEQ ID NO 36
<211> LENGTH: 556
<212> TYPE: PRT
<213> ORGANISM: Artificial Sequence
<220> FEATURE:
<223> OTHER INFORMATION: Synthetic

<400> SEQUENCE: 36

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Leu Glu Asn Leu Tyr Phe Gln Gly Glu Phe Gln
                165                 170                 175

Tyr Ser Pro Thr Ser Pro Ser Tyr Ser Leu Thr Ser Pro Ser Tyr Ser
            180                 185                 190

Pro Thr Ser Pro Ser Leu Thr Thr Met Ala Met Lys Val Asn Met Glu
        195                 200                 205

Tyr Thr Lys Glu Lys Lys Val Gly Glu Gly Thr Tyr Ala Val Val Tyr
    210                 215                 220

Leu Gly Cys Gln His Ser Thr Gly Arg Lys Ile Ala Ile Lys Glu Ile
225                 230                 235                 240

Lys Thr Ser Glu Phe Lys Asp Gly Leu Asp Met Ser Ala Ile Arg Glu
                245                 250                 255

Val Lys Tyr Leu Gln Glu Met Gln His Pro Asn Val Ile Glu Leu Ile
            260                 265                 270

Asp Ile Phe Met Ala Tyr Asp Asn Leu Asn Leu Val Leu Glu Phe Leu
        275                 280                 285

Pro Thr Asp Leu Glu Val Val Ile Lys Asp Lys Ser Ile Leu Phe Thr
    290                 295                 300

Pro Ala Asp Ile Lys Ala Trp Met Leu Met Thr Leu Arg Gly Val Tyr
305                 310                 315                 320

His Cys His Arg Asn Phe Ile Leu His Arg Asp Leu Lys Pro Asn Asn
                325                 330                 335
```

-continued

```
Leu Leu Phe Ser Pro Asp Gly Gln Ile Lys Val Ala Asp Phe Gly Leu
            340                 345                 350

Ala Arg Ala Ile Pro Ala Pro His Glu Ile Leu Thr Ser Asn Val Val
        355                 360                 365

Thr Arg Trp Tyr Arg Ala Pro Glu Leu Leu Phe Gly Ala Lys His Tyr
    370                 375                 380

Thr Ser Ala Ile Asp Ile Trp Ser Val Gly Val Ile Phe Ala Glu Leu
385                 390                 395                 400

Met Leu Arg Ile Pro Tyr Leu Pro Gly Gln Asn Asp Val Asp Gln Met
                405                 410                 415

Glu Val Thr Phe Arg Ala Leu Gly Thr Pro Thr Asp Arg Asp Trp Pro
            420                 425                 430

Glu Val Ser Ser Phe Met Thr Tyr Asn Lys Leu Gln Ile Tyr Pro Pro
        435                 440                 445

Pro Ser Arg Asp Glu Leu Arg Lys Arg Phe Ile Ala Ala Ser Glu Tyr
    450                 455                 460

Ala Leu Asp Phe Met Cys Gly Met Leu Thr Met Asn Pro Gln Lys Arg
465                 470                 475                 480

Trp Thr Ala Val Gln Cys Leu Glu Ser Asp Tyr Phe Lys Glu Leu Pro
                485                 490                 495

Pro Pro Ser Asp Pro Ser Ser Ile Lys Ile Arg Asn Val Met Ala Ile
            500                 505                 510

Pro Gly Gly Gly Arg Ile Phe Tyr Pro Tyr Asp Val Pro Asp Tyr Ala
        515                 520                 525

Gly Tyr Pro Tyr Asp Val Pro Asp Tyr Ala Gly Ser Tyr Pro Tyr Asp
    530                 535                 540

Val Pro Asp Tyr Ala Ala Gln Cys Gly Arg Ser Ser
545                 550                 555
```

<210> SEQ ID NO 37
<211> LENGTH: 8330
<212> TYPE: DNA
<213> ORGANISM: Artificial Sequence
<220> FEATURE:
<223> OTHER INFORMATION: Synthetic

<400> SEQUENCE: 37

```
gtggtacata acgaactaat actgtagccc tagacttgat agccatcatc atatcgaagt     60

ttcactaccc tttttccatt tgccatctat tgaagtaata ataggcgcat gcaacttctt    120

ttcttttttt ttcttttctc tctcccccgt tgttgtctca ccatatccgc aatgacaaaa    180

aaatgatgga agacactaaa ggaaaaaatt aacgacaaag acagcaccaa cagatgtcgt    240

tgttccagag ctgatgaggg gtatctcgaa gcacacgaaa ctttttcctt ccttcattga    300

cctgcaatta ttaatctttt gtttcctcgt cattgttctc gttccctttc ttccttgttt    360

ctttttctgc acaatatttc aagctatacc aagcatacaa tcaactccaa gcttgaagca    420

agcctcctga aagatgaagc tactgtcttc tatcgaacaa gcatgcgata tttgccgact    480

taaaaagctc aagtgctcca aagaaaaacc gaagtgcgcc aagtgtctga agaacaactg    540

ggagtgtcgc tactctccca aaaccaaaag gtctccgctg actagggcac atctgacaga    600

agtggaatca aggctagaaa gactggaaca gctatttcta ctgatttttc ctcgagaaga    660

ccttgacatg attttgaaaa tggattcttt acaggatata aaagcattgt taacaggatt    720

atttgtacaa gataatgtga ataaagatgc cgtcacagat agattggctt cagtggagac    780

tgatatgcct ctaacattga gacagcatag aataagtgcg acatcatcat cggaagagag    840
```

-continued

```
tagtaacaaa ggtcaaagac agttgactgt atcgaactat ctattcgatg atgaagatac    900
cccaccaaac ccaaaaaaag agatcgaatt ggagaatttg tattttcagg gtgaattcca    960
gtattcgcca actagtcctt cgtattcgcc aactagtcct tcgtattcgc caactagtcc   1020
ttcgctgacc accatggcaa tgaaagtgaa tatggagtac acaaaggaaa agaaagttgg   1080
tgagggtact tatgcggttg tttacttggg ttgtcaacac tctactggaa gaaagattgc   1140
tattaaggag atcaaaacat ccgaatttaa agatggttta gatatgtcag ctatccgtca   1200
acttaagtac ctccaagaaa tgcagcatcc gaacgtcata gaactaatag acatatttat   1260
ggcttatgat aatttaaatc tcgttctgga gttcctacca actgatctag aggtggtaat   1320
aaaagacaaa tcaatactgt ttacaccagc agatattaag gcatggatgc ttatgacttt   1380
gaggggcgtg tatcattgcc acagaaattt cattttgcac agggatctga aaccaaacaa   1440
tttattattt tcacctgatg gccagataaa agtagcagat ttcggtctag caagggcgat   1500
accggcccca catgagatac tgacaagtaa cgtcgtaaca agatggtata gagcgccaga   1560
attgttgttt ggagctaaac attacacatc ggctattgat atctggtcag taggcgttat   1620
attcgcggaa ttaatgctaa ggatacctta tttaccagga cagaatgatg tcgatcaaat   1680
ggaagtaacg ttcagggcct tagggacacc tacagataga gattggcccg aagtttcttc   1740
ctttatgacg tataacaagt tacaaatata tccgccccct tcaagagatg aattgaggaa   1800
aaggttcatt gctgctagcg aatacgcctt agattttatg tgtggaatgc taacgatgaa   1860
cccacaaaag aggtggaccg ctgttcagtg tttagaaagt gattatttca aagaattacc   1920
accaccaagt gacccgtctt caataaaaat acgtaacgtc atggcaattc ccggtggcgg   1980
ccgcatcttt tacccatacg atgttcctga ctatgcgggc tatccctatg acgtcccgga   2040
ctatgcagga tcctatccat atgacgttcc agattacgct gctcagtgcg gccgctctag   2100
ctagaactag tggatccccc gataccgtcg acctgcagag atctatgaat cgtagatact   2160
gaaaaacccc gcaagttcac ttcaactgtg catcgtgcac catctcaatt tctttcattt   2220
atacatcgtt ttgccttctt ttatgtaact atactcctct aagtttcaat cttggccatg   2280
taacctctga tctatagaat tttttaaatg actagaatta atgcccatct tttttttgga   2340
cctaaattct tcatgaaaat atattacgag ggcttattca gaagctttgg acttcttcgc   2400
cagaggtttg gtcaagtctc caatcaaggt tgtcggcttg tctaccttgc cagaaattta   2460
cgaaaagatg gaaaagggtc aaatcgttgg tagatacgtt gttgacactt ctaaataagc   2520
gaatttctta tgatttatga tttttattat taaataagtt ataaaaaaaa taagtgtata   2580
caaattttaa agtgactctt aggttttaaa acgaaaattc ttattcttga gtaactcttt   2640
cctgtaggtc aggttgcttt ctcaggtata gcatgaggtc gctcttattg accacacctc   2700
taccggcatg ccgagcaaat gcctgcaaat cgctccccat ttcacccaat tgtagatatg   2760
ctaactccag caatgagttg atgaatctcg gtgtgtattt tatgtcctca gaggacaaca   2820
cctgttgtaa tcgttcttcc acacggatcc tggcgtaata gcgaagaggc ccgcaccgat   2880
cgcccttccc aacagttgcg cagcctgaat ggcgaatggc gcctgatgcg gtattttctc   2940
cttacgcatc tgtgcggtat ttcacaccgc atatatcgct gggccattct catgaagaat   3000
atcttgaatt tattgtcata ttactagttg gtgtggaagt ccatatatcg gtgatcaata   3060
tagtggttga catgctggct agtcaacatt gagccttttg atcatgcaaa tatattacgg   3120
tattttacaa tcaaatatca aacttaacta ttgactttat aacttattta ggtggtaaca   3180
```

-continued ttcttataaa aaagaaaaaa attactgcaa aacagtacta gcttttaact tgtatcctag 3240
gttatctatg ctgtctcacc atagagaata ttacctattt cagaatgtat gtccatgatt 3300
cgccgggtaa atacatataa tacacaaatc tggcttaata aagtctataa tatatctcat 3360
aaagaagtgc taaattggct agtgctatat atttttaaga aaatttcttt tgactaagtc 3420
catatcgact ttgtaaaagt tcactttagc atacatatat tacacgagcc agaaattgta 3480
acttttgcct aaaatcacaa attgcaaaat ttaattgctt gcaaaaggtc acatgcttat 3540
aatcaacttt tttaaaaatt taaaatactt ttttattttt tatttttaaa cataaatgaa 3600
ataatttatt tattgtttat gattaccgaa acataaaacc tgctcaagaa aaagaaactg 3660
ttttgtcctt ggaaaaaaag cactacctag gagcggccaa aatgccgagg ctttcatagc 3720
ttaaactctt tacagaaaat aggcattata gatcagttcg agttttctta ttcttccttc 3780
cggttttatc gtcacagttt tacagtaaat aagtatcacc tcttagagtt cgatgataag 3840
ctgtcaaaca tgagaattaa ttccacatgt taaaatagtg aaggagcatg ttcggcacac 3900
agtggaccga acgtggggta agtgcactag ggtccggtta aacggatctc gcattgatga 3960
ggcaacgcta attatcaaca tatagattgt tatctatctg catgaacacg aaatctttac 4020
ttgacgactt gaggctgatg gtgtttatgc aaagaaacca ctgtgtttaa tatgtgtcac 4080
tgtttgatat tactgtcagc gtagaagata atagtaaaag cggttaataa gtgtatttga 4140
gataagtgtg ataaagtttt tacagcgaaa agacgataaa tacaagaaaa tgattacgag 4200
gatacggaga gaggtatgta catgtgtatt tatatactaa gctgccggcg gttgtttgca 4260
agaccgagaa aaggctagca agaatcgggt cattgtagcg tatgcgcctg tgaacattct 4320
cttcaacaag tttgattcca ttgcggtgaa atggtaaaag tcaacccccct gcgatgtata 4380 ttttcctgta caatcaatca aaaagccaaa tgatttagca ttatctttac atcttgttat 4440
tttacagatt ttatgtttag atcttttatg cttgcttttc aaaaggcttg caggcaagtg 4500
cacaaacaat acttaaataa atactactca gtaataacct atttcttagc atttttgacg 4560
aaatttgcta ttttgttaga gtcttttaca ccatttgtct ccacacctcc gcttacatca 4620
acaccaataa cgccatttaa tctaagcgca tcaccaacat tttctggcgt cagtccacca 4680
gctaacataa aatgtaagct ctcggggctc tcttgccttc caacccagtc agaaatcgag 4740
ttccaatcca aaagttcacc tgtcccacct gcttctgaat caaacaaggg aataaacgaa 4800
tgaggtttct gtgaagctgc actgagtagt atgttgcagt cttttggaaa tacgagtctt 4860
ttaataactg gcaaaccgag gaactcttgg tattcttgcc acgactcatc tccatgcagt 4920
tggacgatat caatgccgta atcattgacc agagccaaaa catcctcctt aggttgatta 4980
cgaaacacgc caaccaagta tttcggagtg cctgaactat ttttatatgc ttttacaaga 5040
cttgaaattt tccttgcaat aaccgggtca attgttctct ttctattggg cacacatata 5100
atacccagca agtcagcatc ggaatctagt gcacattctg cggcctctgt gctctgcaag 5160
ccgcaaactt tcaccaatgg accagaacta cctgtgaaat taataacaga catactccaa 5220
gctgcctttg tgtgcttaat cacgtatact cacgtgctca atagtcacca atgccctccc 5280
tcttggccct ctccttttct tttttcgacc gaattaattc ttgaagacga aagggcctcg 5340
tgatacgcct atttttatag gttaatgtca tgataataat ggtttcttag acgtcaggtg 5400
gcacttttcg gggaaatgtg cgcggaaccc ctatttgttt atttttctaa atacattcaa 5460
atatgtatcc gctcatgaga caataaccct gataaatgct tcaataatat tgaaaaagga 5520
agagtatgag tattcaacat ttccgtgtcg cccttattcc cttttttgcg gcattttgcc 5580

-continued

```
ttcctgtttt tgctcaccca gaaacgctgg tgaaagtaaa agatgctgaa gatcagttgg   5640
gtgcacgagt gggttacatc gaactggatc tcaacagcgg taagatcctt gagagttttc   5700
gccccgaaga acgttttcca atgatgagca cttttaaagt tctgctatgt ggcgcggtat   5760
tatcccgtat tgacgccggg caagagcaac tcggtcgccg catacactat tctcagaatg   5820
acttggttga gtactcacca gtcacagaaa agcatcttac ggatggcatg acagtaagag   5880
aattatgcag tgctgccata accatgagtg ataacactgc ggccaactta cttctgacaa   5940
cgatcggagg accgaaggag ctaaccgctt ttttgcacaa catgggggat catgtaactc   6000
gccttgatcg ttgggaaccg gagctgaatg aagccatacc aaacgacgag cgtgacacca   6060
cgatgcctgt agcaatggca acaacgttgc gcaaactatt aactggcgaa ctacttactc   6120
tagcttcccg gcaacaatta atagactgga tggaggcgga taaagttgca ggaccacttc   6180
tgcgctcggc ccttccggct ggctggttta ttgctgataa atctggagcc ggtgagcgtg   6240
ggtctcgcgg tatcattgca gcactggggc cagatggtaa gccctcccgt atcgtagtta   6300
tctacacgac ggggagtcag gcaactatgg atgaacgaaa tagacagatc gctgagatag   6360
gtgcctcact gattaagcat tggtaactgt cagaccaagt ttactcatat atactttaga   6420
ttgatttaaa acttcatttt taatttaaaa ggatctaggt gaagatcctt tttgataatc   6480
tcatgaccaa aatcccttaa cgtgagtttt cgttccactg agcgtcagac cccgtagaaa   6540
agatcaaagg atcttcttga gatccttttt ttctgcgcgt aatctgctgc ttgcaaacaa   6600
aaaaaccacc gctaccagcg gtggtttgtt tgccggatca agagctacca actctttttc   6660
cgaaggtaac tggcttcagc agagcgcaga taccaaatac tgtccttcta gtgtagccgt   6720
agttaggcca ccacttcaag aactctgtag caccgcctac atacctcgct ctgctaatcc   6780
tgttaccagt ggctgctgcc agtggcgata agtcgtgtct taccgggttg gactcaagac   6840
gatagttacc ggataaggcg cagcggtcgg gctgaacggg gggttcgtgc acacagccca   6900
gcttggagcg aacgacctac accgaactga gatacctaca gcgtgagcta tgagaaagcg   6960
ccacgcttcc cgaagggaga aaggcggaca ggtatccggt aagcggcagg gtcggaacag   7020
gagagcgcac gagggagctt ccagggggaa acgcctggta tctttatagt cctgtcgggt   7080
ttcgccacct ctgacttgag cgtcgatttt tgtgatgctc gtcagggggg cggagcctat   7140
ggaaaaacgc cagcaacgcg gcctttttac ggttcctggc cttttgctgg ccttttgctc   7200
acatgttctt tcctgcgtta tcccctgatt ctgtggataa ccgtattacc gcctttgagt   7260
gagctgatac cgctcgccgc agccgaacga ccgagcgcag cgagtcagtg agcgaggaag   7320
cggaagagcg cccaatacgc aaaccgcctc tccccgcgcg ttggccgatt cattaatgca   7380
ggatccggga tcgaagaaat gatggtaaat gaaataggaa atcaaggagc atgaaggcaa   7440
aagacaaata taagggtcga acgaaaaata aagtgaaaag tgttgatatg atgtatttgg   7500
ctttgcggcg ccgaaaaaac gagtttacgc aattgcacaa tcatgctgac tctgtggcgg   7560
acccgcgctc ttgccggccc ggcgataacg ctgggcgtga ggctgtgccc ggcggagttt   7620
tttgcgcctg cattttccaa ggtttaccct gcgctaaggg gcgagattgg agaagcaata   7680
agaatgccgg ttggggttgc gatgatgacg accacgacaa ctggtgtcat tatttaagtt   7740
gccgaaagaa cctgagtgca tttgcaacat gagtatacta gaagaatgag ccaagacttg   7800
cgagacgcga gtttgccggt ggtgcgaaca atagagcgac catgaccttg aaggtgagac   7860
gcgcataacc gctagagtac tttgaagagg aaacagcaat agggttgcta ccagtataaa   7920
```

-continued

```
tagacaggta catacaacac tggaaatggt tgtctgtttg agtacgcttt caattcattt   7980

gggtgtgcac tttattatgt tacaatatgg aagggaactt tacacttctc ctatgcacat   8040

atattaatta aagtccaatg ctagtagaga agggggggtaa cacccctccg cgctcttttc   8100

cgattttttt ctaaaccgtg gaatatttcg gatatccttt tgttgtttcc gggtgtacaa   8160

tatggacttc ctcttttctg gcaaccaaac ccatacatcg ggattcctat aataccttcg   8220

ttggtctccc taacatgtag gtggcggagg ggagatatac aatagaacag ataccagaca   8280

agacataatg ggctaaacaa gactacacca attacactgc ctcattgatg              8330
```

<210> SEQ ID NO 38
<211> LENGTH: 556
<212> TYPE: PRT
<213> ORGANISM: Artificial Sequence
<220> FEATURE:
<223> OTHER INFORMATION: Synthetic

<400> SEQUENCE: 38

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Asn Tyr Leu Phe Asp Asp Glu Asp Thr Pro Pro Asn Pro
145                 150                 155                 160

Lys Lys Glu Ile Glu Leu Glu Asn Leu Tyr Phe Gln Gly Glu Phe Gln
                165                 170                 175

Tyr Ser Pro Thr Ser Pro Ser Tyr Ser Leu Thr Ser Pro Ser Tyr Ser
            180                 185                 190

Pro Thr Ser Pro Ser Leu Thr Thr Met Ala Met Lys Val Asn Met Glu
        195                 200                 205

Tyr Thr Lys Glu Lys Lys Val Gly Glu Gly Thr Tyr Ala Val Val Tyr
    210                 215                 220

Leu Gly Cys Gln His Ser Thr Gly Arg Lys Ile Ala Ile Lys Glu Ile
225                 230                 235                 240

Lys Thr Ser Glu Phe Lys Asp Gly Leu Asp Met Ser Ala Ile Arg Gln
                245                 250                 255

Val Lys Tyr Leu Gln Glu Met Gln His Pro Asn Val Ile Glu Leu Ile
            260                 265                 270

Asp Ile Phe Met Ala Tyr Asp Asn Leu Asn Leu Val Leu Glu Phe Leu
        275                 280                 285

Pro Thr Asp Leu Glu Val Val Ile Lys Asp Lys Ser Ile Leu Phe Thr
```

-continued

```
290                 295                 300

Pro Ala Asp Ile Lys Ala Trp Met Leu Met Thr Leu Arg Gly Val Tyr
305                 310                 315                 320

His Cys His Arg Asn Phe Ile Leu His Arg Asp Leu Lys Pro Asn Asn
                325                 330                 335

Leu Leu Phe Ser Pro Asp Gly Gln Ile Lys Val Ala Asp Phe Gly Leu
            340                 345                 350

Ala Arg Ala Ile Pro Ala Pro His Glu Ile Leu Thr Ser Asn Val Val
        355                 360                 365

Thr Arg Trp Tyr Arg Ala Pro Glu Leu Leu Phe Gly Ala Lys His Tyr
    370                 375                 380

Thr Ser Ala Ile Asp Ile Trp Ser Val Gly Val Ile Phe Ala Glu Leu
385                 390                 395                 400

Met Leu Arg Ile Pro Tyr Leu Pro Gly Gln Asn Asp Val Asp Gln Met
                405                 410                 415

Glu Val Thr Phe Arg Ala Leu Gly Thr Pro Thr Asp Arg Asp Trp Pro
            420                 425                 430

Glu Val Ser Ser Phe Met Thr Tyr Asn Lys Leu Gln Ile Tyr Pro Pro
        435                 440                 445

Pro Ser Arg Asp Glu Leu Arg Lys Arg Phe Ile Ala Ala Ser Glu Tyr
    450                 455                 460

Ala Leu Asp Phe Met Cys Gly Met Leu Thr Met Asn Pro Gln Lys Arg
465                 470                 475                 480

Trp Thr Ala Val Gln Cys Leu Glu Ser Asp Tyr Phe Lys Glu Leu Pro
                485                 490                 495

Pro Pro Ser Asp Pro Ser Ser Ile Lys Ile Arg Asn Val Met Ala Ile
            500                 505                 510

Pro Gly Gly Gly Arg Ile Phe Tyr Pro Tyr Asp Val Pro Asp Tyr Ala
        515                 520                 525

Gly Tyr Pro Tyr Asp Val Pro Asp Tyr Ala Gly Ser Tyr Pro Tyr Asp
    530                 535                 540

Val Pro Asp Tyr Ala Ala Gln Cys Gly Arg Ser Ser
545                 550                 555
```